(12) United States Patent
Booker et al.

(10) Patent No.: US 11,845,760 B2
(45) Date of Patent: Dec. 19, 2023

(54) PRMT5 INHIBITORS

(71) Applicant: AMGEN INC., Thousand Oaks, CA (US)

(72) Inventors: Shon Booker, Sherman Oaks, CA (US); Matthew Paul Bourbeau, Woodland Hills, CA (US); John R. Butler, Thousand Oaks, CA (US); Sanne Ormholt Schroder Glad, Ballerup (DK); Brian Alan Lanman, Woodland Hills, CA (US); Patricia Lopez, Woodland Hills, CA (US); Francesco Manoni, Newbury Park, CA (US); Liping H. Pettus, Thousand Oaks, CA (US); Ian Sarvary, Greve (DK); Nuria A. Tamayo, Newbury Park, CA (US); Mikkel Vestergaard, Greve (DK); Nicholas Anthony Weires, Thousand Oaks, CA (US)

(73) Assignee: AMGEN INC., Thousand Oaks, CA (US)

(*) Notice: Subject to any disclaimer, the term of this patent is extended or adjusted under 35 U.S.C. 154(b) by 30 days.

(21) Appl. No.: 17/552,016

(22) Filed: Dec. 15, 2021

(65) Prior Publication Data

US 2022/0194955 A1 Jun. 23, 2022

Related U.S. Application Data

(60) Provisional application No. 63/126,416, filed on Dec. 16, 2020.

(51) Int. Cl.

| | | |
|---|---|---|
| *C07D 471/04* | (2006.01) | |
| *C07D 471/14* | (2006.01) | |
| *C07D 491/04* | (2006.01) | |
| *C07D 491/14* | (2006.01) | |
| *C07D 495/04* | (2006.01) | |
| *A61K 31/4355* | (2006.01) | |
| *A61K 31/436* | (2006.01) | |
| *A61K 31/4365* | (2006.01) | |
| *A61K 31/437* | (2006.01) | |
| *A61K 31/4375* | (2006.01) | |
| *A61P 35/00* | (2006.01) | |
| *C07D 491/06* | (2006.01) | |
| *C07D 471/06* | (2006.01) | |
| *C07D 471/16* | (2006.01) | |
| *C07D 491/16* | (2006.01) | |

(52) U.S. Cl.
CPC .......... *C07D 491/06* (2013.01); *A61P 35/00* (2018.01); *C07D 471/06* (2013.01); *C07D 471/16* (2013.01); *C07D 491/16* (2013.01)

(58) Field of Classification Search
CPC .. C07D 471/04; C07D 471/14; C07D 491/04; C07D 491/14; C07D 495/04; A61K 31/4355; A61K 31/436; A61K 31/4365; A61K 31/437; A61K 31/4375; A61P 35/00

See application file for complete search history.

(56) References Cited

FOREIGN PATENT DOCUMENTS

| | | |
|---|---|---|
| WO | 2016026549 | 2/2016 |
| WO | 2019032859 W | 2/2019 |
| WO | 2020033282 W | 2/2020 |
| WO | 2020033285 W | 2/2020 |
| WO | 2021163344 W | 8/2021 |

OTHER PUBLICATIONS

Feustel et al., Protein Arginine Methyltransferase 5 (PRMT5) Inhibitors in Oncology Clinical Trials: A Review, Journal of Immunotherapy and Precision Oncology, vol. 5, No. 3, pp. 58-67 (Year: 2022).*
Elayne Chan-Penebre et al., "A selective inhibitor of PRMT5 with in vivo and in vitro potency in MCL models", Nature Chemical Biology, vol. 11, No. 6, Apr. 27, 2015, pp. 432-437.
International Search Report and Written Opinion dated Mar. 28, 2022 in PCT/US21/063540.
Mao et al., "Potent, Selective, and Cell Active Protein Arginine Methyltransferase 5 (PRMT 5) Inhibitor Developed by Structure-Based Virtual Screening and Hit Optimization", Journal of Medicinal Chemistry, vol. 60, No. 14, Jun. 26, 2017.

* cited by examiner

*Primary Examiner* — Brenda L Coleman
(74) *Attorney, Agent, or Firm* — Olga Mekhovich

(57) ABSTRACT

Described herein are novel PRMT5 inhibitors of Formula I and pharmaceutically acceptable salts thereof, as well as the pharmaceutical compositions thereof. Compounds of the present invention are useful for inhibiting PRMT5 activity and may have use in treating proliferative, metabolic and blood disorders. Compounds of Formula I have the following structure:

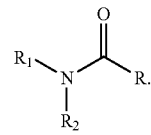

46 Claims, No Drawings

PRMT5 INHIBITORS

CROSS-REFERENCE TO RELATED APPLICATION

This application claims the benefit of U.S. Provisional Application No. 63/126,416 filed Dec. 16, 2020, which is incorporated in its entirety by referenced herein.

BACKGROUND OF THE INVENTION

Epigenetic regulation of gene expression is an important biological determinant of protein production and cellular differentiation and plays a significant pathogenic role in a number of human diseases.

Epigenetic regulation involves heritable modification of genetic material without changing its nucleotide sequence. Typically, epigenetic regulation is mediated by selective and reversible modification (e.g., methylation) of DNA and proteins (e.g., histones) that control the conformational transition between transcriptionally active and inactive states of chromatin. These covalent modifications can be controlled by enzymes such as methyltransferases (e.g., PRMT5), many of which are associated with specific genetic alterations that can cause human disease. PRMT5 plays a role in diseases such as proliferative disorders, metabolic disorders, and blood disorders.

The homozygous deletion of tumor suppressor genes is a key driver of cancer, frequently resulting in the collateral loss of passenger genes located in close genomic proximity to the tumor suppressor. Deletion of these passenger genes can create therapeutically tractable vulnerabilities that are specific to tumor cells. Homozygous deletion of the chromosome 9p21 locus, which harbors the well-known tumor suppressor CDKN2A (cyclin dependent kinase inhibitor 2A), occurs in 15% of all tumors and frequently includes the passenger gene MTAP (methylthioadenosine phosphorylase), a key enzyme in the methionine and adenine salvage pathways. Deletion of MTAP results in accumulation of its substrate, methylthioadenosine (MTA). MTA shares close structural similarity to S-adenosylmethionine (SAM), the substrate methyl donor for the type II methyltransferase PRMT5. Elevated MTA levels, driven by loss of MTAP, selectively compete with SAM for binding to PRMT5, placing the methyltransferase in a hypomorphic state, vulnerable to further PRMT5 inhibition. Multiple genome scale shRNA drop out screens performed in large tumor cell line panels have identified a strong correlation between MTAP loss and cell line dependency on PRMT5, further highlighting the strength of this metabolic vulnerability. However, PRMT5 is a known cell essential gene and conditional PRMT5 knockout and siRNA knockdown studies suggest that significant liabilities could be associated with inhibiting PRMT5 in normal tissues (e.g., pan-cytopenia, infertility, skeletal muscle loss, cardiac hypertrophy). Therefore, novel strategies are required to exploit this metabolic vulnerability and preferentially target PRMT5 in MTAP null tumors while sparing PRMT5 in normal tissues (MTAP WT). Targeting PRMT5 with an MTA-cooperative small molecule inhibitor could preferentially target the MTA bound state of PRMT5, enriched in MTAP null tumor cells, while providing an improved therapeutic index over normal cells where MTAP is intact and MTA levels are low.

SUMMARY OF THE INVENTION

In one aspect, the invention provides a compound of Formula I

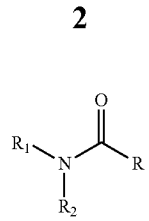

I a tautomer thereof, a stereoisomer thereof, or a pharmaceutically acceptable salt of any of the foregoing:
wherein $R^1$, $R^2$ and the nitrogen atom to which they are attached form a five, six or seven membered ring that may be saturated or partially saturated, and comprises 0, 1 or 2 additional heteroatoms, independently selected from O, N or S, wherein the S atom is optionally substituted with one or two oxo groups;
wherein the ring formed by $R^1$, $R^2$ and the nitrogen atom to which they are attached can be substituted with 0, 1, 2 or 3 $R^3$;
wherein $R^3$ is in each instance selected independently from $C_{1-6}$ alkyl, halo, $C_{1-6}$ haloalkyl, —$OC_{1-6}$ alkyl, —$OC_{1-6}$ haloalkyl, —$C(O)C_{1-6}$ alkyl, —$C(O)C_{1-6}$haloalkyl, —$C(O)OC_{1-6}$ alkyl, —$C(O)OC_{1-6}$ haloalkyl, and five or six membered cycle that may be saturated, partially saturated, or aromatic, and comprises 0, 1 or 2 heteroatoms, independently selected from O, N and S, wherein the cycle may be optionally substituted with one or more $R^a$,
wherein $R^a$ is in each instance independently selected from halo, CN, $C_{1-6}$ alkyl, $C_{1-6}$ haloalkyl, pentafluorosulfanyl, —$OC_{1-3}$ alkyl, and —$OC_{1-3}$ haloalkyl;
wherein R is a tricycle selected from the formulae IA and IB:

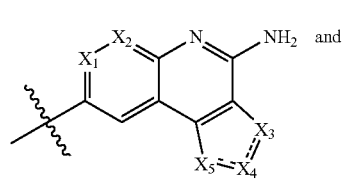

IA

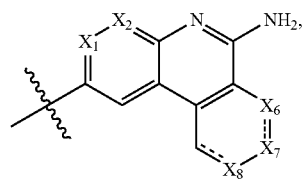

IB wherein ⇌ is a single or double bond,
$X^1$, $X^2$, $X^6$, $X^7$ and $X^8$ are in each instance independently selected from optionally substituted N and C, wherein substituents are independently selected from $C_{1-3}$ alkyl;
wherein both $X^1$ and $X^2$ cannot be N at the same time, and $X^6$ and $X^7$, and $X^7$ and $X^8$ cannot be N at the same time;
further wherein if $X^1$ is C, it can be optionally substituted with halo;
$X^3$, $X^4$ and $X^5$ are at each instance independently selected from optionally substituted C, O, N and S, wherein the substituents are independently selected from $C_{1-3}$ alkyl, and $C_{1-3}$ alkyl(OH), wherein alkyl can be optionally substituted with halo.

The invention provides compounds, the tautomer thereof, the stereoisomer thereof, or the pharmaceutically acceptable salt of any of the foregoing, wherein R is a tricycle of Formula IA

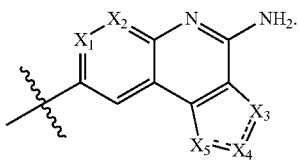
IA

In one aspect, R can be

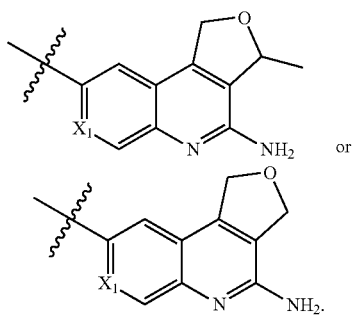

or

In a further aspect, R can be

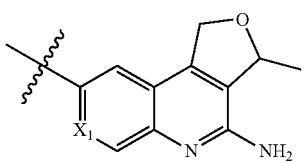

In another aspect, R can be

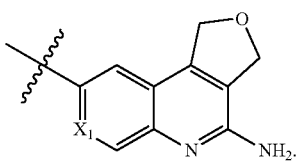

The invention provides compounds, the tautomer thereof, the stereoisomer thereof, or the pharmaceutically acceptable salt of any of the foregoing, wherein R is

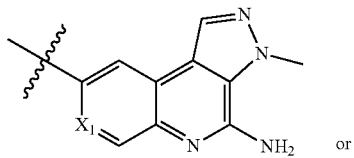

or

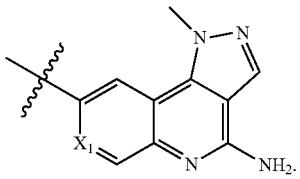

In one aspect, R can be

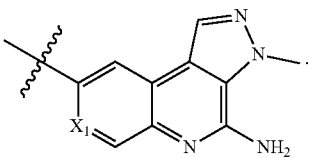

In another aspect, R can be

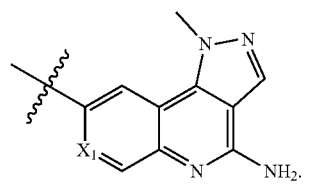

The invention encompasses compound as described above, the tautomer thereof, the stereoisomer thereof, or the pharmaceutically acceptable salt of any of the foregoing, wherein $X^1$ is C. In one aspect, $X^1$ can be substituted with halo.

The invention further encompasses compound as described above, the tautomer thereof, the stereoisomer thereof, or the pharmaceutically acceptable salt of any of the foregoing, wherein $X^1$ can be N.

The invention further provides compounds, the tautomer thereof, the stereoisomer thereof, or the pharmaceutically acceptable salt of any of the foregoing, wherein R is a tricycle of Formula IB

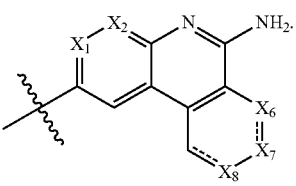
IB

In one aspect, in compounds of Formula IB $X^1$ can be N.
In a further aspect, $X^7$ can be N.
In one aspect of the invention, R can be

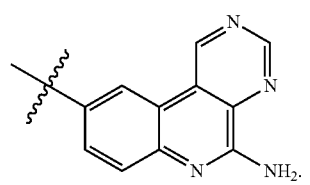 [SMILES: *c1ccc2nc(N)c3ncncc3c2c1]

In another aspect, R can be

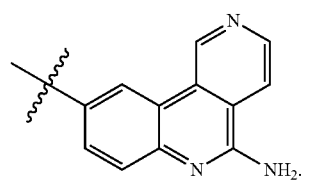 [SMILES: *c1ccc2nc(N)c3ccncc3c2c1]

The invention further provides compounds as described above, the tautomer thereof, the stereoisomer thereof, or the pharmaceutically acceptable salt of any of the foregoing, wherein $R^1$, $R^2$ and the nitrogen atom to which they are attached form a six membered ring that may be saturated or partially saturated, and comprises 0, 1 or 2 additional heteroatoms independently selected from O, N or S, wherein the six membered ring is

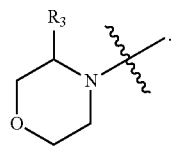

In one aspect, $R^3$ can be selected from phenyl, pyridinyl, pyrazidinyl, or pyrimidinyl, optionally independently substituted with one or more R.

In a further aspect, $R^3$ can be phenyl, optionally independently substituted with one or more $R^a$.

In a further aspect, $R^a$ can be, for example, $C_{1-6}$ haloalkyl or $-OC_{1-3}$ haloalkyl.

The invention provides compounds as described above, the tautomer thereof, the stereoisomer thereof, or the pharmaceutically acceptable salt of any of the foregoing, wherein $X^1$ is C, optionally substituted with halo. In one aspect, halo can be Cl or F.

The invention provides compounds the tautomer thereof, the stereoisomer thereof, or the pharmaceutically acceptable salt of any of the foregoing, wherein $R^1$, $R^2$ and the nitrogen atom to which they are attached form a six membered ring that may be saturated or partially saturated, and comprises 0, 1 or 2 additional heteroatoms selected from O, N or S, wherein the six membered ring can be

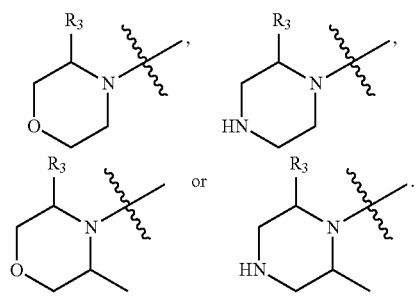

In one aspect, the six membered ring can be

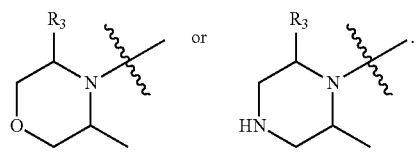

In a further aspect, $R^3$ can be independently selected from phenyl, pyridinyl, pyrazidinyl or pyrimidinyl, optionally independently substituted with one or more $R^a$.

In a different aspect, the invention provides compounds, the tautomer thereof, the stereoisomer thereof, or the pharmaceutically acceptable salt of any of the foregoing, wherein $R^1$, $R^2$ and the nitrogen atom to which they are attached form pyrrolidinyl.

In a further aspect, these compounds include $R^3$ as phenyl, optionally independently substituted with one or more $R^a$. In one aspect, $R^a$ can be $C_{1-6}$ haloalkyl or $-OC_{1-3}$ haloalkyl.

The invention encompasses compounds as described above, the tautomer thereof, the stereoisomer thereof, or the pharmaceutically acceptable salt of any of the foregoing, wherein $X^1$ is C, optionally substituted with $C_{1-3}$ alkyl or halo. In one aspect, $C_{1-3}$ alkyl can be methyl. In another aspect, halo can be Cl or Br.

The invention encompasses compounds as described above, the tautomer thereof, the stereoisomer thereof, or the pharmaceutically acceptable salt of any of the foregoing, wherein $X^1$ is N.

In one aspect, the invention provides compounds as described above, the tautomer thereof, the stereoisomer thereof, or the pharmaceutically acceptable salt of any of the foregoing, wherein $R^1$, $R^2$ and the nitrogen atom to which they are attached form a six membered ring that may be saturated or partially saturated, and comprises 0, 1 or 2 additional heteroatoms selected from O, N or S, wherein the six membered ring can be

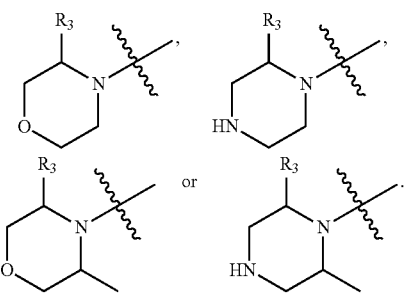

In one aspect, $R^3$ can be independently selected from phenyl, pyridinyl, pyrazidinyl and pyrimidinyl, optionally substituted with one or more $R^a$. In a further aspect, $R^a$ can be in each instance selected from halo, CN, $C_{1-6}$ alkyl, $C_{1-6}$haloalkyl, $-OC_{1-3}$ alkyl, and $-OC_{1-3}$ haloalkyl.

In one aspect, the invention provides compounds as described above, the tautomer thereof, the stereoisomer thereof, or the pharmaceutically acceptable salt of any of the foregoing, wherein $R^1$, $R^2$ and the nitrogen atom to which they are attached form a six membered ring that may be saturated or partially saturated, and comprises 0, 1 or 2 additional heteroatoms selected from O, N or S, wherein the six membered ring can be

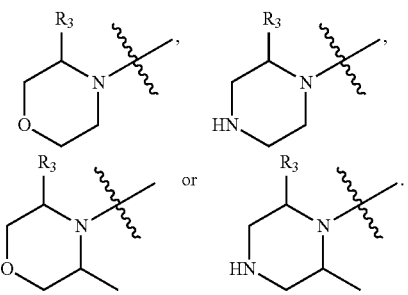

In one aspect, $R^3$ can be independently selected from phenyl, pyridinyl, pyrazidinyl and pyrimidinyl, optionally substituted with one or more $R^a$. In a further aspect, $R^a$ can be in each instance independently selected from halo, CN, $C_{1-6}$ alkyl, $C_{1-6}$haloalkyl, —$OC_{1-3}$ alkyl, and —$OC_{1-3}$haloalkyl.

In another embodiment, $R^3$ can be pyridinyl, optionally substituted with one or more $R^a$. In a further embodiment, $R^a$ can be $C_{1-6}$ haloalkyl. In another embodiment, $R^a$ can be pentafluorosulfanyl.

In one aspect, the invention provides the compound, the tautomer thereof, the stereoisomer thereof, or the pharmaceutically acceptable salt of any of the foregoing, wherein the compound is selected from:

(4-amino-1,3-dihydrofuro[3,4-c]quinolin-8-yl)((3R,5S)-3-(2-fluoro-4-(trifluoromethyl)phenyl)-5-methyl-4-morpholinyl)methanone, ((3R)-4-amino-3-methyl-1,3-dihydrofuro[3,4-c][1,7]naphthyridin-8-yl)((3R)-3-(4-fluoro-3-(trifluoromethoxy)phenyl)-4-morpholinyl)methanone, ((3R)-4-amino-3-methyl-1,3-dihydrofuro[3,4-c][1,7]naphthyridin-8-yl)((3R)-3-(4-fluoro-3-(trifluoromethyl)phenyl)-4-morpholinyl)methanone, ((3R)-4-amino-3-methyl-1,3-dihydrofuro[3,4-c][1,7]naphthyridin-8-yl)((3R)-3-(5-(trifluoromethyl)-2-pyridinyl)-4-morpholinyl)methanone, ((3R)-4-amino-3-methyl-1,3-dihydrofuro[3,4-c][1,7]naphthyridin-8-yl)((3R)-3-(6-ethoxy-3-pyridazinyl)-4-morpholinyl)methanone, ((3R)-4-amino-3-methyl-1,3-dihydrofuro[3,4-c][1,7]naphthyridin-8-yl)((3R,5S)-3-(3,5-difluorophenyl)-5-methyl-4-morpholinyl)methanone, ((3R)-4-amino-3-methyl-1,3-dihydrofuro[3,4-c][1,7]naphthyridin-8-yl)((3R,5S)-3-(6-(difluoromethoxy)-3-pyridazinyl)-5-methyl-4-morpholinyl)methanone, ((3R)-4-amino-3-methyl-1,3-dihydrofuro[3,4-c][1,7]naphthyridin-8-yl)((3R,5S)-3-(6-chloro-3-pyridinyl)-5-methyl-4-morpholinyl)methanone, ((3R)-4-amino-3-methyl-1,3-dihydrofuro[3,4-c][1,7]naphthyridin-8-yl)((3R,5S)-3-(6-ethoxy-3-pyridazinyl)-5-methyl-4-morpholinyl)methanone, ((3R)-4-amino-3-methyl-1,3-dihydrofuro[3,4-c][1,7]naphthyridin-8-yl)((3R,5S)-3-methyl-5-(5-(trifluoromethoxy)-2-pyridinyl)-4-morpholinyl)methanone, ((3R)-4-amino-3-methyl-1,3-dihydrofuro[3,4-c][1,7]naphthyridin-8-yl)((3R,5S)-3-methyl-5-(5-(trifluoromethyl)-2-pyridinyl)-4-morpholinyl)methanone, ((3R)-4-amino-3-methyl-1,3-dihydrofuro[3,4-c][1,7]naphthyridin-8-yl)((3R,5S)-3-methyl-5-(6-(trifluoromethyl)-3-pyridinyl)-4-morpholinyl)methanone, ((3R)-4-amino-3-methyl-1,3-dihydrofuro[3,4-c][1,7]naphthyridin-8-yl)((3S)-3-(4-(pentafluoroethyl)phenyl)-4-morpholinyl)methanone, ((3R)-4-amino-3-methyl-1,3-dihydrofuro[3,4-c][1,7]naphthyridin-8-yl)((3S)-3-(4-(pentafluoro-lambda~6~-sulfanyl)phenyl)-4-morpholinyl)methanone, ((3R)-4-amino-3-methyl-1,3-dihydrofuro[3,4-c][1,7]naphthyridin-8-yl)((3S)-3-(4-(trifluoromethoxy)phenyl)-4-morpholinyl)methanone, ((3R)-4-amino-3-methyl-1,3-dihydrofuro[3,4-c][1,7]naphthyridin-8-yl)((3S)-3-(4-(trifluoromethyl)phenyl)-4-morpholinyl)methanone, ((3R)-4-amino-3-methyl-1,3-dihydrofuro[3,4-c][1,7]naphthyridin-8-yl)((3S)-3-(4-fluoro-3-(trifluoromethoxy)phenyl)-4-morpholinyl)methanone, ((3R)-4-amino-3-methyl-1,3-dihydrofuro[3,4-c][1,7]naphthyridin-8-yl)((3S)-3-(4-fluoro-3-(trifluoromethyl)phenyl)-4-morpholinyl)methanone, ((3R)-4-amino-3-methyl-1,3-dihydrofuro[3,4-c][1,7]naphthyridin-8-yl)((3S)-3-(5-(trifluoromethyl)-2-pyridinyl)-4-morpholinyl)methanone, ((3R)-4-amino-3-methyl-1,3-dihydrofuro[3,4-c][1,7]naphthyridin-8-yl)((3S)-3-(6-ethoxy-3-pyridazinyl)-4-morpholinyl)methanone, ((3R)-4-amino-3-methyl-1,3-dihydrofuro[3,4-c][1,7]naphthyridin-8-yl)((3S,5R)-3-(3,5-difluorophenyl)-5-methyl-4-morpholinyl)methanone, ((3R)-4-amino-3-methyl-1,3-dihydrofuro[3,4-c][1,7]naphthyridin-8-yl)((3S,5R)-3-(6-(difluoromethoxy)-3-pyridazinyl)-5-methyl-4-morpholinyl)methanone, ((3R)-4-amino-3-methyl-1,3-dihydrofuro[3,4-c][1,7]naphthyridin-8-yl)((3S,5R)-3-(6-chloro-3-pyridinyl)-5-methyl-4-morpholinyl)methanone, ((3R)-4-amino-3-methyl-1,3-dihydrofuro[3,4-c][1,7]naphthyridin-8-yl)((3S,5R)-3-(6-ethoxy-3-pyridazinyl)-5-methyl-4-morpholinyl)methanone, ((3R)-4-amino-3-methyl-1,3-dihydrofuro[3,4-c][1,7]naphthyridin-8-yl)((3S,5R)-3-methyl-5-(5-(trifluoromethoxy)-2-pyridinyl)-4-morpholinyl)methanone, ((3R)-4-amino-3-methyl-1,3-dihydrofuro[3,4-c][1,7]naphthyridin-8-yl)((3S,5R)-3-methyl-5-(5-(trifluoromethyl)-2-pyridinyl)-4-morpholinyl)methanone, ((3R)-4-amino-3-methyl-1,3-dihydrofuro[3,4-c][1,7]naphthyridin-8-yl)((3S,5R)-3-methyl-5-(6-(trifluoromethyl)-3-pyridinyl)-4-morpholinyl)methanone, ((3R)-4-amino-3-methyl-1,3-dihydrofuro[3,4-c]quinolin-8-yl)((2R,4R)-4-(4-chlorophenyl)-2-cyclopropyl-1-pyrrolidinyl)methanone, ((3R)-4-amino-3-methyl-1,3-dihydrofuro[3,4-c]quinolin-8-yl)((2R,4S)-4-(4-chlorophenyl)-2-cyclopropyl-1-pyrrolidinyl)methanone, ((3R)-4-amino-3-methyl-1,3-dihydrofuro[3,4-c]quinolin-8-yl)((2S,4R)-4-(4-chlorophenyl)-2-cyclopropyl-1-pyrrolidinyl)methanone, ((3R)-4-amino-3-methyl-1,3-dihydrofuro[3,4-c]quinolin-8-yl)((2S,4S)-4-(4-chlorophenyl)-2-cyclopropyl-1-pyrrolidinyl)methanone, ((3R)-4-amino-3-methyl-1,3-dihydrofuro[3,4-c]quinolin-8-yl)((3R)-3-(2-(trifluoromethyl)-4-pyridinyl)-4-morpholinyl)methanone, ((3R)-4-amino-3-methyl-1,3-dihydrofuro[3,4-c]quinolin-8-yl)((3R)-3-(4-fluoro-3-(trifluoromethoxy)phenyl)-4-morpholinyl)methanone, ((3R)-4-amino-3-methyl-1,3-dihydrofuro[3,4-c]quinolin-8-yl)((3R)-3-(4-fluoro-3-(trifluoromethyl)phenyl)-4-morpholinyl)methanone, ((3R)-4-amino-3-methyl-1,3-dihydrofuro[3,4-c]quinolin-8-yl)((3R)-3-(5-(trifluoromethyl)-2-pyridinyl)-4-morpholinyl)methanone, ((3R)-4-amino-3-methyl-1,3-dihydrofuro[3,4-c]quinolin-8-yl)((3R)-3-(6-ethoxy-3-pyridazinyl)-4-morpholinyl)methanone, ((3R)-4-amino-3-methyl-1,3-dihydrofuro[3,4-c]quinolin-8-yl)((3R,3aR,6aR)-3-phenylhexahydrocyclopenta[b]pyrrol-1(2H)-yl)methanone, ((3R)-4-amino-3-methyl-1,3-dihydrofuro[3,4-c]quinolin-8-yl)((3R,3aR,6aS)-3-phenylhexahydrocyclopenta[b]pyrrol-1(2H)-yl)methanone, ((3R)-4-amino-3-methyl-1,3-dihydrofuro[3,4-c]quinolin-8-yl)((3R,3aR,7aR)-3-phenylhexahydropyrano[4,3-b]pyrrol-1(4H)-yl)methanone, ((3R)-4-amino-3-methyl-1,3-dihydrofuro[3,4-c]quinolin-8-yl)((3R,3aR,7aS)-3-phenylhexahydropyrano[4,3-b]pyrrol-1(4H)-yl)methanone, ((3R)-4-amino-3-methyl-1,3-dihydrofuro[3,4-c]quinolin-8-yl)((3R,3aS,6aR)-3-phenylhexahydrocyclopenta[b]pyrrol-1(2H)-yl)methanone,
((3R)-4-amino-3-methyl-1,3-dihydrofuro[3,4-c]quinolin-8-yl)((3R,3aS,6aS)-3-phenylhexahydrocyclopenta[b]pyrrol-1(2H)-yl)methanone,
((3R)-4-amino-3-methyl-1,3-dihydrofuro[3,4-c]quinolin-8-yl)((3R,3aS,7aR)-3-phenylhexahydropyrano[4,3-b]pyrrol-1(4H)-yl)methanone,
((3R)-4-amino-3-methyl-1,3-dihydrofuro[3,4-c]quinolin-8-yl)((3R,3aS,7aS)-3-phenylhexahydropyrano[4,3-b]pyrrol-1(4H)-yl)methanone,
((3R)-4-amino-3-methyl-1,3-dihydrofuro[3,4-c]quinolin-8-yl)((3R,4R)-3-(4-bromophenyl)-4-methyl-1-pyrrolidinyl)methanone,
((3R)-4-amino-3-methyl-1,3-dihydrofuro[3,4-c]quinolin-8-yl)((3R,4R)-3,4-diphenyl-1-pyrrolidinyl)methanone,
((3R)-4-amino-3-methyl-1,3-dihydrofuro[3,4-c]quinolin-8-yl)((3R,4S)-3-(4-bromophenyl)-4-methyl-1-pyrrolidinyl)methanone,
((3R)-4-amino-3-methyl-1,3-dihydrofuro[3,4-c]quinolin-8-yl)((3R,4S)-3-(4-chlorophenyl)-4-hydroxy-1-pyrrolidinyl)methanone,
((3R)-4-amino-3-methyl-1,3-dihydrofuro[3,4-c]quinolin-8-yl)((3R,4S)-3-(4-fluorophenyl)-4-(1H-pyrazol-3-yl)-1-pyrrolidinyl)methanone,
((3R)-4-amino-3-methyl-1,3-dihydrofuro[3,4-c]quinolin-8-yl)((3R,5S)-3-(2-fluoro-4-(trifluoromethoxy)phenyl)-5-methyl-4-morpholinyl)methanone,
((3R)-4-amino-3-methyl-1,3-dihydrofuro[3,4-c]quinolin-8-yl)((3R,5S)-3-(2-fluoro-4-(trifluoromethyl)phenyl)-5-methyl-4-morpholinyl)methanone,
((3R)-4-amino-3-methyl-1,3-dihydrofuro[3,4-c]quinolin-8-yl)((3R,5S)-3-(6-(difluoromethoxy)-3-pyridazinyl)-5-methyl-4-morpholinyl)methanone,
((3R)-4-amino-3-methyl-1,3-dihydrofuro[3,4-c]quinolin-8-yl)((3R,5S)-3-(6-chloro-3-pyridinyl)-5-methyl-4-morpholinyl)methanone,
((3R)-4-amino-3-methyl-1,3-dihydrofuro[3,4-c]quinolin-8-yl)((3R,5S)-3-(6-ethoxy-3-pyridazinyl)-5-methyl-4-morpholinyl)methanone,
((3R)-4-amino-3-methyl-1,3-dihydrofuro[3,4-c]quinolin-8-yl)((3R,5S)-3-methyl-5-(4-(trifluoromethoxy)phenyl)-4-morpholinyl)methanone,
((3R)-4-amino-3-methyl-1,3-dihydrofuro[3,4-c]quinolin-8-yl)((3R,5S)-3-methyl-5-(5-(trifluoromethoxy)-2-pyridinyl)-4-morpholinyl)methanone,
((3R)-4-amino-3-methyl-1,3-dihydrofuro[3,4-c]quinolin-8-yl)((3R,5S)-3-methyl-5-(5-(trifluoromethyl)-2-pyridinyl)-4-morpholinyl)methanone,
((3R)-4-amino-3-methyl-1,3-dihydrofuro[3,4-c]quinolin-8-yl)((3R,5S)-3-methyl-5-(6-(trifluoromethyl)-3-pyridinyl)-4-morpholinyl)methanone,
((3R)-4-amino-3-methyl-1,3-dihydrofuro[3,4-c]quinolin-8-yl)((3S)-3-(2-(trifluoromethyl)-4-pyridinyl)-4-morpholinyl)methanone,
((3R)-4-amino-3-methyl-1,3-dihydrofuro[3,4-c]quinolin-8-yl)((3S)-3-(4-(pentafluoroethyl)phenyl)-4-morpholinyl)methanone,
((3R)-4-amino-3-methyl-1,3-dihydrofuro[3,4-c]quinolin-8-yl)((3S)-3-(4-(pentafluoro-lambda~6~-sulfanyl)phenyl)-4-morpholinyl)methanone,
((3R)-4-amino-3-methyl-1,3-dihydrofuro[3,4-c]quinolin-8-yl)((3S)-3-(4-fluoro-3-(trifluoromethoxy)phenyl)-4-morpholinyl)methanone,
((3R)-4-amino-3-methyl-1,3-dihydrofuro[3,4-c]quinolin-8-yl)((3S)-3-(4-fluoro-3-(trifluoromethyl)phenyl)-4-morpholinyl)methanone,
((3R)-4-amino-3-methyl-1,3-dihydrofuro[3,4-c]quinolin-8-yl)((3S)-3-(5-(trifluoromethyl)-2-pyridinyl)-4-morpholinyl)methanone,
((3R)-4-amino-3-methyl-1,3-dihydrofuro[3,4-c]quinolin-8-yl)((3S)-3-(6-ethoxy-3-pyridazinyl)-4-morpholinyl)methanone,
((3R)-4-amino-3-methyl-1,3-dihydrofuro[3,4-c]quinolin-8-yl)((3S)-3-fluoro-3-(4-(trifluoromethyl)phenyl)-1-pyrrolidinyl)methanone,
((3R)-4-amino-3-methyl-1,3-dihydrofuro[3,4-c]quinolin-8-yl)((3S)-3-hydroxy-3-(4-(trifluoromethyl)phenyl)-1-pyrrolidinyl)methanone,
((3R)-4-amino-3-methyl-1,3-dihydrofuro[3,4-c]quinolin-8-yl)((3S,3aR,6aR)-3-phenylhexahydrocyclopenta[b]pyrrol-1(2H)-yl)methanone,
((3R)-4-amino-3-methyl-1,3-dihydrofuro[3,4-c]quinolin-8-yl)((3S,3aR,6aS)-3-phenylhexahydrocyclopenta[b]pyrrol-1(2H)-yl)methanone,
((3R)-4-amino-3-methyl-1,3-dihydrofuro[3,4-c]quinolin-8-yl)((3S,3aR,7aR)-3-phenylhexahydropyrano[4,3-b]pyrrol-1(4H)-yl)methanone,
((3R)-4-amino-3-methyl-1,3-dihydrofuro[3,4-c]quinolin-8-yl)((3S,3aR,7aS)-3-phenylhexahydropyrano[4,3-b]pyrrol-1(4H)-yl)methanone,
((3R)-4-amino-3-methyl-1,3-dihydrofuro[3,4-c]quinolin-8-yl)((3S,3aS,6aR)-3-phenylhexahydrocyclopenta[b]pyrrol-1(2H)-yl)methanone,
((3R)-4-amino-3-methyl-1,3-dihydrofuro[3,4-c]quinolin-8-yl)((3S,3aS,6aS)-3-phenylhexahydrocyclopenta[b]pyrrol-1(2H)-yl)methanone,
((3R)-4-amino-3-methyl-1,3-dihydrofuro[3,4-c]quinolin-8-yl)((3S,3aS,7aR)-3-phenylhexahydropyrano[4,3-b]pyrrol-1(4H)-yl)methanone,
((3R)-4-amino-3-methyl-1,3-dihydrofuro[3,4-c]quinolin-8-yl)((3S,3aS,7aS)-3-phenylhexahydropyrano[4,3-b]pyrrol-1(4H)-yl)methanone,
((3R)-4-amino-3-methyl-1,3-dihydrofuro[3,4-c]quinolin-8-yl)((3S,4R)-3-(4-bromophenyl)-4-methyl-1-pyrrolidinyl)methanone,
((3R)-4-amino-3-methyl-1,3-dihydrofuro[3,4-c]quinolin-8-yl)((3S,4R)-3-(4-chlorophenyl)-4-hydroxy-1-pyrrolidinyl)methanone,
((3R)-4-amino-3-methyl-1,3-dihydrofuro[3,4-c]quinolin-8-yl)((3S,4R)-3-(4-fluorophenyl)-4-(1H-pyrazol-3-yl)-1-pyrrolidinyl)methanone,
((3R)-4-amino-3-methyl-1,3-dihydrofuro[3,4-c]quinolin-8-yl)((3S,4R)-3-ethyl-4-(4-methylphenyl)-1-pyrrolidinyl)methanone,
((3R)-4-amino-3-methyl-1,3-dihydrofuro[3,4-c]quinolin-8-yl)((3S,4S)-3-(4-bromophenyl)-4-methyl-1-pyrrolidinyl)methanone,
((3R)-4-amino-3-methyl-1,3-dihydrofuro[3,4-c]quinolin-8-yl)((3S,4S)-3,4-diphenyl-1-pyrrolidinyl)methanone,
((3R)-4-amino-3-methyl-1,3-dihydrofuro[3,4-c]quinolin-8-yl)((3S,5R)-3-(2-fluoro-4-(trifluoromethoxy)phenyl)-5-methyl-4-morpholinyl)methanone,
((3R)-4-amino-3-methyl-1,3-dihydrofuro[3,4-c]quinolin-8-yl)((3S,5R)-3-(2-fluoro-4-(trifluoromethyl)phenyl)-5-methyl-4-morpholinyl)methanone,
((3R)-4-amino-3-methyl-1,3-dihydrofuro[3,4-c]quinolin-8-yl)((3S,5R)-3-(6-(difluoromethoxy)-3-pyridazinyl)-5-methyl-4-morpholinyl)methanone, ((3R)-4-amino-3-methyl-1,3-dihydrofuro[3,4-c]quinolin-8-yl)((3S,5R)-3-(6-chloro-3-pyridinyl)-5-methyl-4-morpholinyl)methanone,
((3R)-4-amino-3-methyl-1,3-dihydrofuro[3,4-c]quinolin-8-yl)((3S,5R)-3-(6-ethoxy-3-pyridazinyl)-5-methyl-4-morpholinyl)methanone,
((3R)-4-amino-3-methyl-1,3-dihydrofuro[3,4-c]quinolin-8-yl)((3S,5R)-3-methyl-5-(5-(trifluoromethoxy)-2-pyridinyl)-4-morpholinyl)methanone,
((3R)-4-amino-3-methyl-1,3-dihydrofuro[3,4-c]quinolin-8-yl)((3S,5R)-3-methyl-5-(5-(trifluoromethyl)-2-pyridinyl)-4-morpholinyl)methanone,
((3R)-4-amino-3-methyl-1,3-dihydrofuro[3,4-c]quinolin-8-yl)((3S,5R)-3-methyl-5-(6-(trifluoromethyl)-3-pyridinyl)-4-morpholinyl)methanone,
((3R)-4-amino-3-methyl-1,3-dihydrofuro[3,4-c]quinolin-8-yl)((4R)-4-(4-fluorophenyl)-3,3-dimethyl-1-pyrrolidinyl)methanone,
((3R)-4-amino-3-methyl-1,3-dihydrofuro[3,4-c]quinolin-8-yl)((4S)-4-(4-fluorophenyl)-3,3-dimethyl-1-pyrrolidinyl)methanone,
((3R)-4-amino-3-methyl-1,3-dihydrofuro[3,4-c]quinolin-8-yl)(3-(5-(trifluoromethyl)-2-pyridinyl)-1-azetidinyl)methanone,
((3R)-4-amino-7-fluoro-3-methyl-1,3-dihydrofuro[3,4-c]quinolin-8-yl)((3R,5S)-3-methyl-5-(6-(3,3,3-trifluoropropoxy)-3-pyridazinyl)-4-morpholinyl)methanone,
((3R)-4-amino-7-fluoro-3-methyl-1,3-dihydrofuro[3,4-c]quinolin-8-yl)((3S,5R)-3-(6-(difluoromethoxy)-3-pyridazinyl)-5-methyl-4-morpholinyl)methanone,
((3R)-4-amino-7-fluoro-3-methyl-1,3-dihydrofuro[3,4-c]quinolin-8-yl)((3S,5R)-3-(6-methoxy-3-pyridazinyl)-5-methyl-4-morpholinyl)methanone,
((3S)-4-amino-3-methyl-1,3-dihydrofuro[3,4-c][1,7]naphthyridin-8-yl)((3R)-3-(4-fluoro-3-(trifluoromethyl)phenyl)-4-morpholinyl)methanone,
((3S)-4-amino-3-methyl-1,3-dihydrofuro[3,4-c][1,7]naphthyridin-8-yl)((3R,5S)-3-(2-fluoro-4-(trifluoromethoxy)phenyl)-5-methyl-4-morpholinyl)methanone,
((3S)-4-amino-3-methyl-1,3-dihydrofuro[3,4-c][1,7]naphthyridin-8-yl)((3R,5S)-3-(2-fluoro-4-(trifluoromethyl)phenyl)-5-methyl-4-morpholinyl)methanone,
((3S)-4-amino-3-methyl-1,3-dihydrofuro[3,4-c][1,7]naphthyridin-8-yl)((3R,5S)-3-methyl-5-(5-(trifluoromethoxy)-2-pyridinyl)-4-morpholinyl)methanone,
((3S)-4-amino-3-methyl-1,3-dihydrofuro[3,4-c][1,7]naphthyridin-8-yl)((3S)-3-(4-(pentafluoroethyl)phenyl)-4-morpholinyl)methanone,
((3S)-4-amino-3-methyl-1,3-dihydrofuro[3,4-c][1,7]naphthyridin-8-yl)((3S)-3-(4-(trifluoromethyl)phenyl)-4-morpholinyl)methanone,
((3S)-4-amino-3-methyl-1,3-dihydrofuro[3,4-c][1,7]naphthyridin-8-yl)((3S)-3-(4-fluoro-3-(trifluoromethyl)phenyl)-4-morpholinyl)methanone,
((3S)-4-amino-3-methyl-1,3-dihydrofuro[3,4-c][1,7]naphthyridin-8-yl)((3S,5R)-3-(2-fluoro-4-(trifluoromethoxy)phenyl)-5-methyl-4-morpholinyl)methanone,
((3S)-4-amino-3-methyl-1,3-dihydrofuro[3,4-c][1,7]naphthyridin-8-yl)((3S,5R)-3-(2-fluoro-4-(trifluoromethyl)phenyl)-5-methyl-4-morpholinyl)methanone,
((3S)-4-amino-3-methyl-1,3-dihydrofuro[3,4-c][1,7]naphthyridin-8-yl)((3S,5R)-3-methyl-5-(5-(trifluoromethoxy)-2-pyridinyl)-4-morpholinyl)methanone,
(4-amino-1,3-dihydrofuro[3,4-c][1,7]naphthyridin-8-yl)((1R,3S)-1-oxido-3-(4-(trifluoromethyl)phenyl)-4-thiomorpholinyl)methanone,
(4-amino-1,3-dihydrofuro[3,4-c][1,7]naphthyridin-8-yl)((1S,3S)-1-oxido-3-(4-(trifluoromethyl)phenyl)-4-thiomorpholinyl)methanone,
(4-amino-1,3-dihydrofuro[3,4-c][1,7]naphthyridin-8-yl)((2S)-2-(4-(trifluoromethyl)phenyl)-1-piperazinyl)methanone,
(4-amino-1,3-dihydrofuro[3,4-c][1,7]naphthyridin-8-yl)((2R)-2-(4-(trifluoromethyl)phenyl)-1-piperazinyl)methanone,
(4-amino-1,3-dihydrofuro[3,4-c][1,7]naphthyridin-8-yl)((3R)-3-(2-fluoro-4-(trifluoromethoxy)phenyl)-4-morpholinyl)methanone,
(4-amino-1,3-dihydrofuro[3,4-c][1,7]naphthyridin-8-yl)((3R)-3-(2-fluoro-4-(trifluoromethyl)phenyl)-4-morpholinyl)methanone,
(4-amino-1,3-dihydrofuro[3,4-c][1,7]naphthyridin-8-yl)((3R)-3-(4-(2,2,2-trifluoroethyl)phenyl)-4-morpholinyl)methanone,
(4-amino-1,3-dihydrofuro[3,4-c][1,7]naphthyridin-8-yl)((3R)-3-(4-(difluoromethoxy)-3-fluorophenyl)-4-morpholinyl)methanone,
(4-amino-1,3-dihydrofuro[3,4-c][1,7]naphthyridin-8-yl)((3R)-3-(4-(trifluoromethyl)-2-thiophenyl)-4-morpholinyl)methanone,
(4-amino-1,3-dihydrofuro[3,4-c][1,7]naphthyridin-8-yl)((3R)-3-(4,5-dichloro-2-thiophenyl)-4-morpholinyl)methanone,
(4-amino-1,3-dihydrofuro[3,4-c][1,7]naphthyridin-8-yl)((3R)-3-(4-bromo-2,6-difluorophenyl)-4-morpholinyl)methanone,
(4-amino-1,3-dihydrofuro[3,4-c][1,7]naphthyridin-8-yl)((3R)-3-(4-fluoro-3-(trifluoromethoxy)phenyl)-4-morpholinyl)methanone,
(4-amino-1,3-dihydrofuro[3,4-c][1,7]naphthyridin-8-yl)((3R)-3-(4-fluoro-3-(trifluoromethyl)phenyl)-4-morpholinyl)methanone,
(4-amino-1,3-dihydrofuro[3,4-c][1,7]naphthyridin-8-yl)((3R)-3-(5-(trifluoromethyl)-2-thiophenyl)-4-morpholinyl)methanone,
(4-amino-1,3-dihydrofuro[3,4-c][1,7]naphthyridin-8-yl)((3R)-3-(6-(2-propanyloxy)-3-pyridinyl)-4-morpholinyl)methanone,
(4-amino-1,3-dihydrofuro[3,4-c][1,7]naphthyridin-8-yl)((3R)-3-(6-(difluoromethoxy)-3-pyridinyl)-4-morpholinyl)methanone,
(4-amino-1,3-dihydrofuro[3,4-c][1,7]naphthyridin-8-yl)((3R,5S)-3-(2-fluoro-4-(trifluoromethoxy)phenyl)-5-methyl-4-morpholinyl)methanone,
(4-amino-1,3-dihydrofuro[3,4-c][1,7]naphthyridin-8-yl)((3R,5S)-3-(2-fluoro-4-(trifluoromethyl)phenyl)-5-methyl-4-morpholinyl)methanone,
(4-amino-1,3-dihydrofuro[3,4-c][1,7]naphthyridin-8-yl)((3R,5S)-3-(4-(difluoromethoxy)-3-fluorophenyl)-5-methyl-4-morpholinyl)methanone,
(4-amino-1,3-dihydrofuro[3,4-c][1,7]naphthyridin-8-yl)((3R,5S)-3-(6-(difluoromethoxy)-3-pyridazinyl)-5-methyl-4-morpholinyl)methanone,
(4-amino-1,3-dihydrofuro[3,4-c][1,7]naphthyridin-8-yl)((3R,5S)-3-(6-(difluoromethoxy)-3-pyridinyl)-5-methyl-4-morpholinyl)methanone,
(4-amino-1,3-dihydrofuro[3,4-c][1,7]naphthyridin-8-yl)((3R,5S)-3-(6-chloro-3-pyridinyl)-5-methyl-4-morpholinyl)methanone,
(4-amino-1,3-dihydrofuro[3,4-c][1,7]naphthyridin-8-yl)((3R,5S)-3-(6-ethoxy-3-pyridazinyl)-5-methyl-4-morpholinyl)methanone, (4-amino-1,3-dihydrofuro[3,4-c][1,7]naphthyridin-8-yl)
((3R,5S)-3-methyl-5-(4-(trifluoromethoxy)phenyl)-4-morpholinyl)methanone,
(4-amino-1,3-dihydrofuro[3,4-c][1,7]naphthyridin-8-yl)
((3R,5S)-3-methyl-5-(4-(trifluoromethyl)phenyl)-4-morpholinyl)methanone,
(4-amino-1,3-dihydrofuro[3,4-c][1,7]naphthyridin-8-yl)
((3R,5S)-3-methyl-5-(5-(trifluoromethoxy)-2-pyridinyl)-4-morpholinyl)methanone,
(4-amino-1,3-dihydrofuro[3,4-c][1,7]naphthyridin-8-yl)
((3R,5S)-3-methyl-5-(5-(trifluoromethyl)-2-pyridinyl)-4-morpholinyl)methanone,
(4-amino-1,3-dihydrofuro[3,4-c][1,7]naphthyridin-8-yl)
((3R,5S)-3-methyl-5-(6-(2,2,2-trifluoroethoxy)-3-pyridazinyl)-4-morpholinyl)methanone,
(4-amino-1,3-dihydrofuro[3,4-c][1,7]naphthyridin-8-yl)
((3R,5S)-3-methyl-5-(6-(2-propanyloxy)-3-pyridinyl)-4-morpholinyl)methanone,
(4-amino-1,3-dihydrofuro[3,4-c][1,7]naphthyridin-8-yl)
((3R,5S)-3-methyl-5-(6-(3,3,3-trifluoropropoxy)-3-pyridazinyl)-4-morpholinyl)methanone,
(4-amino-1,3-dihydrofuro[3,4-c][1,7]naphthyridin-8-yl)
((3R,5S)-3-methyl-5-(6-(trifluoromethyl)-3-pyridazinyl)-4-morpholinyl)methanone,
(4-amino-1,3-dihydrofuro[3,4-c][1,7]naphthyridin-8-yl)
((3R,5S)-3-methyl-5-(6-(trifluoromethyl)-3-pyridinyl)-4-morpholinyl)methanone,
(4-amino-1,3-dihydrofuro[3,4-c][1,7]naphthyridin-8-yl)
((3S)-3-(2-fluoro-4-(trifluoromethoxy)phenyl)-4-morpholinyl)methanone,
(4-amino-1,3-dihydrofuro[3,4-c][1,7]naphthyridin-8-yl)
((3S)-3-(2-fluoro-4-(trifluoromethyl)phenyl)-4-morpholinyl)methanone,
(4-amino-1,3-dihydrofuro[3,4-c][1,7]naphthyridin-8-yl)
((3S)-3-(4-(2,2,2-trifluoroethyl)phenyl)-4-morpholinyl)methanone,
(4-amino-1,3-dihydrofuro[3,4-c][1,7]naphthyridin-8-yl)
((3S)-3-(4-(difluoromethoxy)-3-fluorophenyl)-4-morpholinyl)methanone,
(4-amino-1,3-dihydrofuro[3,4-c][1,7]naphthyridin-8-yl)
((3S)-3-(4-(pentafluoroethyl)phenyl)-4-morpholinyl)methanone,
(4-amino-1,3-dihydrofuro[3,4-c][1,7]naphthyridin-8-yl)
((3S)-3-(4-(trifluoromethyl)phenyl)-1,4-oxazepan-4-yl)methanone,
(4-amino-1,3-dihydrofuro[3,4-c][1,7]naphthyridin-8-yl)
((3R)-3-(4-(trifluoromethyl)phenyl)-1,4-oxazepan-4-yl)methanone,
(4-amino-1,3-dihydrofuro[3,4-c][1,7]naphthyridin-8-yl)
((3S)-3-(4-(trifluoromethyl)phenyl)-4-morpholinyl)methanethione,
(4-amino-1,3-dihydrofuro[3,4-c][1,7]naphthyridin-8-yl)
((3S)-3-(4-(trifluoromethyl)phenyl)-4-thiomorpholinyl)methanone,
(4-amino-1,3-dihydrofuro[3,4-c][1,7]naphthyridin-8-yl)
((3R)-3-(4-(trifluoromethyl)phenyl)-4-thiomorpholinyl)methanone,
(4-amino-1,3-dihydrofuro[3,4-c][1,7]naphthyridin-8-yl)
((3S)-3-(4-bromo-2,6-difluorophenyl)-4-morpholinyl)methanone,
(4-amino-1,3-dihydrofuro[3,4-c][1,7]naphthyridin-8-yl)
((3S)-3-(4-fluoro-3-(trifluoromethoxy)phenyl)-4-morpholinyl)methanone,
(4-amino-1,3-dihydrofuro[3,4-c][1,7]naphthyridin-8-yl)
((3S)-3-(4-fluoro-3-(trifluoromethyl)phenyl)-4-morpholinyl)methanone,
(4-amino-1,3-dihydrofuro[3,4-c][1,7]naphthyridin-8-yl)
((3S)-3-(5-(difluoromethoxy)-2-pyridinyl)-4-morpholinyl)methanone,
(4-amino-1,3-dihydrofuro[3,4-c][1,7]naphthyridin-8-yl)
((3S)-3-(5-(trifluoromethyl)-2-thiophenyl)-4-morpholinyl)methanone,
(4-amino-1,3-dihydrofuro[3,4-c][1,7]naphthyridin-8-yl)
((3S)-3-(5-bromo-3-fluoro-2-pyridinyl)-4-morpholinyl)methanone,
(4-amino-1,3-dihydrofuro[3,4-c][1,7]naphthyridin-8-yl)
((3S)-3-(6-(2-propanyloxy)-3-pyridinyl)-4-morpholinyl)methanone,
(4-amino-1,3-dihydrofuro[3,4-c][1,7]naphthyridin-8-yl)
((3S)-3-(6-(difluoromethoxy)-3-pyridinyl)-4-morpholinyl)methanone,
(4-amino-1,3-dihydrofuro[3,4-c][1,7]naphthyridin-8-yl)
((3S)-3-(6-(trifluoromethyl)-3-pyridazinyl)-4-morpholinyl)methanone,
(4-amino-1,3-dihydrofuro[3,4-c][1,7]naphthyridin-8-yl)
((3S,5R)-3-(2-fluoro-4-(trifluoromethoxy)phenyl)-5-methyl-4-morpholinyl)methanone,
(4-amino-1,3-dihydrofuro[3,4-c][1,7]naphthyridin-8-yl)
((3S,5R)-3-(2-fluoro-4-(trifluoromethyl)phenyl)-5-methyl-4-morpholinyl)methanone,
(4-amino-1,3-dihydrofuro[3,4-c][1,7]naphthyridin-8-yl)
((3S,5R)-3-(4-(difluoromethoxy)-3-fluorophenyl)-5-methyl-4-morpholinyl)methanone,
(4-amino-1,3-dihydrofuro[3,4-c][1,7]naphthyridin-8-yl)
((3S,5R)-3-(6-(cyclopropyloxy)-3-pyridazinyl)-5-methyl-4-morpholinyl)methanone,
(4-amino-1,3-dihydrofuro[3,4-c][1,7]naphthyridin-8-yl)
((3S,5R)-3-(6-(difluoromethoxy)-3-pyridazinyl)-5-methyl-4-morpholinyl)methanone,
(4-amino-1,3-dihydrofuro[3,4-c][1,7]naphthyridin-8-yl)
((3S,5R)-3-(6-(difluoromethoxy)-3-pyridinyl)-5-methyl-4-morpholinyl)methanone,
(4-amino-1,3-dihydrofuro[3,4-c][1,7]naphthyridin-8-yl)
((3S,5R)-3-(6-chloro-3-pyridinyl)-5-methyl-4-morpholinyl)methanone,
(4-amino-1,3-dihydrofuro[3,4-c][1,7]naphthyridin-8-yl)
((3S,5R)-3-(6-ethoxy-3-pyridazinyl)-5-methyl-4-morpholinyl)methanone,
(4-amino-1,3-dihydrofuro[3,4-c][1,7]naphthyridin-8-yl)
((3S,5R)-3-(6-methoxy-3-pyridazinyl)-5-methyl-4-morpholinyl)methanone,
(4-amino-1,3-dihydrofuro[3,4-c][1,7]naphthyridin-8-yl)
((3S,5R)-3-methyl-5-(5-(trifluoromethoxy)-2-pyridinyl)-4-morpholinyl)methanone,
(4-amino-1,3-dihydrofuro[3,4-c][1,7]naphthyridin-8-yl)
((3S,5R)-3-methyl-5-(5-(trifluoromethyl)-2-pyridinyl)-4-morpholinyl)methanone,
(4-amino-1,3-dihydrofuro[3,4-c][1,7]naphthyridin-8-yl)
((3S,5R)-3-methyl-5-(6-(2-propanyloxy)-3-pyridinyl)-4-morpholinyl)methanone,
(4-amino-1,3-dihydrofuro[3,4-c][1,7]naphthyridin-8-yl)
((3S,5R)-3-methyl-5-(6-(trifluoromethyl)-3-pyridinyl)-4-morpholinyl)methanone,
(4-amino-1,3-dihydrofuro[3,4-c][1,7]naphthyridin-8-yl)-
[(2R)-2-[4-(trifluoromethyl)phenyl]-1-piperidyl]methanone,
(4-amino-1,3-dihydrofuro[3,4-c][1,7]naphthyridin-8-yl)-
[(2R)-4,4-difluoro-2-[4-(trifluoromethoxy)phenyl]-1-piperidyl]methanone,
(4-amino-1,3-dihydrofuro[3,4-c][1,7]naphthyridin-8-yl)-
[(2R)-4,4-difluoro-2-[4-(trifluoromethyl)phenyl]-1-piperidyl]methanone, (4-amino-1,3-dihydrofuro[3,4-c][1,7]naphthyridin-8-yl)-[(2S)-2-[4-(trifluoromethyl)phenyl]-1-piperidyl]methanone,
(4-amino-1,3-dihydrofuro[3,4-c][1,7]naphthyridin-8-yl)-[(2S)-4,4-difluoro-2-[4-(trifluoromethoxy)phenyl]-1-piperidyl]methanone,
(4-amino-1,3-dihydrofuro[3,4-c][1,7]naphthyridin-8-yl)-[(2S)-4,4-difluoro-2-[4-(trifluoromethyl)phenyl]-1-piperidyl]methanone,
(4-amino-1,3-dihydrofuro[3,4-c][1,7]naphthyridin-8-yl)-[(3R)-3-(6-methyl-3-pyridyl)morpholin-4-yl]methanone,
(4-amino-1,3-dihydrofuro[3,4-c][1,7]naphthyridin-8-yl)-[(3R)-3-[2-(trifluoromethyl)pyrimidin-5-yl]morpholin-4-yl]methanone,
(4-amino-1,3-dihydrofuro[3,4-c][1,7]naphthyridin-8-yl)-[(3R)-3-[4-(trifluoromethyl)phenyl]morpholin-4-yl]methanone,
(4-amino-1,3-dihydrofuro[3,4-c][1,7]naphthyridin-8-yl)-[(3R)-3-[5-(trifluoromethyl)pyrazin-2-yl]morpholin-4-yl]methanone,
(4-amino-1,3-dihydrofuro[3,4-c][1,7]naphthyridin-8-yl)-[(3R,5S)-3-isobutyl-5-[4-(trifluoromethyl)phenyl]morpholin-4-yl]methanone,
(4-amino-1,3-dihydrofuro[3,4-c][1,7]naphthyridin-8-yl)-[(3S)-3-(6-methyl-3-pyridyl)morpholin-4-yl]methanone,
(4-amino-1,3-dihydrofuro[3,4-c][1,7]naphthyridin-8-yl)-[(3S)-3-[2-(trifluoromethyl)pyrimidin-5-yl]morpholin-4-yl]methanone,
(4-amino-1,3-dihydrofuro[3,4-c][1,7]naphthyridin-8-yl)-[(3S)-3-[4-(trifluoromethoxy)phenyl]morpholin-4-yl]methanone,
(4-amino-1,3-dihydrofuro[3,4-c][1,7]naphthyridin-8-yl)-[(3S)-3-[4-(trifluoromethyl)phenyl]morpholin-4-yl]methanone,
(4-amino-1,3-dihydrofuro[3,4-c][1,7]naphthyridin-8-yl)-[(3S)-3-[5-(trifluoromethyl)pyrazin-2-yl]morpholin-4-yl]methanone,
(4-amino-1,3-dihydrofuro[3,4-c][1,7]naphthyridin-8-yl)-[(3S,5R)-3-isobutyl-5-[4-(trifluoromethyl)phenyl]morpholin-4-yl]methanone,
(4-amino-1,3-dihydrofuro[3,4-c][1,7]naphthyridin-8-yl)-[rac-(3S)-3-(6-cyclopropyl-3-pyridyl)morpholin-4-yl]methanone,
(4-amino-1,3-dihydrofuro[3,4-c][1,7]naphthyridin-8-yl)-[rac-(3S)-3-[5-(trifluoromethyl)-2-pyridyl]morpholin-4-yl]methanone,
(4-amino-1,3-dihydrofuro[3,4-c][1,8]naphthyridin-8-yl)((3R)-3-(4-(trifluoromethyl)phenyl)-4-morpholinyl)methanone,
(4-amino-1,3-dihydrofuro[3,4-c][1,8]naphthyridin-8-yl)((3S)-3-(4-(trifluoromethyl)phenyl)-4-morpholinyl)methanone,
(4-amino-1,3-dihydrofuro[3,4-c][1,8]naphthyridin-8-yl)-[(3S)-3-[4-(trifluoromethoxy)phenyl]morpholin-4-yl]methanone,
(4-amino-1,3-dihydrofuro[3,4-c]quinolin-8-yl)((3R)-3-(4-(2,2,2-trifluoroethyl)phenyl)-4-morpholinyl)methanone,
(4-amino-1,3-dihydrofuro[3,4-c]quinolin-8-yl)((3R)-3-(4-(difluoromethoxy)phenyl)-4-morpholinyl)methanone,
(4-amino-1,3-dihydrofuro[3,4-c]quinolin-8-yl)((3R)-3-(4-fluoro-3-(trifluoromethoxy)phenyl)-4-morpholinyl)methanone,
(4-amino-1,3-dihydrofuro[3,4-c]quinolin-8-yl)((3R)-3-(4-fluoro-3-(trifluoromethyl)phenyl)-4-morpholinyl)methanone,
(4-amino-1,3-dihydrofuro[3,4-c]quinolin-8-yl)((3R,5S)-3-(6-(difluoromethoxy)-3-pyridazinyl)-5-methyl-4-morpholinyl)methanone,
(4-amino-1,3-dihydrofuro[3,4-c]quinolin-8-yl)((3R,5S)-3-(6-ethoxy-3-pyridazinyl)-5-methyl-4-morpholinyl)methanone,
(4-amino-1,3-dihydrofuro[3,4-c]quinolin-8-yl)((3R,5S)-3-methyl-5-(4-(trifluoromethyl)phenyl)-4-morpholinyl)methanone,
(4-amino-1,3-dihydrofuro[3,4-c]quinolin-8-yl)((3R,5S)-3-methyl-5-(5-(trifluoromethoxy)-2-pyridinyl)-4-morpholinyl)methanone,
(4-amino-1,3-dihydrofuro[3,4-c]quinolin-8-yl)((3R,5S)-3-methyl-5-(6-(trifluoromethyl)-3-pyridinyl)-4-morpholinyl)methanone,
(4-amino-1,3-dihydrofuro[3,4-c]quinolin-8-yl)((3S)-3-(4-(2,2,2-trifluoroethyl)phenyl)-4-morpholinyl)methanone,
(4-amino-1,3-dihydrofuro[3,4-c]quinolin-8-yl)((3S)-3-(4-(difluoromethoxy)phenyl)-4-morpholinyl)methanone,
(4-amino-1,3-dihydrofuro[3,4-c]quinolin-8-yl)((3S)-3-(4-(pentafluoroethyl)phenyl)-4-morpholinyl)methanone,
(4-amino-1,3-dihydrofuro[3,4-c]quinolin-8-yl)((3S)-3-(4-(trifluoromethyl)phenyl)-4-morpholinyl)methanethione,
(4-amino-1,3-dihydrofuro[3,4-c]quinolin-8-yl)((3S)-3-(4-fluoro-3-(trifluoromethoxy)phenyl)-4-morpholinyl)methanone,
(4-amino-1,3-dihydrofuro[3,4-c]quinolin-8-yl)((3S)-3-(4-fluoro-3-(trifluoromethyl)phenyl)-4-morpholinyl)methanone,
(4-amino-1,3-dihydrofuro[3,4-c]quinolin-8-yl)((3S)-3-(5-bromo-3-fluoro-2-pyridinyl)-4-morpholinyl)methanone,
(4-amino-1,3-dihydrofuro[3,4-c]quinolin-8-yl)((3S)-3-(6-(trifluoromethyl)-3-pyridazinyl)-4-morpholinyl)methanone,
(4-amino-1,3-dihydrofuro[3,4-c]quinolin-8-yl)((3S,5R)-3-(2-fluoro-4-(trifluoromethyl)phenyl)-5-methyl-4-morpholinyl)methanone,
(4-amino-1,3-dihydrofuro[3,4-c]quinolin-8-yl)((3S,5R)-3-(6-(difluoromethoxy)-3-pyridazinyl)-5-methyl-4-morpholinyl)methanone,
(4-amino-1,3-dihydrofuro[3,4-c]quinolin-8-yl)((3S,5R)-3-(6-ethoxy-3-pyridazinyl)-5-methyl-4-morpholinyl)methanone,
(4-amino-1,3-dihydrofuro[3,4-c]quinolin-8-yl)((3S,5R)-3-methyl-5-(5-(trifluoromethoxy)-2-pyridinyl)-4-morpholinyl)methanone,
(4-amino-1,3-dihydrofuro[3,4-c]quinolin-8-yl)((3S,5R)-3-methyl-5-(6-(trifluoromethyl)-3-pyridinyl)-4-morpholinyl)methanone,
(4-amino-1,3-dihydrofuro[3,4-c]quinolin-8-yl)((5S)-2,2-dimethyl-5-(5-(trifluoromethyl)-2-pyridinyl)-4-morpholinyl)methanone,
(4-amino-1,3-dihydrofuro[3,4-c]quinolin-8-yl)-[(2R,5R)-2-methyl-5-[5-(trifluoromethyl)-2-pyridyl]morpholin-4-yl]methanone,
(4-amino-1,3-dihydrofuro[3,4-c]quinolin-8-yl)-[(2R,5S)-2-methyl-5-[4-(trifluoromethoxy)phenyl]morpholin-4-yl]methanone,
(4-amino-1,3-dihydrofuro[3,4-c]quinolin-8-yl)-[(2R,5S)-2-methyl-5-[5-(trifluoromethyl)-2-pyridyl]morpholin-4-yl]methanone,
(4-amino-1,3-dihydrofuro[3,4-c]quinolin-8-yl)-[(2S,5R)-2-methyl-5-[4-(trifluoromethoxy)phenyl]morpholin-4-yl]methanone,
(4-amino-1,3-dihydrofuro[3,4-c]quinolin-8-yl)-[(3R)-3-(3-chlorophenyl)morpholin-4-yl]methanone, (4-amino-1,3-dihydrofuro[3,4-c]quinolin-8-yl)-[(3R)-3-(4-chlorophenyl)morpholin-4-yl]methanone,
(4-amino-1,3-dihydrofuro[3,4-c]quinolin-8-yl)-[(3R)-3-(5-bromo-2-pyridyl)morpholin-4-yl]methanone,
(4-amino-1,3-dihydrofuro[3,4-c]quinolin-8-yl)-[(3R)-3-(6-methyl-3-pyridyl)morpholin-4-yl]methanone,
(4-amino-1,3-dihydrofuro[3,4-c]quinolin-8-yl)-[(3R)-3-[4-(trifluoromethyl)phenyl]morpholin-4-yl]methanone,
(4-amino-1,3-dihydrofuro[3,4-c]quinolin-8-yl)-[(3R)-3-[5-(trifluoromethyl)-2-pyridyl]morpholin-4-yl]methanone,
(4-amino-1,3-dihydrofuro[3,4-c]quinolin-8-yl)-[(3R)-3-[6-(trifluoromethoxy)-3-pyridyl]morpholin-4-yl]methanone,
(4-amino-1,3-dihydrofuro[3,4-c]quinolin-8-yl)-[(3R,5S)-3-methyl-5-[4-(trifluoromethoxy)phenyl]morpholin-4-yl]methanone,
(4-amino-1,3-dihydrofuro[3,4-c]quinolin-8-yl)-[(3S)-3-(3-chlorophenyl)morpholin-4-yl]methanone,
(4-amino-1,3-dihydrofuro[3,4-c]quinolin-8-yl)-[(3S)-3-(4-chlorophenyl)morpholin-4-yl]methanone,
(4-amino-1,3-dihydrofuro[3,4-c]quinolin-8-yl)-[(3S)-3-(5-bromo-2-pyridyl)morpholin-4-yl]methanone,
(4-amino-1,3-dihydrofuro[3,4-c]quinolin-8-yl)-[(3S)-3-(6-methyl-3-pyridyl)morpholin-4-yl]methanone,
(4-amino-1,3-dihydrofuro[3,4-c]quinolin-8-yl)-[(3S)-3-[4-(trifluoromethoxy)phenyl]morpholin-4-yl]methanone,
(4-amino-1,3-dihydrofuro[3,4-c]quinolin-8-yl)-[(3S)-3-[4-(trifluoromethyl)phenyl]morpholin-4-yl]methanone,
(4-amino-1,3-dihydrofuro[3,4-c]quinolin-8-yl)-[(3S)-3-[5-(trifluoromethyl)-2-pyridyl]morpholin-4-yl]methanone,
(4-amino-1,3-dihydrofuro[3,4-c]quinolin-8-yl)-[(3S)-3-[6-(trifluoromethoxy)-3-pyridyl]morpholin-4-yl]methanone,
(4-amino-1,3-dihydrofuro[3,4-c]quinolin-8-yl)-[(3S)-3-[6-(trifluoromethyl)-3-pyridyl]morpholin-4-yl]methanone,
(4-amino-1,3-dihydrofuro[3,4-c]quinolin-8-yl)-[(3S,5R)-3-methyl-5-[4-(trifluoromethoxy)phenyl]morpholin-4-yl]methanone,
(4-amino-1,3-dihydrofuro[3,4-c]quinolin-8-yl)-[(3S,5R)-3-methyl-5-[5-(trifluoromethyl)-2-pyridyl]morpholin-4-yl]methanone,
(4-amino-1,3-dihydrofuro[3,4-c]quinolin-8-yl)-[(3S,5S)-3-methyl-5-[5-(trifluoromethyl)-2-pyridyl]morpholin-4-yl]methanone,
(4-amino-1,3-dihydrofuro[3,4-c]quinolin-8-yl)-[rac-(2R)-2-(4-bromophenyl)-4,4-difluoro-1-piperidyl]methanone,
(4-amino-1,3-dihydrofuro[3,4-c]quinolin-8-yl)-[rac-(3R)-3-(6-methyl-3-pyridyl)morpholin-4-yl]methanone,
(4-amino-1,3-dihydrofuro[3,4-c]quinolin-8-yl)-[rac-(3S)-3-(2-chlorophenyl)morpholin-4-yl]methanone,
(4-amino-1,3-dihydrofuro[3,4-c]quinolin-8-yl)-[rac-(3S)-3-(3-bromophenyl)morpholin-4-yl]methanone,
(4-amino-1,3-dihydrofuro[3,4-c]quinolin-8-yl)-[rac-(3S)-3-(3-fluorophenyl)morpholin-4-yl]methanone,
(4-amino-1,3-dihydrofuro[3,4-c]quinolin-8-yl)-[rac-(3S)-3-(4-bromophenyl)morpholin-4-yl]methanone,
(4-amino-1,3-dihydrofuro[3,4-c]quinolin-8-yl)-[rac-(3S)-3-(4-fluorophenyl)morpholin-4-yl]methanone,
(4-amino-1,3-dihydrofuro[3,4-c]quinolin-8-yl)-[rac-(3S)-3-(4-methoxyphenyl)morpholin-4-yl]methanone,
(4-amino-1,3-dihydrofuro[3,4-c]quinolin-8-yl)-[rac-(3S)-3-(6-bromopyridazin-3-yl)morpholin-4-yl]methanone,
(4-amino-1,3-dihydrofuro[3,4-c]quinolin-8-yl)-[rac-(3S)-3-(o-tolyl)morpholin-4-yl]methanone,
(4-amino-1,3-dihydrofuro[3,4-c]quinolin-8-yl)-[rac-(3S)-3-(p-tolyl)morpholin-4-yl]methanone,
(4-amino-1,3-dihydrofuro[3,4-c]quinolin-8-yl)-[rac-(3S)-3-[6-(trifluoromethyl)-3-pyridyl]morpholin-4-yl]methanone,
(4-amino-1,3-dihydrofuro[3,4-c]quinolin-8-yl)-[rac-(3S)-3-phenylmorpholin-4-yl]methanone,
(4-amino-1,3-dihydrofuro[3,4-c]quinolin-8-yl)-[rac-(3S)-3-pyrimidin-2-ylmorpholin-4-yl]methanone,
(4-amino-1,7-dimethyl-1H-pyrazolo[4,3-c][1,8]naphthyridin-8-yl)((3S)-3-(4-(trifluoromethyl)phenyl)-4-morpholinyl)methanone,
(4-amino-1,7-dimethyl-1H-pyrazolo[4,3-c]quinolin-8-yl)((3S)-3-(4-(trifluoromethyl)phenyl)-4-morpholinyl)methanone,
(4-amino-1-methyl-1H-pyrazolo[4,3-c][1,7]naphthyridin-8-yl)((3R)-3-(4-(trifluoromethyl)benzyl)-1-pyrrolidinyl)methanone,
(4-amino-1-methyl-1H-pyrazolo[4,3-c][1,7]naphthyridin-8-yl)((3R)-3-(4-(trifluoromethyl)phenoxy)-1-pyrrolidinyl)methanone,
(4-amino-1-methyl-1H-pyrazolo[4,3-c][1,7]naphthyridin-8-yl)((3R)-3-(4-(trifluoromethyl)phenyl)-1-pyrrolidinyl)methanone,
(4-amino-1-methyl-1H-pyrazolo[4,3-c][1,7]naphthyridin-8-yl)((3R,5S)-3-methyl-5-(5-(trifluoromethyl)-2-pyridinyl)-4-morpholinyl)methanone,
(4-amino-1-methyl-1H-pyrazolo[4,3-c][1,7]naphthyridin-8-yl)((3S)-3-(4-(pentafluoroethyl)phenyl)-4-morpholinyl)methanone,
(4-amino-1-methyl-1H-pyrazolo[4,3-c][1,7]naphthyridin-8-yl)((3S)-3-(4-(pentafluoro-lambda~6~-sulfanyl)phenyl)-4-morpholinyl)methanone,
(4-amino-1-methyl-1H-pyrazolo[4,3-c][1,7]naphthyridin-8-yl)((3S)-3-(4-(trifluoromethyl)benzyl)-1-pyrrolidinyl)methanone,
(4-amino-1-methyl-1H-pyrazolo[4,3-c][1,7]naphthyridin-8-yl)((3S)-3-(4-(trifluoromethyl)phenoxy)-1-pyrrolidinyl)methanone,
(4-amino-1-methyl-1H-pyrazolo[4,3-c][1,7]naphthyridin-8-yl)((3S)-3-(4-(trifluoromethyl)phenyl)-4-morpholinyl)methanone,
(4-amino-1-methyl-1H-pyrazolo[4,3-c][1,7]naphthyridin-8-yl)((3S)-3-(6-(difluoromethoxy)-3-pyridazinyl)-4-morpholinyl)methanone,
(4-amino-1-methyl-1H-pyrazolo[4,3-c]quinolin-8-yl)((3R)-3-(4-(trifluoromethyl)phenyl)-1-pyrrolidinyl)methanone,
(4-amino-1-methyl-1H-pyrazolo[4,3-c]quinolin-8-yl)((3S)-3-(4-(pentafluoroethyl)phenyl)-4-morpholinyl)methanone,
(4-amino-1-methyl-1H-pyrazolo[4,3-c]quinolin-8-yl)((3S)-3-(4-(pentafluoro-lambda~6~-sulfanyl)phenyl)-4-morpholinyl)methanone,
(4-amino-1-methyl-1H-pyrazolo[4,3-c]quinolin-8-yl)((3S)-3-(4-(trifluoromethyl)phenyl)-4-morpholinyl)methanone,
(4-amino-1-methyl-1H-pyrazolo[4,3-c]quinolin-8-yl)((3S)-3-(6-(difluoromethoxy)-3-pyridazinyl)-4-morpholinyl)methanone,
(4-amino-1-methyl-1H-pyrazolo[4,3-c]quinolin-8-yl)(3-(4-(trifluoromethyl)phenyl)-1-azetidinyl)methanone,
(4-amino-1-methyl-7-(trifluoromethyl)-1H-pyrazolo[4,3-c]quinolin-8-yl)((3R)-3-(4-(trifluoromethyl)phenyl)-1-pyrrolidinyl)methanone,
(4-amino-1-methyl-7-(trifluoromethyl)-1H-pyrazolo[4,3-c]quinolin-8-yl)((3S)-3-(4-(trifluoromethyl)phenyl)-4-morpholinyl)methanone,
(4-amino-2,3-dihydrofuro[3,2-c][1,7]naphthyridin-8-yl)((3S)-3-(4-(trifluoromethyl)phenyl)-4-morpholinyl)methanone,
(4-amino-3,3-dimethyl-1H-furo[3,4-c]quinolin-8-yl)-[(3S)-3-[4-(trifluoromethoxy)phenyl]morpholin-4-yl]methanone, (4-amino-3,7-dimethyl-3H-pyrazolo[3,4-c]quinolin-8-yl)
((3S)-3-(4-(trifluoromethyl)phenyl)-4-morpholinyl)
methanone,
(4-amino-3-methyl-1H-pyrazolo[4,3-c][1,7]naphthyridin-8-
yl)((3S)-3-(4-(trifluoromethyl)phenyl)-4-morpholinyl)
methanone,
(4-amino-3-methyl-1H-pyrazolo[4,3-c]quinolin-8-yl)((3S)-
3-(4-(trifluoromethyl)phenyl)-4-morpholinyl)methanone,
(4-amino-3-methyl-3H-pyrazolo[3,4-c]quinolin-8-yl)((3R)-
3-(4-(trifluoromethoxy)phenyl)-4-morpholinyl)metha-
none,
(4-amino-3-methyl-3H-pyrazolo[3,4-c]quinolin-8-yl)((3R)-
3-(4-(trifluoromethyl)phenyl)-4-morpholinyl)methanone,
(4-amino-3-methyl-3H-pyrazolo[3,4-c]quinolin-8-yl)((3R)-
3-(5-(trifluoromethyl)-2-pyridinyl)-4-morpholinyl)
methanone,
(4-amino-3-methyl-3H-pyrazolo[3,4-c]quinolin-8-yl)((3R,
5S)-3-methyl-5-(4-(trifluoromethoxy)phenyl)-4-mor-
pholinyl)methanone,
(4-amino-3-methyl-3H-pyrazolo[3,4-c]quinolin-8-yl)((3R,
5S)-3-methyl-5-(4-(trifluoromethyl)phenyl)-4-morpholi-
nyl)methanone,
(4-amino-3-methyl-3H-pyrazolo[3,4-c]quinolin-8-yl)((3R,
5S)-3-methyl-5-(5-(trifluoromethyl)-2-pyridinyl)-4-mor-
pholinyl)methanone,
(4-amino-3-methyl-3H-pyrazolo[3,4-c]quinolin-8-yl)((3S)-
3-(4-(trifluoromethoxy)phenyl)-4-morpholinyl)metha-
none,
(4-amino-3-methyl-3H-pyrazolo[3,4-c]quinolin-8-yl)((3S)-
3-(4-(trifluoromethyl)phenyl)-4-morpholinyl)methanone,
(4-amino-3-methyl-3H-pyrazolo[3,4-c]quinolin-8-yl)((3S)-
3-(5-(difluoromethoxy)-2-pyridinyl)-4-morpholinyl)
methanone,
(4-amino-3-methyl-3H-pyrazolo[3,4-c]quinolin-8-yl)((3S)-
3-(5-(trifluoromethyl)-2-pyridinyl)-4-morpholinyl)
methanone,
(4-amino-3-methyl-3H-pyrazolo[3,4-c]quinolin-8-yl)((3S,
5R)-3-(6-methoxy-3-pyridazinyl)-5-methyl-4-morpholi-
nyl)methanone,
(4-amino-7-chloro-1,3-dihydrofuro[3,4-c]quinolin-8-yl)
((3R)-3-(2-(trifluoromethyl)-4-pyridinyl)-4-morpholinyl)
methanone,
(4-amino-7-chloro-1,3-dihydrofuro[3,4-c]quinolin-8-yl)
((3R)-3-(4-fluoro-3-(trifluoromethoxy)phenyl)-4-mor-
pholinyl)methanone,
(4-amino-7-chloro-1,3-dihydrofuro[3,4-c]quinolin-8-yl)
((3R)-3-(4-fluoro-3-(trifluoromethyl)phenyl)-4-mor-
pholinyl)methanone,
(4-amino-7-chloro-1,3-dihydrofuro[3,4-c]quinolin-8-yl)
((3R)-3-(5-(trifluoromethyl)-2-pyridinyl)-1-pyrrolidinyl)
methanone,
(4-amino-7-chloro-1,3-dihydrofuro[3,4-c]quinolin-8-yl)
((3R)-3-(5-(trifluoromethyl)-2-pyridinyl)-4-morpholinyl)
methanone,
(4-amino-7-chloro-1,3-dihydrofuro[3,4-c]quinolin-8-yl)
((3R)-3-(6-(difluoromethoxy)-3-pyridinyl)-4-morpholi-
nyl)methanone,
(4-amino-7-chloro-1,3-dihydrofuro[3,4-c]quinolin-8-yl)
((3R)-3-(6-ethoxy-3-pyridazinyl)-4-morpholinyl)metha-
none,
(4-amino-7-chloro-1,3-dihydrofuro[3,4-c]quinolin-8-yl)
((3R)-3-hydroxy-3-(4-(trifluoromethyl)phenyl)-1-pyrro-
lidinyl)methanone,
(4-amino-7-chloro-1,3-dihydrofuro[3,4-c]quinolin-8-yl)
((3R,4S)-3-(4-fluorophenyl)-4-(1H-pyrazol-3-yl)-1-pyr-
rolidinyl)methanone,
(4-amino-7-chloro-1,3-dihydrofuro[3,4-c]quinolin-8-yl)
((3R,4S)-3-ethyl-4-(4-methylphenyl)-1-pyrrolidinyl)
methanone,
(4-amino-7-chloro-1,3-dihydrofuro[3,4-c]quinolin-8-yl)
((3R,5S)-3-(6-ethoxy-3-pyridazinyl)-5-methyl-4-mor-
pholinyl)methanone,
(4-amino-7-chloro-1,3-dihydrofuro[3,4-c]quinolin-8-yl)
((3R,5S)-3-methyl-5-(4-(trifluoromethoxy)phenyl)-4-
morpholinyl)methanone,
(4-amino-7-chloro-1,3-dihydrofuro[3,4-c]quinolin-8-yl)
((3R,5S)-3-methyl-5-(5-(trifluoromethoxy)-2-pyridinyl)-
4-morpholinyl)methanone,
(4-amino-7-chloro-1,3-dihydrofuro[3,4-c]quinolin-8-yl)
((3R,5S)-3-methyl-5-(5-(trifluoromethyl)-2-pyridinyl)-4-
morpholinyl)methanone,
(4-amino-7-chloro-1,3-dihydrofuro[3,4-c]quinolin-8-yl)
((3R,5S)-3-methyl-5-(6-(trifluoromethyl)-3-pyridinyl)-4-
morpholinyl)methanone,
(4-amino-7-chloro-1,3-dihydrofuro[3,4-c]quinolin-8-yl)
((3S)-3-(2-(trifluoromethyl)-4-pyridinyl)-4-morpholinyl)
methanone,
(4-amino-7-chloro-1,3-dihydrofuro[3,4-c]quinolin-8-yl)
((3S)-3-(4-(pentafluoro-lambda~6~-sulfanyl)phenyl)-4-
morpholinyl)methanone,
(4-amino-7-chloro-1,3-dihydrofuro[3,4-c]quinolin-8-yl)
((3S)-3-(4-(trifluoromethyl)phenyl)-4-morpholinyl)
methanone,
(4-amino-7-chloro-1,3-dihydrofuro[3,4-c]quinolin-8-yl)
((3S)-3-(4-fluoro-3-(trifluoromethoxy)phenyl)-4-mor-
pholinyl)methanone,
(4-amino-7-chloro-1,3-dihydrofuro[3,4-c]quinolin-8-yl)
((3S)-3-(4-fluoro-3-(trifluoromethyl)phenyl)-4-morpholi-
nyl)methanone,
(4-amino-7-chloro-1,3-dihydrofuro[3,4-c]quinolin-8-yl)
((3S)-3-(5-(trifluoromethyl)-2-pyridinyl)-1-pyrrolidinyl)
methanone,
(4-amino-7-chloro-1,3-dihydrofuro[3,4-c]quinolin-8-yl)
((3S)-3-(5-(trifluoromethyl)-2-pyridinyl)-4-morpholinyl)
methanone,
(4-amino-7-chloro-1,3-dihydrofuro[3,4-c]quinolin-8-yl)
((3S)-3-(6-(difluoromethoxy)-3-pyridinyl)-4-morpholi-
nyl)methanone,
(4-amino-7-chloro-1,3-dihydrofuro[3,4-c]quinolin-8-yl)
((3S)-3-(6-ethoxy-3-pyridazinyl)-4-morpholinyl)metha-
none,
(4-amino-7-chloro-1,3-dihydrofuro[3,4-c]quinolin-8-yl)
((3S,4R)-3-ethyl-4-(4-methylphenyl)-1-pyrrolidinyl)
methanone,
(4-amino-7-chloro-1,3-dihydrofuro[3,4-c]quinolin-8-yl)
((3S,5R)-3-(6-ethoxy-3-pyridazinyl)-5-methyl-4-mor-
pholinyl)methanone,
(4-amino-7-chloro-1,3-dihydrofuro[3,4-c]quinolin-8-yl)
((3S,5R)-3-methyl-5-(5-(trifluoromethoxy)-2-pyridinyl)-
4-morpholinyl)methanone,
(4-amino-7-chloro-1,3-dihydrofuro[3,4-c]quinolin-8-yl)
((3S,5R)-3-methyl-5-(5-(trifluoromethyl)-2-pyridinyl)-4-
morpholinyl)methanone,
(4-amino-7-chloro-1,3-dihydrofuro[3,4-c]quinolin-8-yl)
((3S,5R)-3-methyl-5-(6-(trifluoromethyl)-3-pyridinyl)-4-
morpholinyl)methanone,
(4-amino-7-chloro-1,3-dihydrofuro[3,4-c]quinolin-8-yl)(3-
(4-(trifluoromethyl)phenyl)-1-azetidinyl)methanone,
(4-amino-7-chloro-1-methyl-1H-pyrazolo[4,3-c]quinolin-8-
yl)((3R)-3-(4-(trifluoromethyl)phenyl)-1-pyrrolidinyl)
methanone, (4-amino-7-chloro-1-methyl-1H-pyrazolo[4,3-c]quinolin-8-yl)((3R)-3-(5-(trifluoromethyl)-2-pyridinyl)-1-pyrrolidinyl)methanone,
(4-amino-7-chloro-1-methyl-1H-pyrazolo[4,3-c]quinolin-8-yl)((3R,4S)-3-(2-fluoro-4-(trifluoromethyl)phenyl)-4-(hydroxymethyl)-1-pyrrolidinyl)methanone,
(4-amino-7-chloro-1-methyl-1H-pyrazolo[4,3-c]quinolin-8-yl)((3S)-3-(4-(trifluoromethyl)phenyl)-4-morpholinyl)methanone,
(4-amino-7-chloro-1-methyl-1H-pyrazolo[4,3-c]quinolin-8-yl)((3S)-3-(5-(trifluoromethyl)-2-pyridinyl)-1-pyrrolidinyl)methanone,
(4-amino-7-chloro-1-methyl-1H-pyrazolo[4,3-c]quinolin-8-yl)(3-(4-(trifluoromethyl)phenyl)-1-azetidinyl)methanone,
(4-amino-7-chloro-1-methyl-1H-pyrazolo[4,3-c]quinolin-8-yl)(3-(5-(trifluoromethyl)-2-pyridinyl)-1-azetidinyl)methanone,
(4-amino-7-chloro-1-methyl-1H-pyrazolo[4,3-c]quinolin-8-yl)(3-hydroxy-3-(4-(trifluoromethyl)phenyl)-1-azetidinyl)methanone,
(4-amino-7-chloro-3-methyl-3H-pyrazolo[3,4-c]quinolin-8-yl)((3S)-3-(4-(pentafluoro-lambda~6~-sulfanyl)phenyl)-4-morpholinyl)methanone,
(4-amino-7-fluoro-1,3-dihydrofuro[3,4-c]quinolin-8-yl)((3R)-3-(2-(trifluoromethyl)-4-pyridinyl)-4-morpholinyl)methanone,
(4-amino-7-fluoro-1,3-dihydrofuro[3,4-c]quinolin-8-yl)((3R)-3-(4-(trifluoromethyl)phenyl)-1-pyrrolidinyl)methanone,
(4-amino-7-fluoro-1,3-dihydrofuro[3,4-c]quinolin-8-yl)((3R)-3-(4-fluoro-3-(trifluoromethoxy)phenyl)-4-morpholinyl)methanone,
(4-amino-7-fluoro-1,3-dihydrofuro[3,4-c]quinolin-8-yl)((3R)-3-(4-fluoro-3-(trifluoromethyl)phenyl)-4-morpholinyl)methanone,
(4-amino-7-fluoro-1,3-dihydrofuro[3,4-c]quinolin-8-yl)((3R)-3-(5-(trifluoromethyl)-2-pyridinyl)-1-pyrrolidinyl)methanone,
(4-amino-7-fluoro-1,3-dihydrofuro[3,4-c]quinolin-8-yl)((3R)-3-(5-(trifluoromethyl)-2-pyridinyl)-4-morpholinyl)methanone,
(4-amino-7-fluoro-1,3-dihydrofuro[3,4-c]quinolin-8-yl)((3R)-3-(6-(difluoromethoxy)-3-pyridinyl)-4-morpholinyl)methanone,
(4-amino-7-fluoro-1,3-dihydrofuro[3,4-c]quinolin-8-yl)((3R)-3-(6-ethoxy-3-pyridazinyl)-4-morpholinyl)methanone,
(4-amino-7-fluoro-1,3-dihydrofuro[3,4-c]quinolin-8-yl)((3R)-3-hydroxy-3-(4-(trifluoromethyl)phenyl)-1-pyrrolidinyl)methanone,
(4-amino-7-fluoro-1,3-dihydrofuro[3,4-c]quinolin-8-yl)((3R,5S)-3-(6-(difluoromethoxy)-3-pyridazinyl)-5-methyl-4-morpholinyl)methanone,
(4-amino-7-fluoro-1,3-dihydrofuro[3,4-c]quinolin-8-yl)((3R,5S)-3-(6-chloro-3-pyridinyl)-5-methyl-4-morpholinyl)methanone,
(4-amino-7-fluoro-1,3-dihydrofuro[3,4-c]quinolin-8-yl)((3R,5S)-3-(6-ethoxy-3-pyridazinyl)-5-methyl-4-morpholinyl)methanone,
(4-amino-7-fluoro-1,3-dihydrofuro[3,4-c]quinolin-8-yl)((3R,5S)-3-methyl-5-(4-(trifluoromethyl)phenyl)-4-morpholinyl)methanone,
(4-amino-7-fluoro-1,3-dihydrofuro[3,4-c]quinolin-8-yl)((3R,5S)-3-methyl-5-(5-(trifluoromethoxy)-2-pyridinyl)-4-morpholinyl)methanone,
(4-amino-7-fluoro-1,3-dihydrofuro[3,4-c]quinolin-8-yl)((3R,5S)-3-methyl-5-(5-(trifluoromethyl)-2-pyridinyl)-4-morpholinyl)methanone,
(4-amino-7-fluoro-1,3-dihydrofuro[3,4-c]quinolin-8-yl)((3R,5S)-3-methyl-5-(6-(trifluoromethyl)-3-pyridinyl)-4-morpholinyl)methanone,
(4-amino-7-fluoro-1,3-dihydrofuro[3,4-c]quinolin-8-yl)((3S)-3-(2-(trifluoromethyl)-4-pyridinyl)-4-morpholinyl)methanone,
(4-amino-7-fluoro-1,3-dihydrofuro[3,4-c]quinolin-8-yl)((3S)-3-(4-(trifluoromethyl)phenyl)-4-morpholinyl)methanone,
(4-amino-7-fluoro-1,3-dihydrofuro[3,4-c]quinolin-8-yl)((3S)-3-(4-fluoro-3-(trifluoromethoxy)phenyl)-4-morpholinyl)methanone,
(4-amino-7-fluoro-1,3-dihydrofuro[3,4-c]quinolin-8-yl)((3S)-3-(4-fluoro-3-(trifluoromethyl)phenyl)-4-morpholinyl)methanone,
(4-amino-7-fluoro-1,3-dihydrofuro[3,4-c]quinolin-8-yl)((3S)-3-(5-(trifluoromethyl)-2-pyridinyl)-1-pyrrolidinyl)methanone,
(4-amino-7-fluoro-1,3-dihydrofuro[3,4-c]quinolin-8-yl)((3S)-3-(5-(trifluoromethyl)-2-pyridinyl)-4-morpholinyl)methanone,
(4-amino-7-fluoro-1,3-dihydrofuro[3,4-c]quinolin-8-yl)((3S)-3-(5-bromo-3-fluoro-2-pyridinyl)-4-morpholinyl)methanone,
(4-amino-7-fluoro-1,3-dihydrofuro[3,4-c]quinolin-8-yl)((3S)-3-(6-(difluoromethoxy)-3-pyridinyl)-4-morpholinyl)methanone,
(4-amino-7-fluoro-1,3-dihydrofuro[3,4-c]quinolin-8-yl)((3S)-3-(6-ethoxy-3-pyridazinyl)-4-morpholinyl)methanone,
(4-amino-7-fluoro-1,3-dihydrofuro[3,4-c]quinolin-8-yl)((3S)-3-hydroxy-3-(4-(trifluoromethyl)phenyl)-1-pyrrolidinyl)methanone,
(4-amino-7-fluoro-1,3-dihydrofuro[3,4-c]quinolin-8-yl)((3S,5R)-3-(6-(difluoromethoxy)-3-pyridazinyl)-5-methyl-4-morpholinyl)methanone,
(4-amino-7-fluoro-1,3-dihydrofuro[3,4-c]quinolin-8-yl)((3S,5R)-3-(6-chloro-3-pyridinyl)-5-methyl-4-morpholinyl)methanone,
(4-amino-7-fluoro-1,3-dihydrofuro[3,4-c]quinolin-8-yl)((3S,5R)-3-(6-ethoxy-3-pyridazinyl)-5-methyl-4-morpholinyl)methanone,
(4-amino-7-fluoro-1,3-dihydrofuro[3,4-c]quinolin-8-yl)((3S,5R)-3-(6-methoxy-3-pyridazinyl)-5-methyl-4-morpholinyl)methanone,
(4-amino-7-fluoro-1,3-dihydrofuro[3,4-c]quinolin-8-yl)((3S,5R)-3-methyl-5-(5-(trifluoromethoxy)-2-pyridinyl)-4-morpholinyl)methanone,
(4-amino-7-fluoro-1,3-dihydrofuro[3,4-c]quinolin-8-yl)((3S,5R)-3-methyl-5-(5-(trifluoromethyl)-2-pyridinyl)-4-morpholinyl)methanone,
(4-amino-7-fluoro-1,3-dihydrofuro[3,4-c]quinolin-8-yl)((3S,5R)-3-methyl-5-(6-(trifluoromethyl)-3-pyridinyl)-4-morpholinyl)methanone,
(4-amino-7-fluoro-1,3-dihydrofuro[3,4-c]quinolin-8-yl)((4R)-3,3-dimethyl-4-(4-(trifluoromethyl)phenyl)-1-pyrrolidinyl)methanone,
(4-amino-7-fluoro-1,3-dihydrofuro[3,4-c]quinolin-8-yl)((4S)-3,3-dimethyl-4-(4-methylphenyl)-1-pyrrolidinyl)methanone,
(4-amino-7-fluoro-1,3-dihydrofuro[3,4-c]quinolin-8-yl)((4S)-4-(4-bromophenyl)-3,3-dimethyl-1-pyrrolidinyl)methanone, (4-amino-7-fluoro-1,3-dihydrofuro[3,4-c]quinolin-8-yl)
((4S)-4-(4-fluorophenyl)-3,3-dimethyl-1-pyrrolidinyl)
methanone,
(4-amino-7-fluoro-1,3-dihydrofuro[3,4-c]quinolin-8-yl)(3-
(4-(trifluoromethyl)phenyl)-1-azetidinyl)methanone,
(4-amino-7-fluoro-1,3-dihydrofuro[3,4-c]quinolin-8-yl)(3-
(5-(trifluoromethyl)-2-pyridinyl)-1-azetidinyl)methanone,
(4-amino-7-fluoro-1,3-dihydrofuro[3,4-c]quinolin-8-yl)(3-
hydroxy-3-(4-(trifluoromethyl)phenyl)-1-azetidinyl)
methanone,
(4-amino-7-fluoro-1-methyl-1H-pyrazolo[4,3-c]quinolin-8-
yl)((1R,5S)-1-(4-(trifluoromethyl)phenyl)-3-azabicyclo
[3.1.0]hexan-3-yl)methanone,
(4-amino-7-fluoro-1-methyl-1H-pyrazolo[4,3-c]quinolin-8-
yl)((1S,5R)-1-(4-(trifluoromethyl)phenyl)-3-azabicyclo
[3.1.0]hexan-3-yl)methanone,
(4-amino-7-fluoro-1-methyl-1H-pyrazolo[4,3-c]quinolin-8-
yl)((3R)-3-((5-(trifluoromethyl)-2-pyridinyl)oxy)-1-pyrrolidinyl)methanone,
(4-amino-7-fluoro-1-methyl-1H-pyrazolo[4,3-c]quinolin-8-
yl)((3R)-3-(4-(trifluoromethyl)benzyl)-1-pyrrolidinyl)
methanone,
(4-amino-7-fluoro-1-methyl-1H-pyrazolo[4,3-c]quinolin-8-
yl)((3R)-3-(4-(trifluoromethyl)phenoxy)-1-pyrrolidinyl)
methanone,
(4-amino-7-fluoro-1-methyl-1H-pyrazolo[4,3-c]quinolin-8-
yl)((3R)-3-(4-(trifluoromethyl)phenyl)-1-pyrrolidinyl)
methanone,
(4-amino-7-fluoro-1-methyl-1H-pyrazolo[4,3-c]quinolin-8-
yl)((3R)-3-(5-(trifluoromethyl)-2-pyridinyl)-1-pyrrolidinyl)methanone,
(4-amino-7-fluoro-1-methyl-1H-pyrazolo[4,3-c]quinolin-8-
yl)((3R)-3-(5-(trifluoromethyl)-2-pyridinyl)-4-morpholinyl)methanone,
(4-amino-7-fluoro-1-methyl-1H-pyrazolo[4,3-c]quinolin-8-
yl)((3R,4S)-3-(2-fluoro-4-(trifluoromethyl)phenyl)-4-
(hydroxymethyl)-1-pyrrolidinyl)methanone,
(4-amino-7-fluoro-1-methyl-1H-pyrazolo[4,3-c]quinolin-8-
yl)((3R,5S)-3-methyl-5-(5-(trifluoromethyl)-2-pyridinyl)-4-morpholinyl)methanone,
(4-amino-7-fluoro-1-methyl-1H-pyrazolo[4,3-c]quinolin-8-
yl)((3S)-3-((5-(trifluoromethyl)-2-pyridinyl)oxy)-1-pyrrolidinyl)methanone,
(4-amino-7-fluoro-1-methyl-1H-pyrazolo[4,3-c]quinolin-8-
yl)((3S)-3-(4-(pentafluoroethyl)phenyl)-4-morpholinyl)
methanone,
(4-amino-7-fluoro-1-methyl-1H-pyrazolo[4,3-c]quinolin-8-
yl)((3S)-3-(4-(pentafluoro-lambda~6~-sulfanyl)phenyl)-
4-morpholinyl)methanone,
(4-amino-7-fluoro-1-methyl-1H-pyrazolo[4,3-c]quinolin-8-
yl)((3S)-3-(4-(trifluoromethyl)benzyl)-1-pyrrolidinyl)
methanone,
(4-amino-7-fluoro-1-methyl-1H-pyrazolo[4,3-c]quinolin-8-
yl)((3S)-3-(4-(trifluoromethyl)phenoxy)-1-pyrrolidinyl)
methanone,
(4-amino-7-fluoro-1-methyl-1H-pyrazolo[4,3-c]quinolin-8-
yl)((3S)-3-(4-(trifluoromethyl)phenyl)-4-morpholinyl)
methanone,
(4-amino-7-fluoro-1-methyl-1H-pyrazolo[4,3-c]quinolin-8-
yl)((3S)-3-(4-fluorophenyl)-4-morpholinyl)methanone,
(4-amino-7-fluoro-1-methyl-1H-pyrazolo[4,3-c]quinolin-8-
yl)((3S)-3-(5-(trifluoromethyl)-2-pyridinyl)-1-pyrrolidinyl)methanone,
(4-amino-7-fluoro-1-methyl-1H-pyrazolo[4,3-c]quinolin-8-
yl)((3S)-3-(5-(trifluoromethyl)-2-pyridinyl)-4-morpholinyl)methanone,
(4-amino-7-fluoro-1-methyl-1H-pyrazolo[4,3-c]quinolin-8-
yl)((3S)-3-(6-(difluoromethoxy)-3-pyridazinyl)-4-morpholinyl)methanone,
(4-amino-7-fluoro-1-methyl-1H-pyrazolo[4,3-c]quinolin-8-
yl)((3S)-3-(6-(trifluoromethyl)-3-pyridazinyl)-4-morpholinyl)methanone,
(4-amino-7-fluoro-1-methyl-1H-pyrazolo[4,3-c]quinolin-8-
yl)((3S,5R)-3-(6-(difluoromethoxy)-3-pyridazinyl)-5-
methyl-4-morpholinyl)methanone,
(4-amino-7-fluoro-1-methyl-1H-pyrazolo[4,3-c]quinolin-8-
yl)((3S,5R)-3-(6-methoxy-3-pyridazinyl)-5-methyl-4-
morpholinyl)methanone,
(4-amino-7-fluoro-1-methyl-1H-pyrazolo[4,3-c]quinolin-8-
yl)((4R)-3,3-dimethyl-4-(4-(trifluoromethyl)phenyl)-1-
pyrrolidinyl)methanone,
(4-amino-7-fluoro-1-methyl-1H-pyrazolo[4,3-c]quinolin-8-
yl)((4S)-3,3-dimethyl-4-(4-(trifluoromethyl)phenyl)-1-
pyrrolidinyl)methanone,
(4-amino-7-fluoro-1-methyl-1H-pyrazolo[4,3-c]quinolin-8-
yl)(3-(4-(trifluoromethyl)phenyl)-1-azetidinyl)methanone,
(4-amino-7-fluoro-1-methyl-1H-pyrazolo[4,3-c]quinolin-8-
yl)(3-(5-(trifluoromethyl)-2-pyridinyl)-1-azetidinyl)
methanone,
(4-amino-7-fluoro-1-methyl-1H-pyrazolo[4,3-c]quinolin-8-
yl)(3-hydroxy-3-(4-(trifluoromethyl)phenyl)-1-azetidinyl)methanone,
(4-amino-7-fluoro-2,3-dihydrofuro[3,2-c]quinolin-8-yl)
((3S)-3-(4-(trifluoromethyl)phenyl)-4-morpholinyl)
methanone,
(4-amino-7-fluoro-3-methyl-3H-pyrazolo[3,4-c]quinolin-8-
yl)((3R)-3-(4-(trifluoromethyl)phenyl)-1-pyrrolidinyl)
methanone,
(4-amino-7-fluoro-3-methyl-3H-pyrazolo[3,4-c]quinolin-8-
yl)((3R,5S)-3-methyl-5-(4-(trifluoromethoxy)phenyl)-4-
morpholinyl)methanone,
(4-amino-7-fluoro-3-methyl-3H-pyrazolo[3,4-c]quinolin-8-
yl)((3R,5S)-3-methyl-5-(4-(trifluoromethyl)phenyl)-4-
morpholinyl)methanone,
(4-amino-7-fluoro-3-methyl-3H-pyrazolo[3,4-c]quinolin-8-
yl)((3R,5S)-3-methyl-5-(5-(trifluoromethyl)-2-pyridinyl)-4-morpholinyl)methanone,
(4-amino-7-fluoro-3-methyl-3H-pyrazolo[3,4-c]quinolin-8-
yl)((3S)-3-(4-(pentafluoro-lambda~6~-sulfanyl)phenyl)-
4-morpholinyl)methanone,
(4-amino-7-fluoro-3-methyl-3H-pyrazolo[3,4-c]quinolin-8-
yl)((3S)-3-(4-(trifluoromethyl)phenyl)-4-morpholinyl)
methanone,
(4-amino-7-fluoro-3-methyl-3H-pyrazolo[3,4-c]quinolin-8-
yl)((3S)-3-(6-(difluoromethoxy)-3-pyridazinyl)-4-morpholinyl)methanone,
(4-amino-7-fluoro-3-methyl-3H-pyrazolo[3,4-c]quinolin-8-
yl)((3S,5R)-3-(6-methoxy-3-pyridazinyl)-5-methyl-4-
morpholinyl)methanone,
(4-aminoimidazo[1,2-a]quinoxalin-8-yl)((3S)-3-(4-(trifluoromethyl)phenyl)-4-morpholinyl)methanone,
(4-aminothieno[2,3-c]quinolin-8-yl)-[(2R)-2-[4-(trifluoromethyl)phenyl]-1-piperidyl]methanone,
(4-aminothieno[2,3-c]quinolin-8-yl)-[(2S)-2-[4-(trifluoromethyl)phenyl]-1-piperidyl]methanone,
(4-aminothieno[2,3-c]quinolin-8-yl)-[(3R)-3-[4-(trifluoromethyl)phenyl]morpholin-4-yl]methanone,
(4-aminothieno[2,3-c]quinolin-8-yl)-[(3S)-3-[4-(trifluoromethyl)phenyl]morpholin-4-yl]methanone,
(5-amino-1,4-dihydro-2H-pyrano[3,4-c]quinolin-9-yl)
((3S)-3-(4-(trifluoromethoxy)phenyl)-4-morpholinyl)
methanone, (5-aminobenzo[c][2,6]naphthyridin-9-yl)((3S)-3-(4-(trifluoromethyl)phenyl)-4-morpholinyl)methanone,
(5-aminopyrido[4,3-c][1,7]naphthyridin-9-yl)((3S)-3-(4-(trifluoromethyl)phenyl)-4-morpholinyl)methanone,
(5-aminopyrimido[4,5-c][1,7]naphthyridin-9-yl)((3S)-3-(4-(trifluoromethyl)phenyl)-4-morpholinyl)methanone,
(5-aminopyrimido[4,5-c]quinolin-9-yl)((3S)-3-(4-(trifluoromethyl)phenyl)-4-morpholinyl)methanone,
(6-amino-8,9-dihydro-7H-cyclopenta[c][1,7]naphthyridin-2-yl)((3R,5S)-3-methyl-5-(5-(trifluoromethyl)-2-pyridinyl)-4-morpholinyl)methanone,
(6-amino-8,9-dihydro-7H-cyclopenta[c][1,7]naphthyridin-2-yl)((3S)-3-(4-(trifluoromethoxy)phenyl)-4-morpholinyl)methanone,
(R)-(4-amino-1,3-dihydrofuro[3,4-c][1,7]naphthyridin-8-yl)(3-(4-(pentafluoro-16-sulfaneyl)phenyl)morpholino)methanone,
(R)-(4-amino-1,3-dihydrofuro[3,4-c]quinolin-8-yl)(3-(6-(trifluoromethyl)pyridin-3-yl)morpholino)methanone,
(S)-(4-amino-1,3-dihydrofuro[3,4-c][1,7]naphthyridin-8-yl)(3-(4-(pentafluoro-16-sulfaneyl)phenyl)morpholino)methanone,
[(3R)-4-amino-3-methyl-1,3-dihydrofuro[3,4-c]quinolin-8-yl]-[(3S)-3-[4-(trifluoromethoxy)phenyl]morpholin-4-yl]methanone,
[(3S)-4-amino-3-methyl-1,3-dihydrofuro[3,4-c]quinolin-8-yl]-[(3S)-3-[4-(trifluoromethoxy)phenyl]morpholin-4-yl]methanone,
1-((3S)-4-((4-amino-1,3-dihydrofuro[3,4-c][1,7]naphthyridin-8-yl)carbonyl)-3-(4-(trifluoromethyl)phenyl)-1-piperazinyl)ethanone,
4-((3R)-4-((4-amino-1,3-dihydrofuro[3,4-c][1,7]naphthyridin-8-yl)carbonyl)-3-morpholinyl)benzonitrile,
4-((3R,5S)-4-((4-amino-1,3-dihydrofuro[3,4-c][1,7]naphthyridin-8-yl)carbonyl)-5-methyl-3-morpholinyl)benzonitrile,
4-((3S)-4-((4-amino-1,3-dihydrofuro[3,4-c][1,7]naphthyridin-8-yl)carbonyl)-3-morpholinyl)benzonitrile,
4-((3S,5R)-4-((4-amino-1,3-dihydrofuro[3,4-c][1,7]naphthyridin-8-yl)carbonyl)-5-methyl-3-morpholinyl)benzonitrile,
4-chloro-6-[rac-(3S)-4-(4-amino-1,3-dihydrofuro[3,4-c]quinoline-8-carbonyl)morpholin-3-yl]pyridine-3-carbonitrile,
6-[(3R)-4-(4-amino-1,3-dihydrofuro[3,4-c]quinoline-8-carbonyl)morpholin-3-yl]pyridine-3-carbonitrile,
6-[(3S)-4-(4-amino-1,3-dihydrofuro[3,4-c]quinoline-8-carbonyl)morpholin-3-yl]pyridine-3-carbonitrile,
methyl (3R,4S)-1-((4-amino-7-fluoro-1,3-dihydrofuro[3,4-c]quinolin-8-yl)carbonyl)-4-(4-(trifluoromethyl)phenyl)-3-pyrrolidinecarboxylate,
methyl (3S,4R)-1-((4-amino-7-fluoro-1,3-dihydrofuro[3,4-c]quinolin-8-yl)carbonyl)-4-(4-(trifluoromethyl)phenyl)-3-pyrrolidinecarboxylate,
tert-butyl (3R)-4-(4-amino-1,3-dihydrofuro[3,4-c][1,7]naphthyridine-8-carbonyl)-3-[4-(trifluoromethyl)phenyl]piperazine-1-carboxylate, and
tert-butyl (3S)-4-(4-amino-1,3-dihydrofuro[3,4-c][1,7]naphthyridine-8-carbonyl)-3-[4-(trifluoromethyl)phenyl]piperazine-1-carboxylate.
In one aspect, the invention provides the following compounds:
(4-amino-1-methyl-1H-pyrazolo[4,3-c][1,7]naphthyridin-8-yl)((3S)-3-(4-(trifluoromethyl)phenyl)-4-morpholinyl)methanone;
(4-amino-1,3-dihydrofuro[3,4-c][1,7]naphthyridin-8-yl)((3S,5R)-3-(6-(cyclopropyloxy)-3-pyridazinyl)-5-methyl-4-morpholinyl)methanone;
(4-amino-1,3-dihydrofuro[3,4-c][1,7]naphthyridin-8-yl)((3R,5S)-3-methyl-5-(6-(2,2,2-trifluoroethoxy)-3-pyridazinyl)-4-morpholinyl)methanone;
((3R)-4-amino-3-methyl-1,3-dihydrofuro[3,4-c]quinolin-8-yl)((3S,5R)-3-(6-ethoxy-3-pyridazinyl)-5-methyl-4-morpholinyl)methanone;
(4-amino-1,3-dihydrofuro[3,4-c][1,7]naphthyridin-8-yl)((3S,5R)-3-(6-(difluoromethoxy)-3-pyridazinyl)-5-methyl-4-morpholinyl)methanone;
(4-amino-1-methyl-1H-pyrazolo[4,3-c]quinolin-8-yl)((3S)-3-(4-(pentafluoro-lambda~6~-sulfanyl)phenyl)-4-morpholinyl)methanone;
(4-amino-1,3-dihydrofuro[3,4-c]quinolin-8-yl)-[(3S)-3-[4-(trifluoromethyl)phenyl]morpholin-4-yl]methanone;
(4-amino-1,3-dihydrofuro[3,4-c]quinolin-8-yl)-[(3S,5S)-3-methyl-5-[5-(trifluoromethyl)-2-pyridyl]morpholin-4-yl]methanone;
(4-amino-1,3-dihydrofuro[3,4-c]quinolin-8-yl)-[(3S)-3-[6-(trifluoromethyl)-3-pyridyl]morpholin-4-yl]methanone;
(4-amino-1,3-dihydrofuro[3,4-c]quinolin-8-yl)-[(3S)-3-[5-(trifluoromethyl)-2-pyridyl]morpholin-4-yl]methanone;
((3R)-4-amino-3-methyl-1,3-dihydrofuro[3,4-c][1,7]naphthyridin-8-yl)((3S)-3-(4-(trifluoromethyl)phenyl)-4-morpholinyl)methanone;
[(3R)-4-amino-3-methyl-1,3-dihydrofuro[3,4-c]quinolin-8-yl]-[(3S)-3-[4-(trifluoromethoxy)phenyl]morpholin-4-yl]methanone;
(4-amino-1,3-dihydrofuro[3,4-c]quinolin-8-yl)-[(3S)-3-[4-(trifluoromethoxy)phenyl]morpholin-4-yl]methanone;
(4-amino-3-methyl-3H-pyrazolo[3,4-c]quinolin-8-yl)((3R,5S)-3-methyl-5-(5-(trifluoromethyl)-2-pyridinyl)-4-morpholinyl)methanone;
(4-amino-1-methyl-1H-pyrazolo[4,3-c]quinolin-8-yl)((3S)-3-(4-(trifluoromethyl)phenyl)-4-morpholinyl)methanone;
(4-amino-7-fluoro-1-methyl-1H-pyrazolo[4,3-c]quinolin-8-yl)((3S)-3-(6-(difluoromethoxy)-3-pyridazinyl)-4-morpholinyl)methanone;
(4-amino-7-fluoro-1-methyl-1H-pyrazolo[4,3-c]quinolin-8-yl)((3S)-3-(6-(trifluoromethyl)-3-pyridazinyl)-4-morpholinyl)methanone;
(4-amino-7-fluoro-1-methyl-1H-pyrazolo[4,3-c]quinolin-8-yl)((3R)-3-(4-(trifluoromethyl)phenyl)-1-pyrrolidinyl)methanone; and
(4-amino-1,3-dihydrofuro[3,4-c][1,7]naphthyridin-8-yl)-[(3S)-3-[4-(trifluoromethyl)phenyl]morpholin-4-yl]methanone.

The invention further provides methods of treating cancer comprising administering to a subject an effective amount of the compound of the invention, the tautomer thereof, the stereoisomer thereof, or the pharmaceutically acceptable salt of any of the foregoing. In one aspect, the cancer is selected from lung, Head and Neck Squamous Cell Carcinoma (HNSCC), esophagus, lymphoid, glioblastoma, colon, melanoma, gastric, pancreatic, bile or bladder cancer. In one aspect, lung cancer could be Non-Small Cell Lung Carcinoma (NSCLC).

The invention further provides pharmaceutical compositions, comprising the compounds of the invention, the tautomer thereof, the stereoisomer thereof, or the pharmaceutically acceptable salt of any of the foregoing or a pharmaceutically acceptable salt thereof, and at least one pharmaceutically acceptable excipient.

The invention also provides methods of manufacturing a medication for treating a cancer, the method comprising administering to a subject an effective amount of the compound of the invention, the tautomer thereof, the stereoisomer thereof, or the pharmaceutically acceptable salt of any of the foregoing. In one aspect, the cancer can be lung, Head and Neck Squamous Cell Carcinoma (HNSCC), esophagus, lymphoid, glioblastoma, colon, bile, melanoma, gastric, pancreatic or bladder cancer. In one aspect, lung cancer could be Non-Small Cell Lung Carcinoma (NSCLC). The invention also provides the compound of the invention, the tautomer thereof, the stereoisomer thereof, or the pharmaceutically acceptable salt of any of the foregoing for use in a method of treating a cancer, the method comprising administering to a subject an effective amount of such compound. In one aspect, the cancer can lung, Head and Neck Squamous Cell Carcinoma (HNSCC), esophagus, lymphoid, glioblastoma, colon, melanoma, gastric, pancreatic bile or bladder cancer. In one aspect, lung cancer could be Non-Small Cell Lung Carcinoma (NSCLC).

The invention also provides the use of the compound of the present invention, the tautomer thereof, the stereoisomer thereof, or the pharmaceutically acceptable salt of any of the foregoing in the manufacture of a medicament for treating a cancer. In one aspect, the cancer can be lung, Head and Neck Squamous Cell Carcinoma (HNSCC), esophagus, lymphoid, glioblastoma, colon, melanoma, gastric, pancreatic, bile or bladder cancer. In one aspect, lung cancer could be Non-Small Cell Lung Carcinoma (NSCLC).

Other objects, features and advantages of the invention will become apparent to those skilled in the art from the following description and claims.

DETAILED DESCRIPTION OF THE INVENTION

Definitions

As used herein, if any variable occurs more than one time in a chemical formula, its definition on each occurrence is independent of its definition at every other occurrence. If the chemical structure and chemical name conflict, the chemical structure is determinative of the identity of the compound. The compounds of the present disclosure may contain one or more chiral centers and/or double bonds and therefore, may exist as stereoisomers, such as double-bond isomers (i.e., geometric isomers), enantiomers, or diastereomers. Accordingly, any chemical structures within the scope of the specification depicted, in whole or in part, with a relative configuration encompass all possible enantiomers and stereoisomers of the illustrated compounds including the stereoisomerically pure form (e.g., geometrically pure, enantiomerically pure or diastereomerically pure) and enantiomeric and stereoisomeric mixtures. Enantiomeric and stereoisomeric mixtures can be resolved into the component enantiomers or stereoisomers using separation techniques or chiral synthesis techniques well known to the skilled artisan.

Certain compounds of the invention may possess asymmetric carbon atoms (optical centers) or double bonds; the racemates, enantiomers, diastereomers, geometric isomers and individual isomers are all intended to be encompassed within the scope of the invention. Furthermore, atropisomers and mixtures thereof such as those resulting from restricted rotation about two aromatic or heteroaromatic rings bonded to one another are intended to be encompassed within the scope of the invention. For example, when substituent is a phenyl group and is substituted with two groups bonded to the C atoms adjacent to the point of attachment to the N atom of the triazole, then rotation of the phenyl may be restricted. In some instances, the barrier of rotation is high enough that the different atropisomers may be separated and isolated.

As used herein and unless otherwise indicated, the term "stereoisomer" or "stereomerically pure" means one stereoisomer of a compound that is substantially free of other stereoisomers of that compound. For example, a stereomerically pure compound having one chiral center will be substantially free of the mirror image enantiomer of the compound. A stereomerically pure compound having two chiral centers will be substantially free of other diastereomers of the compound. A typical stereomerically pure compound comprises greater than about 80% by weight of one stereoisomer of the compound and less than about 20% by weight of other stereoisomers of the compound, more preferably greater than about 90% by weight of one stereoisomer of the compound and less than about 10% by weight of the other stereoisomers of the compound, even more preferably greater than about 95% by weight of one stereoisomer of the compound and less than about 5% by weight of the other stereoisomers of the compound, and most preferably greater than about 97% by weight of one stereoisomer of the compound and less than about 3% by weight of the other stereoisomers of the compound. If the stereochemistry of a structure or a portion of a structure is not indicated with, for example, bold or dashed lines, the structure or portion of the structure is to be interpreted as encompassing all stereoisomers of it. A bond drawn with a wavy line indicates that both stereoisomers are encompassed. This is not to be confused with a wavy line drawn perpendicular to a bond which indicates the point of attachment of a group to the rest of the molecule.

As known by those skilled in the art, certain compounds of the invention may exist in one or more tautomeric forms. Because one chemical structure may only be used to represent one tautomeric form, it will be understood that for convenience, referral to a compound of a given structural formula includes tautomers of the structure represented by the structural formula. Depending on the compound, some compounds may exist primarily in one form more than another. Also, depending on the compound and the energy required to convert one tautomer to the other, some compounds may exist as mixtures at room temperature whereas others may be isolated in one tautomeric form or the other. Examples of other tautomers associated with compounds of the invention are those with a pyridone group (a pyridinyl) for which hydroxypyridine is a tautomer and compounds with a ketone group with the enol tautomer. Examples of these are shown below.

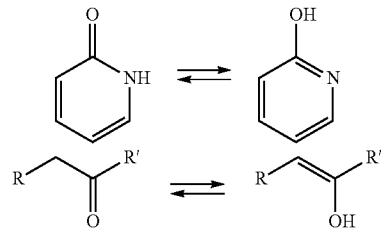

Compounds of the present disclosure include, but are not limited to, compounds of Formula I and all pharmaceutically acceptable forms thereof. The invention includes pharmaceutically acceptable forms of the compounds pharmaceutically acceptable salts, solvates, crystal forms (including polymorphs and clathrates), chelates, non-covalent complexes, prodrugs, and mixtures thereof. The invention discloses compounds, and a pharmaceutically acceptable salt thereof, a solvate thereof, a chelate thereof, a non-covalent complex thereof, a prodrug thereof, and ester prodrugs such as ($C_1$-$C_4$)alkyl esters and mixtures of any of the foregoing.

Pharmaceutically acceptable salts of the compounds of the present invention include acid addition salts formed with inorganic acids such as hydrochloric, hydrobromic, hydroiodic, phosphoric, metaphosphoric, nitric and sulfuric acids, and with organic acids, such as tartaric, acetic, trifluoroacetic, citric, malic, lactic, fumaric, benzoic, formic, propionic, glycolic, gluconic, maleic, succinic, camphorsulfuric, isothionic, mucic, gentisic, isonicotinic, saccharic, glucuronic, furoic, glutamic, ascorbic, anthranilic, salicylic, phenylacetic, mandelic, embonic (pamoic), methanesulfonic, ethanesulfonic, pantothenic, stearic, sulfinilic, alginic, galacturonic and arylsulfonic, for example benzenesulfonic and p-toluenesulfonic, acids; base addition salts formed with alkali metals and alkaline earth metals and organic bases such as N,N-dibenzylethylenediamine, chloroprocaine, choline, diethanolamine, ethylenediamine, meglumaine (N-methylglucamine), lysine and procaine; and internally formed salts. Suitable salts include those described in P. Heinrich Stahl, Camille G. Wermuth (Eds.), Handbook of Pharmaceutical Salts Properties, Selection and Use; 2002. Salts having a non-pharmaceutically acceptable anion or cation are within the scope of the invention as useful intermediates for the preparation of pharmaceutically acceptable salts and/or for use in non-therapeutic, for example, in vitro, situations.

The term "solvate" refers to the compound formed by the interaction of a solvent and a compound. Solvates of a compound includes solvates of all forms of the compound. In certain embodiments, solvents are volatile, non-toxic, and/or acceptable for administration to humans in trace amounts. Suitable solvates are pharmaceutically acceptable solvates, such as hydrates, including monohydrates and hemi-hydrates.

The invention discloses compounds which may also contain naturally occurring or unnatural proportions of atomic isotopes at one or more of the atoms that constitute such compounds. For example, the compounds may be radiolabeled with radioactive isotopes, such as for example tritium (H), iodine-125 ($^{125}$I) or carbon-14 ($^{14}$C). Radiolabeled compounds are useful as therapeutic or prophylactic agents, research reagents, e.g., assay reagents, and diagnostic agents, e.g., in vivo imaging agents. All isotopic variations of the compounds of the invention, whether radioactive or not, are intended to be encompassed within the scope of the invention. For example, the invention also includes deuterium (D) or tritium (T) containing compounds.

"Alkyl" refers to a saturated branched or straight-chain monovalent hydrocarbon group derived by the removal of one hydrogen atom from a single carbon atom of a parent alkane. Typical alkyl groups include, but are not limited to, methyl, ethyl, propyls such as propan-1-yl and propan-2-yl, butyls such as butan-1-yl, butan-2-yl, 2-methyl-propan-1-yl, 2-methyl-propan-2-yl, tert-butyl, and the like. In certain embodiments, an alkyl group comprises 1 to 20 carbon atoms. In some embodiments, alkyl groups include 1 to 10 carbon atoms or 1 to 6 carbon atoms whereas in other embodiments, alkyl groups include 1 to 4 carbon atoms. In still other embodiments, an alkyl group includes 1 or 2 carbon atoms. Branched chain alkyl groups include at least 3 carbon atoms and typically include 3 to 7, or in some embodiments, 3 to 6 carbon atoms. An alkyl group having 1 to 6 carbon atoms may be referred to as a ($C_1$-$C_6$)alkyl group and an alkyl group having 1 to 4 carbon atoms may be referred to as a ($C_1$-$C_4$)alkyl. This nomenclature may also be used for alkyl groups with differing numbers of carbon atoms.

"Alkenyl" refers to an unsaturated branched or straight-chain hydrocarbon group having at least one carbon-carbon double bond derived by the removal of one hydrogen atom from a single carbon atom of a parent alkene. The group may be in either the Z- or E-form (cis or trans) about the double bond(s). Typical alkenyl groups include, but are not limited to, ethenyl; propenyls such as prop-1-en-1-yl, prop-1-en-2-yl, prop-2-en-1-yl (allyl), and prop-2-en-2-yl; butenyls such as but-1-en-1-yl, but-1-en-2-yl, 2-methyl-prop-1-en-1-yl, but-2-en-1-yl, but-2-en-1-yl, but-2-en-2-yl, buta-1,3-dien-1-yl, and buta-1,3-dien-2-yl; and the like. In certain embodiments, an alkenyl group has 2 to 20 carbon atoms and in other embodiments, has 2 to 6 carbon atoms. An alkenyl group having 2 to 6 carbon atoms may be referred to as a ($C_2$-$C_6$)alkenyl group.

"Alkynyl" refers to an unsaturated branched or straight-chain hydrocarbon having at least one carbon-carbon triple bond derived by the removal of one hydrogen atom from a single carbon atom of a parent alkyne. Typical alkynyl groups include, but are not limited to, ethynyl; propynyl; butynyl, 2-pentynyl, 3-pentynyl, 2-hexynyl, 3-hexynyl and the like. In certain embodiments, an alkynyl group has 2 to 20 carbon atoms and in other embodiments, has 2 to 6 carbon atoms. An alkynyl group having 2 to 6 carbon atoms may be referred to as a —($C_2$-$C_6$)alkynyl group.

"Alkoxy" refers to a radical —OR where R represents an alkyl group as defined herein. Representative examples include, but are not limited to, methoxy, ethoxy, propoxy, butoxy, and the like. Typical alkoxy groups include 1 to 10 carbon atoms, 1 to 6 carbon atoms or 1 to 4 carbon atoms in the R group. Alkoxy groups that include 1 to 6 carbon atoms may be designated as —O—($C_1$-$C_6$) alkyl or as —O—($C_1$-$C_6$ alkyl) groups. In some embodiments, an alkoxy group may include 1 to 4 carbon atoms and may be designated as —O—($C_1$-$C_4$) alkyl or as —O—($C_1$-$C_4$ alkyl) groups group.

"Aryl" refers to a monovalent aromatic hydrocarbon group derived by the removal of one hydrogen atom from a single carbon atom of a parent aromatic ring system. Aryl encompasses monocyclic carbocyclic aromatic rings, for example, benzene. Aryl also encompasses bicyclic carbocyclic aromatic ring systems where each of the rings is aromatic, for example, naphthalene. Aryl groups may thus include fused ring systems where each ring is a carbocyclic aromatic ring. In certain embodiments, an aryl group includes 6 to 10 carbon atoms. Such groups may be referred to as $C_6$-$C_{10}$ aryl groups. Aryl, however, does not encompass or overlap in any way with heteroaryl as separately defined below. Hence, if one or more carbocyclic aromatic rings is fused with an aromatic ring that includes at least one heteroatom, the resulting ring system is a heteroaryl group, not an aryl group, as defined herein.

"Carbonyl" refers to the radical —C(O) which may also be referred to as —C(=O) group.

"Carboxy" refers to the radical —C(O)OH which may also be referred to as —C(=O)OH.

"Cyano" refers to the radical —CN.

"Cycloalkyl" refers to a saturated cyclic alkyl group derived by the removal of one hydrogen atom from a single carbon atom of a parent cycloalkane. Typical cycloalkyl groups include, but are not limited to, groups derived from cyclopropane, cyclobutane, cyclopentane, cyclohexane, cycloheptane, cyclooctane, and the like. Cycloalkyl groups may be described by the number of carbon atoms in the ring.

For example, a cycloalkyl group having 3 to 8 ring members may be referred to as a $(C_3-C_8)$cycloalkyl, a cycloalkyl group having 3 to 7 ring members may be referred to as a $(C_3-C_7)$cycloalkyl and a cycloalkyl group having 4 to 7 ring members may be referred to as a $(C_4-C_7)$cycloalkyl. In certain embodiments, the cycloalkyl group can be a $(C_3-C_{10})$cycloalkyl, a $(C_3-C_8)$cycloalkyl, a $(C_3-C_7)$cycloalkyl, a $(C_3-C_6)$cycloalkyl, or a $(C_4-C_7)$cycloalkyl group and these may be referred to as $C_3-C_{10}$ cycloalkyl, $C_3-C_8$ cycloalkyl, $C_3-C_7$ cycloalkyl, $C_3-C_6$ cycloalkyl, or $C_4-C_7$ cycloalkyl groups using alternative language.

"Heterocyclyl" refers to a cyclic group that includes at least one saturated, partially unsaturated, cyclic ring. Heterocyclyl groups include at least one heteroatom as a ring member. Typical heteroatoms include O, S and N and are independently chosen. Heterocyclyl groups include monocyclic ring systems and bicyclic ring systems. Bicyclic heterocyclyl groups include at least one non-aromatic ring with at least one heteroatom ring member that may be fused to a cycloalkyl ring or may be fused to an aromatic ring where the aromatic ring may be carbocyclic or may include one or more heteroatoms. The point of attachment of a bicyclic heterocyclyl group may be at the non-aromatic cyclic ring that includes at least one heteroatom or at another ring of the heterocyclyl group. For example, a heterocyclyl group derived by removal of a hydrogen atom from one of the 9 membered heterocyclic compounds shown below may be attached to the rest of the molecule at the 5-membered ring or at the 6-membered ring.

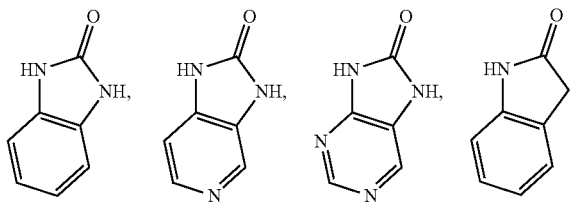 [SMILES: O=c1[nH]c2ccccc2[nH]1 ; O=c1[nH]c2ccncc2[nH]1 ; O=c1[nH]c2cncnc2[nH]1 ; O=C1Cc2ccccc2N1]

In some embodiments, a heterocyclyl group includes 5 to 10 ring members of which 1, 2, 3 or 4 are heteroatoms independently selected from O, S, or N. In other embodiments, a heterocyclyl group includes 3 to 7 ring members of which 1, 2, or 3 heteroatom are independently selected from O, S, or N. In such 3-7 membered heterocyclyl groups, only 1 of the ring atoms is a heteroatom when the ring includes only 3 members and includes 1 or 2 heteroatoms when the ring includes 4 members. In some embodiments, a heterocyclyl group includes 3 or 4 ring members of which 1 is a heteroatom selected from O, S, or N. In other embodiments, a heterocyclyl group includes 5 to 7 ring members of which 1, 2, or 3 are heteroatoms independently selected from O, S, or N. Typical heterocyclyl groups include, but are not limited to, groups derived from epoxides, aziridine, azetidine, imidazolidine, morpholine, piperazine, piperidine, hexahydropyrimidine, 1,4,5,6-tetrahydropyrimidine, pyrazolidine, pyrrolidine, quinuclidine, tetrahydrofuran, tetrahydropyran, benzimidazolone, pyridinone, and the like. Heterocyclyl groups may be fully saturated but may also include one or more double bonds. Examples of such heterocyclyl groups include, but are not limited to, 1,2,3,6-tetrahydropyridinyl, 3,6-dihydro-2H-pyranyl, 3,4-dihydro-2H-pyranyl, 2,5-dihydro-1H-pyrolyl, 2,3-dihydro-1H-pyrolyl, 1H-azirinyl, 1,2-dihydroazetenyl, and the like. Substituted heterocyclyl also includes ring systems substituted with one or more oxo (=O) or oxide (—O—) substituents, such as piperidinyl N-oxide, morpholinyl-N-oxide, 1-oxo-1-thiomorpholinyl, pyridinonyl, benzimidazolonyl, benzo[d]oxazol-2(3H)-onyl, 3,4-dihydroisoquinolin-1(2H)-onyl, indolin-onyl, 1H-imidazo[4,5-c]pyridin-2(3H)-onyl, 7H-purin-8 (9H)-onyl, imidazolidin-2-onyl, 1H-imidazol-2(3H)-onyl, 1,1-dioxo-1-thiomorpholinyl, and the like.

The term "comprising" is meant to be open ended, i.e., all-encompassing and non-limiting. It may be used herein synonymously with "having" or "including". Comprising is intended to include each and every indicated or recited component or element(s) while not excluding any other components or elements.

"Disease" refers to any disease, disorder, condition, symptom, or indication.

"Halo" or "halogen" refers to a fluoro, chloro, bromo, or iodo group.

"Haloalkyl" refers to an alkyl group in which at least one hydrogen is replaced with a halogen. Thus, the term "haloalkyl" includes monohaloalkyl (alkyl substituted with one halogen atom) and polyhaloalkyl (alkyl substituted with two or more halogen atoms). Representative "haloalkyl" groups include difluoromethyl, 2,2,2-trifluoroethyl, 2,2,2-trichloroethyl, and the like. The term "perhaloalkyl" means, unless otherwise stated, an alkyl group in which each of the hydrogen atoms is replaced with a halogen atom. For example, the term "perhaloalkyl", includes, but is not limited to, trifluoromethyl, pentachloroethyl, 1,1,1-trifluoro-2-bromo-2-chloroethyl, and the like.

"Heteroaryl" refers to a monovalent heteroaromatic group derived by the removal of one hydrogen atom from a single atom of a parent heteroaromatic ring system. Heteroaryl groups typically include 5- to 14-membered, but more typically include 5- to 10-membered aromatic, monocyclic, bicyclic, and tricyclic rings containing one or more, for example, 1, 2, 3, or 4, or in certain embodiments, 1, 2, or 3, heteroatoms chosen from O, S, or N, with the remaining ring atoms being carbon. In monocyclic heteroaryl groups, the single ring is aromatic and includes at least one heteroatom. In some embodiments, a monocyclic heteroaryl group may include 5 or 6 ring members and may include 1, 2, 3, or 4 heteroatoms, 1, 2, or 3 heteroatoms, 1 or 2 heteroatoms, or 1 heteroatom where the heteroatom(s) are independently selected from O, S, or N. In bicyclic aromatic rings, both rings are aromatic. In bicyclic heteroaryl groups, at least one of the rings must include a heteroatom, but it is not necessary that both rings include a heteroatom although it is permitted for them to do so. For example, the term "heteroaryl" includes a 5- to 7-membered heteroaromatic ring fused to a carbocyclic aromatic ring or fused to another heteroaromatic ring. In tricyclic aromatic rings, all three of the rings are aromatic and at least one of the rings includes at least one heteroatom. For fused, bicyclic and tricyclic heteroaryl ring systems where only one of the rings contains one or more heteroatoms, the point of attachment may be at the ring including at least one heteroatom or at a carbocyclic ring. When the total number of S and O atoms in the heteroaryl group exceeds 1, those heteroatoms are not adjacent to one another. In certain embodiments, the total number of S and O atoms in the heteroaryl group is not more than 2. In certain embodiments, the total number of S and O atoms in the aromatic heterocycle is not more than 1. Heteroaryl does not encompass or overlap with aryl as defined above. Examples of heteroaryl groups include, but are not limited to, groups derived from acridine, carbazole, cinnoline, furan, imidazole, indazole, indole, indolizine, isobenzofuran, isochromene, isoindole, isoquinoline, isothiazole, 2H-benzo[d][1,2,3]triazole, isoxazole, naphthyridine, oxadiazole, oxazole, perimidine, phenanthridine, phenanthroline, phenazine, phthalazine, pteridine, purine, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, and the like. In certain embodiments, the heteroaryl group can be between 5 to 20 membered heteroaryl, such as, for example, a 5 to 14 membered or 5 to 10 membered heteroaryl. In certain embodiments, heteroaryl groups can be those derived from thiophene, pyrrole, benzothiophene, 2H-benzo[d][1,2,3]triazole benzofuran, indole, pyridine, quinoline, imidazole, benzimidazole, oxazole, tetrazole, and pyrazine.

"MTAP" refers to a mammalian methylthioadenosine phosphorylase enzyme.

"Pharmaceutically acceptable" refers to generally recognized for use in animals, and more particularly in humans.

"Pharmaceutically acceptable salt" refers to a salt of a compound that is pharmaceutically acceptable and that possesses the desired pharmacological activity of the parent compound.

"Pharmaceutically acceptable excipient" refers to a broad range of ingredients that may be combined with a compound or salt of the present invention to prepare a pharmaceutical composition or formulation. Typically, excipients include, but are not limited to, diluents, colorants, vehicles, anti-adherents, glidants, disintegrants, flavoring agents, coatings, binders, sweeteners, lubricants, sorbents, preservatives, and the like.

"PRMT5" refers to a mammalian Protein Arginine N-Methyl Transferase 5 (PRMT5) enzyme.

"PRMT5 inhibitor" refers to compounds that inhibit or negatively modulate all or a portion of the PRMT5 enzymatic activity.

"MTA-cooperative PRMT5 inhibitor" refers to compounds that inhibit or negatively modulate all or a portion of the PRMT5 enzymatic activity in the presence of bound MTA, in vitro or in vivo, in the cells with elevated levels of MTA.

"Stereoisomer" refers to an isomer that differs in the arrangement of the constituent atoms in space. Stereoisomers that are mirror images of each other and optically active are termed "enantiomers," and stereoisomers that are not mirror images of one another and are optically active are termed "diastereomers."

"Subject" includes mammals and humans. The terms "human" and "subject" are used interchangeably herein.

"Therapeutically effective amount" refers to the amount of a compound that, when administered to a subject for treating a disease, or at least one of the clinical symptoms of a disease or disorder, is sufficient to affect such treatment for the disease, disorder, or symptom. As those skilled in the art will recognize. this amount is typically not limited to a single dose but may comprise multiple dosages over a significant period of time as required to bring about a therapeutic or prophylactic response in the subject. Thus, a "therapeutically effective amount" is not limited to the amount in a single capsule or tablet, but may include more than one capsule or tablet, which is the dose prescribed by a qualified physician or medical care provider. The "therapeutically effective amount" can vary depending on the compound, the disease, disorder, and/or symptoms of the disease or disorder, severity of the disease, disorder, and/or symptoms of the disease or disorder, the age of the subject to be treated, and/or the weight of the subject to be treated. An appropriate amount in any given instance can be readily apparent to those skilled in the art or capable of determination by routine experimentation.

"Treating" or "treatment" of any disease or disorder refers to arresting or ameliorating a disease, disorder, or at least one of the clinical symptoms of a disease or disorder, reducing the risk of acquiring a disease, disorder, or at least one of the clinical symptoms of a disease or disorder, reducing the development of a disease, disorder or at least one of the clinical symptoms of the disease or disorder, or reducing the risk of developing a disease or disorder or at least one of the clinical symptoms of a disease or disorder. "Treating" or "treatment" also refers to inhibiting the disease or disorder, either physically, (e.g., stabilization of a discernible symptom), physiologically, (e.g., stabilization of a physical parameter), or both, or inhibiting at least one physical parameter which may not be discernible to the subject. Further, "treating" or "treatment" refers to delaying the onset of the disease or disorder or at least symptoms thereof in a subject which may be exposed to or predisposed to a disease or disorder even though that subject does not yet experience or display symptoms of the disease or disorder.

Also provided are pharmaceutical compositions that include the compound or the pharmaceutically acceptable salt thereof, the tautomer thereof, the pharmaceutically acceptable salt of the tautomer, the stereoisomer of any of the foregoing, or the mixture thereof according to any one of the examples and at least one pharmaceutically acceptable excipient, carrier or diluent. In some examples, the compound or the pharmaceutically acceptable salt thereof, the tautomer thereof, the pharmaceutically acceptable salt of the tautomer, the stereoisomer of any of the foregoing, or the mixture thereof according to any one of the aspects is present in an amount effective for the treatment of PRMT5-dependent cancers. In some aspects, the pharmaceutical composition is formulated for oral delivery whereas in other embodiments, the pharmaceutical composition is formulated for intravenous delivery. In some embodiments, the pharmaceutical composition is formulated for oral administration once a day or QD, and in some such formulations is a tablet where the effective amount of the active ingredient ranges from 1 mg to 1000 mg.

In some aspects, the subject is a mammal. In some such aspects, the mammal is a rodent. In other aspects, the mammal is a canine. In still other embodiments, the subject is a primate and, in some embodiments, is a human.

The pharmaceutical compositions or formulations for the administration of the compounds of this invention may conveniently be presented in unit dosage form and may be prepared by any of the methods well known in the art. All methods include the step of bringing the active ingredient into association with the carrier which constitutes one or more accessory ingredients. In general, the pharmaceutical compositions are prepared by uniformly and intimately bringing the active ingredient into association with a liquid carrier or a finely divided solid carrier or both, and then, if necessary, shaping the product into the desired formulation. In the pharmaceutical composition, the active object compound is included in an amount sufficient to produce the desired effect upon the process or condition of diseases.

The compounds of the invention may be administered via oral, mucosal (including sublingual, buccal, rectal, nasal, or vaginal), parenteral (including subcutaneous, intramuscular, bolus injection, intra-arterial, or intravenous), transdermal, or topical administration. In some aspects, the compounds of the invention are administered via mucosal (including sublingual, buccal, rectal, nasal, or vaginal), parenteral (including subcutaneous, intramuscular, bolus injection, intra-arterial, or intravenous), transdermal, or topical administration.

In other aspects, the compounds of the invention are administered via oral administration.

The compounds of the invention, the pharmaceutically acceptable salt thereof, the tautomer thereof, the pharmaceutically acceptable salt of the tautomer, the stereoisomer of any of the foregoing, or the mixture thereof may find use in treating a number of conditions.

Compounds and compositions described herein are generally useful for the inhibition of PRMT5. In some aspects, methods of treating PRMT5-mediated disorder in a subject are provided which comprise administering an effective amount of a compound described herein (e.g., a compound of Formula I or a pharmaceutically acceptable salt thereof), to a subject in need of treatment. In certain aspects, the effective amount is a therapeutically effective amount. In certain aspects, the effective amount is a prophylactically effective amount. In certain aspects, the subject is suffering from a PRMT5-mediated disorder (e.g., a cancer, for example a lymphoma, breast cancer, or pancreatic cancer). In other aspects, the subject is susceptible to a PRMT5-mediated disorder (e.g., a cancer, for example a lymphoma, breast cancer, or pancreatic cancer).

As used herein, the term "PRMT5-mediated disorder" means any disease, disorder, or other pathological condition in which PRMT5 is known to play a role. Accordingly, in some aspects, the present disclosure relates to treating or lessening the severity of one or more diseases in which PRMT5 is known to play a role.

In some aspects, herein provided is a method of inhibiting PRMT5 activity in a subject in need thereof comprising administering to the subject an effective amount of a compound described herein (e.g., a compound of Formula I, or a pharmaceutically acceptable salt thereof, or a pharmaceutical composition thereof.

The invention provides methods of treating cancers and other disorders arising from homozygous deletion of the chromosome 9p21 locus, which harbors the well-known tumor suppressor CDKN2A (cyclin dependent kinase inhibitor 2A). In one aspect, the invention encompasses methods of treating cancers and tumors which are MTAP (methylthioadenosine phosphorylase)-null. In some embodiments, these types of cancer display accumulation of MTAP substrate, methylthioadenosine (MTA).

The methods of treating PRMT5 disorders encompassed by the invention preferentially target PRMT5 in MTAP null tumors while sparing PRMT5 in normal tissues (MTAP WT). The compounds of the present invention thus include MTA-cooperative small molecule inhibitors which could preferentially target the MTA bound state of PRMT5, enriched in MTAP null tumor cells, while providing an improved therapeutic index over normal cells where MTAP is intact and MTA levels are low.

In further aspects, a PRMT5 inhibitor MTA cooperative compound contemplated by the present invention is useful in treating a proliferative disorder, such as cancer. In some embodiments, the cancer compounds described herein are useful for treating pancreatic cancer. In some aspects, the cancer compounds described herein are useful for treating multiple myeloma (MM). In further embodiments, the cancer compounds described herein are useful for treating breast cancer. The breast cancer can be estrogen receptor negative (ER−) or the breast cancer can be progesterone receptor negative (PR−). In further embodiments, the breast cancer can be HER2 negative. In some embodiments, the breast cancer is estrogen receptor negative, progesterone receptor negative and HER2 negative, also referred to herein as "triple negative breast cancer".

In further aspects, a breast cancer can be a lobular carcinoma in situ (LCIS), a ductal carcinoma in situ (DCIS), an invasive ductal carcinoma (IDC), inflammatory breast cancer, Paget disease of the nipple, Phyllodes tumor, Angiosarcoma, adenoid cystic carcinoma, low-grade adenosquamous carcinoma, medullary carcinoma, mucinous carcinoma, papillary carcinoma, tubular carcinoma, metaplastic carcinoma, micropapary carcinoma, mixed carcinoma, or another breast cancer, including but not limited to triple negative, HER positive, estrogen receptor positive, progesterone receptor positive, HER and estrogen receptor positive, HER and progesterone receptor positive, estrogen and progesterone receptor positive, and HER and estrogen and progesterone receptor positive.

In one embodiment, compounds of the invention are useful for treating pancreatic cancer.

In another embodiment, compounds of the invention are useful for treating NSCLC (non-small cell lung carcinoma. In one embodiment, the NSCLC can be squamous NSCLC. In another embodiment, it can be adenocarcinoma.

In a further aspect, cancer can be glioblastoma (GBM). In a further aspect, cancer can be mesothelioma. In one aspect, cancer can be bladder cancer. In another aspect, cancer can be esophageal cancer. In a further aspect, cancer can be melanoma. In one aspect, cancer can be DLBCL, HNSCC or cholangiocarcinoma.

In some aspects, one or more compounds described herein are useful for treating any PRMT5-mediated or PRMT5-responsive proliferative cell disorder, for example a cancer that is PRMT5 responsive.

In one aspect, a cancer that lacks p53 (e.g., a p53 null cancer) is less sensitive to PRMT5 inhibition than a cancer that is p53 positive. Accordingly, a cancer that is PRMT5 responsive can be a p53 positive cancer. The term "p53 positive" refers to a cancer that does not lack p53 expression and/or activity. In some embodiments, one or more compounds described herein are useful for treating a p53 positive cancer. In some aspects, a greater amount of one or more compounds described herein may be required to treat a p53 negative cancer (e.g., a p53 null cancer) than a p53 positive cancer.

In some aspects, the disclosure provides a method for identifying subjects having a cancer that is sensitive to treatment with a PRMT5 inhibitor. In some embodiments, the method comprises obtaining a sample from the subject; detecting the presence or absence of p53; and, identifying the subject as having a cancer that is sensitive to treatment with a PRMT5 inhibitor if p53 is present in the sample. Accordingly, in some embodiments, a subject having a p53 positive cancer is identified as a subject for treatment with a PRMT5 inhibitor. In some embodiments, the method further comprises administering to the subject a composition comprising a PRMT5 inhibitor.

In some embodiments, aspects of the disclosure relate to a method for identifying subjects having a cancer that is insensitive (or that has low sensitivity) to treatment with a PRMT5 inhibitor. In some embodiments, the method comprises obtaining a sample from the subject; detecting the presence or absence of p53; and, identifying the subject as having a cancer that is not sensitive (for example, a cancer that is less sensitive than a p53 positive cancer) to treatment with a PRMT5 inhibitor if p53 is absent from the sample (e.g., if the cancer is a p53 null cancer). In some embodiments, a p53 negative cancer (e.g., a p53 null cancer) is treated with a PRMT5 inhibitor, but a greater amount of PRMT5 inhibitor may be required to treat the p53 negative cancer than a p53 positive cancer. However, in some embodiments, a subject having a p53 negative cancer (e.g., a p53 null cancer) is treated with a therapeutic agent that is not a PRMT5 inhibitor.

By "sample" is meant any biological sample derived from the subject, includes but is not limited to, cells, tissues samples, body fluids (including, but not limited to, mucus, blood, plasma, serum, urine, saliva, and semen), cancer cells, and cancer tissues. Detection of the presence or absence of p53 in the sample may be achieved by any suitable method for detecting p53 nucleic acid or protein, for example, nucleic acid sequencing (e.g., DNA or RNA sequencing), quantitative PCR, Western blotting, etc., or any combination of thereof.

It should be appreciated that in some aspects, one or more of the compounds described herein may be useful for treating other types of cancer, including, but not limited to, acoustic neuroma, adenocarcinoma, adrenal gland cancer, anal cancer, angiosarcoma (e.g., lymphangiosarcoma, lymphangioendotheliosarcoma, hemangio sarcoma), appendix cancer, benign monoclonal gammopathy, biliary cancer (e.g., cholangiocarcinoma), bladder cancer, brain cancer (e.g., meningioma; glioma, e.g, astrocytoma, oligodendroglioma; medulloblastoma), bronchus cancer, carcinoid tumor, cervical cancer (e.g., cervical adenocarcinoma), choriocarcinoma, chordoma, craniopharyngioma, colorectal cancer (e.g., colon cancer, rectal cancer, colorectal adenocarcinoma), epithelial carcinoma, ependymoma, endothelio sarcoma (e.g., Kaposi's sarcoma, multiple idiopathic hemorrhagic sarcoma), endometrial cancer (e.g., uterine cancer, uterine sarcoma), esophageal cancer (e.g., adenocarcinoma of the esophagus, Barrett's adenocarinoma), Ewing sarcoma, eye cancer (e.g., intraocular melanoma, retinoblastoma), familiar hypereosinophilia, gall bladder cancer, gastric cancer (e.g., stomach adenocarcinoma), gastrointestinal stromal tumor (GIST), head and neck cancer (e.g., head and neck squamous cell carcinoma, oral cancer (e.g., oral squamous cell carcinoma (OSCC), throat cancer (e.g., laryngeal cancer, pharyngeal cancer, nasopharyngeal cancer, oropharyngeal cancer)), hematopoietic cancers (e.g., leukemia such as acute lymphocytic leukemia (ALL) (e.g., B-cell ALL, T-cell ALL), acute myelocytic leukemia (AML) (e.g., B-cell AML, T-cell AML), chronic myelocytic leukemia (CML) (e.g., B-cell CML, T-cell CML), and chronic lymphocytic leukemia (CLL) (e.g., B-cell CLL, T-cell CLL), follicular lymphoma, chronic lymphocytic leukemia/small lymphocytic lymphoma (CLL/SLL), marginal zone B-cell lymphomas (e.g., mucosa-associated lymphoid tissue (MALT) lymphomas, nodal marginal zone B-cell lymphoma, splenic marginal zone B-cell lymphoma), primary mediastinal B-cell lymphoma, Burkitt lymphoma, lymphoplasmacytic lymphoma (e.g., "Waldenstrom's macro globulinemia"), hairy cell leukemia (HCL), immunoblastic large cell lymphoma, precursor B-lymphoblastic lymphoma and primary central nervous system (CNS) lymphoma; and T-cell NHL such as precursor T-lymphoblastic lymphoma/leukemia, peripheral T-cell lymphoma (PTCL) (e.g., cutaneous T-cell lymphoma (CTCL) (e.g., mycosis fungiodes, Sezary syndrome), angioimmunoblastic T-cell lymphoma, extranodal natural killer T-cell lymphoma, enteropathy type T-cell lymphoma, subcutaneous panniculitis-like T-cell lymphoma, anaplastic large cell lymphoma); a mixture of one or more leukemia/lymphoma as described above; and multiple myeloma (MM)), heavy chain disease (e.g., alpha chain disease, gamma chain disease, mu chain disease)), hemangioblastoma, inflammatory myofibroblastic tumors, immunocytic amyloidosis, kidney cancer (e.g., nephroblastoma a.k.a. Wilms' tumor, renal cell carcinoma), liver cancer (e.g., hepatocellular cancer (HCC), malignant hepatoma), lung cancer (e.g., bronchogenic carcinoma, small cell lung cancer (SCLC), non-small cell lung cancer (NSCLC), adenocarcinoma of the lung), leiomyosarcoma (LMS), mastocytosis (e.g., systemic mastocytosis), myelodysplasia syndrome (MDS), mesothelioma, myeloproliferative disorder (MPD) (e.g., polycythemia Vera (PV), essential thrombocytosis (ET), agnogenic myeloid metaplasia (AMM) a.k.a. myelofibrosis (MF), chronic idiopathic myelofibrosis, chronic myelocytic leukemia (CML), chronic neutrophilic leukemia (CNL), hypereosinophilic syndrome (HES)), neuroblastoma, neurofibroma (e.g., neurofibromatosis (NF) type 1 or type 2, schwannomatosis), neuroendocrine cancer (e.g., gastroenteropancreatic neuroendoctrine tumor (GEP-NET), carcinoid tumor), osteosarcoma, ovarian cancer (e.g., cystadenocarcinoma, ovarian embryonal carcinoma, ovarian adenocarcinoma), papillary adenocarcinoma, penile cancer (e.g., Paget's disease of the penis and scrotum), pinealoma, primitive neuroectodermal tumor (PNT), prostate cancer (e.g., prostate adenocarcinoma), rectal cancer, rhabdomyosarcoma, salivary gland cancer, skin cancer (e.g., squamous cell carcinoma (SCC), keratoacanthoma (KA), melanoma, basal cell carcinoma (BCC)), small bowel cancer (e.g., appendix cancer), soft tissue sarcoma (e.g., malignant fibrous histiocytoma (MFH), liposarcoma, malignant peripheral nerve sheath tumor (MPNST), chondrosarcoma, fibrosarcoma, myxosarcoma), sebaceous gland carcinoma, sweat gland carcinoma, synovioma, testicular cancer (e.g., seminoma, testicular embryonal carcinoma), thyroid cancer (e.g., papillary carcinoma of the thyroid, papillary thyroid carcinoma (PTC), medullary thyroid cancer), urethral cancer, vaginal cancer and vulvar cancer (e.g., Paget's disease of the vulva).

In some aspects, the method of treating cancer in a subject comprises administering a composition comprising a PRMT5 inhibitor to the subject, wherein treatment with the PRMT5 inhibitor inhibits tumor growth of the cancer by more than about 25%, more than about 50%, more than about 75%, more than about 90% (e.g., 25%-50%, 50%-75%, 75%-90%, or 90%-100% for example). In some embodiments, the method of treating cancer in a subject comprises administering a composition comprising a PRMT5 inhibitor to the subject, wherein methyl mark of the cancer is reduced more than about 50%, more than about 75%, more than about 80% (e.g., 50%-75%, 50%-80%, 80%-90%, 80%-100%, or 90%-100% for example). A methyl mark refers to protein methylation, for example a histone methylation (e.g., methylation of one or more lysines and/or arginines of a histone protein), or DNA methylation (e.g., epigenetic DNA methylation, for example methylated CpG sites). In some embodiments, the methyl mark level of a cell is a measure of the extent to which histones are methylated in the cell (e.g., at one or more particular lysine and/or arginine positions).

The invention is further described by reference to the following examples, which are intended to exemplify the claimed invention but not to limit it in any way.

EXAMPLES

Unless otherwise noted in the intermediate section, all materials were obtained from commercial suppliers and were used without further purification.

The following abbreviations are used to refer to various reagents, solvents, or instruments:

| | |
|---|---|
| AcOH | acetic acid |
| aq or aq. | aqueous |
| Boc | tert-butyloxycarbonyl |
| CLND | chemiluminescent nitrogen detection |
| CMPI | 2-Chloro-1-methylpyridinium iodide |
| DAD | diode array detector |
| DCE | 1,2-dichloroethane |
| DCM | dichloromethane |
| DEA | diethylamine |
| DIAD | diisopropyl azodicarboxylate |
| DMA or DMAc | N,N-dimethylacetamide |
| DMF | N,N-dimethylformamide |
| DMSO | dimethyl sulfoxide |
| dppf | 1,1'-bis(diphenylphosphino)ferrocene |
| EDC•HCl or EDCI | 3-((ethylimino)methyleneamino)-N,N-dimethylpropan-1-amonium chloride |
| ESI or ES | electrospray ionization |
| Et | ethyl |
| $Et_2O$ | diethyl ether |
| EtOH | ethyl alcohol |
| EtOAc | ethyl acetate |
| g | grams |
| h | hour |
| HPLC | high pressure liquid chromatography |
| HATU | 1-[bis(dimethylamino)methylene]-1H-1,2,3-triazolo[4,5-b]pyridinium 3-oxid hexafluorophosphate |
| HBTU | N,N,N',N'-Tetramethyl-O-(1H-benzotriazol-1-yl)uronium hexafluorophosphate, O-(Benzotriazol-1-yl)-N,N,N',N'-tetramethyluronium hexafluorophosphate |
| HOAt | 1-hydroxy-7-azabenzotriazole |
| iPr | isopropyl |
| $iPr_2NEt$ or DIPEA | N-ethyl diisopropylamine (Hünig's base) |
| LC MS, LCMS, LC-MS or LC/MS | liquid chromatography mass spectroscopy |
| LG | leaving group (e.g., halogen, mesylate, triflate) |
| LiHMDS | lithium bis(trimethylsilyl)amide |
| m/z | mass divided by charge |
| Me | methyl |
| MeCN/ACN | acetonitrile |
| MeOH | methanol |
| Met | metal species for cross-coupling (e.g., MgX, ZnX, $SnR_3$, $SiR_3$, $B(OR)_2$) |
| mg | milligrams |
| min | minutes |
| mL | milliliters |
| MS | mass spectra |
| MsCl | methanesulfonyl chloride |
| MTBE | tert-butyl methyl ether |
| NMP | 1-methyl-2-pyrrolidine |
| n-BuLi | n-butyllithium |
| NMR | nuclear magnetic resonance |
| $Pd_2(dba)_3$ | tris(dibenzylideneacetone)dipalladium(0) |
| $Pd(dppf)Cl_2$•DCM | [1,1'-bis(diphenylphosphino)ferrocene]dichloropalladium(II), complex with DCM |
| $Pd(PPh_3)_4$ | tetrakis(triphenylphosphine)palladium(0) |
| Ph | phenyl |
| PG or Prot. group | protecting group |
| Prep | preparative |
| PyBrOP | bromotripyrrolidinophosphonium hexafluorophosphate |
| rbf | round-bottom flask |
| RP-HPLC | reverse phase high pressure liquid chromatography |
| RT or rt | room temperature |
| R.T. | retention time |
| RuPhos | 2-dicyclohexylphosphino-2',6'-diisopropoxybiphenyl |
| sat. or sat'd | saturated |
| SFC | supercritical fluid chromatography |
| t-BuOH | tert-butanol |
| TEA or $Et_3N$ | triethylamine |
| TEOS | tetraethyl orthosilicate |
| TFA | trifluoroacetic acid |
| THF | tetrahydrofuran |
| TBTU | N,N,N',N'-Tetramethyl-O-(benzotriazol-1-yl)uronium tetrafluoroborate |
| TOF | time of flight |
| UHPLC | ultra-high-performance liquid chromatography |
| Xantphos | 4,5-bis(diphenylphosphino)-9,9-dimethylxanthene |

General Synthetic Schemes:
Method A

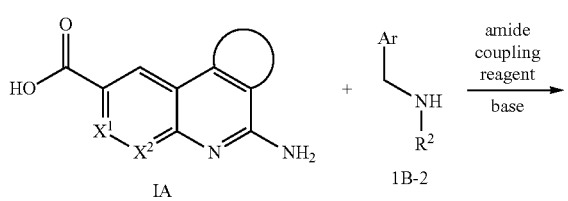

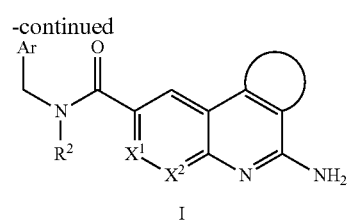

Method A-SFC

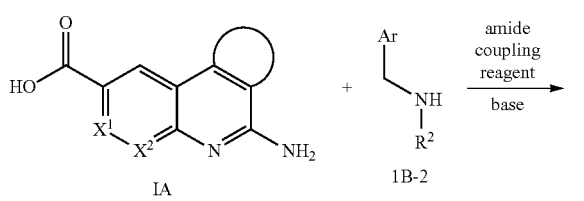

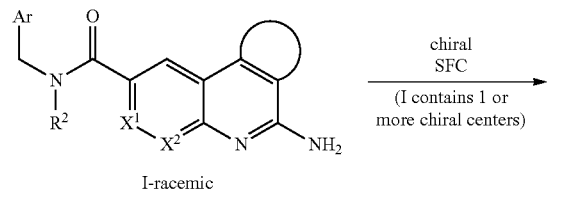

Method B

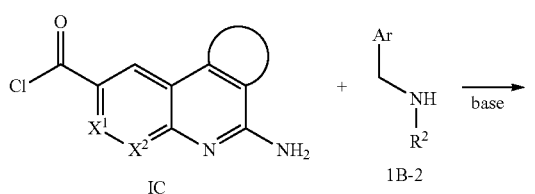

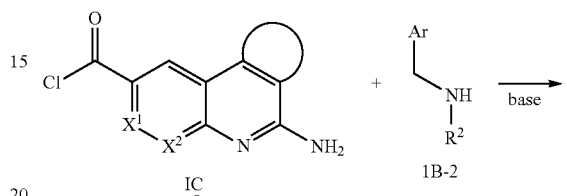

Method B-SFC

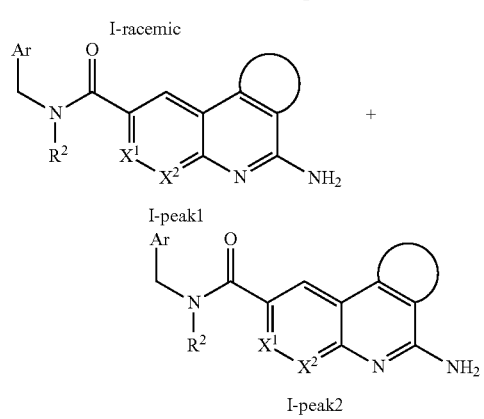

Method A: Compound I can be prepared from the reaction of acid IA and secondary amine IB-1 in the presence of a base such as Et$_3$N or DIPEA, an activating reagent such as HATU or PyBrOP, in a solvent such as DMF or DMAc. If racemic amine or acid is employed in Method A, chiral SFC can be used to separate the stereoisomers, in which case stereochemistry was arbitrarily assigned to each isomer.

Method B: Compound I can be prepared from the reaction of acid chloride IC and secondary amine IB in the presence of a base such as Et$_3$N or DIPEA or pyridine, in a solvent such as THF or dioxane or DCM or DCE. Alternatively, compound I can be prepared from the reaction of acid chloride IC and secondary amine IB in the presence of DMAP in pyridine. If racemic amine or acid is employed in Method B, chiral SFC can be used to separate the stereoisomers, in which case stereochemistry was arbitrarily assigned to each isomer.

Analytical U/HPLC

The following equipment was used for analytical UHPLC:

Waters Acquity system equipped with an Acquity BEH C18 (1.7 µm, 2.1×50 mm) with a linear gradient of a binary solvent system using a flow rate of 0.5 mL/min and DAD at ambient temperature, combined with MS detection SQD I.

Linear gradients used (H₂O/CH₃CN/HCO₂H (95/5/0.1% to 0/100/0.1%)). Agilent Infinity I/II-TOF6230B/CLND Antek 8060 equipped with Acquity BEH C18 (1.7 μm, 2.1×50 mm) with a linear gradient of a binary solvent system using a flow rate of 0.75 mL/min combined with DAD. Linear gradients used (H₂O/MeOH/HCO₂H (95/5/0.1% to 0/100/0.1%)).

Preparative HPLC

The following equipment was used for Prep-HPLC: Shimadzu Nexera X2 equipped with a Merck Chromolith SpeedROD RP-18E (5 μm, 10×100 mm) with a linear gradient of a binary solvent system using a flow rate between 4 and 7 mL/min and UV detection at 254 nm, combined with MS detecting on a Shimadzu LCMS-2020. Linear gradients used (H₂O/MeOH/HCO₂H (95/5/0.1% to 0/100/0.1%)).

INTERMEDIATES

Intermediate 1:
6-(difluoromethoxy)pyridazine-3-carbaldehyde

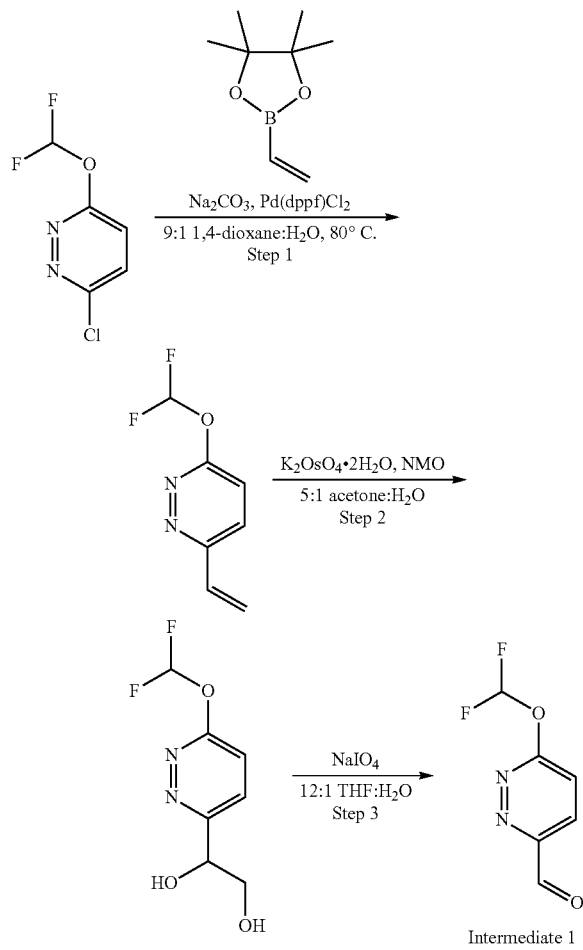

Step 1. A vial was charged with 3-chloro-6-(difluoromethoxy)pyridazine (675 mg, 3.74 mmol), sodium carbonate (1190 mg, 11.2 mmol), and [1,1'-bis(diphenylphosphino)ferrocene] dichloropalladium (II) (274 mg, 0.374 mmol). 1,4-dioxane (16.8 mL) and water (1.87 mL) were then added, followed by vinylboronic acid pinacol ester (1.73 g, 1.90 mL, 11.2 mmol). The resulting mixture was sparged with nitrogen for 15 min and then heated to 80° C. After 15 h, the mixture was cooled to 23° C. and transferred to a separatory funnel with EtOAc (20 mL) and H₂O (20 mL). The aqueous layer was extracted with EtOAc (20 mL), and the combined organic extracts were dried with Na₂SO₄ and concentrated to dryness. The resulting crude residue was purified by flash chromatography (0 to 50% 3:1 EtOAc:EtOH in heptane) to afford 3-(difluoromethoxy)-6-vinylpyridazine (573 mg, 3.33 mmol, 89% yield) as a light-brown solid. m/z (ESI): 173.2 [M+H]⁺.

Step 2. A vial was charged with 3-(difluoromethoxy)-6-vinylpyridazine (573 mg, 3.33 mmol), acetone (7.93 mL), and water (1.59 mL). To the resulting solution was added potassium osmate (VI) dihydrate (123 mg, 0.333 mmol) followed by 4-methylmorpholine 4-oxide (1.37 g, 11.7 mmol), and the resulting mixture was allowed to stir at 23° C. After 1.5 h, the reaction mixture was concentrated in vacuo then co-evaporated with toluene (5 mL), and the resulting crude residue was purified by flash column chromatography (0 to 100% 3:1 EtOAc:EtOH in heptane) to afford 1-(6-(difluoromethoxy)pyridazin-3-yl)ethane-1,2-diol (300 mg, 1.45 mmol, 43.7% yield) as a black oil. m/z (ESI): 207.1 [M+H]⁺.

Step 3. A vial was charged with 1-(6-(difluoromethoxy)pyridazin-3-yl)ethane-1,2-diol (300 mg, 1.45 mmol) and tetrahydrofuran (13.4 mL). To the resulting solution were added sodium (meta)periodate (933 mg, 4.36 mmol) and water (1.12 mL), and the resulting mixture was allowed to stir at 23° C. After 1 h, the reaction mixture was diluted with H₂O (10 mL), transferred to a separatory funnel with CH₂Cl₂ (20 mL) and brine (20 mL), and extracted with CH₂Cl₂ (2×20 mL). The combined organic layers were dried over anhydrous Na₂SO₄, filtered, and concentrated to dryness. The resulting crude residue was purified by flash column chromatography (0 to 100% 3:1 EtOAc:EtOH in heptane) to afford 6-(difluoromethoxy)pyridazine-3-carbaldehyde (1, 217 mg, 1.25 mmol, 86% yield) as a clear oil. m/z (ESI): 175.2 [M+H]⁺.

Intermediate 2:
6-cyclopropoxypyridazine-3-carbaldehyde

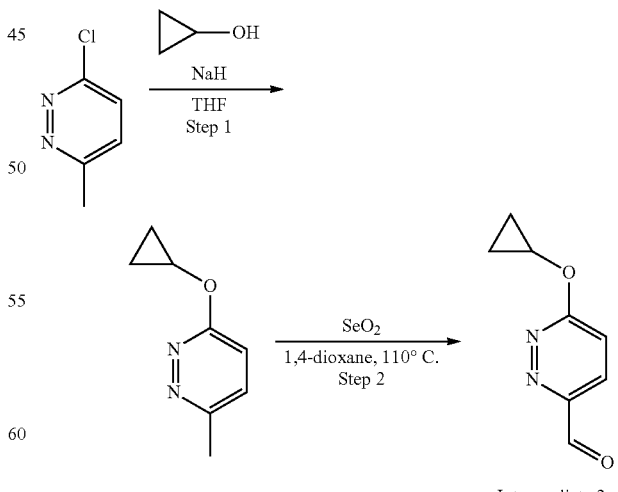

Step 1. A round-bottom flask was charged with sodium hydride (60% dispersion in mineral oil, 1.556 g, 38.9 mmol) and tetrahydrofuran (31.1 mL). The headspace was flushed with nitrogen, and the mixture was cooled to 0° C. Subsequently, cyclopropanol (2.281 g, 1.901 mL, 39.3 mmol) was added, and the resulting mixture was allowed to warm to 23° C. under nitrogen for 1 h. 3-chloro-6-methylpyridazine (1.00 g, 7.78 mmol) was then added dropwise as a solution in tetrahydrofuran (8.0 mL), and the reaction mixture was allowed to stir at 23° C. After 16 h, the reaction mixture was transferred to a separatory funnel w/CH$_2$Cl$_2$ (30 mL), H$_2$O (20 mL), and sat. aq. NH$_4$Cl (30 mL), the layers were separated, and the aqueous layer was extracted with CH$_2$Cl$_2$ (2×20 mL). The combined organic layers were dried over anhydrous Na$_2$SO$_4$, filtered, and concentrated to dryness. The resulting crude residue was purified by flash chromatography (0 to 100% EtOAc in heptane) to afford 3-cyclopropoxy-6-methylpyridazine (308.5 mg, 2.054 mmol, 26.4% yield) as a light yellow oil. m/z (ESI): 151.2 [M+H]$^+$.

Step 2. A vial was charged with 3-cyclopropoxy-6-methylpyridazine (308.5 mg, 2.054 mmol), selenium dioxide (365 mg, 3.29 mmol), and 1,4-dioxane (8.22 mL). The resulting mixture was sparged with nitrogen for 10 min, and the vial was subsequently heated to 110° C. After 30 min, the reaction mixture was allowed to cool to 23° C. and was filtered over a pad of Celite (30 mL 3:1 EtOAc:EtOH eluent) and concentrated to dryness. The resulting crude residue was purified by flash chromatography (0 to 50% 3:1 EtOAc: EtOH in heptane) to afford 6-cyclopropoxypyridazine-3-carbaldehyde (2, 111.7 mg, 0.680 mmol, 33.1% yield) as an orange oil. m/z (ESI): 165.1 [M+H]$^+$.

Intermediate 3: 6-ethoxypyridazine-3-carbaldehyde

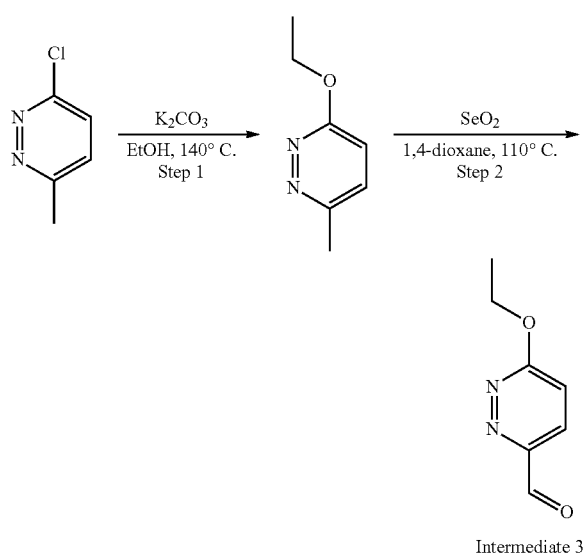

Intermediate 3

A microwave vial was charged with 3-chloro-6-methylpyridazine (1.00 g, 7.78 mmol, Combi Blocks) and ethanol (15.6 mL). To the resulting solution was added potassium carbonate (2.69 g, 19.45 mmol), and the mixture was heated to 140° C. in the microwave for 14 h. The reaction mixture was then transferred to a separatory funnel with CH$_2$Cl$_2$ (30 mL), H$_2$O (20 mL), and sat. aq. NH$_4$Cl (30 mL), the layers were separated, and the aqueous layer was extracted with CH$_2$Cl$_2$ (2×20 mL). The combined organic layers were dried over anhydrous Na$_2$SO$_4$, filtered, and concentrated to dryness. The resulting crude residue was purified by flash chromatography (0 to 100% 3:1 EtOAc:EtOH in heptane) to afford 3-ethoxy-6-methylpyridazine (1.07 g, 7.72 mmol, 99% yield) as a light-yellow oil. m/z (ESI): 139.15 [M+H]$^+$.

A vial was charged with 3-ethoxy-6-methylpyridazine (1.07 g, 7.72 mmol), selenium dioxide (1.37 g, 12.3 mmol), and 1,4-dioxane (30.9 mL). The resulting mixture was sparged with nitrogen for 10 min, and the vial was subsequently heated to 110° C. After 30 min, the reaction mixture was allowed to cool to 23° C. and was filtered over a 1 cm pad of Celite (30 mL 3:1 EtOAc:EtOH eluent) and conc. to dryness. The resulting crude residue was purified by flash chromatography (0 to 50% 3:1 EtOAc:EtOH in heptane) to afford 6-ethoxypyridazine-3-carbaldehyde (3, 332.7 mg, 2.187 mmol, 28% yield) as a light-yellow solid. $^1$H NMR (400 MHz, CHLOROFORM-d) δ ppm 10.26 (d, J=0.8 Hz, 1H), 7.96 (d, J=9.1 Hz, 1H), 7.08 (dd, J=9.0, 0.9 Hz, 1H), 4.75 (q, J=7.0 Hz, 2H), 1.52 (t, J=7.2 Hz, 3H); m/z (ESI): 153.1 [M+H]$^+$. This route can be applied to other non-commercial aldehyde intermediates in Table 1.

Intermediates 4-6:
3-(6-methoxypyridazin-3-yl)-5-methylmorpholine

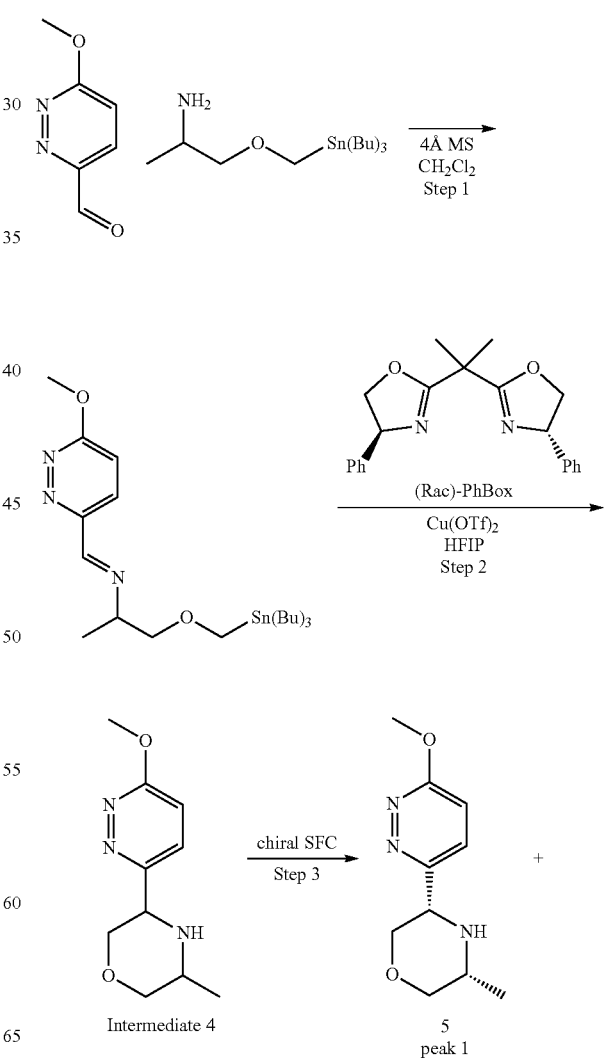

-continued

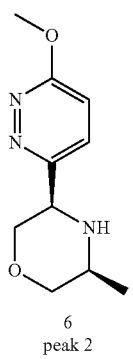

6
peak 2

Step 1. An oven-dried vial was charged with 4 Å Molecular Sieves (2.00 g, 2.64 mmol), dichloromethane (10.6 mL), and 6-methoxypyridazine-3-carbaldehyde (365 mg, 2.64 mmol, Enamine). To the resulting suspension was added 1-((tributylstannyl)methoxy)propan-2-amine (SnAP 3Me-M reagent, 0.907 mL, 2.64 mmol) via syringe, and the resulting mixture was allowed to stir at 23° C. After 17 h, the reaction mixture was filtered (20 mL dichloromethane eluent) and the filtrate was concentrated in vacuo to afford (E)-1-(6-methoxypyridazin-3-yl)-N-(1-((tributylstannyl)methoxy)propan-2-yl)methanimine as a brown oil. $^1$H NMR (400 MHz, CHLOROFORM-d) δ ppm 8.55 (s, 1H), 8.10 (d, J=9.0 Hz, 1H), 7.00 (dd, J=9.2, 0.6 Hz, 1H), 4.20 (s, 3H), 3.62-3.81 (m, 3H), 3.38-3.49 (m, 2H), 1.18-1.69 (m, 20H), 0.76-1.01 (m, 18H). The material was used in the subsequent step without further purification.

Step 2. A vial was charged oven-dried copper (II) trifluoromethanesulfonate (191 mg, 0.528 mmol), (4S,4'S)-2,2'-(propane-2,2-diyl)bis(4-phenyl-4,5-dihydrooxazole) (88 mg, 0.264 mmol), (4R,4'R)-2,2'-(propane-2,2-diyl)bis(4-phenyl-4,5-dihydrooxazole) (88 mg, 0.264 mmol), and hexafluoroisopropanol (4 mL). The resulting mixture was stirred at 23° C. for 7 h. The mixture was then added via syringe to a solution of (E)-1-(6-methoxypyridazin-3-yl)-N-(1-((tributylstannyl)methoxy)propan-2-yl)methanimine (1316 mg, 2.64 mmol) in hexafluoroisopropanol (19.1 mL). The resulting mixture was sparged with nitrogen for 10 min, and then allowed to stir at 23° C. After 16 h, the reaction mixture was treated with 30% aq NH$_4$OH and brine (1:1, 10 mL) and stirred vigorously for 1 h at 23° C. The mixture was transferred to a separatory funnel with CH$_2$Cl$_2$ (20 mL) and brine (20 mL), the layers were separated, and the aqueous layer was extracted with CH$_2$Cl$_2$ (2×20 mL). The combined organic layers were dried over anhydrous Na$_2$SO$_4$, filtered, and concentrated in vacuo. The resulting crude residue was purified by flash chromatography (0 to 100% 3:1 EtOAc:EtOH in heptane) to afford 3-(6-methoxypyridazin-3-yl)-5-methylmorpholine (4, 337 mg, 1.611 mmol, 61% yield) as a yellow solid. $^1$H NMR (400 MHz, CHLOROFORM-d) δ ppm 7.50 (d, J=9.1 Hz, 1H), 6.97 (d, J=9.1 Hz, 1H), 4.27-4.38 (m, 1H), 4.14 (s, 3H), 4.07 (dd, J=11.0, 3.3 Hz, 1H), 3.81-3.92 (m, 1H), 3.41 (t, J=10.7 Hz, 1H), 3.07-3.25 (m, 2H), 1.92 (br s, 1H), 1.07 (d, J=6.0 Hz, 3H); m/z (ESI): 210.1 [M+H]$^+$.

Step 3. The racemic secondary amine 4 (337 mg) was purified via preparative SFC using a Chiral Technologies IG column (250×21 mm, 5 mm) with a mobile phase of 50% liquid CO$_2$ and 50% MeOH with 0.2% TEA using a flowrate of 80 mL/min. Peak assignment determined by SFC with IG column with 50% MeOH with 0.2% TEA. The 1st eluting peak was arbitrarily assigned as (3S,5R)-3-(6-methoxypyridazin-3-yl)-5-methylmorpholine (5, 150.7 mg, >99% ee) and the 2$^{nd}$ eluting peak was arbitrarily assigned as (3R,5S)-3-(6-methoxypyridazin-3-yl)-5-methylmorpholine (6, 152.7 mg, >99% ee).

Racemic amines summarized in Table 1 were prepared in a fashion similar to that described above for amine 4.

TABLE 1

| Int | Structure | Name | m/z (ESI): [M + H]$^+$ |
|---|---|---|---|
| 7 | 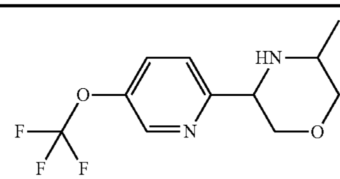 | 3-methyl-5-(5-(trifluoromethoxy)pyridin-2-yl)morpholine | 263.1 |
| 8 | 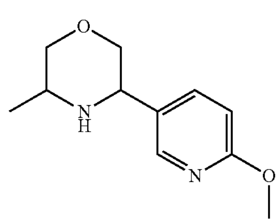 | 3-(6-ethoxypyridin-3-yl)-5-methylmorpholine | 232.2 |
| 9 | 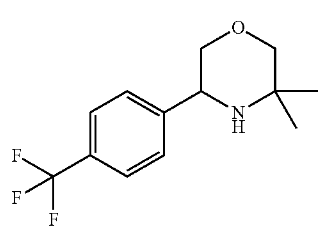 [SMILES: CC1(C)COCC(c2ccc(C(F)(F)F)cc2)N1] | 3,3-dimethyl-5-(4-(trifluoromethyl)phenyl)morpholine | 260.1 |

TABLE 1-continued

| Int | Structure | Name | m/z (ESI): [M + H]+ |
|---|---|---|---|
| 10 | 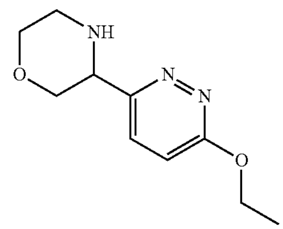 | 3-(6-ethoxypyridazin-3-yl)morpholine | 210.1 |
| 11 | 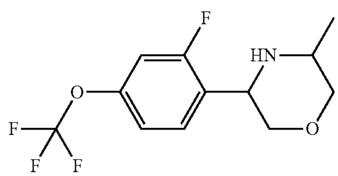 [SMILES: CC1COCC(c2ccc(OC(F)(F)F)cc2F)N1] | 3-(2-fluoro-4-(trifluoromethoxy)phenyl)-5-methylmorpholine | 280.0 |
| 12 | 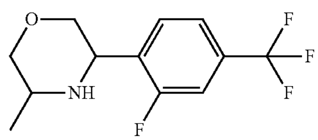 [SMILES: CC1COCC(c2ccc(C(F)(F)F)cc2F)N1] | 3-(2-fluoro-4-(trifluoromethyl)phenyl)-5-methylmorpholine | 264.1 |
| 13 | 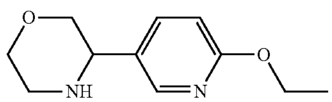 | 3-(6-ethoxypyridin-3-yl)morpholine | 209.2 |
| 14 | 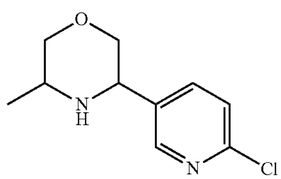 | 3-(6-chloropyridin-3-yl)-5-methylmorpholine | 312.0 |
| 15 | 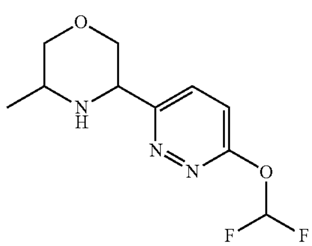 [SMILES: CC1COCC(c2ccc(OC(F)F)nn2)N1] | 3-(6-(difluoromethoxy)pyridazin-3-yl)-5-methylmorpholine | 246.0 |
| 16 | 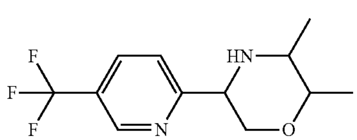 [SMILES: CC1NC(c2ccc(C(F)(F)F)cn2)COC1C] | 2,3-dimethyl-5-(5-(trifluoromethyl)pyridin-2-yl)morpholine | 261.1 |
| 17 | 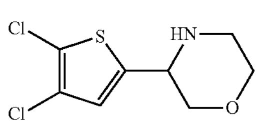 [SMILES: Clc1cc(C2COCCN2)sc1Cl] | 3-(4,5-dichlorothiophen-2-yl)morpholine | 238.2 |
| 18 | 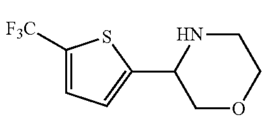 | 3-(5-(trifluoromethyl)thiophen-2-yl)morpholine | 238.0 |

TABLE 1-continued

| Int | Name | m/z (ESI): [M + H]+ |
|---|---|---|
| 19 | 3-(4-(trifluoromethyl)thiophen-2-yl)morpholine | 238.0 |
| 20 | 2-methyl-5-(5-(trifluoromethyl)pyridin-2-yl)morpholine | 247.1 |
| 21 | 6-(morpholin-3-yl)nicotinonitrile | 190.1 |
| 22 | 3-(5-bromopyridin-2-yl)morpholine | 243.1, 245.1 |
| 23 | 3-(6-bromopyridazin-3-yl)morpholine | 244.0, 246.0 |
| 24 | 3-(5-chloropyridin-2-yl)morpholine | 199.1 |
| 25 | 3-(6-(trifluoromethyl)pyridazin-3-yl)morpholine | 234.1 |
| 26 | 3-(6-methoxypyridazin-3-yl)morpholine | 196.1 |
| 27 | 3-(6-(trifluoromethoxy)pyridin-3-yl)morpholine | 249.1 |
| 28 | 2,2-dimethyl-5-(5-(trifluoromethyl)pyridin-2-yl)morpholine | 261.1 |
| 29 | 3-(6-(trifluoromethyl)pyridin-3-yl)morpholine | 233.2 |
| 30 | 3-(4-(2,2,2-trifluoroethyl)phenyl)morpholine | 246 |
| 31 | 3-(4-(pentafluoro-16-sulfaneyl)phenyl)morpholine | 290.1 |

TABLE 1-continued

| Int | Structure | Name | m/z (ESI): [M + H]+ |
|---|---|---|---|
| 32 | 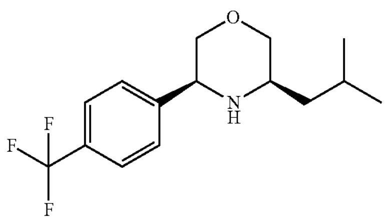 [SMILES: CC(C)C[C@@H]1COC[C@H](c2ccc(C(F)(F)F)cc2)N1] | Rac-cis-(3R,5S)-3-isobutyl-5-(4-(trifluoromethyl)phenyl)morpholine | 288.0 |
| 33 | 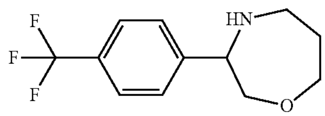 [SMILES: FC(F)(F)c1ccc(C2COCCCN2)cc1] | 3-(4-(trifluoromethyl)phenyl)-1,4-oxazepane | 246.2 |
| 34 | 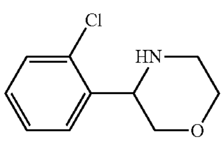 [SMILES: Clc1ccccc1C1COCCN1] | 3-(2-chlorophenyl)morpholine | 198.2 |
| 35 | 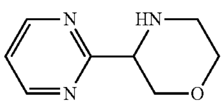 [SMILES: c1cnc(C2COCCN2)nc1] | 3-(pyrimidin-2-yl)morpholine | 166.3 |
| 36 | 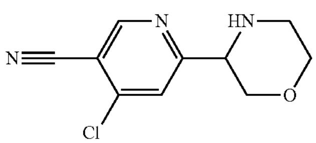 [SMILES: N#Cc1cnc(C2COCCN2)cc1Cl] | 4-chloro-6-(morpholin-3-yl)nicotinonitrile | 224.0 |
| 37 | 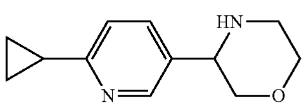 [SMILES: c1cc(C2CC2)ncc1C1COCCN1] | 3-(6-cyclopropylpyridin-3-yl)morpholine | 205.1 |
| 38 | 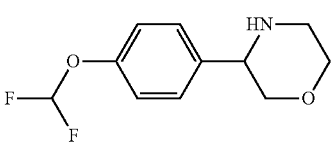 [SMILES: FC(F)Oc1ccc(C2COCCN2)cc1] | 3-(4-(difluoromethoxy)phenyl)morpholine | 230.2 |
| 39 | 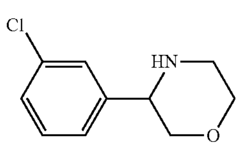 | 3-(3-chlorophenyl)morpholine | 198.1 |
| 40 | 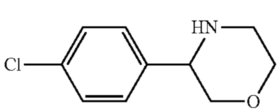 | 3-(4-chlorophenyl)morpholine | 198.2 |

Chiral amines in Table 2 were prepared in a fashion similar to that described above for amine 5 and 6. The racemic amines were subjected to chiral SFC to provide enantiomerically pure amines (>99% ee).

TABLE 2

| Int | Structure | SFC Conditions | m/z (ESI): [M + H]+ |
|---|---|---|---|
| 41 | 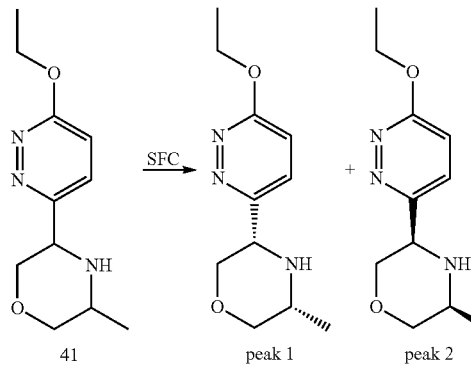 | Chiralpak AD column (150 × 20 mm, 5 μm) with a mobile phase of 80% Liquid $CO_2$ and 20% MeOH with 0.2% $Et_2NH$ using a flow rate of 80 mL/min. | 224.2 |
| 42 | 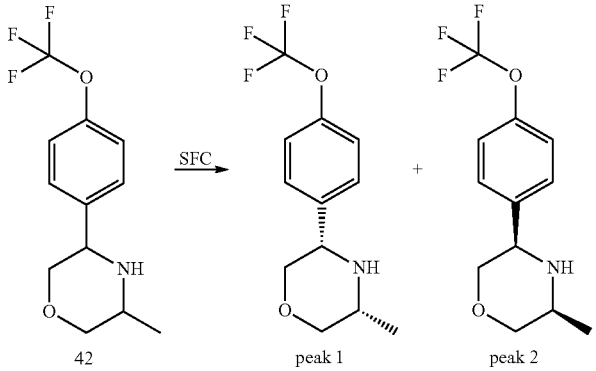 | Chiral Technologies IG column (250 × 21 mm, 5 μm) with a mobile phase of 85% Liquid $CO_2$ and 15% $CH_3CN$ using a flow rate of 65 mL/min. | 262.0 |
| 43 | 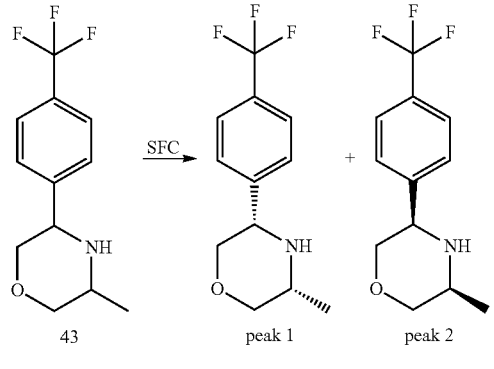 | Chiral Technologies IG column (250 × 21 mm, 5 μm) with a mobile phase of 70% Liquid $CO_2$ and 30% $CH_3CN$ using a flow rate of 80 mL/min. | 246.25 |
| 44 | 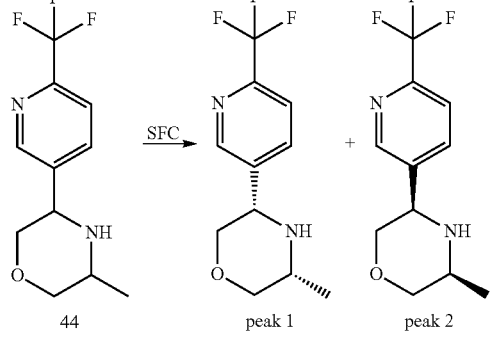 | Chiralcel AD-H column (250 × 21 mm, 5 μm) with a mobile phase of 85% Liquid $CO_2$ and 15% MeOH with 0.2% $Et_3N$ using a flow rate of 80 mL/min. | 247.15 |

TABLE 2-continued

| Int | Structure | SFC Conditions | m/z (ESI): [M + H]+ |
|---|---|---|---|
| 45 | 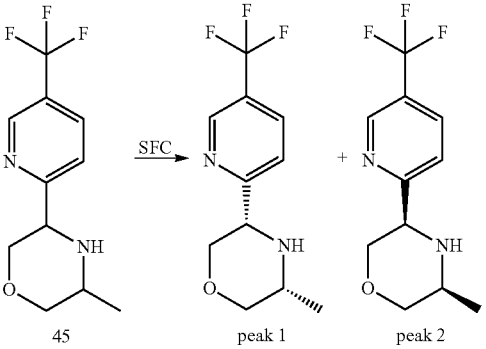 | Chiral Technologies AD column (250 × 21 mm, 5 μm) with a mobile phase of 90% Liquid $CO_2$ and 10% MeOH with 0.2% $Et_3N$ using a flow rate of 80 mL/min. | 247.15 |
| 46 | 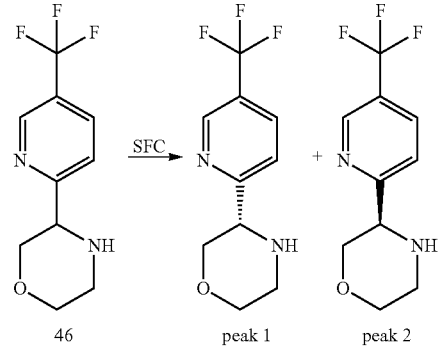 | IG column with a mobile phase of 60% Liquid $CO_2$ and 40% MeOH with DEA | 233.0 |
| 47 | 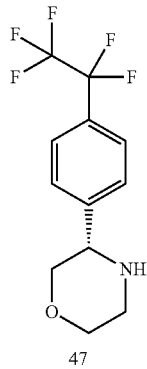 | $2^{nd}$ peak, Chiral Technologies IG column (250 × 21 mm, 5 mm) × 2 with a mobile phase of 90% Liquid $CO_2$ and 10% MeOH with 0.2% TEA using a flowrate of 70 mL/min. | 282.0 |
| 48 | 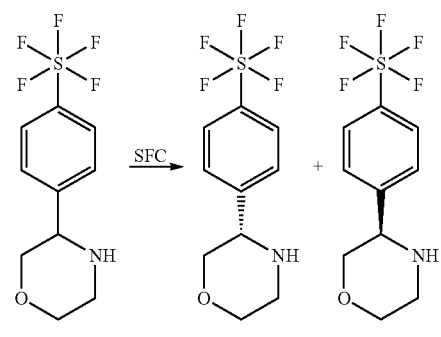 | Chiralpak AD column (250 × 21 mm, 5 um) with a mobile phase of 90% Liquid $CO_2$ and 10% methanol with 0.2% TEA using a flowrate 80 mL/min | 290.1 |

TABLE 2-continued

| Int | Structure | SFC Conditions | m/z (ESI): [M + H]+ |
|---|---|---|---|
| 49 | 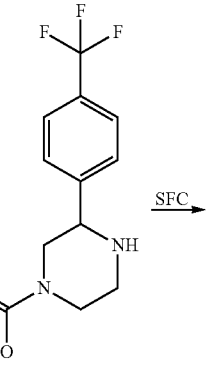 | ChiralPak IG column (250 × 4.6 mm, 5 μm) with a mobile Phase of 90% Liquid CO$_2$ and 10% MeOH with 0.2% DEA using a flow rate of 3 mL/min. | 331.1 |
| 50 | 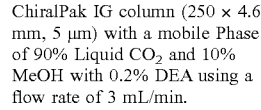 | SFC Chiralpak AD-H column (250 × 21 mm, 5 μm) with a mobile phase of 75% Liquid CO$_2$ and 25% MeOH with 0.2% TEA using a flowrate 100 mL/min. | 234.1 |
| 51 | 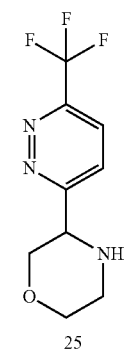 | SFC Chiral Technologies IG column (250 × 21 mm, 5 mm) with a mobile phase of 50% Liquid CO$_2$ and 50% MeOH with 0.2% TEA using a flowrate of 55 mL/min. | 246.3 |
| 52 | 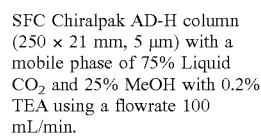 | SFC Chiralpak AD column (21 × 150 mm, 5 μm) with a mobile phase of 80% Liquid CO$_2$ and 20% MeOH with 0.2% diethylamine using a flowrate of 80 mL/min. | 248.1 |

TABLE 2-continued

| Int | Structure | SFC Conditions | m/z (ESI): [M + H]+ |
|---|---|---|---|
| 53 | 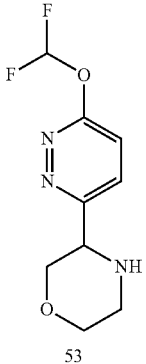 | SFC Chiralpak AD column (21 × 150 mm, 5 μm) with a mobile phase of 75% Liquid $CO_2$ and 25% MeOH with 0.2% diethylamine using a flowrate of 80 mL/min. | 232.2 |
| 54 | 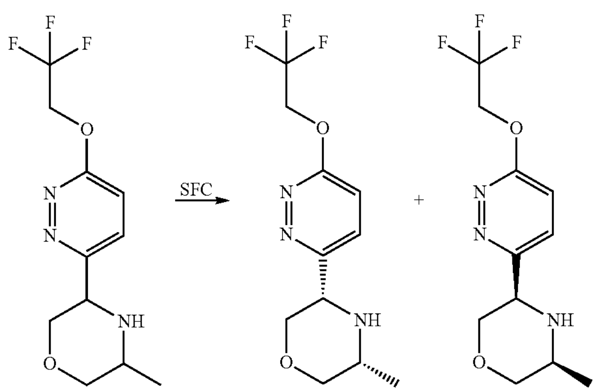 | SFC Chiralpak AD column (250 × 21 mm, 5 μm) with a mobile phase of 85% Liquid $CO_2$ and 15% MeOH with 0.2% TEA using a flowrate 80 mL/min. | 278.2 |
| 55 | 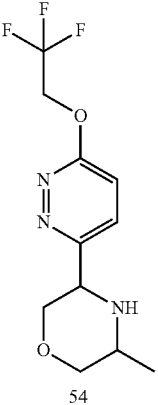 | SFC Chiralpak IG column (21 × 150 mm, 5 μm) with a mobile phase of 65% Liquid $CO_2$ and 35% MeOH with 0.2% diethylamine using a flowrate of 80 mL/min. | 292.2 |

| Int | Structure | SFC Conditions | m/z (ESI): [M + H]+ |
|---|---|---|---|
| 56 | 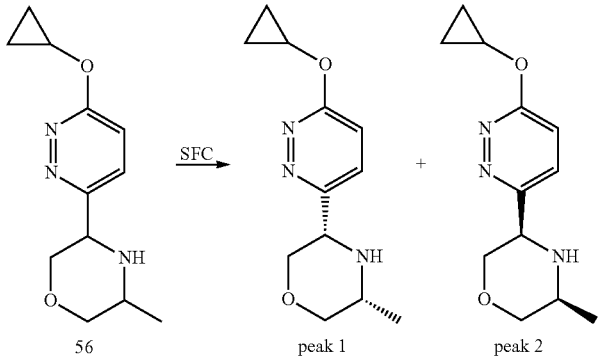 56  peak 1  peak 2 | SFC Chiral Technologies OJ column (250 × 21 mm, 5 mm) with a mobile phase of 90% Liquid $CO_2$ and 10% MeOH with 0.2% TEA using a flowrate of 80 mL/min. | 236.2 |

Intermediate 57:
2-(4-bromophenyl)-4,4-difluoropiperidine

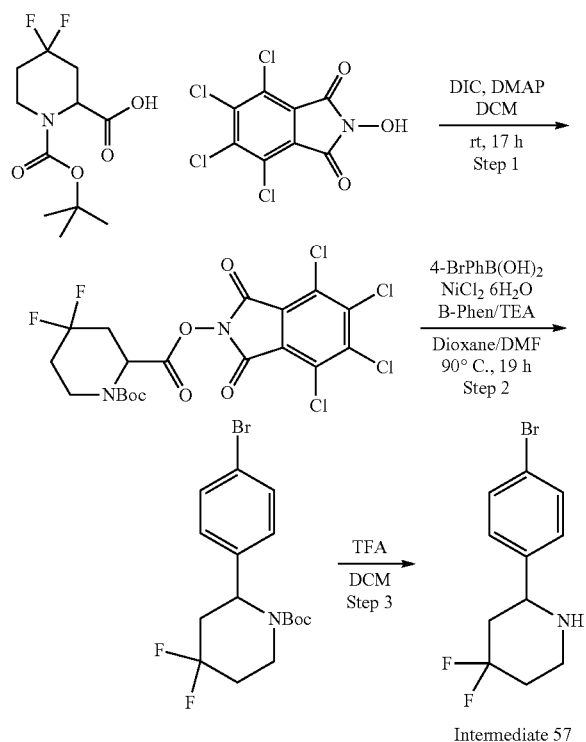

Intermediate 57

Step 1. As performed in Angew. Chem. Int. Ed. 2016, 55, 9676-9: to a vigorously stirred mixture in a 25-mL reaction vial of Boc-1-homoPro(4,4-difluoro) (1.050 g, 3.96 mmol, RSP Amino Acids, LLC), 4,5,6,7-tetrachloro-2-hydroxyisoindoline-1,3-dione (1.191 g, 3.96 mmol, Aldrich) and 4-(dimethylamino) pyridine (0.048 g, 0.396 mmol, Sigma-Aldrich Corporation) in DCM (25 mL) was dropwise added at rt N,N'-Diisopropylcarbodiimide (0.550 g, 0.674 mL, 4.35 mmol, Sigma-Aldrich Corporation) via a syringe. The resulting mixture was stirred at rt for 17 h. The crude mixture was directly loaded onto a silica gel precolumn (25 g) and subjected to combi-flash column chromatography using a 40-g ISCO gold column eluting with EtOAc/heptane (17 min from 10 to 70%) to give 1-(tert-butyl) 2-(4,5,6,7-tetrachloro-1,3-dioxoisoindolin-2-yl) 4,4-difluoropiperidine-1,2-dicarboxylate (1.45 g, 2.65 mmol, 66.8% yield) as a white solid. $^1$H NMR (CHLOROFORM-d, 400 MHz) δ 5.2-5.7 (m, 1H), 4.1-4.4 (m, 1H), 3.2-3.5 (m, 1H), 2.85 (br d, 1H, J=1.3 Hz), 2.1-2.5 (m, 2H), 1.8-2.0 (m, 1H), 1.51 (s, 9H). m/z (ESI): 569.0, 570.8 and 572.8 (M+Na)+.

Step 2. A 25-mL reaction vessel charged with nickel (ii) chloride hexahydrate (50.3 mg, 0.212 mmol, Sigma-Aldrich Corporation) and 1,10-bathophenanthroline (70.3 mg, 0.212 mmol, Combi-Blocks Inc.) was subjected to evacuation followed by back-filling with argon (3x) before N, N-dimethylformamide (4.10 mL) was introduced. The resulting mixture was stirred under argon at rt for 2.5 h as a green solution. Separately, a 250-mL single-necked reaction vessel charged with 1-(tert-butyl) 2-(4,5,6,7-tetrachloro-1,3-dioxoisoindolin-2-yl) 4,4-difluoropiperidine-1,2-dicarboxylate (580 mg, 1.058 mmol, form Step 1) and (4-bromophenyl)boranediol (1062 mg, 5.29 mmol, Oakwood Products, Inc.) was subjected to evacuation followed by back-filling with nitrogen (3x) before 1,4-dioxane (41 mL) was introduced. The resulting mixture was stirred under nitrogen at rt for 2 min before triethylamine (1071 mg, 1.487 mL, 10.58 mmol, Sigma-Aldrich Corporation) was added. The resulting mixture was stirred at rt for 5 min before the afore-prepared catalyst solution was introduced via a syringe under nitrogen. The resulting mixture was immediately placed in an oil bath pre-heated at 90° C. and stirred for 17 h. The volume was reduced and the crude residue was loaded onto a silica gel precolumn (25 g) and subjected to combi-flash column chromatography using a 24-g ISCO gold column eluting with MeOH/DCM (20 min from 0 to 5%), monitored at 215 nm UV channel, to give 290 mg of an impure tert-butyl 2-(4-bromophenyl)-4,4-difluoropiperidine-1-carboxylate as a colorless film. This was taken onto the next step without further purification. m/z (ESI): 398.0 and 400.0 (M+Na)+.

Step 3. To a stirred solution of tert-butyl 2-(4-bromophenyl)-4,4-difluoropiperidine-1-carboxylate (290 mg, 0.771 mmol, impure from Step 2) in DCM (5 mL) was added at rt 2,2,2-trifluoroacetic acid (88 mg, 4.0 mL, 0.771 mmol, Aldrich). The resulting mixture was stirred at rt for 1 h. The volatiles were removed in vacuo and the residue was loaded onto a silica gel precolumn (25 g) and subjected to combi-flash column chromatography using a 12-g ISCO gold column eluting with 20% MeOH (with 0.5% ammonium hydroxide)/DCM (12 min from 1% to 20%) to give an impure desired product 57, which was dissolved in DCM/MeOH and loaded onto a silica gel precolumn (25 g) and subjected to combi-flash column chromatography using a 12-g ISCO gold column eluting with (EtOH/EtOAc, 1/3, v/v)/heptane (15 min from 0 to 80%), monitored at 215 nm UV channel, to give 2-(4-bromophenyl)-4,4-difluoropiperidine (142 mg, 0.514 mmol, 49% yield in two steps) (57) as a colorless film. $^1$H NMR (CHLOROFORM-d, 400 MHz) δ 7.48 (d, 2H, J=8.4 Hz), 7.26 (d, 2H, J=8.4 Hz), 3.82 (br d, 1H, J=11.7 Hz), 3.23 (tdd, 1H, J=2.6, 5.3, 12.1 Hz), 2.9-3.0 (m, 1H), 2.1-2.3 (m, 2H), 1.7-2.0 (m, 3H). $^{19}$F NMR (CHLOROFORM-d, 376 MHz) δ−88.35 (d, 1F, J=237.6 Hz), −101.82 (d, 1F, J=237.6 Hz). m/z (ESI): 276.0 and 278.0 [M+H]$^+$.

Racemic amines in Table 3 were prepared in a fashion similar to that described above for amine 57.

TABLE 3

| Int | Structure | Name | m/z (ESI): [M + H]$^+$ |
|---|---|---|---|
| 58 | (Br-phenyl-piperidine with 2 F) | 2-(4-bromophenyl)-4,4-difluoropiperidine | 276.0 and 278.0 |
| 59 | (Br-phenyl-morpholine) | 3-(4-bromophenyl)morpholine | 242.0 and 244.0 |
| 60 | (F$_3$C-phenyl-difluoropiperidine) | 4,4-difluoro-2-(4-(trifluoromethyl)phenyl)piperidine | 266.0 |
| 61 | (F$_3$CO-phenyl-difluoropiperidine) | 4,4-difluoro-2-(4-(trifluoromethoxy)phenyl)piperidine | 282.2 |

Intermediate 100: 4-Amino-1,3-dihydrofuro[3,4-c]quinoline-8-carboxylic acid

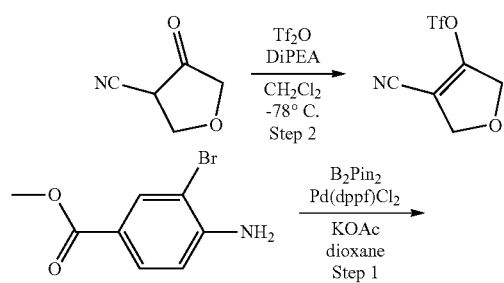

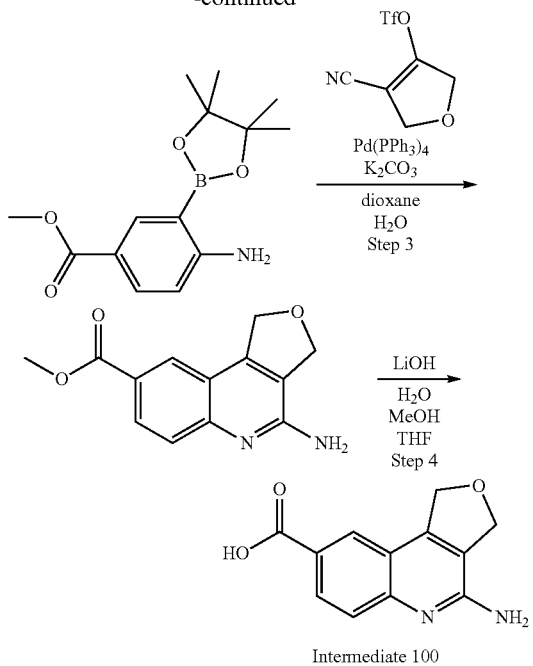

Intermediate 100

Step 1. To a 150-mL round-bottomed flask was added methyl 4-amino-3-bromobenzoate (4 g, 17.39 mmol, Combi-Blocks Inc.) and bis(pinacolato)diboron (8.83 g, 34.8 mmol, Frontier Scientific, Inc.) in 1,4-dioxane (58.0 mL). To the solution was then added potassium acetate (5.12 g, 52.2 mmol, Sigma-Aldrich Corporation), the mixture was degassed by bubbling through with Argon for 5 minutes. Then, [1,1'-bis(diphenylphosphino)ferrocene]dichloropalladium (ii), complex with dichloromethane (1.420 g, 1.739 mmol, Strem Chemicals, Inc.) was added. The reaction was then left stirring at 100° C. After 18 h the reaction was cooled down and the solid filtered under vacuum and the washed with DCM. The mother liquor was then concentrated to give a semisolid residue. DCM was added, and the solid formed collected by vacuum filtration. The mother liquor concentrated again, and this step was repeated. The desired methyl 4-amino-3-(4,4,5,5-tetramethyl-1,3,2-dioxaborolan-2-yl)benzoate (2.6 g, 9.38 mmol, 54.0% yield) was isolated as a grey solid. m/z (ESI): 196.1 [M+H]$^+$ (boronic acid). $^1$H NMR (400 MHz, CHLOROFORM-d) δ ppm 8.33 (d, J=2.1 Hz, 1H), 7.90 (dd, J=8.6, 2.2 Hz, 1H), 6.57 (d, J=8.5 Hz, 1H), 5.20 (br s, 2H), 3.87 (s, 3H), 1.37 (s, 12H).

Step 2. To a stirred solution of 4-oxotetrahydrofuran-3-carbonitrile (0.500 g, 4.50 mmol) in dichloromethane (5.00 mL) was added DIPEA (0.943 mL, 5.40 mmol) and the reaction mixture was cooled to −78° C. Then, triflic anhydride (0.760 mL, 4.50 mmol) was added dropwise at −78° C. for 1 min and the reaction mixture stirred at same temperature for 15 min. After completion of reaction, the reaction mixture was diluted with water, the organic layer was separated, washed with brine (2×10 mL), dried over sodium sulfate, and concentrated to give crude 4-cyano-2,5-dihydrofuran-3-yl trifluoromethanesulfonate (1.05 g, 4.32 mmol, 96% yield), which was used in the next step without further purification.

Step 3. To a stirred solution of 4-cyano-2,5-dihydrofuran-3-yl trifluoromethanesulfonate (10 g, 41.1 mmol) in 1,4-dioxane (200 mL) and water (20.00 mL) was added methyl 4-amino-3-(4,4,5,5-tetramethyl-1,3,2-dioxaborolan-2-yl)

benzoate (9.12 g, 32.9 mmol), K$_2$CO$_3$ (17.05 g, 123 mmol), and Pd(PPh$_3$)$_4$ (4.75 g, 4.11 mmol) under nitrogen purging. Then, the reaction mixture heated at 80° C. for 16 h. The reaction mixture was concentrated, then diluted with ethyl acetate (50 mL) and water (50 mL) stirred at room temperature for 30 min. Then, the solid formed was filtered and washed with ethyl acetate (50 mL) and 2% MeOH in DCM (50 mL), then dried under vacuum to give methyl 4-amino-1,3-dihydrofuro[3,4-c]quinoline-8-carboxylate (6.6 g, 27.0 mmol, 65.7% yield) as gray solid. m/z (ESI): 245.3 [M+H]+. $^1$H NMR (400 MHz, TFA-d) 6 ppm 8.59-8.67 (2H, m), 7.97 (1H, d, J=9.3 Hz), 5.94 (2H, t, J=3.5 Hz), 5.65 (2H, t, J=3.4 Hz), 4.24 (3H, s). Note: for some heterocycles Pd(dppf)Cl$_2$ was used in place of Pd(PPh$_3$)$_4$.

Step 4. To a stirred solution of methyl 4-amino-1,3-dihydrofuro[3,4-c]quinoline-8-carboxylate (30 g, 123 mmol) in water (300 mL):tetrahydrofuran (300 mL):methanol (300 mL) was added LiOH (11.77 g, 491 mmol) and the reaction mixture heated at 75° C. for 3 h. The reaction mixture concentrated and then the aqueous layer acidified with 1.5 N HCl up to pH 6.0. The solid obtained was filtered, washed with methanol (300 mL), and dried to give 4-amino-1,3-dihydrofuro[3,4-c]quinoline-8-carboxylic acid (28 g, 122 mmol, 99% yield) as off-white solid. m/z (ESI): 231.2 [M+H]$^+$. $^1$H NMR (400 MHz, DMSO-d) 6 ppm 12.83 (1H, s), 7.88-8.30 (2H, in), 7.59 (1H, d, J=8.8 Hz), 7.02 (2H, s), 5.40 (2H, t, J=3.5 Hz), 5.03 (2H, t, J=3.6 Hz).

Acids in Table 4 were prepared in a manner similar to that described for Intermediate 100.

TABLE 4

| Int. # | Chemical Structure | Name | m/z (ESI): [M + H]$^+$ |
|---|---|---|---|
| 101 | 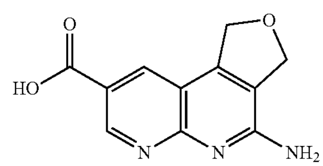 | 4-amino-1,3-dihydrofuro[3,4-c][1,8]naphthyridine-8-carboxylic acid | 232.1 |
| 102 | 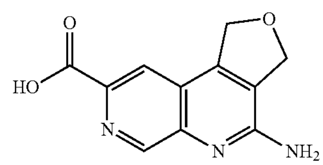 [SMILES: Nc1nc2ncc(C(=O)O)cc2c2c1COC2] | 4-amino-1,3-dihydrofuro[3,4-c][1,7]naphthyridine-8-carboxylic acid | 232.0 |
| 103 | 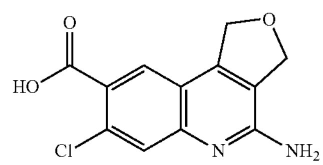 [SMILES: Nc1nc2cc(Cl)c(C(=O)O)cc2c2c1COC2] | 4-amino-7-chloro-1,3-dihydrofuro[3,4-c]quinoline-8-carboxylic acid | 264.9 |
| 104 | 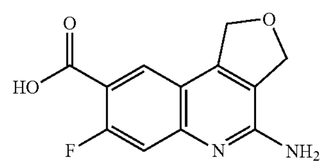 | 4-amino-7-fluoro-1,3-dihydrofuro[3,4-c]quinoline-8-carboxylic acid | 249.0 |
| 105 | 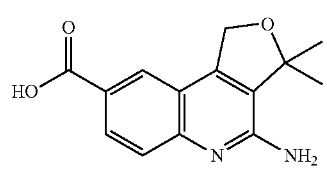 [SMILES: CC1(C)OCc2c1c(N)nc1ccc(C(=O)O)cc21] | 4-amino-3,3-dimethyl-1,3-dihydrofuro[3,4-c]quinoline-8-carboxylic acid | 259.1 |
| 106 | 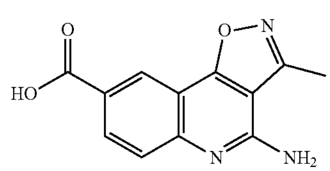 [SMILES: Cc1noc2c1c(N)nc1ccc(C(=O)O)cc12] | 4-amino-3-methylisoxazolo[4,5-c]quinoline-8-carboxylic acid | 244.0 |

TABLE 4-continued

| Int. # | Chemical Structure | Name | m/z (ESI): [M + H]+ |
|---|---|---|---|
| 107 | 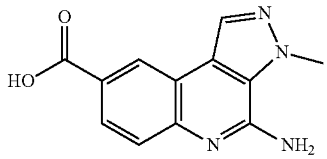 [SMILES: Cn1ncc2c3cc(C(=O)O)ccc3nc(N)c21] | 4-amino-3-methyl-3H-pyrazolo[3,4-c]quinoline-8-carboxylic acid | 243.1 |
| 108 | 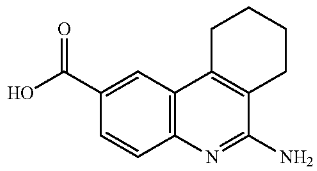 | 6-amino-7,8,9,10-tetrahydrophenanthridine-2-carboxylic acid | 243.2 |
| 109 | 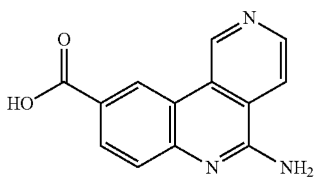 [SMILES: Nc1nc2ccc(C(=O)O)cc2c2cnccc12] | 5-aminobenzo[c][2,6]naphthyridine-9-carboxylic acid | 240.1 |
| 110 | 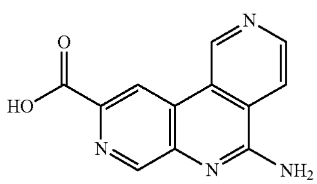 | 5-aminopyrido[4,3-c][1,7]naphthyridine-9-carboxylic acid | 241.1 |
| 111 | 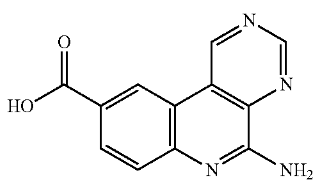 | 5-aminopyrimido[4,5-c]quinoline-9-carboxylic acid | 241.2 |
| 112 | 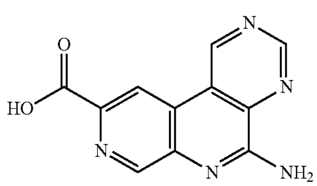 | 5-aminopyrimido[4,5-c][1,7]naphthyridine-9-carboxylic acid | 241.1 |
| 113 | 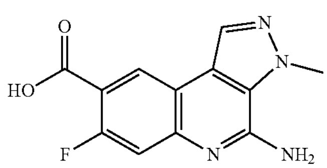 [SMILES: Cn1ncc2c3cc(C(=O)O)c(F)cc3nc(N)c21] | 4-amino-7-fluoro-3-methyl-3H-pyrazolo[3,4-c]quinoline-8-carboxylic acid | 261.1 |
| 114 | 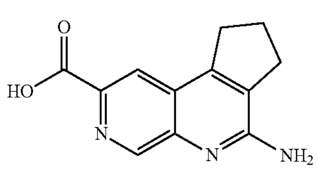 [SMILES: Nc1nc2cnc(C(=O)O)cc2c2c1CCC2] | 6-amino-8,9-dihydro-7H-cyclopenta[c][1,7]naphthyridine-2-carboxylic acid | 230.0 |

TABLE 4-continued

| Int. # | Chemical Structure | Name | m/z (ESI): [M + H]+ |
|---|---|---|---|
| 115 | 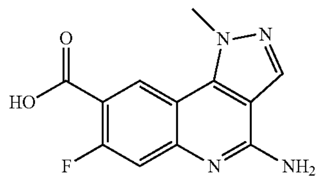 [SMILES: Cn1ncc2c(N)nc3cc(F)c(C(=O)O)cc3c21] | 4-amino-7-fluoro-1-methyl-1H-pyrazolo[4,3-c]quinoline-8-carboxylic acid | 261.0 |
| 116 | 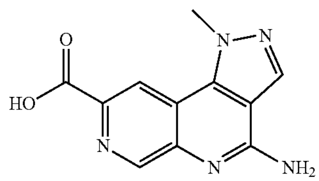 | 4-amino-1-methyl-1H-pyrazolo [4,3-c][1,7]naphthyridine-8-carboxylic acid | 244.0 |
| 117 | 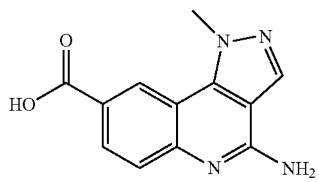 [SMILES: Cn1ncc2c(N)nc3cnc(C(=O)O)cc3c21] | 4-amino-1-methyl-1H-pyrazolo[4,3-c]quinoline-8-carboxylic acid | 243.0 |
| 118 | 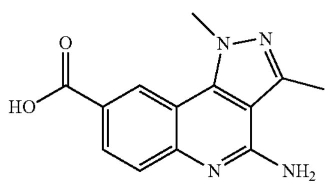 [SMILES: Cc1nn(C)c2c1c(N)nc1ccc(C(=O)O)cc12] | 4-amino-1,3-dimethyl-1H-pyrazolo[4,3-c]quinoline-8-carboxylic acid | 257.0 |
| 119 | 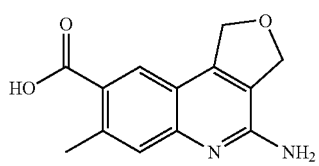 [SMILES: Cc1cc2nc(N)c3c(c2cc1C(=O)O)COC3] | 4-amino-7-methyl-1,3-dihydrofuro[3,4-c]quinoline-8-carboxylic acid | 245.2 |
| 120 | 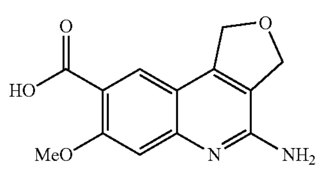 [SMILES: COc1cc2nc(N)c3c(c2cc1C(=O)O)COC3] | 4-amino-7-methoxy-1,3-dihydrofuro[3,4-c]quinoline-8-carboxylic acid | 261.0 |
| 121 | 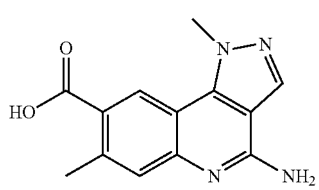 [SMILES: Cc1cc2nc(N)c3cnn(C)c3c2cc1C(=O)O] | 4-amino-1,7-dimethyl-1H-pyrazolo[4,3-c]quinoline-8-carboxylic acid | 257.0 |
| 122 | 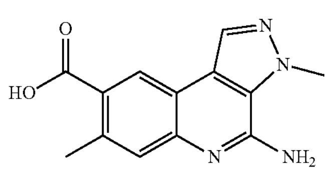 [SMILES: Cc1cc2nc(N)c3c(cnn3C)c2cc1C(=O)O] | 4-amino-3,7-dimethyl-3H-pyrazolo[3,4-c]quinoline-8-carboxylic acid | 257.1 |

TABLE 4-continued

| Int. # | Chemical Structure | Name | m/z (ESI): [M + H]+ |
|---|---|---|---|
| 123 | 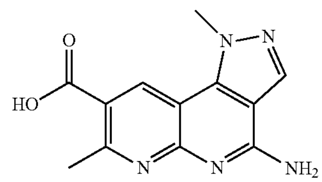 | 4-amino-1,7-dimethyl-1H-pyrazolo[4,3-c][1,8]naphthyridine-8-carboxylic acid | 258.0 |
| 124 | 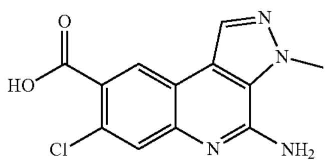 [SMILES: Cn1ncc2c3cc(C(=O)O)c(Cl)cc3nc(N)c21] | 4-amino-7-chloro-3-methyl-3H-pyrazolo[3,4-c]quinoline-8-carboxylic acid | 476.9 |
| 125 | 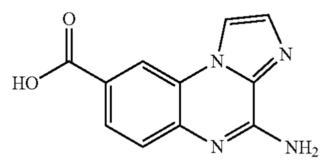 [SMILES: Nc1nc2ccc(C(=O)O)cc2n2ccnc12] | 4-aminoimidazo[1,2-a]quinoxaline-8-carboxylic acid | 228.9 |
| 126 | 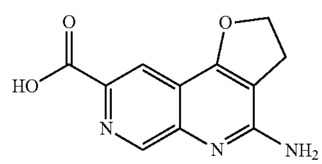 | 4-amino-2,3-dihydrofuro[3,2-c][1,7]naphthyridine-8-carboxylic acid | 232.2 |
| 127 | 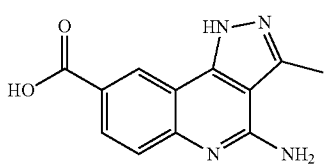 | 4-amino-3-methyl-1H-pyrazolo[4,3-c]quinoline-8-carboxylic acid | 243.1 |
| 128 | 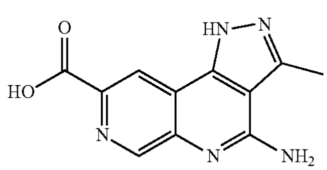 [SMILES: Cc1n[nH]c2c1c(N)nc1cnc(C(=O)O)cc12] | 4-amino-3-methyl-1H-pyrazolo[4,3-c][1,7]naphthyridine-8-carboxylic acid | 258.0 (Me ester) Acid mass not observed |
| 129 | 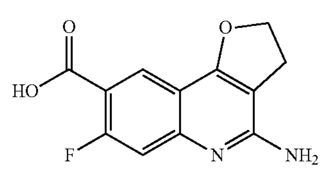 [SMILES: Nc1nc2cc(F)c(C(=O)O)cc2c2c1CCO2] | 4-amino-7-fluoro-2,3-dihydrofuro[3,2-c]quinoline-8-carboxylic acid | 249.1 |
| 130 | 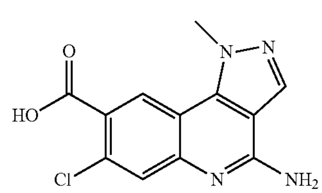 | 4-amino-7-chloro-1-methyl-1H-pyrazolo[4,3-c]quinoline-8-carboxylic acid | 277.0 |

TABLE 4-continued

| Int. # | Chemical Structure | Name | m/z (ESI): [M + H]+ |
|---|---|---|---|
| 131 | 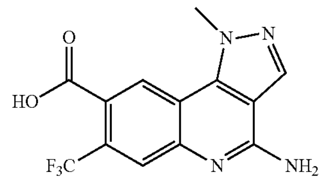 [SMILES: Cn1ncc2c(N)nc3cc(C(F)(F)F)c(C(=O)O)cc3c21] | 4-amino-1-methyl-7-(trifluoromethyl)-1H-pyrazolo[4,3-c]quinoline-8-carboxylic acid | 310.9 |

Intermediate 132: 6-amino-8,9-dihydro-7H-cyclopenta[c][1,8]naphthyridine-2-carboxylic acid Intermediate 132

Step 1. A mixture of methyl 2-oxocyclopentanecarboxylate (1.0 g, 0.877 mL, 7.03 mmol, Matrix Scientific) and 1,1'-dimethyltriethylamine (1.000 g, 1.352 mL, 7.74 mmol, Sigma-Aldrich Corporation) in DCM (15 mL) was cooled to −78° C. and trifluoromethanesulfonic acid anhydride (7.03 mL, 7.03 mmol, Sigma-Aldrich Corporation) was added. After complete addition, the mixture was stirred at −78° C. for 5 min, then the dry ice-bath was removed and stirred at rt. After 15 min, the mixture was concentrated to afford methyl 2-(((trifluoromethyl)sulfonyl)oxy)cyclopent-1-ene-1-carboxylate with quant. yield as a light-yellow solid to be used as is. m/z (ESI): 275 [M+H]+.

Step 2. A mixture of methyl 2-(((trifluoromethyl)sulfonyl)oxy)cyclopent-1-ene-1-carboxylate (1.982 g, 7.23 mmol), (2-amino-5-(methoxycarbonyl)pyridin-3-yl)boronic acid (1.70 g, 8.67 mmol), potassium phosphate, tribasic (3.78 g, 21.69 mmol, Acros) and [1,1'-bis(diphenylphosphino)ferrocene]dichloropalladium(ii), complex with dichloromethane (0.177 g, 0.217 mmol, Strem Chemicals, Inc.) in 1,4-dioxane/water (10/0.60 mL) was heated at 80° C. for 1 h. When the reaction reached completion, it was brought to rt and diluted with EtOAc. A precipitate was formed which corresponded to the desired product. It was filtered and washed with EtOAc to yield methyl 6-oxo-6,7,8,9-tetrahydro-5H-cyclopenta[c][1,8]naphthyridine-2-carboxylate as a light gray solid with quant. yield. m/z (ESI): 245 [M+H]+. 1H NMR (400 MHz, DMSO-d6) δ ppm 11.93-12.58 (m, 1H), 8.96 (d, J=2.1 Hz, 1H), 8.33 (d, J=2.1 Hz, 1H), 3.89 (s, 3H), 3.13 (br t, J=7.6 Hz, 2H), 2.78 (br t, J=7.3 Hz, 2H), 2.08-2.18 (m, 2H).

Step 3. A mixture of methyl 6-oxo-6,7,8,9-tetrahydro-5H-cyclopenta[c][1,8]naphthyridine-2-carboxylate (1.76 g, 7.21 mmol) in POCl3 (24.68 g, 15 mL, 161 mmol, Aldrich) was heated to reflux for 30 min. The reaction went to completion and was carefully added to cold-sat. aq NaHCO3 to basify the reaction. After stirring for 15 min, the mixture was extracted with EtOAc and the combined organics were concentrated to afford methyl 6-chloro-8,9-dihydro-7H-cyclopenta[c][1,8]naphthyridine-2-carboxylate as a yellow solid with quant. yield. m/z (ESI): 263 [M+H]+.

Step 4. To a suspension of methyl 6-chloro-8,9-dihydro-7H-cyclopenta[c][1,8]naphthyridine-2-carboxylate (1.89 g, 7.19 mmol) in DMSO (15 mL) was added DIPEA (2.79 g, 3.77 mL, 21.58 mmol, Aldrich) followed by the addition of (2,4-dimethoxyphenyl)methanamine (1.564 g, 1.405 mL, 9.35 mmol, Aldrich). The resulting mixture was heated at 90° C. overnight. The reaction was cooled to rt, diluted with water, washed with sat. NH₄Cl and extracted with EtOAc. The combined organics were dried over Na₂SO₄, filtered and concentrated to afford methyl 6-((2,4-dimethoxybenzyl)amino)-8,9-dihydro-7H-cyclopenta[c][1,8]naphthyridine-2-carboxylate (2.18 g, 5.54 mmol, 77% yield) as a yellow solid to be used as is. m/z (ESI): 394 [M+H]⁺.

Step 5. To a solution of methyl 6-((2,4-dimethoxybenzyl)amino)-8,9-dihydro-7H-cyclopenta[c][1,8]naphthyridine-2-carboxylate (2.18 g, 5.54 mmol) in THF/MeOH (10/10 mL) was added NaOH (10 mL, 10.00 mmol) and the resulting solution was heated at 70° C. for 2 h. When the reaction reached completion, it was brought to rt and acidified with 10 mL 1M HCl. A light yellow precipitate was formed filtered off and azeotropically dried with toluene to afford 6-((2,4-dimethoxybenzyl)amino)-8,9-dihydro-7H-cyclopenta[c][1,8]naphthyridine-2-carboxylic acid hydrochloride (1.44 g, 3.46 mmol, 62.5% yield) as a yellow solid. m/z (ESI): 380.2 [M+H]⁺.

Intermediate 138: 4-((2,4-dimethoxybenzyl)amino)-1,3-dihydrofuro[3,4-c][1,7]naphthyridine-8-carboxylic acid

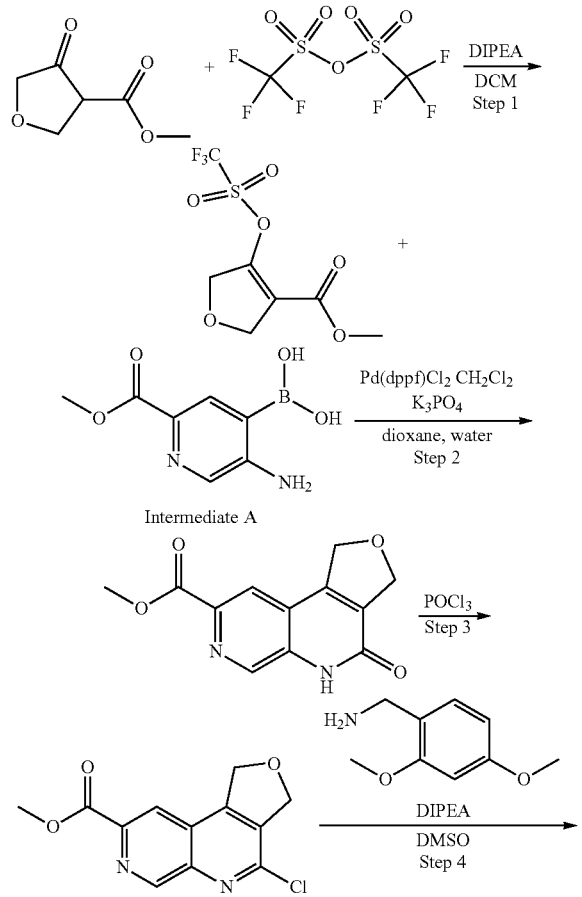

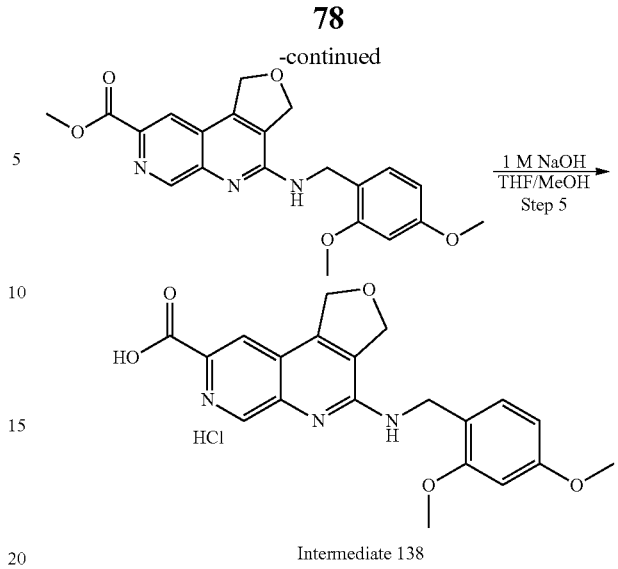

Intermediate 138

Step 1. A mixture of 3-furancarboxylic acid, tetrahydro-4-oxo methyl ester (3.0 g, 3.00 mL, 20.82 mmol, Ambeed, Inc.) and DIPEA (2.96 g, 4.00 mL, 22.90 mmol, Aldrich) in DCM (20 mL) was cooled to −78° C. and trifluoromethanesulfonic anhydride (20.82 mL, 20.82 mmol, Sigma-Aldrich Corporation) was added. After complete addition, the mixture was stirred at −78° C. for 5 min then the dry ice-bath was removed and stirred at rt. After 15 min the LCMS showed desired mass. The mixture was concentrated to afford methyl 4-(((trifluoromethyl)sulfonyl)oxy)-2,5-dihydrofuran-3-carboxylate to be used as is. m/z (ESI): 277 (M+H)⁺.

Step 2. A mixture of methyl 4-(((trifluoromethyl)sulfonyl)oxy)-2,5-dihydrofuran-3-carboxylate (2.349 g, 8.50 mmol), (5-amino-2-(methoxycarbonyl)pyridin-4-yl)boronic acid (2.0 g, 10.21 mmol), potassium phosphate, tribasic (4.44 g, 25.5 mmol, Acros) and [1,1'-bis(diphenylphosphino)ferrocene]dichloropalladium (ii), complex with dichloromethane (0.347 g, 0.425 mmol, Strem Chemicals, Inc.) in 1,4-dioxane/water (20/1.20 mL) was heated at 90° C. for 1 h. Then, it was brought to rt and diluted with EtOAc. A precipitate was formed which corresponded to the desired product. It was filtered and washed with EtOAc. Methyl 4-oxo-1,3,4,5-tetrahydrofuro[3,4-c][1,7]naphthyridine-8-carboxylate was obtained as a gray solid. m/z (ESI): 247 (M+H)⁺. Theoretical yield was considered.

Step 3. A mixture of methyl 4-oxo-1,3,4,5-tetrahydrofuro[3,4-c][1,7]naphthyridine-8-carboxylate (2.0 g, 8.12 mmol) and POCl₃ (32.9 g, 20 mL, 215 mmol, Aldrich) was heated to reflux for 3 h. The reaction was brought to rt and carefully added to cold-sat. NaHCO₃ to basify the reaction. After stirring for 15 min, the mixture was extracted with EtOAc and the combined organics were concentrated to afford methyl 4-chloro-1,3-dihydrofuro[3,4-c][1,7]naphthyridine-8-carboxylate. m/z (ESI): 265 (M+H)⁺. Theoretical yield was considered.

Step 4. To a mixture methyl 4-chloro-1,3-dihydrofuro[3,4-c][1,7]naphthyridine-8-carboxylate (2.15 g, 8.12 mmol) in DMSO (20 mL) was added DIPEA (3.15 g, 4.26 mL, 24.37 mmol, Aldrich) followed by the addition of (2,4-dimethoxyphenyl)methanamine (1.630 g, 1.464 mL, 9.75 mmol, Aldrich). The resulting mixture was heated at 90° C. overnight. The reaction was brought to rt, diluted with water and extracted with EtOAc. The combined organics were chromatographed on silica gel using 0-30% 3:1 EtOAc/EtOH in heptane to afford methyl 4-((2,4-dimethoxybenzyl)amino)-1,3-dihydrofuro[3,4-c][1,7]naphthyridine-8-carboxylate (0.500 g, 1.264 mmol, 15.57% yield) as a brown solid. m/z (ESI): 396 (M+H)+.

Step 5. To a solution of methyl 4-((2,4-dimethoxybenzyl)amino)-1,3-dihydrofuro[3,4-c][1,7]naphthyridine-8-carboxylate (0.500 g, 1.264 mmol) in THF/MeOH (10/10 mL) was added NaOH (5.0 mL, 5.00 mmol, EDM) and the resulting solution was heated at 70° C. for 2 h. Then, the reaction was brought to rt and acidified with 1M HCl (5 mL). The resulting mixture was concentrated and azeotropically dried with toluene to afford 4-((2,4-dimethoxybenzyl)amino)-1,3-dihydrofuro[3,4-c][1,7]naphthyridine-8-carboxylic acid hydrochloride as a brown solid. m/z (ESI): 382 (M+H)+. Theoretical yield was considered.

Acids in Table 5 were prepared in a manner similar to that described for Intermediates 132 and 138.

TABLE 5

| Int. # | Chemical Structure | Name | m/z (ESI): [M + H]+ |
|---|---|---|---|
| 132 | 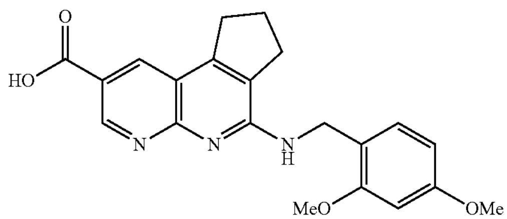 [SMILES: COc1ccc(CNc2nc3ncc(C(=O)O)cc3c3c2CCC3)c(OC)c1] | 6-((2,4-dimethoxybenzyl)amino)-8,9-dihydro-7H-cyclopenta[c][1,8]naphthyridine-2-carboxylic | 380.2 |
| 133 | 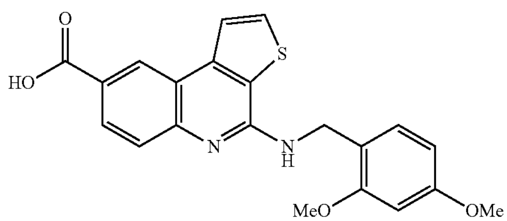 [SMILES: COc1ccc(CNc2nc3ccc(C(=O)O)cc3c3ccsc23)c(OC)c1] | 4-((2,4-dimethoxybenzyl)amino)thieno[2,3-c]quinoline-8-carboxylic acid | 395.0 |
| 134 | 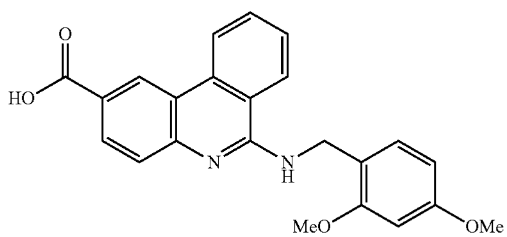 [SMILES: COc1ccc(CNc2nc3ccc(C(=O)O)cc3c3ccccc23)c(OC)c1] | 6-((2,4-dimethoxybenzyl)amino)phenanthridine-2-carboxylic acid | 389.2 |
| 135 | 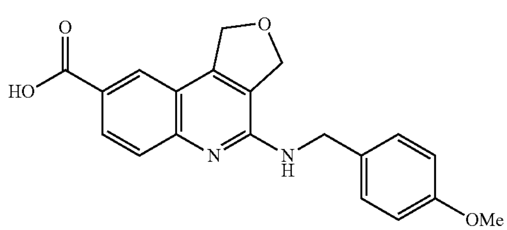 [SMILES: COc1ccc(CNc2nc3ccc(C(=O)O)cc3c3c2COC3)cc1] | 4-((4-methoxybenzyl)amino)-1,3-dihydrofuro[3,4-c]quinoline-8-carboxylic acid | 351.0 |
| 136 | 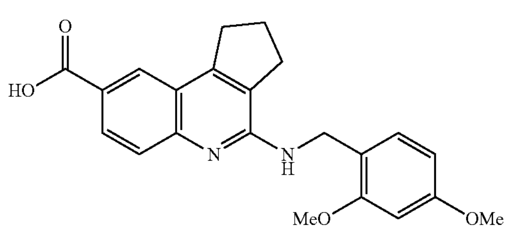 [SMILES: COc1ccc(CNc2nc3ccc(C(=O)O)cc3c3c2CCC3)c(OC)c1] | 4-((2,4-dimethoxybenzyl)amino)-2,3-dihydro-1H-cyclopenta[c]quinoline-8-carboxylic acid | 379.2 |

TABLE 5-continued

| Int. # | Chemical Structure | Name | m/z (ESI): [M + H]+ |
|---|---|---|---|
| 137 | 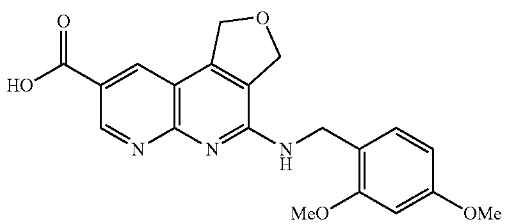 [SMILES: COc1ccc(CNc2nc3ncc(C(=O)O)cc3c3c2COC3)c(OC)c1] | 4-((2,4-dimethoxybenzyl)amino)-1,3-dihydrofuro[3,4-c][1,8]naphthyridine-8-carboxylic acid | 382.2 |
| 139 | 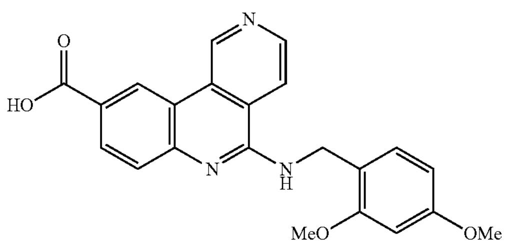 [SMILES: COc1ccc(CNc2nc3ccc(C(=O)O)cc3c3cnccc23)c(OC)c1] | 5-((2,4-dimethoxybenzyl)amino)benzo[c][2,6]naphthyridine-9-carboxylic acid | 390.2 |
| 140 | 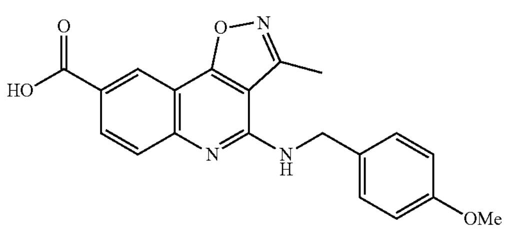 [SMILES: COc1ccc(CNc2nc3ccc(C(=O)O)cc3c3onc(C)c23)cc1] | 4-((4-methoxybenzyl)amino)-3-methylisoxazolo[4,5-c]quinoline-8-carboxylic acid | 364.1 |
| 141 | 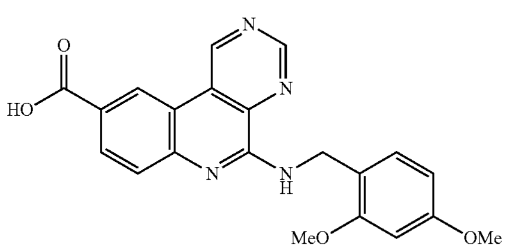 [SMILES: COc1ccc(CNc2nc3ccc(C(=O)O)cc3c3cncnc23)c(OC)c1] | 5-((2,4-dimethoxybenzyl)amino)pyrimido[4,5-c]quinoline-9-carboxylic acid | 391.2 |
| 142 | 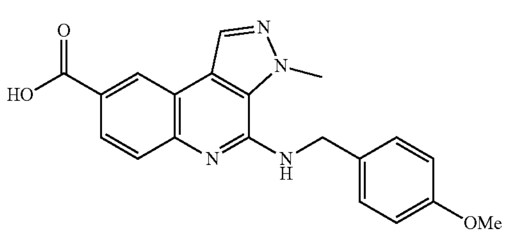 [SMILES: COc1ccc(CNc2nc3ccc(C(=O)O)cc3c3cnn(C)c23)cc1] | 4-((4-methoxybenzyl)amino)-3-methyl-3H-pyrazolo[3,4-c]quinoline-8-carboxylic acid | 363.0 |
| 143 | 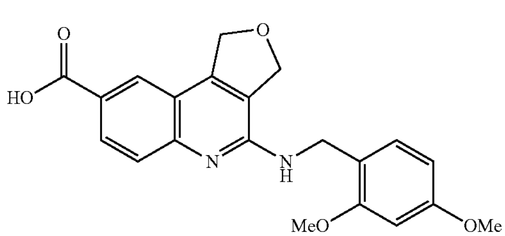 [SMILES: COc1ccc(CNc2nc3ccc(C(=O)O)cc3c3c2COC3)c(OC)c1] | 4-((2,4-dimethoxybenzyl)amino)-1,3-dihydrofuro[3,4-c]quinoline-8-carboxylic acid | 381.1 |

TABLE 5-continued

| Int. # | Chemical Structure | Name | m/z (ESI): [M + H]+ |
|---|---|---|---|
| 144 | 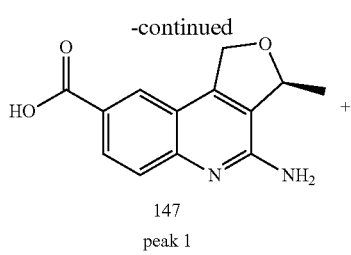 | 4-((4-methoxybenzyl)amino)-2,3-dihydrofuro[3,2-c]quinoline-8-carboxylic acid | 351.2 |
| 145 | 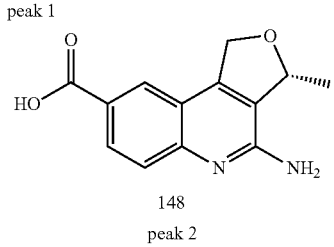 | 5-((4-methoxybenzyl)amino)-1,4-dihydro-2H-pyrano[3,4-c]quinoline-9-carboxylic acid | 365.1 |

Intermediate 146: 4-amino-3-methyl-1,3-dihydro-furo[3,4-c]quinoline-8-carboxylic acid

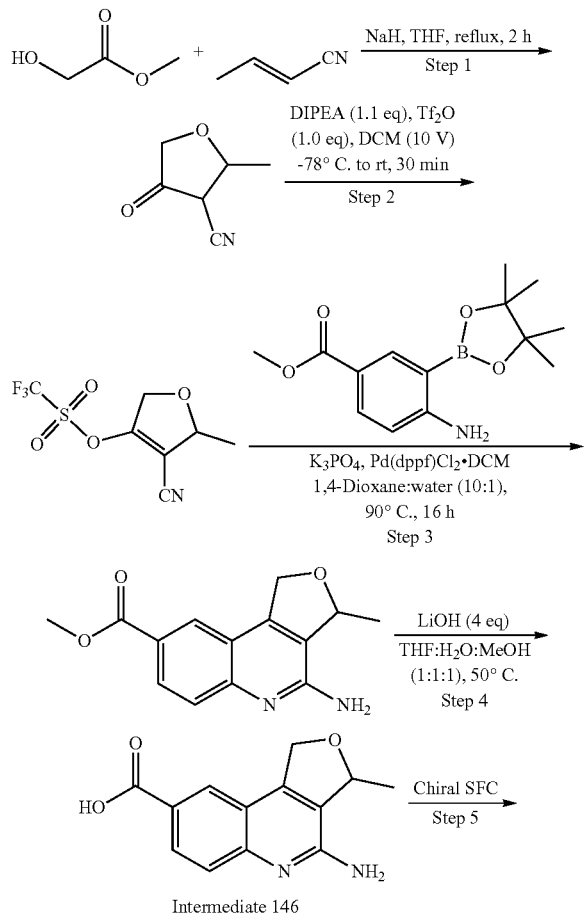

Intermediate 146

147 peak 1

148 peak 2

Note: Stereochemistry is arbitrarily assigned

Step 1: To a suspension of sodium hydride (11.10 g, 278 mmol 0.5 equiv., 60% in mineral oil) in anhydrous tetrahydrofuran (250 mL) was added methyl 2-hydroxyacetate (42.4 mL, 555 mmol, 1.0 equiv) at room temperature under $N_2$ atmosphere. To the reaction mixture (E)-but-2-enenitrile (54.5 mL, 666 mmol, 1.0 equiv) was added slowly at 65° C. and stirred for 2 h at same temperature. The reaction mixture was cooled and quenched with 2N NaOH solution (250 mL) and extracted with diethyl ether (500 mL). The aqueous layer was acidified with conc. HCl to adjust the pH to ~1 and extracted with dichloromethane (2×500 mL). The combined organic layer was washed with brine (200 mL) and dried over sodium sulfate, filtered and concentrated under reduced pressure. The crude residue was purified by column chromatography over silica gel (230-400 mesh) using 10% ethyl acetate with hexanes as an eluent to give 2-methyl-4-oxotetrahydrofuran-3-carbonitrile (22 g, 176 mmol, 32% yield) as a brown solid. Product's $R_f$: 0.3 (50% Ethyl acetate in hexanes) m/z (ESI, Negative): 124.3 [M-1]. $^1$H NMR (400 MHz, Chloroform-d): δ ppm 4.40-4.27 (m, 2H), 4.26-4.19 (m, 1H), 3.24-2.99 (m, 1H), 1.61 (dd, J=18.6, 6.2 Hz, 3H).

Step 2: To a stirred solution of 2-methyl-4-oxotetrahydrofuran-3-carbonitrile (25.0 g, 200 mmol, 1.0 equiv) in dichloromethane (500 mL) was added DIPEA (69.8 mL, 400 mmol, 2.0 equiv) and triflic anhydride (47.1 mL, 280 mmol, 1.4 equiv) at −78° C. and stirred at same temperature for 15 min. The reaction mixture was quenched with slow addition of water (250 mL) and after attaining the room temperature was extracted with dichloromethane (2×500 mL). The combined organic layer was dried over sodium sulfate, filtered and concentrated under reduced pressure. The crude residue was stirred in diethyl ether and filtered. The mother liquor was concentrated under reduced pressure to give 4-cyano-5-methyl-2,5-dihydrofuran-3-yl trifluoromethanesulfonate (35.0 g, crude) as a light brown adduct. The crude material was used for next step without further purification. Product's $R_f$: 0.5 (40% Ethyl acetate in hexanes). m/z: 257.1 [Not ionized].

Step 3: To a stirred solution of 4-cyano-5-methyl-2,5-dihydrofuran-3-yl trifluoromethanesulfonate (35 g, 136 mmol, 1.0 equiv) in 1,4-dioxane (1400 mL) and water (70.0 mL), was added methyl 4-amino-3-(4,4,5,5-tetramethyl-1,3,2-dioxaborolan-2-yl)benzoate (37.7 g, 136 mmol, 1.0 equiv) and potassium phosphate tribasic (87 g, 408 mmol, 3.0 equiv) under nitrogen atmosphere. The reaction mixture was degassed with nitrogen for 15 min and then $PdCl_2(dppf)$-DCM adduct (9.96 g, 13.61 mmol, 0.1 equiv) was added and the reaction mixture was heated at 90° C. for 16 h. LCMS indicated completion of the reaction. The reaction mass was concentrated under reduced pressure to get crude product. The crude residue was purified by column chromatography over silica gel (60-120 mesh) using 50% ethyl acetate with hexanes as an eluent to give methyl 4-amino-3-methyl-1,3-dihydrofuro[3,4-c]quinoline-8-carboxylate (25 g, 97 mmol, 71% yield) as a brown solid. Product $R_f$: 0.3 (100% Ethyl acetate). m/z: 259.2 [M+H]$^1$H NMR (400 MHz, DMSO-$d_6$): δ 8.11 (d, J=2.0 Hz, 1H), 8.00 (dd, J=8.8, 2.0 Hz, 1H), 7.58 (d, J=8.8 Hz, 1H), 6.87 (s, 2H), 4.11 (q, J=5.3 Hz, 1H), 3.87 (s, 2H), 3.17 (d, J=5.3 Hz, 3H), 1.41 (d, J=5.9 Hz, 3H).

Step 4: To a stirred solution of methyl 4-amino-3-methyl-1,3-dihydrofuro[3,4-c]quinoline-8-carboxylate (26.0 g, 101 mmol, 1.0 equiv) in tetrahydrofuran (130 mL), methanol (78 mL) and water (52 mL), was added lithium hydroxide (9.64 g, 403 mmol, 4.0 equiv) and stirred at 75° C. for 4 h. LCMS indicated completion of the reaction. The reaction mixture was concentrated under reduced pressure. The crude residue was dissolved in water (100 mL) and filtered to removed insoluble particles. The aqueous layer was acidified with con. HCl (pH 6 to 6.5). The precipitated solid was filtered, washed with water and dried under vacuum to get compound 146 (17.5 g, 71.6 mmol, 71% yield) as an off-white solid. Product $R_f$: 0.1 (100% Ethyl acetate). m/z: 245.1 [M+H]$^+$ $^1$H NMR (TFA, 400 MHz): δ (ppm) 8.68 (t, J=6.2 Hz, 2H), 8.01 (dd, J=9.1, 4.2 Hz, 1H), 6.15 (s, 1H), 5.94 (m, 2H), 1.86 (t, J=5.4 Hz, 3H)

Step 5: Chiral SFC separation: 44.5 g of racemic 4-amino-3-methyl-1,3-dihydrofuro[3,4-c]quinoline-8-carboxylic acid was separated by chiral SFC to get 14 g of each isomer. Stereochemistry is assigned arbitrarily.

Separation Information:

| Key | | Value |
|---|---|---|
| 1 | Instrument | SFC 200 |
| 2 | Column | ChiralPak-IC(250 × 30 mm, 5μ) |
| 3 | Mobile Phase | Liquid $CO_2$: 0.5% DEA in Methanol (40:60) |
| 4 | Flow rate | 100 mL/min |
| 5 | Pressure Drop | 130 bar |
| 6 | BPR | 100 bar |
| 7 | UV Detector Wavelength | 210 nm |
| 8 | Dissolution | 14.0 g dissolved in 280 mL of 2% of DEA in Methanol |
| 9 | Test Injections | 2.5, 1.5, 1.8 mL |
| 10 | Processing | NA |
| 11 | Injection Volume | 2.0 mL |
| 12 | Cycle time | 4.14 min |

Acids in Table 6 were prepared in a manner similar to that described for Intermediate 146.

TABLE 6

| Acids | | SFC Conditions | m/z (ESI): [M + H]$^+$ |
|---|---|---|---|
| 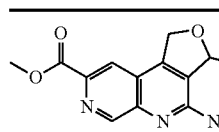<br>Intermediate 149 | 1. SFC<br>2. LiOH → 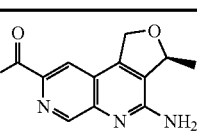<br>peak 1 | Chiralpak IG-3 column, (50 × 4.6 mm I.D., 3 um) Liquid $CO_2$: MeOH (0.05% isopropylamine, v/v); 95:5→1:1; 3 min gradient | 246.0 |
| | 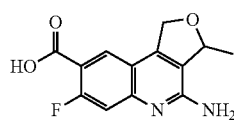<br>peak 2 | | |
| 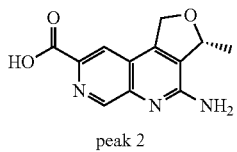 [SMILES: C[C@H]1OCc2c1c(N)nc1cnc(C(=O)O)cc21]<br>Intermediate 150 | SFC → peak 1 | SFC CHIRALPAK IG column (250 × 50 mm, 10 μm) with a mobile phase of 75% Liquid $CO_2$ and 25% MeOH with 0.3% $NH_4OH$ using a flowrate of 200 mL/min. | 263.1 |

Intermediate 151: 4-amino-3-((benzyloxy)methyl)-1,3-dihydrofuro[3,4-c]quinoline-8-carboxylic acid

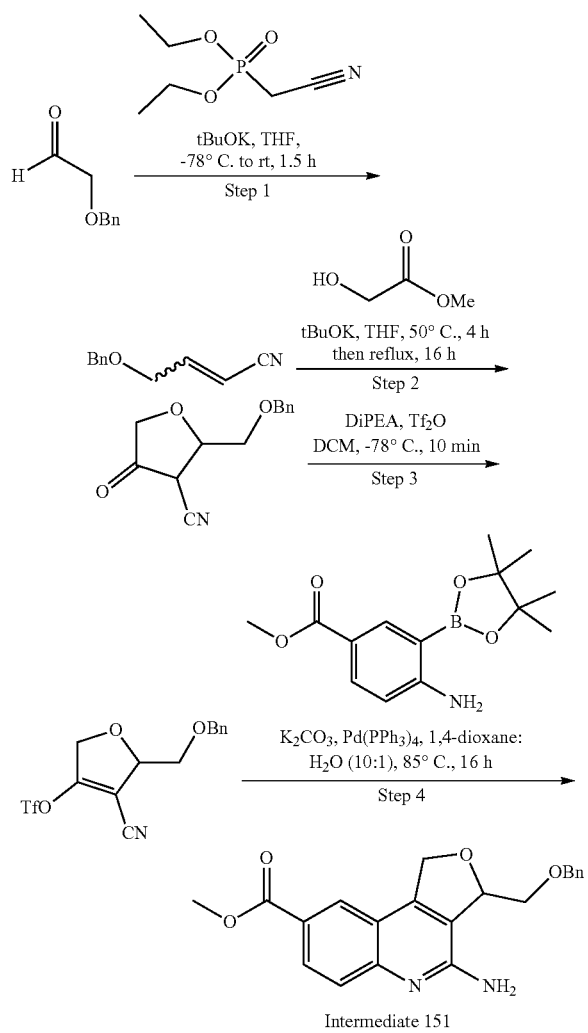

Intermediate 151

Step 1: To a stirred solution of diethyl (cyanomethyl) phosphonate (130 g, 732 mmol, 1.1 equiv) in tetrahydrofuran (2000 mL) was added potassium tert-butoxide (1M solution in THF; 732 mL, 732 mmol, 1.1 equiv) at −78° C. and stirred for 30 min. To the reaction mixture, 2-(benzyloxy)acetaldehyde (100 g, 666 mmol, 1.0 equiv) was added at −78° C. and allowed the mixture to warm to rt over 1 h. After completion, the reaction mixture was quenched with saturated NH$_4$Cl solution (1500 mL) and extracted with ethyl acetate (2×3000 mL). The combined organic layers were washed with brine solution (1000 mL) and dried over anhydrous Na$_2$SO$_4$, filtered and concentrated under vacuum. The crude residue was purified by column chromatography over silica gel (60-120 mesh) using 15% ethyl acetate with pet ether as eluent to give 4-(benzyloxy)but-2-enenitrile (100.6 g, 87% yield) as a colorless oil. Product's R$_f$: 0.5 (30% Ethyl acetate in hexanes). m/z: 174.1 [M+H]$^+$. $^1$H NMR (Chloroform-d, 400 MHz): δ (ppm) 7.47-7.32 (m, 5H), 6.80-6.62 (m, 1H), 5.77-5.72 (m, 1H), 4.59 (d, J=2.8 Hz, 2H), 4.18-4.16 (m, 2H). Proton NMR showed mixture of isomers.

Step 2: To a stirred solution of potassium tert-butoxide (1M solution in THF; 289.0 mL, 289 mmol, 1.0 equiv) in tetrahydrofuran (260 mL) was added methyl 2-hydroxyacetate (22.03 mL, 289 mmol, 1.0 equiv) at RT and heated to 50° C. under nitrogen atmosphere. To this, 4-(benzyloxy)but-2-enenitrile (50.0 g, 289 mmol, 1.0 equiv) was added and stirred at same temperature for 4 h. Reaction monitored by TLC. Reaction temperature was increased up to 70° C. and stirred for 16 h. After completion, the reaction mixture was cooled to 0° C. and quenched with ice water (500 mL). The resultant solution was washed with diethyl ether (2×200 mL) and then acidified with conc. HCl (until pH of ~1-2) and then extracted with DCM (2×500 mL). The combined organic layers were dried over anhydrous Na$_2$SO$_4$, filtered and concentrated under vacuum. The crude residue was purified by column chromatography over silica gel (60-120 mesh) using 26% ethyl acetate with pet ether as an eluent to give 2-((benzyloxy)methyl)-4-oxotetrahydrofuran-3-carbonitrile (9.2 g, 14% yield) as a colorless oil. Product's R$_f$: 0.2 (80% Ethyl acetate in hexanes). LCMS (ESI, Positive) m/z: 232.0 [M+H]$^+$. $^1$H NMR (400 MHz, Chloroform-d) δ 7.41-7.28 (m, 5H), 4.83-4.60 (m, 2H), 4.52 (dd, J=11.8, 6.6 Hz, 1H), 4.33 (dd, J=17.0, 9.0 Hz, 1H), 4.11-3.89 (m, 2H), 3.82-3.68 (m, 2H).

Step 3: To a stirred solution of 2-((benzyloxy)methyl)-4-oxotetrahydrofuran-3-carbonitrile (5.8 g, 25.08 mmol, 1.0 equiv) in dichloromethane (116 mL) were added Triflic anhydride (6.75 mL, 40.1 mmol, 1.6 equiv) and DIPEA (8.76 mL, 50.2 mmol, 2.0 equiv) at −78° C. under N$_2$ atmosphere and stirred for 10 min. The reaction mixture was quenched with water (50 mL) and extracted with dichloromethane (2×200 mL). The combined organic layers were washed with brine solution (100 mL) and dried over anhydrous Na$_2$SO$_4$, filtered and concentrated under reduced pressure. The crude residue was washed with diethyl ether (200 mL) and filtered. The organic layer was concentrated under reduced pressure to give 5-((benzyloxy)methyl)-4-cyano-2,5-dihydrofuran-3-yl trifluoromethane sulfonate (7.65 g) as a light brown liquid, which was taken as such for next step. Product's R$_f$: 0.4 (40% Ethyl acetate in hexanes).

Step 4: To a stirred solution of 5-((benzyloxy)methyl)-4-cyano-2,5-dihydrofuran-3-yl trifluoromethane sulfonate (7.65 g, 20.93 mmol, 1.0 equiv) in 1,4-dioxane (232 mL) and water (11.60 mL) were added methyl 4-amino-3-(4,4,5,5-tetramethyl-1,3,2-dioxaborolan-2-yl)benzoate (5.8 g, 20.93 mmol, 1.0 equiv), potassium carbonate (8.68 g, 62.8 mmol, 3.0 equiv) at room temperature. Reaction mixture was purged with $N_2$ gas for 15 min and then added $Pd(PPh_3)_4$ (1.209 g, 1.046 mmol, 0.05 equiv). The reaction mixture was heated at 80° C. for 16 h. After completion, the reaction mixture was concentrated under reduced pressure and the crude residue was purified by column chromatography over silica gel (60-120 mesh) using 80% ethyl acetate with pet ether as eluent to give 4-amino-3-((benzyloxy)methyl)-1,3-dihydrofuro[3,4-c]quinoline-8-carboxylate (4.4 g, 58% yield) as an off white solid. Product's $R_f$: 0.2 (100% Ethyl acetate in hexanes). LCMS (ESI, Positive/negative ion) m/z: 365.2 $[M+H]^+$. $^1H$ NMR (400 MHz, DMSO-$d_6$) δ 8.12 (d, J=2.0 Hz, 1H), 8.01 (dd, J=8.9, 2.0 Hz, 1H), 7.59 (d, J=8.8 Hz, 1H), 7.34-7.20 (m, 5H), 6.91 (br s, 2H), 5.49 (dq, J=5.6, 3.6, 2.7 Hz, 1H), 5.44-5.32 (m, 2H), 4.56-4.44 (m, 2H), 3.90-3.73 (m, 5H).

Ester 151 was treated with LiOH in THF (similar to Step 4 to intermediate 146) and the lithium salt of 151 was used crude in amide coupling reactions.

Intermediate 152: 4-aminoimidazo[1,2-a]quinoxaline-8-carboxylic acid

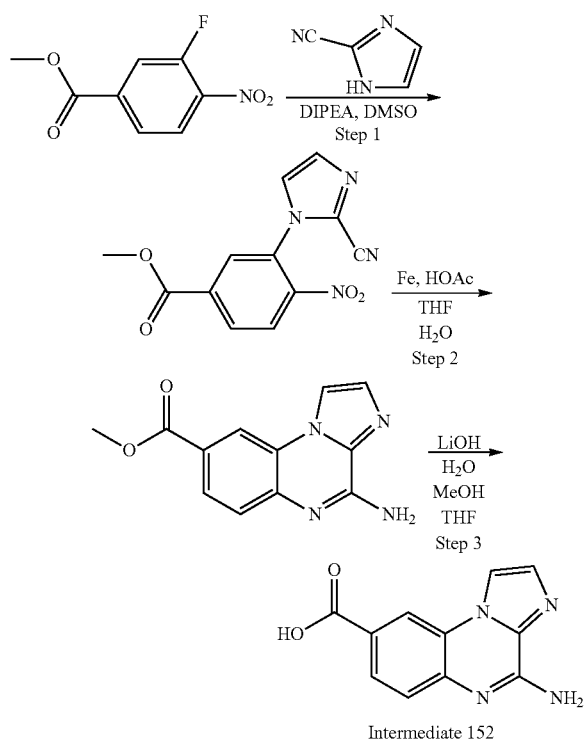

Step 1: To a stirred suspension of methyl 3-fluoro-4-nitrobenzoate (1.07 g, 5.37 mmol, 1.00 equiv) and 1H-imidazole-2-carbonitrile (0.500 g, 5.37 mmol, 1.0 equiv) in dimethyl sulfoxide (5.00 mL) was added DIPEA (2.35 mL, 13.43 mmol, 2.5 equiv.) at room temperature and the reaction mixture was stirred 16 hours. The reaction mixture was then concentrated under reduced pressure to obtain crude material that was diluted with EtOAc and washed with water. The layers were separated and organic layer was dried over anhydrous $Na_2SO_4$ and concentrated under reduced pressure. The residue was purified by medium pressure chromatography (silica, 35% EtOAc in heptanes, to obtain methyl 3-(2-cyano-1H-imidazol-1-yl)-4-nitrobenzoate (1.20 g, 4.41 mmol, 82% yield) as a pale brown solid. m/z: 273.1 $[M+H]^+$.

Step 2: To a stirred solution of methyl 3-(2-cyano-1H-imidazol-1-yl)-4-nitrobenzoate (0.900 g, 3.31 mmol, 1.0 equiv) in tetrahydrofuran (10.0 mL) and water (2.00 mL) was added acetic acid (0.946 mL, 16.53 mmol, 5.0 equiv.) and iron powder (1.85 g, 33.1 mmol, 10.0 equiv) at room temperature. The reaction mixture was stirred for 16 hours. The reaction mixture was then diluted with EtOAc and washed with satd. aq $NaHCO_3$ solution. The organic layer was then concentrated and then the residue was recrystallized using EtOAc to obtain methyl 4-aminoimidazo[1,2-a]quinoxaline-8-carboxylate (350 mg, 1.45 mmol, 44% yield) as pale yellow solid. m/z: 243.1 $[M+H]^+$.

Step 3: To a suspension of methyl 4-aminoimidazo[1,2-a]quinoxaline-8-carboxylate (0.650 g, 2.68 mmol, 1.0 equiv) in a mixture of tetrahydrofuran (12.0 mL), methanol (4.00 mL) and water (4.00 mL), was added lithium hydroxide monohydride (0.450 g, 10.7 mmol, 4.0 equiv) at 0° C. The reaction mixture was then heated to 60° C. for two hours. The reaction mixture was concentrated under reduced pressure to the crude product, which was diluted with water and acidified to pH=6 by 1.50 N HCl solution. An off white solid was formed as a precipitate and filtered and washed with diethyl ether to obtain 4-aminoimidazo[1,2-a]quinoxaline-8-carboxylic acid (480 mg, 2.10 mmol, 78% yield) as off-white solid. m/z: 228.9 $[M+H]^+$.

Intermediate 153: 4-amino-3-methyl-1H-pyrazolo[4,3-c]quinoline-8-carboxylic acid

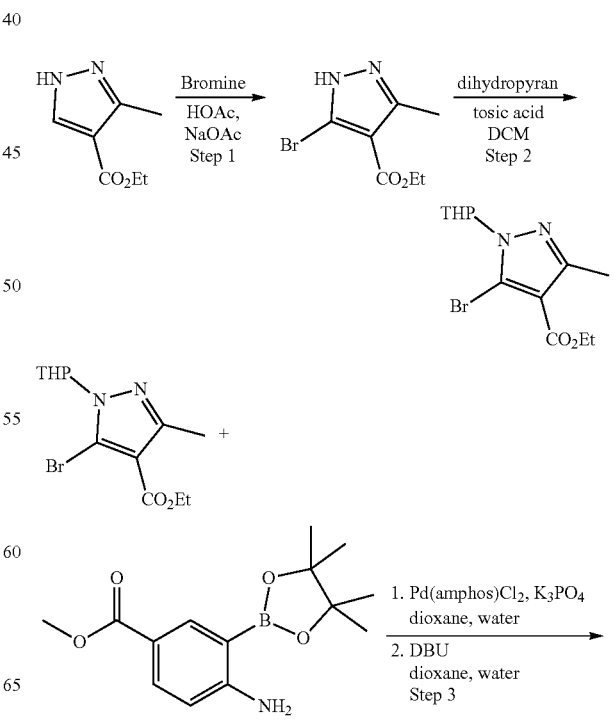

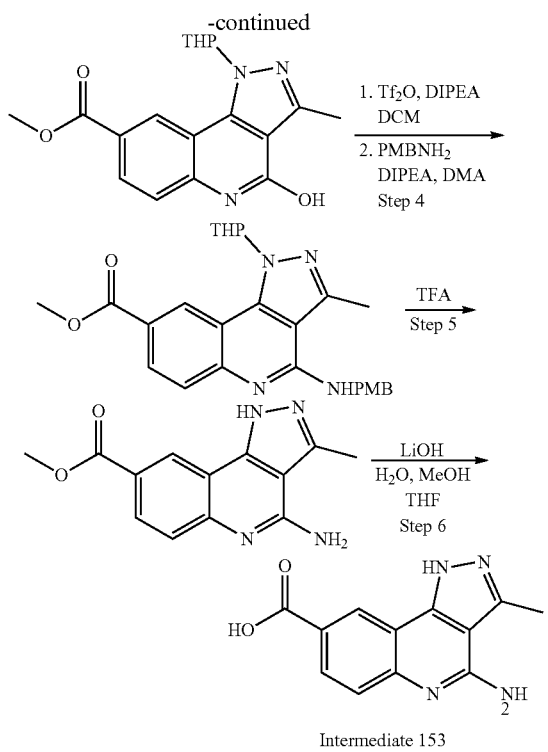

Intermediate 153

Step 1: To the solution of ethyl 5-methyl-1H-pyrazole-4-carboxylate (5.00 g, 32.4 mmol, 1.0 equiv, Combi-Blocks) in acetic acid (100 mL) was added bromine (5.01 mL, 97.0 mmol, 3.0 equiv) and sodium acetate (10.6 g, 130 mmol, 4.0 equiv.) at rt. Then the reaction mixture was stirred and heated for 16 h. The reaction was slowly quenched with sodium bicarbonate and extracted with ethyl acetate. The organic layer was dried over sodium sulphate and concentrated under reduced pressure to get pure crude ethyl 3-bromo-5-methyl-1H-pyrazole-4-carboxylate (4.80 g, 20.6 mmol, 63.5% yield). m/z: 230.8, 232.9 [M+H]$^+$.

Step 2: To a stirred solution of ethyl 3-bromo-5-methyl-1H-pyrazole-4-carboxylate (4.80 g, 20.6 mmol, 1.0 equiv) in dichloromethane (15 mL) was added DHP (2.26 mL, 24.7 mmol, 1.2 equiv) and tosic acid (0.78 g, 4.12 mmol, 0.2 equiv) at 0° C. The resulting reaction mixture was stirred for 16 h to completion. The reaction was quenched with water (20 mL) and extracted with ethyl acetate (20 mL×3). The combined organic layer was washed with brine solution, dried over anhydrous sodium sulphate and concentrated to get crude material. The crude material was purified by chromatography (silica, 40% Ethyl acetate in hexane) to obtain ethyl 3-bromo-5-methyl-1-(tetrahydro-2H-pyran-2-yl)-1H-pyrazole-4-carboxylate (4.80 g, 15.1 mmol, 73.5% yield) as colorless sticky liquid. m/z: 314.9, 317.0 [M+H]$^+$.

Step 3: To a stirred solution of methyl 4-amino-3-(4,4,5,5-tetramethyl-1,3,2-dioxaborolan-2-yl)benzoate (7.34 g, 26.5 mmol, 1.2 equiv, LabNetwork) in 1,4-dioxane (112 mL) and water (28.0 mL) was added ethyl 3-bromo-5-methyl-1-(tetrahydro-2H-pyran-2-yl)-1H-pyrazole-4-carboxylate (7.00 g, 22.1 mmol, 1.0 equiv), potassium phosphate, tribasic (9.36 g, 44.1 mmol, 2.0 equiv) under nitrogen purging for 10 min at room temperature. Then Pd(amphos) Cl$_2$ adduct (0.781 g, 1.10 mmol, 0.05 equiv) was added and the reaction mixture was heated at 90° C. for 16 h. The reaction mixture was quenched with water and extracted with ethyl acetate. The organic layer was dried over by sodium sulphate and concentrated under reduced pressure to get 7.00 grams of the crude ethyl 5-(2-amino-5-(methoxycarbonyl)phenyl)-3-methyl-1-(tetrahydro-2H-pyran-2-yl)-1H-pyrazole-4-carboxylate.

To a stirred solution of ethyl 5-(2-amino-5-(methoxycarbonyl)phenyl)-3-methyl-1-(tetrahydro-2H-pyran-2-yl)-1H-pyrazole-4-carboxylate (600 mg, 1.55 mmol, 1.0 equiv) in 1,4-dioxane (9.60 mL) and water (2.40 mL) was added DBU (2.00 mL, 13.3 mmol, 12 equiv) under nitrogen at room temperature and the reaction mixture heated to 90° C. for 16 h. The reaction mixture was quenched with water and extracted with ethyl acetate. The organic layer was dried over by sodium sulphate and concentrated under reduced pressure to get the crude material, which was purified by column chromatography (silica, 5% MeOH in DCM) to yield pure methyl 4-hydroxy-3-methyl-1-(tetrahydro-2H-pyran-2-yl)-1H-pyrazolo[4,3-c]quinoline-8-carboxylate (220 mg, 0.644 mmol, 41.6% yield). m/z: 258.0 [M-THP+H]$^+$ Step 4: To a stirred solution of methyl 4-hydroxy-3-methyl-1-(tetrahydro-2H-pyran-2-yl)-1H-pyrazolo[4,3-c]quinoline-8-carboxylate (600 mg, 1.76 mmol, 1.0 equiv) in dichloromethane (3.00 mL). Then trifluoromethanesulfonic anhydride (992 mg, 3.52 mmol, 2.0 equiv) and DIPEA (921 μL, 5.27 mmol, 3.0 equiv) was added and the reaction mixture kept between 30-32° C. for 16 h. The reaction mixture was concentrated under reduced pressure to get 300 mg (31% crude yield) of crude methyl 3-methyl-1-(tetrahydro-2H-pyran-2-yl)-4-(((trifluoromethyl)sulfonyl)oxy)-1H-pyrazolo[4,3-c]quinoline-8-carboxylate.

To a stirred solution of this crude methyl 3-methyl-1-(tetrahydro-2H-pyran-2-yl)-4-(((trifluoromethyl)sulfonyl)oxy)-1H-pyrazolo[4,3-c]quinoline-8-carboxylate (300 mg, 0.634 mmol, 1.0 equiv) in N,N-dimethylacetamide (2.00 mL) was added DIPEA (332 μL, 1.90 mmol, 3.0 equiv). Then (4-methoxyphenyl)methanamine (130 mg, 0.950 mmol, 1.5 equiv) was added and the reaction mixture heated at 90° C. for 4 h. The reaction mixture was quenched with water and extracted with ethyl acetate. The organic layer was dried over by sodium sulphate and concentrated under reduced pressure to get crude material which was purified by column chromatography (silica, 50% EtOAc:hexane) to get pure methyl 4-((4-methoxybenzyl)amino)-3-methyl-1-(tetrahydro-2H-pyran-2-yl)-1H-pyrazolo[4,3-c]quinoline-8-carboxylate (250 mg, 0.543 mmol, 86.0% yield). m/z: 377.1 [M-THP+H]$^+$ Step 5: A solution of methyl 4-((4-methoxybenzyl)amino)-3-methyl-1-(tetrahydro-2H-pyran-2-yl)-1H-pyrazolo[4,3-c]quinoline-8-carboxylate (2.80 g, 6.08 mmol, 1.0 equiv) in trifluoroacetic acid (28.0 mL) was heated at 90° C. for 12 h. The reaction mixture was concentrated under reduced pressure to get crude methyl 4-amino-3-methyl-1H-pyrazolo[4,3-c]quinoline-8-carboxylate (3.50 g, 13.7 mmol, 225% crude yield). m/z: 257.3 [M+H]$^+$.

Step 6: To a stirred solution of methyl 4-amino-3-methyl-1H-pyrazolo[4,3-c]quinoline-8-carboxylate (3.50 g, 13.7 mmol, 1.0 equiv) in tetrahydrofuran (35.0 mL), methanol (35.0 mL), water (35.0 mL) at room temperature. Then lithium hydroxide monohydrate (4.02 g, 96.0 mmol, 7.0 equiv) was added and the reaction mixture was stirred at rt for 16 h. The reaction mixture was quenched with water and a solid precipitate was observed. The solid was filtered and dried under vacuum. This solid was washed with diethyl ether and dried to obtain 4-amino-3-methyl-1H-pyrazolo[4,3-c]quinoline-8-carboxylic acid (1.40 g, 5.78 mmol, 42.3% yield). m/z: 243.1 [M+H]$^+$.

Intermediate 154: Lithium 4-amino-1-methyl-7-(trifluoromethyl)-1H-pyrazolo[4,3-c]quinoline-8-carboxylate hydroxide

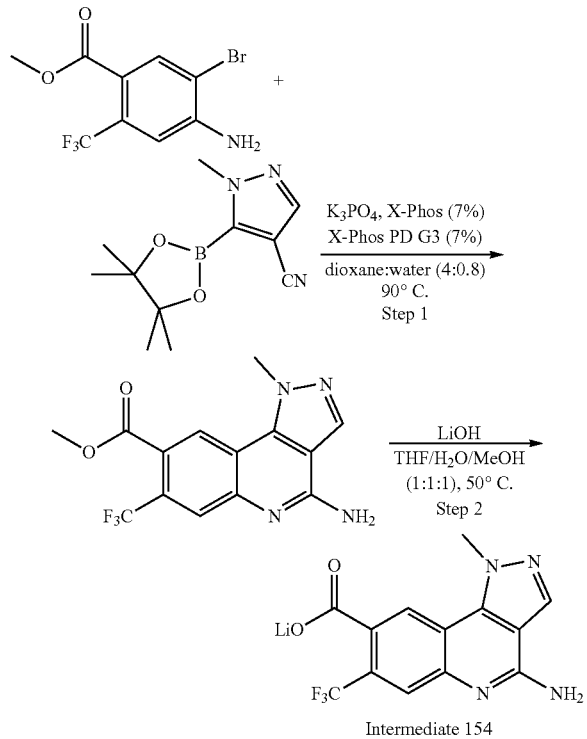

Intermediate 154

Step 1. K$_3$PO$_4$H$_2$O (1.08 g, 4.70 mmol, Sigma-Aldrich Corporation), X-Phos (0.08 g, 0.16 mmol, Sigma-Aldrich Corporation), (2-dicyclohexylphosphino-2',4',6'-triisopropyl-1,1'-biphenyl)[2-(2'-amino-1,1'-biphenyl)]palladium (ii) methanesulfonate (0.14 mg, 0.16 mmol, Sigma-Aldrich Corporation), 1-methyl-5-(4,4,5,5-tetramethyl-1,3,2-dioxaborolan-2-yl)-1 h-pyrazole-4-carbonitrile (1.10 g, 4.70 mmol, Enamine) and methyl 4-amino-5-bromo-2-(trifluoromethyl)benzoate (0.700 g, 2.349 mmol, Combi Blocks) were suspended in a degassed mixture of water (1.0 mL) and 1,4-dioxane (5.0 mL) and stirred at 60° C. over night and then at 90° C. for 18 h. Volatiles were removed in vacuo and the crude product was purified via silica column chromatography (0 to 5% MeOH/DCM+0.5% NH$_3$/MeOH) to yield methyl 4-amino-1-methyl-7-(trifluoromethyl)-1H-pyrazolo[4,3-c]quinoline-8-carboxylate (0.63 g, 1.94 mmol, 83% yield) as an slight brownish solid. m/z (ESI): 324.8 [M+H]$^+$. $^1$H NMR (400 MHz, DMSO-d6) δ ppm 8.71-8.76 (m, 1H), 8.33-8.37 (m, 1H), 7.87-7.92 (m, 1H), 7.54-7.61 (m, 2H), 4.41-4.46 (m, 3H), 3.92 (s, 3H). $^{19}$F NMR (376 MHz, DMSO-d6) δ ppm −58.06.

Step 2. Methyl 4-amino-1-methyl-7-(trifluoromethyl)-1H-pyrazolo[4,3-c]quinoline-8-carboxylate (0.62 g, 1.90 mmol) and lithium hydroxide (0.91 g, 3.79 mmol, Sigma-Aldrich Corporation) were suspended in methanol (3.0 mL), H$_2$O (3.0 mL) and THF (3.0 mL) and stirred at 50° C. for 2 hours. Volatiles of the crude mixture were removed in vacuo and the light brownish solid co-evaporated with DCM twice, followed by co-evaporation with toluene to give lithium 4-amino-1-methyl-7-(trifluoromethyl)-1H-pyrazolo[4,3-c]quinoline-8-carboxylate hydroxide (585 mg, 1.720 mmol, 91% yield) that was used in subsequent steps without further purification. m/z (ESI): 310.9 [M+H]$^+$. $^1$H NMR (400 MHz, DMSO-d6) δ ppm 8.33 (s, 1H), 8.27 (s, 1H), 7.68 (s, 1H), 7.03 (br s, 2H), 4.38 (s, 3H). $^{19}$F NMR (376 MHz, DMSO-d6) δ ppm −57.47.

EXAMPLES

Example 300: Preparation of (4-amino-1,3-dihydrofuro[3,4-c]quinolin-8-yl)(3-(pyrimidin-2-yl)morpholino)methanone

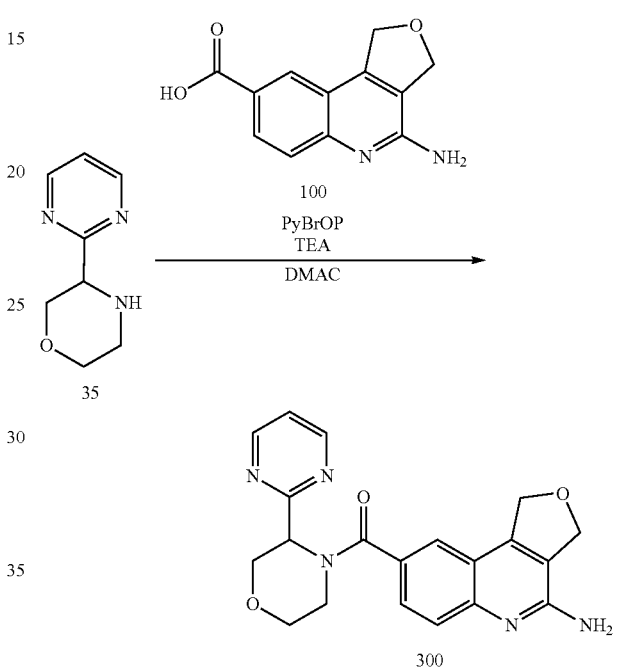

To a 50-mL round-bottomed flask was added 3-(pyrimidin-2-yl)morpholine (35, 0.20 g, 1.21 mmol) and 4-amino-1,3-dihydrofuro[3,4-c]quinoline-8-carboxylic acid (100, 0.33 g, 1.45 mmol) in N, N-dimethylacetamide (6.0 mL). Then bromotripyrrolidinophosphonium hexafluorophosphate (0.56 g, 1.21 mmol, Sigma-Aldrich Corporation) and triethylamine (0.61 g, 0.9 mL, 6.05 mmol, Sigma-Aldrich Corporation) were added to the reaction mixture. The mixture was stirred at rt for 2 h. The reaction mixture was concentrated in vacuo. The crude material was absorbed onto a plug of silica gel and purified by chromatography through an Interchim (15 micron) silica-gel column (40 grams), eluting with a gradient of 0-35% MeOH in DCM. The product was collected, then purified by reverse-phase HPLC: Purification performed with 0.1% NH$_4$OH in H$_2$O (A) and ACN (B) as mobile phase, XBridge column (19×100 mm, 5 μm). This afforded (4-amino-1,3-dihydrofuro[3,4-c]quinolin-8-yl)(3-(pyrimidin-2-yl)morpholino)methanone (0.120 g, 0.318 mmol, 26% yield) as white solid. $^1$H NMR (400 MHz, DMSO-d$_6$) δ ppm 8.88 (br d, J=4.6 Hz, 2H), 7.61 (br s, 2H), 7.46 (t, J=4.8 Hz, 2H), 6.68 (br s, 2H), 5.51-5.69 (m, 1H), 5.37 (br s, 2H), 5.00 (br s, 3H), 4.63 (br s, 1H), 4.18-4.37 (m, 1H), 3.87-3.97 (m, 1H), 3.66-3.79 (m, 1H), 3.54-3.62 (in, 1H). m/z (ESI): 378.1 [M+H]$^+$.

Examples in Table 7 were prepared in a manner similar to that described above for Example 300 using the indicated amide coupling reagent in the table.

TABLE 7

| Ex. | Structure | Name | Coupling Reagent | m/z (ESI): [M + H]+ |
|---|---|---|---|---|
| 301 | | (4-amino-7-chloro-1,3-dihydrofuro[3,4-c]quinolin-8-yl)((3R,5S)-3-methyl-5-(5-(trifluoromethyl)-2-pyridinyl)-4-morpholinyl)methanone and (4-amino-7-chloro-1,3-dihydrofuro[3,4-c]quinolin-8-yl)((3S,5R)-3-methyl-5-(5-(trifluoromethyl)-2-pyridinyl)-4-morpholinyl)methanone | CMPI | 493.0 |
| 302 | | (4-amino-7-chloro-1,3-dihydrofuro[3,4-c]quinolin-8-yl)((3R,5S)-3-methyl-5-(6-(trifluoromethyl)-3-pyridinyl)-4-morpholinyl)methanone and (4-amino-7-chloro-1,3-dihydrofuro[3,4-c]quinolin-8-yl)((3S,5R)-3-methyl-5-(6-(trifluoromethyl)-3-pyridinyl)-4-morpholinyl)methanone | CMPI | 493.1 |
| 303 | 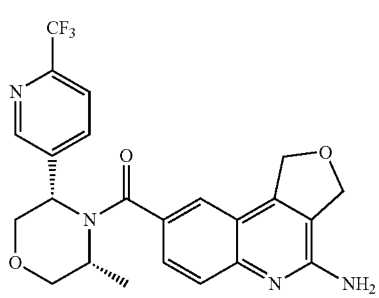 [SMILES: C[C@@H]1COC[C@H](c2ccc(C(F)(F)F)nc2)N1C(=O)c1ccc2nc(N)c3c(c2c1)COC3] | (4-amino-1,3-dihydrofuro[3,4-c]quinolin-8-yl)((3R,5S)-3-methyl-5-(6-(trifluoromethyl)-3-pyridinyl)-4-morpholinyl)methanone and (4-amino-1,3-dihydrofuro[3,4-c]quinolin-8-yl)((3S,5R)-3-methyl-5-(6-(trifluoromethyl)-3-pyridinyl)-4-morpholinyl)methanone | CMPI | 459.2 |

| Ex. | Structure | Name | Coupling Reagent | m/z (ESI): [M + H]+ |
|---|---|---|---|---|
| | 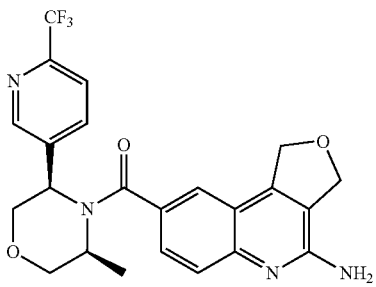 [SMILES: C[C@H]1COC[C@@H](c2ccc(C(F)(F)F)nc2)N1C(=O)c1ccc2nc(N)c3c(c2c1)COC3] | | | |
| 304 | 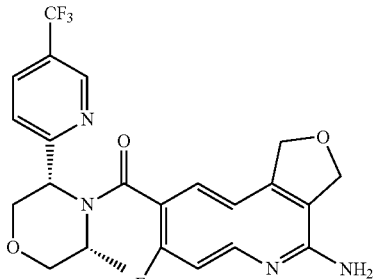 | (4-amino-7-fluoro-1,3-dihydrofuro[3,4-c]quinolin-8-yl)((3R,5S)-3-methyl-5-(5-(trifluoromethyl)-2-pyridinyl)-4-morpholinyl)methanone and (4-amino-7-fluoro-1,3-dihydrofuro[3,4-c]quinolin-8-yl)((3S,5R)-3-methyl-5-(5-(trifluoromethyl)-2-pyridinyl)-4-morpholinyl)methanone | CMPI | 477.0 |
| 305 | 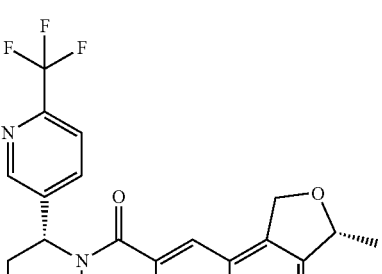 | ((3R)-4-amino-3-methyl-1,3-dihydrofuro[3,4-c]quinolin-8-yl)((3R,5S)-3-methyl-5-(6-(trifluoromethyl)-3-pyridinyl)-4-morpholinyl)methanone and ((3R)-4-amino-3-methyl-1,3-dihydrofuro[3,4-c]quinolin-8-yl)((3S,5R)-3-methyl-5-(6-(trifluoromethyl)-3-pyridinyl)-4-morpholinyl)methanone | CMPI | 473.2 |

TABLE 7-continued

| Ex. | Structure | Name | Coupling Reagent | m/z (ESI): [M + H]+ |
|---|---|---|---|---|
| 306 | | (4-amino-1,3-dihydrofuro[3,4-c][1,7]naphthyridin-8-yl)((3R,5S)-3-methyl-5-(6-(2-propanyloxy)-3-pyridinyl)-4-morpholinyl)methanone and (4-amino-1,3-dihydrofuro[3,4-c][1,7]naphthyridin-8-yl)((3S,5R)-3-methyl-5-(6-(2-propanyloxy)-3-pyridinyl)-4-morpholinyl)methanone | CMPI | 450.2 |
| 307 | | ((3R)-4-amino-3-methyl-1,3-dihydrofuro[3,4-c][1,7]naphthyridin-8-yl)((3R,5S)-3-methyl-5-(5-(trifluoromethyl)-2-pyridinyl)-4-morpholinyl)methanone and ((3R)-4-amino-3-methyl-1,3-dihydrofuro[3,4-c][1,7]naphthyridin-8-yl)((3S,5R)-3-methyl-5-(5-(trifluoromethyl)-2-pyridinyl)-4-morpholinyl)methanone | CMPI | 474.0 |

TABLE 7-continued

| Ex. | Structure | Name | Coupling Reagent | m/z (ESI): [M + H]+ |
|---|---|---|---|---|
| 308 | 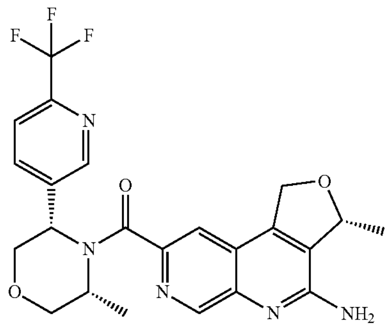 [SMILES: C[C@@H]1COC[C@H](c2ccc(C(F)(F)F)nc2)N1C(=O)c1cc2c3c(c(N)nc2cn1)[C@@H](C)OC3] | ((3R)-4-amino-3-methyl-1,3-dihydrofuro[3,4-c][1,7]naphthyridin-8-yl)((3R,5S)-3-methyl-5-(6-(trifluoromethyl)-3-pyridinyl)-4-morpholinyl)methanone and ((3R)-4-amino-3-methyl-1,3-dihydrofuro[3,4-c][1,7]naphthyridin-8-yl)((3S,5R)-3-methyl-5-(6-(trifluoromethyl)-3-pyridinyl)-4-morpholinyl)methanone | CMPI | 474.0 |
| 309 | 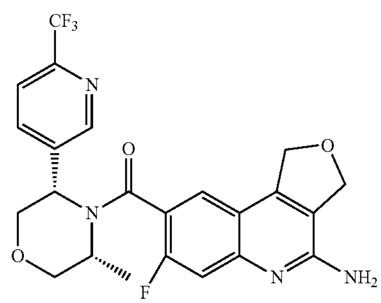 [SMILES: C[C@@H]1COC[C@H](c2ccc(C(F)(F)F)nc2)N1C(=O)c1cc2c3c(c(N)nc2cc1F)COC3] | (4-amino-7-fluoro-1,3-dihydrofuro[3,4-c]quinolin-8-yl)((3R,5S)-3-methyl-5-(6-(trifluoromethyl)-3-pyridinyl)-4-morpholinyl)methanone and (4-amino-7-fluoro-1,3-dihydrofuro[3,4-c]quinolin-8-yl)((3S,5R)-3-methyl-5-(6-(trifluoromethyl)-3-pyridinyl)-4-morpholinyl)methanone | CMPI | 477.0 |
| 310 | 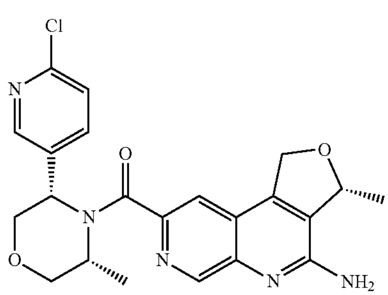 [SMILES: C[C@@H]1COC[C@H](c2ccc(Cl)nc2)N1C(=O)c1cc2c3c(c(N)nc2cn1)[C@@H](C)OC3] | ((3R)-4-amino-3-methyl-1,3-dihydrofuro[3,4-c][1,7]naphthyridin-8-yl)((3R,5S)-3-(6-chloro-3-pyridinyl)-5-methyl-4-morpholinyl)methanone and ((3R)-4-amino-3-methyl-1,3-dihydrofuro[3,4-c][1,7]naphthyridin-8-yl)((3S,5R)-3-(6-chloro-3-pyridinyl)-5-methyl-4-morpholinyl)methanone | CMPI | 440.1 |

| Ex. | Structure | Name | Coupling Reagent | m/z (ESI): [M + H]+ |
|---|---|---|---|---|
| 311 | 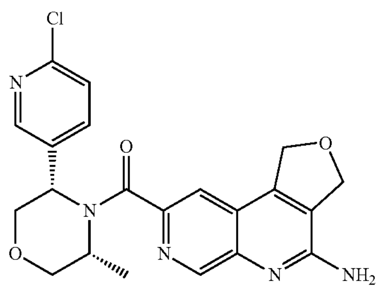 [SMILES: C[C@@H]1COC[C@H](c2ccc(Cl)nc2)N1C(=O)c1cc2c3c(c(N)nc2cn1)COC3] | (4-amino-1,3-dihydrofuro[3,4-c][1,7]naphthyridin-8-yl)((3R,5S)-3-(6-chloro-3-pyridinyl)-5-methyl-4-morpholinyl)methanone and (4-amino-1,3-dihydrofuro[3,4-c][1,7]naphthyridin-8-yl)((3S,5R)-3-(6-chloro-3-pyridinyl)-5-methyl-4-morpholinyl)methanone | CMPI | 426.1 |
| 312 | 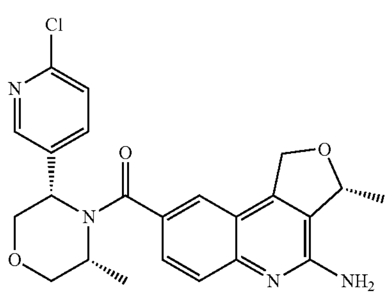 [SMILES: C[C@@H]1COC[C@H](c2ccc(Cl)nc2)N1C(=O)c1ccc2nc(N)c3c(c2c1)CO[C@@H]3C] | ((3R)-4-amino-3-methyl-1,3-dihydrofuro[3,4-c]quinolin-8-yl)((3R,5S)-3-(6-chloro-3-pyridinyl)-5-methyl-4-morpholinyl)methanone and ((3R)-4-amino-3-methyl-1,3-dihydrofuro[3,4-c]quinolin-8-yl)((3S,5R)-3-(6-chloro-3-pyridinyl)-5-methyl-4-morpholinyl)methanone | CMPI | 439.1 |

| Ex. | Structure | Name | Coupling Reagent | m/z (ESI): [M + H]+ |
|---|---|---|---|---|
| 313 | | (4-amino-7-fluoro-1,3-dihydrofuro[3,4-c]quinolin-8-yl)((3R,5S)-3-(6-chloro-3-pyridinyl)-5-methyl-4-morpholinyl)methanone and (4-amino-7-fluoro-1,3-dihydrofuro[3,4-c]quinolin-8-yl)((3S,5R)-3-(6-chloro-3-pyridinyl)-5-methyl-4-morpholinyl)methanone | CMPI | 443.1 |
| 314 | | (4-amino-7-fluoro-1,3-dihydrofuro[3,4-c]quinolin-8-yl)((3R,5S)-3-(6-(difluoromethoxy)-3-pyridazinyl)-5-methyl-4-morpholinyl)methanone and (4-amino-7-fluoro-1,3-dihydrofuro[3,4-c]quinolin-8-yl)((3S,5R)-3-(6-(difluoromethoxy)-3-pyridazinyl)-5-methyl-4-morpholinyl)methanone | CMPI | 476.0 |

TABLE 7-continued

| Ex. | Structure | Name | Coupling Reagent | m/z (ESI): [M + H]+ |
|---|---|---|---|---|
| 315 | 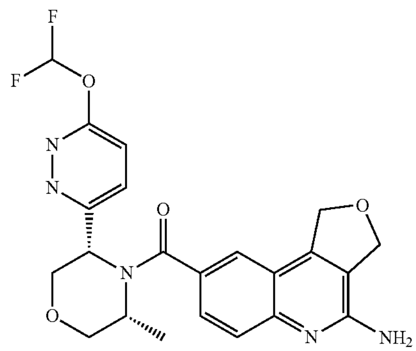 [SMILES: C[C@@H]1COC[C@H](C2=CC=C(OC(F)F)NN2)N1C(=O)c1ccc2nc(N)c3c(c2c1)COC3] | (4-amino-1,3-dihydrofuro[3,4-c]quinolin-8-yl)((3R,5S)-3-(6-(difluoromethoxy)-3-pyridazinyl)-5-methyl-4-morpholinyl)methanone and (4-amino-1,3-dihydrofuro[3,4-c]quinolin-8-yl)((3S,5R)-3-(6-(difluoromethoxy)-3-pyridazinyl)-5-methyl-4-morpholinyl)methanone | CMPI | 458.0 |
| 316 | 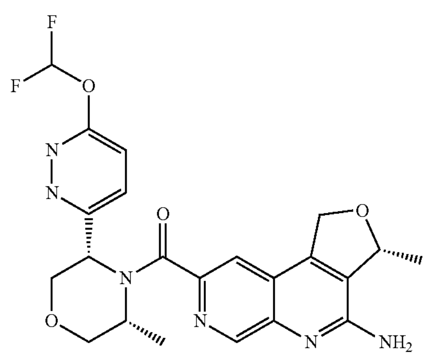 [SMILES: C[C@@H]1COC[C@H](C2=CC=C(OC(F)F)NN2)N1C(=O)c1cc2c3c(c(N)nc2cn1)[C@@H](C)OC3] | ((3R)-4-amino-3-methyl-1,3-dihydrofuro[3,4-c][1,7]naphthyridin-8-yl)((3R,5S)-3-(6-(difluoromethoxy)-3-pyridazinyl)-5-methyl-4-morpholinyl)methanone and ((3R)-4-amino-3-methyl-1,3-dihydrofuro[3,4-c][1,7]naphthyridin-8-yl)((3S,5R)-3-(6-(difluoromethoxy)-3-pyridazinyl)-5-methyl-4-morpholinyl)methanone | CMPI | 473.0 |

| Ex. | Structure | Name | Coupling Reagent | m/z (ESI): [M + H]+ |
|---|---|---|---|---|
| 317 | 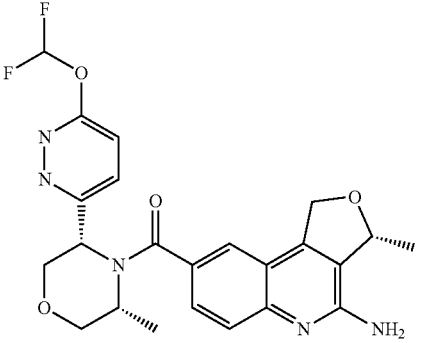 [SMILES: C[C@@H]1COC[C@H](C2=CC=C(OC(F)F)NN2)N1C(=O)c1ccc2nc(N)c3c(c2c1)CO[C@@H]3C]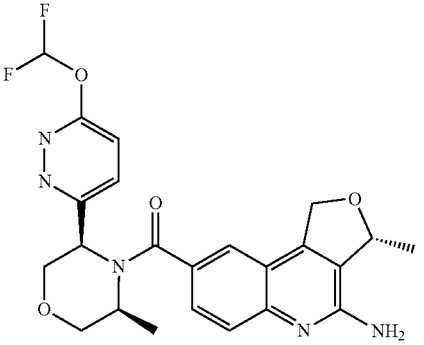 [SMILES: C[C@H]1OCc2c1c(N)nc1ccc(C(=O)N3[C@@H](C)COC[C@H]3C3=CC=C(OC(F)F)NN3)cc21] | ((3R)-4-amino-3-methyl-1,3-dihydrofuro[3,4-c]quinolin-8-yl)((3R,5S)-3-(6-(difluoromethoxy)-3-pyridazinyl)-5-methyl-4-morpholinyl)methanone and ((3R)-4-amino-3-methyl-1,3-dihydrofuro[3,4-c]quinolin-8-yl)((3S,5R)-3-(6-(difluoromethoxy)-3-pyridazinyl)-5-methyl-4-morpholinyl)methanone | CMPI | 472.1 |
| 318 | 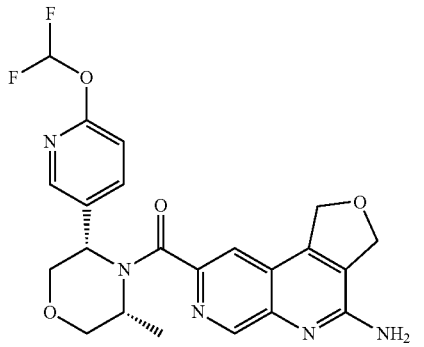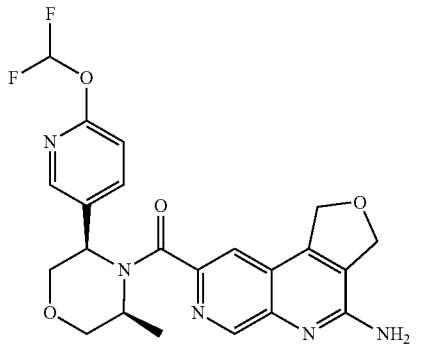 | (4-amino-1,3-dihydrofuro[3,4-c][1,7]naphthyridin-8-yl)((3R,5S)-3-(6-(difluoromethoxy)-3-pyridinyl)-5-methyl-4-morpholinyl)methanone and (4-amino-1,3-dihydrofuro[3,4-c][1,7]naphthyridin-8-yl)((3S,5R)-3-(6-(difluoromethoxy)-3-pyridinyl)-5-methyl-4-morpholinyl)methanone | CMPI | 458.2 |

TABLE 7-continued

| Ex. | Structure | Name | Coupling Reagent | m/z (ESI): [M + H]+ |
|---|---|---|---|---|
| 319 | 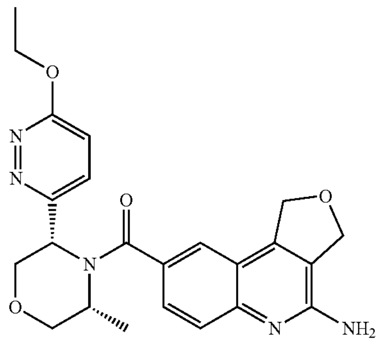 [SMILES: CCOc1ccc([C@H]2COC[C@@H](C)N2C(=O)c2ccc3nc(N)c4c(c3c2)COC4)nn1] | (4-amino-1,3-dihydrofuro[3,4-c]quinolin-8-yl)((3R,5S)-3-(6-ethoxy-3-pyridazinyl)-5-methyl-4-morpholinyl)methanone and (4-amino-1,3-dihydrofuro[3,4-c]quinolin-8-yl)((3S,5R)-3-(6-ethoxy-3-pyridazinyl)-5-methyl-4-morpholinyl)methanone | CMPI | 436.2 |
| 320 | 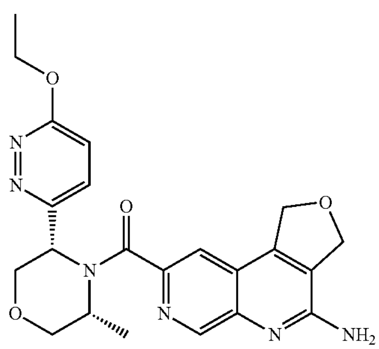 [SMILES: CCOc1ccc([C@H]2COC[C@@H](C)N2C(=O)c2cc3c4c(c(N)nc3cn2)COC4)nn1] | (4-amino-1,3-dihydrofuro[3,4-c][1,7]naphthyridin-8-yl)((3R,5S)-3-(6-ethoxy-3-pyridazinyl)-5-methyl-4-morpholinyl)methanone and (4-amino-1,3-dihydrofuro[3,4-c][1,7]naphthyridin-8-yl)((3S,5R)-3-(6-ethoxy-3-pyridazinyl)-5-methyl-4-morpholinyl)methanone | CMPI | 437.2 |

TABLE 7-continued

| Ex. | Structure | Name | Coupling Reagent | m/z (ESI): [M + H]+ |
|---|---|---|---|---|
| 321 | 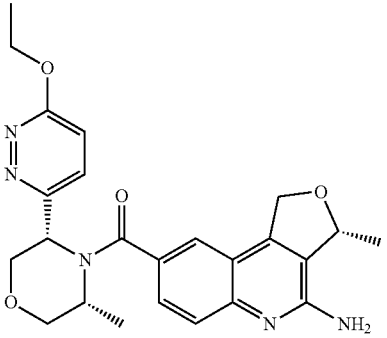 [SMILES: CCOc1ccc([C@H]2COC[C@@H](C)N2C(=O)c2ccc3nc(N)c4c(c3c2)CO[C@@H]4C)nn1] | ((3R)-4-amino-3-methyl-1,3-dihydrofuro[3,4-c]quinolin-8-yl)((3R,5S)-3-(6-ethoxy-3-pyridazinyl)-5-methyl-4-morpholinyl)methanone and ((3R)-4-amino-3-methyl-1,3-dihydrofuro[3,4-c]quinolin-8-yl)((3S,5R)-3-(6-ethoxy-3-pyridazinyl)-5-methyl-4-morpholinyl)methanone | CMPI | 450.2 |
| 322 | 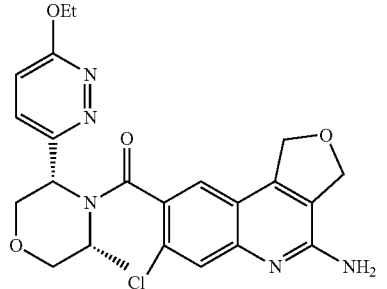 [SMILES: CCOc1ccc([C@H]2COC[C@@H](C)N2C(=O)c2cc3c4c(c(N)nc3cc2Cl)COC4)nn1] | (4-amino-7-chloro-1,3-dihydrofuro[3,4-c]quinolin-8-yl)((3R,5S)-3-(6-ethoxy-3-pyridazinyl)-5-methyl-4-morpholinyl)methanone and (4-amino-7-chloro-1,3-dihydrofuro[3,4-c]quinolin-8-yl)((3S,5R)-3-(6-ethoxy-3-pyridazinyl)-5-methyl-4-morpholinyl)methanone | CMPI | 470.2 |

TABLE 7-continued

| Ex. | Structure | Name | Coupling Reagent | m/z (ESI): [M + H]+ |
|---|---|---|---|---|
| 323 | 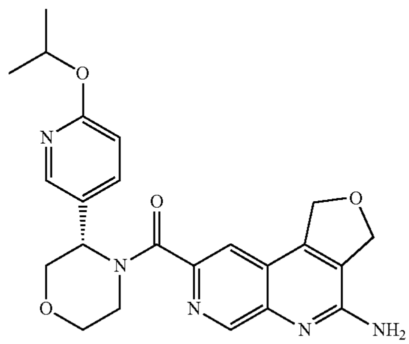 | (4-amino-1,3-dihydrofuro[3,4-c][1,7]naphthyridin-8-yl)((3R)-3-(6-(2-propanyloxy)-3-pyridinyl)-4-morpholinyl)methanone and (4-amino-1,3-dihydrofuro[3,4-c][1,7]naphthyridin-8-yl)((3S)-3-(6-(2-propanyloxy)-3-pyridinyl)-4-morpholinyl)methanone | CMPI | 436.2 |
| 324 | | ((3R)-4-amino-3-methyl-1,3-dihydrofuro[3,4-c][1,7]naphthyridin-8-yl)((3R,5S)-3-(3,5-difluorophenyl)-5-methyl-4-morpholinyl)methanone and ((3R)-4-amino-3-methyl-1,3-dihydrofuro[3,4-c][1,7]naphthyridin-8-yl)((3S,5R)-3-(3,5-difluorophenyl)-5-methyl-4-morpholinyl)methanone | CMPI | 441.1 |
| 325 | 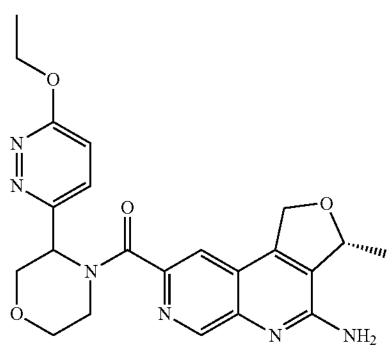 [SMILES: CCOc1ccc(C2COCCN2C(=O)c2cc3c4c(c(N)nc3cn2)[C@@H](C)OC4)nn1] | ((3R)-4-amino-3-methyl-1,3-dihydrofuro[3,4-c][1,7]naphthyridin-8-yl)((3R)-3-(6-ethoxy-3-pyridazinyl)-4-morpholinyl)methanone and ((3R)-4-amino-3-methyl-1,3-dihydrofuro[3,4-c][1,7]naphthyridin-8-yl)((3S)-3-(6-ethoxy-3-pyridazinyl)-4-morpholinyl)methanone | CMPI | 437.2 |
| 326 | 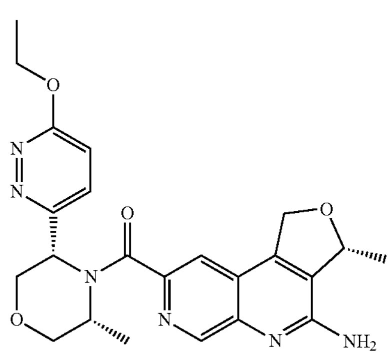 [SMILES: CCOc1ccc([C@H]2COC[C@@H](C)N2C(=O)c2cc3c4c(c(N)nc3cn2)[C@@H](C)OC4)nn1] | ((3R)-4-amino-3-methyl-1,3-dihydrofuro[3,4-c][1,7]naphthyridin-8-yl)((3R,5S)-3-(6-ethoxy-3-pyridazinyl)-5-methyl-4-morpholinyl)methanone and ((3R)-4-amino-3-methyl-1,3-dihydrofuro[3,4-c][1,7]naphthyridin-8-yl)((3S,5R)-3-(6-ethoxy-3-pyridazinyl)-5-methyl-4-morpholinyl)methanone | CMPI | 451.2 |

TABLE 7-continued

| Ex. | Structure | Name | Coupling Reagent | m/z (ESI): [M + H]+ |
|---|---|---|---|---|
| | 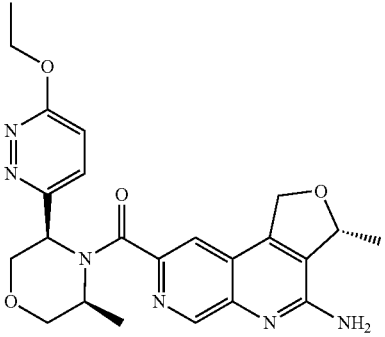 [SMILES: CCOc1ccc([C@@H]2COC[C@H](C)N2C(=O)c2cc3c4c(c(N)nc3cn2)[C@@H](C)OC4)nn1] | | | |
| 327 | 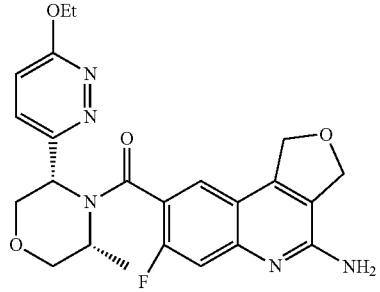 | (4-amino-7-fluoro-1,3-dihydrofuro[3,4-c]quinolin-8-yl)((3R,5S)-3-(6-ethoxy-3-pyridazinyl)-5-methyl-4-morpholinyl)methanone and (4-amino-7-fluoro-1,3-dihydrofuro[3,4-c]quinolin-8-yl)((3S,5R)-3-(6-ethoxy-3-pyridazinyl)-5-methyl-4-morpholinyl)methanone | CMPI | 454.2 |
| 328 | 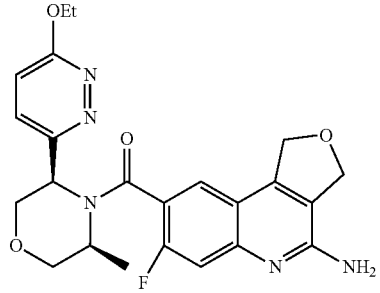 [SMILES: CCOc1ccc([C@@H]2COC[C@H](C)N2C(=O)c2cc3c4c(c(N)nc3cc2F)COC4)nn1] | (4-amino-1,3-dihydrofuro[3,4-c][1,7]naphthyridin-8-yl)((3R,5S)-3-(2-fluoro-4-(trifluoromethoxy)phenyl)-5-methyl-4-morpholinyl)methanone and (4-amino-1,3-dihydrofuro[3,4-c][1,7]naphthyridin-8-yl)((3S,5R)-3-(2-fluoro-4-(trifluoromethoxy)phenyl)-5-methyl-4-morpholinyl)methanone | CMPI | 493.0 |

TABLE 7-continued

| Ex. | Structure | Name | Coupling Reagent | m/z (ESI): [M + H]+ |
|---|---|---|---|---|
| 329 | | ((3R)-4-amino-3-methyl-1,3-dihydrofuro[3,4-c]quinolin-8-yl)((3R,5S)-3-(2-fluoro-4-(trifluoromethoxy)phenyl)-5-methyl-4-morpholinyl)methanone and ((3R)-4-amino-3-methyl-1,3-dihydrofuro[3,4-c]quinolin-8-yl)((3S,5R)-3-(2-fluoro-4-(trifluoromethoxy)phenyl)-5-methyl-4-morpholinyl)methanone | CMPI | 506.0 |
| 330 | 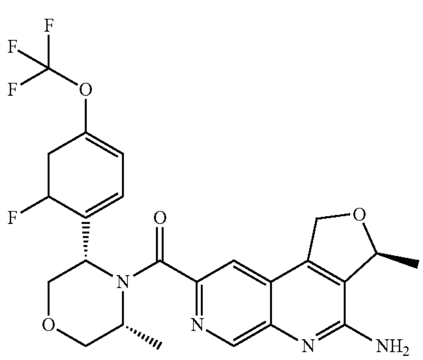 [SMILES: C[C@@H]1OCc2c1c(N)nc1cnc(C(=O)N3[C@H](C)COC[C@@H]3C3=CC=C(OC(F)(F)F)CC3F)cc21] | ((3S)-4-amino-3-methyl-1,3-dihydrofuro[3,4-c][1,7]naphthyridin-8-yl)((3R,5S)-3-(2-fluoro-4-(trifluoromethoxy)phenyl)-5-methyl-4-morpholinyl)methanone and ((3S)-4-amino-3-methyl-1,3-dihydrofuro[3,4-c][1,7]naphthyridin-8-yl)((3S,5R)-3-(2-fluoro-4-(trifluoromethoxy)phenyl)-5-methyl-4-morpholinyl)methanone | CMPI | 507.0 |

| Ex. | Structure | Name | Coupling Reagent | m/z (ESI): [M + H]+ |
|---|---|---|---|---|
| 331 | | ((3R)-4-amino-3-methyl-1,3-dihydrofuro[3,4-c]quinolin-8-yl)((3R,5S)-3-(2-fluoro-4-(trifluoromethyl)phenyl)-5-methyl-4-morpholinyl)methanone and ((3R)-4-amino-3-methyl-1,3-dihydrofuro[3,4-c]quinolin-8-yl)((3S,5R)-3-(2-fluoro-4-(trifluoromethyl)phenyl)-5-methyl-4-morpholinyl)methanone | CMPI | 490.1 |
| 332 | 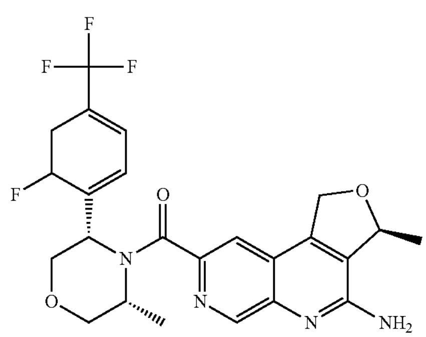 [SMILES: C[C@@H]1OCc2c1c(N)nc1cnc(C(=O)N3[C@H](C)COC[C@@H]3C3=CC=C(C(F)(F)F)CC3F)cc21] | ((3S)-4-amino-3-methyl-1,3-dihydrofuro[3,4-c][1,7]naphthyridin-8-yl)((3R,5S)-3-(2-fluoro-4-(trifluoromethyl)phenyl)-5-methyl-4-morpholinyl)methanone and ((3S)-4-amino-3-methyl-1,3-dihydrofuro[3,4-c][1,7]naphthyridin-8-yl)((3S,5R)-3-(2-fluoro-4-(trifluoromethyl)phenyl)-5-methyl-4-morpholinyl)methanone | CMPI | 491.1 |

TABLE 7-continued

| Ex. | Structure | Name | Coupling Reagent | m/z (ESI): [M + H]+ |
|---|---|---|---|---|
| 333 | 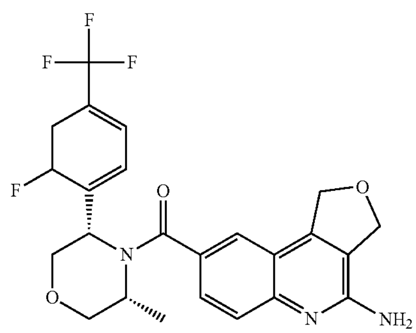 [SMILES: C[C@@H]1COC[C@H](C2=CC=C(C(F)(F)F)CC2F)N1C(=O)c1ccc2nc(N)c3c(c2c1)COC3] | (4-amino-1,3-dihydrofuro[3,4-c]quinolin-8-yl)((3R,5S)-3-(2-fluoro-4-(trifluoromethyl)phenyl)-5-methyl-4-morpholinyl)methanone and (4-amino-1,3-dihydrofuro[3,4-c]quinolin-8-yl)((3S,5R)-3-(2-fluoro-4-(trifluoromethyl)phenyl)-5-methyl-4-morpholinyl)methanone | CMPI | 476.0 |
| 334 | 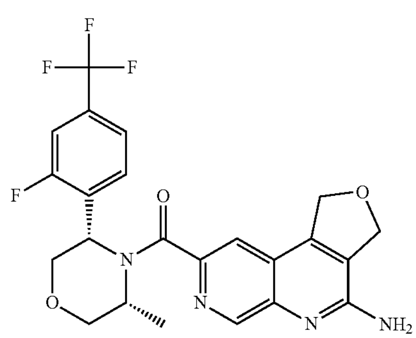 [SMILES: C[C@@H]1COC[C@H](c2ccc(C(F)(F)F)cc2F)N1C(=O)c1cc2c3c(c(N)nc2cn1)COC3] | (4-amino-1,3-dihydrofuro[3,4-c][1,7]naphthyridin-8-yl)((3R,5S)-3-(2-fluoro-4-(trifluoromethyl)phenyl)-5-methyl-4-morpholinyl)methanone and (4-amino-1,3-dihydrofuro[3,4-c][1,7]naphthyridin-8-yl)((3S,5R)-3-(2-fluoro-4-(trifluoromethyl)phenyl)-5-methyl-4-morpholinyl)methanone | CMPI | 477.0 |

TABLE 7-continued

| Ex. | Structure | Name | Coupling Reagent | m/z (ESI): [M + H]+ |
|---|---|---|---|---|
| | | | | |
| 335 | 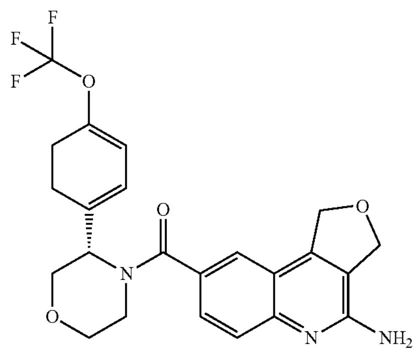 [SMILES: Nc1nc2ccc(C(=O)N3CCOC[C@@H]3C3=CC=C(OC(F)(F)F)CC3)cc2c2c1COC2] | (4-amino-1,3-dihydrofuro[3,4-c]quinolin-8-yl)-[(3S)-3-[4-(trifluoromethoxy)phenyl]morpholin-4-yl]methanone | HATU | 460.0 |
| 336 | 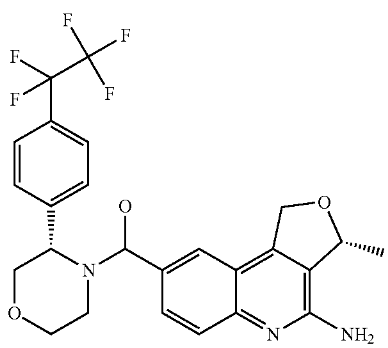 [SMILES: C[C@H]1OCc2c1c(N)nc1ccc(C(O)N3CCOC[C@@H]3c3ccc(C(F)(F)C(F)(F)F)cc3)cc21] | ((3R)-4-amino-3-methyl-1,3-dihydrofuro[3,4-c]quinolin-8-yl)((3S)-3-(4-(pentafluoroethyl)phenyl)-4-morpholinyl)methanone | HATU | 508.0 |
| 337 | 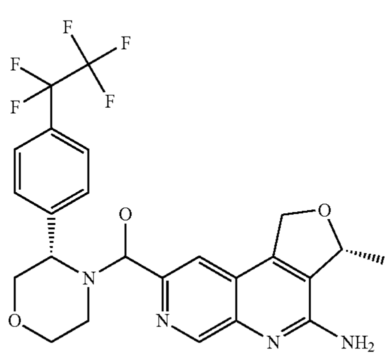 [SMILES: C[C@H]1OCc2c1c(N)nc1cnc(C(O)N3CCOC[C@@H]3c3ccc(C(F)(F)C(F)(F)F)cc3)cc21] | ((3R)-4-amino-3-methyl-1,3-dihydrofuro[3,4-c][1,7]naphthyridin-8-yl)((3S)-3-(4-(pentafluoroethyl)phenyl)-4-morpholinyl)methanone and ((3S)-4-amino-3-methyl-1,3-dihydrofuro[3,4-c][1,7]naphthyridin-8-yl)((3S)-3-(4-(pentafluoroethyl)phenyl)-4-morpholinyl)methanone | HATU | 509.0 |

TABLE 7-continued

| Ex. | Structure | Name | Coupling Reagent | m/z (ESI): [M + H]+ |
|---|---|---|---|---|
| | | | | |
| 338 | 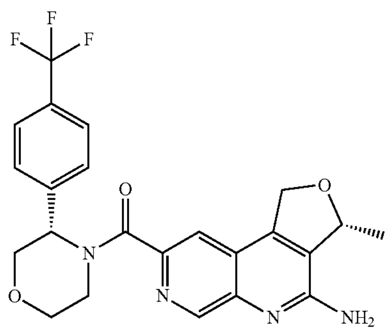 [SMILES: C[C@H]1OCc2c1c(N)nc1cnc(C(=O)N3CCOC[C@@H]3c3ccc(C(F)(F)F)cc3)cc21] | ((3R)-4-amino-3-methyl-1,3-dihydrofuro[3,4-c][1,7]naphthyridin-8-yl)((3S)-3-(4-(trifluoromethyl)phenyl)-4-morpholinyl)methanone and ((3S)-((4-amino-3-methyl-1,3-dihydrofuro[3,4-c][1,7]naphthyridin-8-yl)((3S)-3-(4-(trifluoromethyl)phenyl)-4-morpholinyl)methanone | HATU | 459.0 |
| 339 | 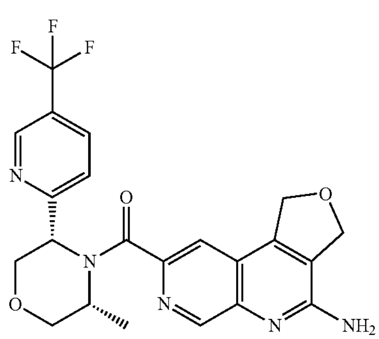 [SMILES: C[C@@H]1COC[C@H](c2ccc(C(F)(F)F)cn2)N1C(=O)c1cc2c3c(c(N)nc2cn1)COC3] | (4-amino-1,3-dihydrofuro[3,4-c][1,7]naphthyridin-8-yl)((3R,5S)-3-methyl-5-(5-(trifluoromethyl)-2-pyridinyl)-4-morpholinyl)methanone and (4-amino-1,3-dihydrofuro[3,4-c][1,7]naphthyridin-8-yl)((3S,5R)-3-methyl-5-(5-(trifluoromethyl)-2-pyridinyl)-4-morpholinyl)methanone | HATU | 460.1 |

TABLE 7-continued

| Ex. | Structure | Name | Coupling Reagent | m/z (ESI): [M + H]+ |
|---|---|---|---|---|
| 340 | | (4-amino-1,3-dihydrofuro[3,4-c][1,7]naphthyridin-8-yl)((3R,5S)-3-methyl-5-(6-(trifluoromethyl)-3-pyridinyl)-4-morpholinyl)methanone and (4-amino-1,3-dihydrofuro[3,4-c][1,7]naphthyridin-8-yl)((3S,5R)-3-methyl-5-(6-(trifluoromethyl)-3-pyridinyl)-4-morpholinyl)methanone | HATU | 460.2 |
| 341 | 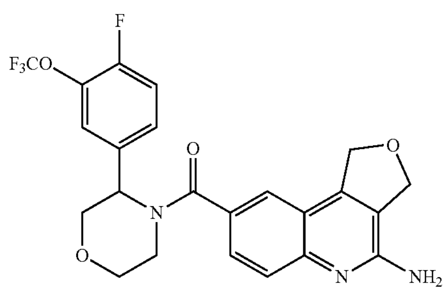 [SMILES: Nc1nc2ccc(C(=O)N3CCOCC3c3ccc(F)c(OC(F)(F)F)c3)cc2c2c1COC2] | (4-amino-1,3-dihydrofuro[3,4-c]quinolin-8-yl)((3R)-3-(4-fluoro-3-(trifluoromethoxy)phenyl)-4-morpholinyl)methanone and (4-amino-1,3-dihydrofuro[3,4-c]quinolin-8-yl)((3S)-3-(4-fluoro-3-(trifluoromethoxy)phenyl)-4-morpholinyl)methanone | HATU | 478.1 |
| 342 | 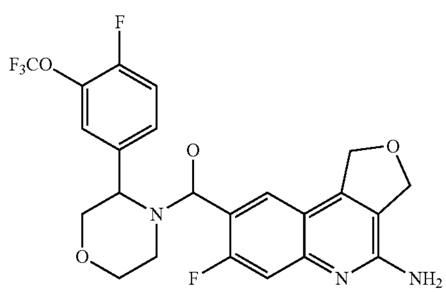 [SMILES: Nc1nc2cc(F)c(C(O)N3CCOCC3c3ccc(F)c(OC(F)(F)F)c3)cc2c2c1COC2] | (4-amino-7-fluoro-1,3-dihydrofuro[3,4-c]quinolin-8-yl)((3R)-3-(4-fluoro-3-(trifluoromethyl)phenyl)-4-morpholinyl)methanone and (4-amino-7-fluoro-1,3-dihydrofuro[3,4-c]quinolin-8-yl)((3S)-3-(4-fluoro-3-(trifluoromethyl)phenyl)-4-morpholinyl)methanone | HATU | 480.1 |

TABLE 7-continued

| Ex. | Structure | Name | Coupling Reagent | m/z (ESI): [M + H]+ |
|---|---|---|---|---|
| 343 | 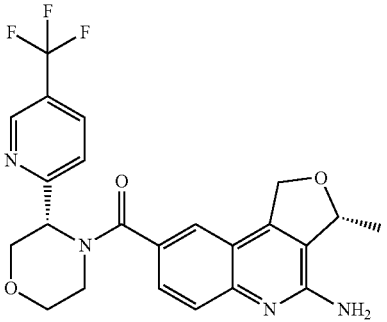 | ((3R)-4-amino-3-methyl-1,3-dihydrofuro[3,4-c]quinolin-8-yl)((3R)-3-(5-(trifluoromethyl)-2-pyridinyl)-4-morpholinyl)methanone and ((3R)-4-amino-3-methyl-1,3-dihydrofuro[3,4-c]quinolin-8-yl)((3S)-3-(5-(trifluoromethyl)-2-pyridinyl)-4-morpholinyl)methanone | HATU | 459.2 |
| 344 | 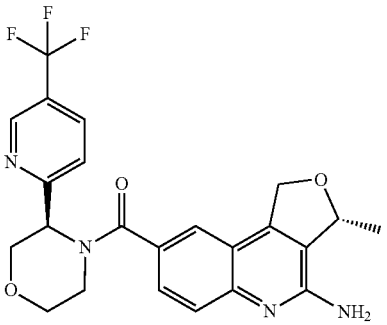 [SMILES: C[C@H]1OCc2c1c(N)nc1ccc(C(=O)N3CCOC[C@H]3c3ccc(C(F)(F)F)cn3)cc21] | (4-amino-7-chloro-1,3-dihydrofuro[3,4-c]quinolin-8-yl)((3R)-3-(5-(trifluoromethyl)-2-pyridinyl)-4-morpholinyl)methanone and (4-amino-7-chloro-1,3-dihydrofuro[3,4-c]quinolin-8-yl)((3S)-3-(5-(trifluoromethyl)-2-pyridinyl)-4-morpholinyl)methanone | HATU | 479.1 |
| 345 | 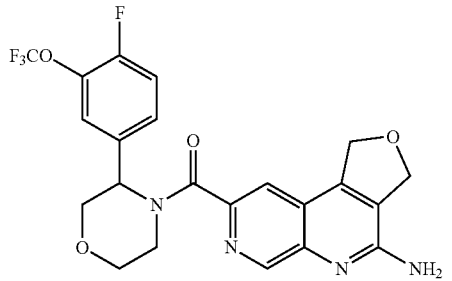 [SMILES: Nc1nc2cnc(C(=O)N3CCOCC3c3ccc(F)c(OC(F)(F)F)c3)cc2c2c1COC2] | (4-amino-1,3-dihydrofuro[3,4-c][1,7]naphthyridin-8-yl)((3R)-3-(4-fluoro-3-(trifluoromethoxy)phenyl)-4-morpholinyl)methanone and (4-amino-1,3-dihydrofuro[3,4-c][1,7]naphthyridin-8-yl)((3S)-3-(4-fluoro-3-(trifluoromethoxy)phenyl)-4-morpholinyl)methanone | HATU | 479.1 |

TABLE 7-continued

| Ex. | Structure | Name | Coupling Reagent | m/z (ESI): [M + H]+ |
|---|---|---|---|---|
| 346 | 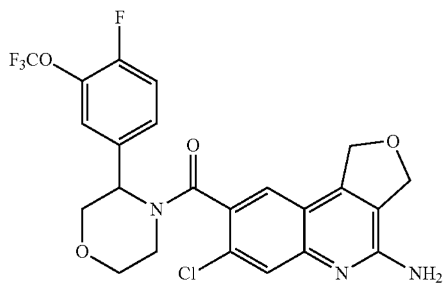 [SMILES: Nc1nc2cc(Cl)c(C(=O)N3CCOCC3c3ccc(F)c(OC(F)(F)F)c3)cc2c2c1COC2] | (4-amino-7-chloro-1,3-dihydrofuro[3,4-c]quinolin-8-yl)((3R)-3-(4-fluoro-3-(trifluoromethoxy)phenyl)-4-morpholinyl)methanone and (4-amino-7-chloro-1,3-dihydrofuro[3,4-c]quinolin-8-yl)((3S)-3-(4-fluoro-3-(trifluoromethoxy)phenyl)-4-morpholinyl)methanone | HATU | 512.0 |
| 347 | 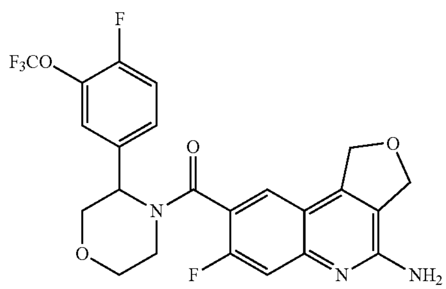 | (4-amino-7-fluoro-1,3-dihydrofuro[3,4-c]quinolin-8-yl)((3R)-3-(4-fluoro-3-(trifluoromethoxy)phenyl)-4-morpholinyl)methanone and (4-amino-7-fluoro-1,3-dihydrofuro[3,4-c]quinolin-8-yl)((3S)-3-(4-fluoro-3-(trifluoromethoxy)phenyl)-4-morpholinyl)methanone | HATU | 496.0 |
| 348 | 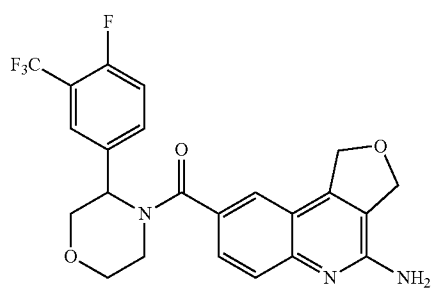 [SMILES: Nc1nc2ccc(C(=O)N3CCOCC3c3ccc(F)c(C(F)(F)F)c3)cc2c2c1COC2] | (4-amino-1,3-dihydrofuro[3,4-c]quinolin-8-yl)((3R)-3-(4-fluoro-3-(trifluoromethyl)phenyl)-4-morpholinyl)methanone and (4-amino-1,3-dihydrofuro[3,4-c]quinolin-8-yl)((3S)-3-(4-fluoro-3-(trifluoromethyl)phenyl)-4-morpholinyl)methanone | HATU | 462.1 |
| 349 | 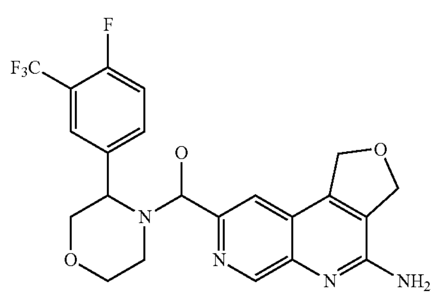 [SMILES: Nc1nc2cnc(C(O)N3CCOCC3c3ccc(F)c(C(F)(F)F)c3)cc2c2c1COC2] | (4-amino-1,3-dihydrofuro[3,4-c][1,7]naphthyridin-8-yl)((3R)-3-(4-fluoro-3-(trifluoromethyl)phenyl)-4-morpholinyl)methanone and (4-amino-1,3-dihydrofuro[3,4-c][1,7]naphthyridin-8-yl)((3S)-3-(4-fluoro-3-(trifluoromethyl)phenyl)-4-morpholinyl)methanone | HATU | 463.1 |
| 350 | 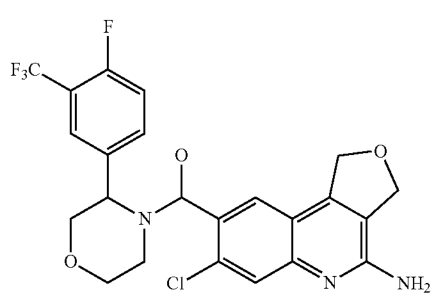 [SMILES: Nc1nc2cc(Cl)c(C(O)N3CCOCC3c3ccc(F)c(C(F)(F)F)c3)cc2c2c1COC2] | (4-amino-7-chloro-1,3-dihydrofuro[3,4-c]quinolin-8-yl)((3R)-3-(4-fluoro-3-(trifluoromethyl)phenyl)-4-morpholinyl)methanone and (4-amino-7-chloro-1,3-dihydrofuro[3,4-c]quinolin-8-yl)((3S)-3-(4-fluoro-3-(trifluoromethyl)phenyl)-4-morpholinyl)methanone | HATU | 496.1 |

TABLE 7-continued

| Ex. | Structure | Name | Coupling Reagent | m/z (ESI): [M + H]+ |
|---|---|---|---|---|
| 351 | 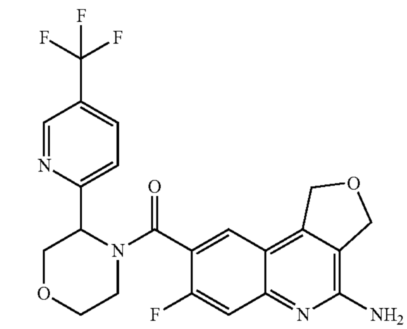 | (4-amino-7-fluoro-1,3-dihydrofuro[3,4-c]quinolin-8-yl)((3R)-3-(5-(trifluoromethyl)-2-pyridinyl)-4-morpholinyl)methanone and (4-amino-7-fluoro-1,3-dihydrofuro[3,4-c]quinolin-8-yl)((3S)-3-(5-(trifluoromethyl)-2-pyridinyl)-4-morpholinyl)methanone | HATU | 463.1 |
| 352 | 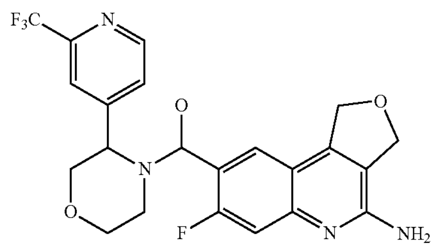 [SMILES: Nc1nc2cc(F)c(C(O)N3CCOCC3c3ccnc(C(F)(F)F)c3)cc2c2c1COC2] | (4-amino-7-fluoro-1,3-dihydrofuro[3,4-c]quinolin-8-yl)((3R)-3-(2-(trifluoromethyl)-4-pyridinyl)-4-morpholinyl)methanone and (4-amino-7-fluoro-1,3-dihydrofuro[3,4-c]quinolin-8-yl)((3S)-3-(2-(trifluoromethyl)-4-pyridinyl)-4-morpholinyl)methanone | HATU | 463.1 |
| 353 | 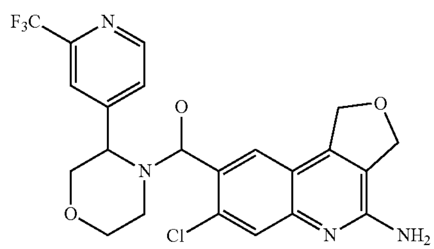 | (4-amino-7-chloro-1,3-dihydrofuro[3,4-c]quinolin-8-yl)((3R)-3-(2-(trifluoromethyl)-4-pyridinyl)-4-morpholinyl)methanone and (4-amino-7-chloro-1,3-dihydrofuro[3,4-c]quinolin-8-yl)((3S)-3-(2-(trifluoromethyl)-4-pyridinyl)-4-morpholinyl)methanone | HATU | 479.0 |
| 354 | | ((3R)-4-amino-3-methyl-1,3-dihydrofuro[3,4-c]quinolin-8-yl)((3R)-3-(2-(trifluoromethyl)-4-pyridinyl)-4-morpholinyl)methanone and ((3R)-4-amino-3-methyl-1,3-dihydrofuro[3,4-c]quinolin-8-yl)((3S)-3-(2-(trifluoromethyl)-4-pyridinyl)-4-morpholinyl)methanone | HATU | 459.2 |

TABLE 7-continued

| Ex. | Structure | Name | Coupling Reagent | m/z (ESI): [M + H]+ |
|---|---|---|---|---|
| 355 | | ((3S)-4-amino-3-methyl-1,3-dihydrofuro[3,4-c][1,7]naphthyridin-8-yl)((3R)-3-(4-fluoro-3-(trifluoromethyl)phenyl)-4-morpholinyl)methanone and ((3S)-4-amino-3-methyl-1,3-dihydrofuro[3,4-c][1,7]naphthyridin-8-yl)((3S)-3-(4-fluoro-3-(trifluoromethyl)phenyl)-4-morpholinyl)methanone | HATU | 477.1 |
| 356 | | ((3R)-4-amino-3-methyl-1,3-dihydrofuro[3,4-c][1,7]naphthyridin-8-yl)((3R)-3-(4-fluoro-3-(trifluoromethyl)phenyl)-4-morpholinyl)methanone and ((3R)-4-amino-3-methyl-1,3-dihydrofuro[3,4-c][1,7]naphthyridin-8-yl)((3S)-3-(4-fluoro-3-(trifluoromethyl)phenyl)-4-morpholinyl)methanone | HATU | 477.1 |
| 357 | 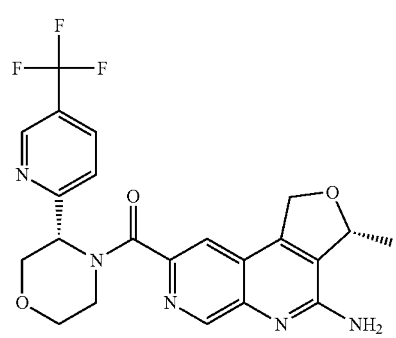 [SMILES: C[C@H]1OCc2c1c(N)nc1cnc(C(=O)N3CCOC[C@@H]3c3ccc(C(F)(F)F)cn3)cc21] | ((3R)-4-amino-3-methyl-1,3-dihydrofuro[3,4-c][1,7]naphthyridin-8-yl)((3R)-3-(5-(trifluoromethyl)-2-pyridinyl)-4-morpholinyl)methanone and ((3R)-4-amino-3-methyl-1,3-dihydrofuro[3,4-c][1,7]naphthyridin-8-yl)((3S)-3-(5-(trifluoromethyl)-2-pyridinyl)-4-morpholinyl)methanone | HATU | 460.0 |

TABLE 7-continued

| Ex. | Structure | Name | Coupling Reagent | m/z (ESI): [M + H]+ |
|---|---|---|---|---|
| | 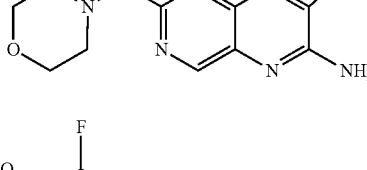 | | | |
| 358 | 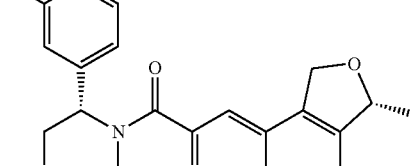<br>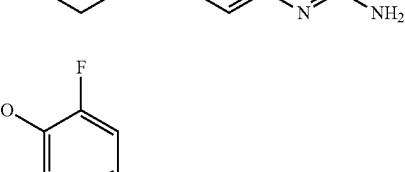 | ((3R)-4-amino-3-methyl-1,3-dihydrofuro[3,4-c][1,7]naphthyridin-8-yl)((3R)-3-(4-fluoro-3-(trifluoromethoxy)phenyl)-4-morpholinyl)methanone and ((3R)-4-amino-3-methyl-1,3-dihydrofuro[3,4-c][1,7]naphthyridin-8-yl)((3S)-3-(4-fluoro-3-(trifluoromethoxy)phenyl)-4-morpholinyl)methanone | HATU | 493.0 |
| 359 | 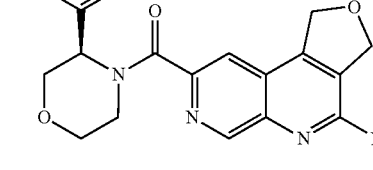<br>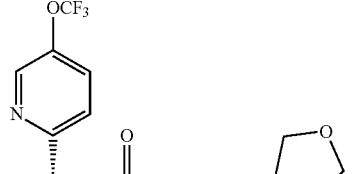 | (4-amino-1,3-dihydrofuro[3,4-c][1,7]naphthyridin-8-yl)((3R,5S)-3-methyl-5-(5-(trifluoromethoxy)-2-pyridinyl)-4-morpholinyl)methanone and (4-amino-1,3-dihydrofuro[3,4-c][1,7]naphthyridin-8-yl)((3S,5R)-3-methyl-5-(5-(trifluoromethoxy)-2-pyridinyl)-4-morpholinyl)methanone | HATU | 476.1 |

TABLE 7-continued

| Ex. | Structure | Name | Coupling Reagent | m/z (ESI): [M + H]+ |
|---|---|---|---|---|
| 360 | 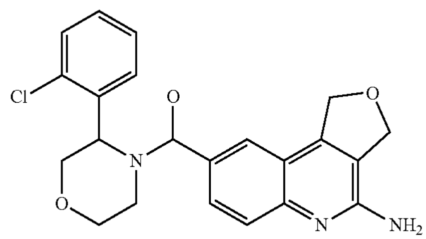 [SMILES: Nc1nc2ccc(C(O)N3CCOCC3c3ccccc3Cl)cc2c2c1COC2] | (4-amino-1,3-dihydrofuro[3,4-c]quinolin-8-yl)-[rac-(3S)-3-(2-chlorophenyl)morpholin-4-yl]methanone | PyBroP | 410.2 |
| 361 | 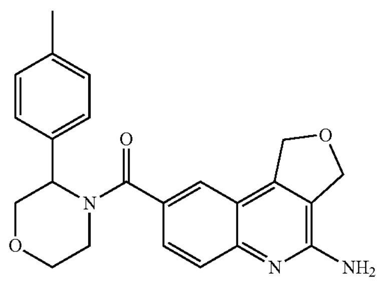 | (4-amino-1,3-dihydrofuro[3,4-c]quinolin-8-yl)-[rac-(3S)-3-(p-tolyl)morpholin-4-yl]methanone | PyBroP | 390.2 |
| 362 | 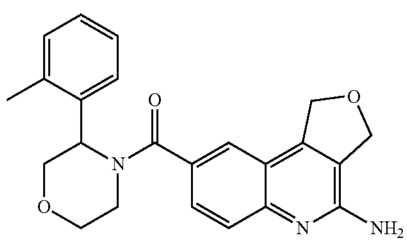 [SMILES: Cc1ccccc1C1COCCN1C(=O)c1ccc2nc(N)c3c(c2c1)COC3] | (4-amino-1,3-dihydrofuro[3,4-c]quinolin-8-yl)-[rac-(3S)-3-(o-tolyl)morpholin-4-yl]methanone | PyBroP | 390.2 |
| 363 | 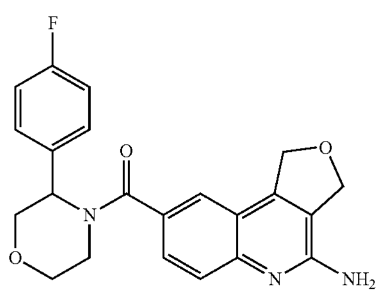 [SMILES: Nc1nc2ccc(C(=O)N3CCOCC3c3ccc(F)cc3)cc2c2c1COC2] | (4-amino-1,3-dihydrofuro[3,4-c]quinolin-8-yl)-[rac-(3S)-3-(4-fluorophenyl)morpholin-4-yl]methanone | PyBroP | 394.2 |
| 364 | 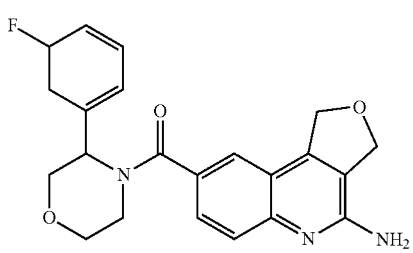 [SMILES: Nc1nc2ccc(C(=O)N3CCOCC3C3=CC=CC(F)C3)cc2c2c1COC2] | (4-amino-1,3-dihydrofuro[3,4-c]quinolin-8-yl)-[rac-(3S)-3-(3-fluorophenyl)morpholin-4-yl]methanone | PyBroP | 394.2 |

TABLE 7-continued

| Ex. | Structure | Name | Coupling Reagent | m/z (ESI): [M + H]+ |
|---|---|---|---|---|
| 365 | 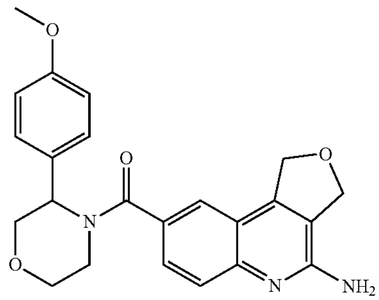 [SMILES: COc1ccc(C2COCCN2C(=O)c2ccc3nc(N)c4c(c3c2)COC4)cc1] | (4-amino-1,3-dihydrofuro[3,4-c]quinolin-8-yl)-[rac-(3S)-3-(4-methoxyphenyl)morpholin-4-yl]methanone | PyBroP | 406.2 |
| 366 | 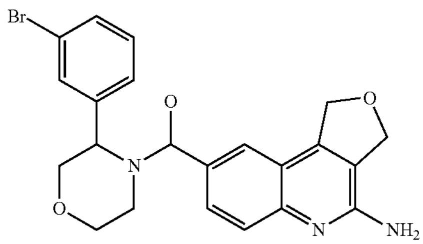 | (4-amino-1,3-dihydrofuro[3,4-c]quinolin-8-yl)-[rac-(3S)-3-(3-bromophenyl)morpholin-4-yl]methanone | PyBroP | 454.0 |
| 367 | 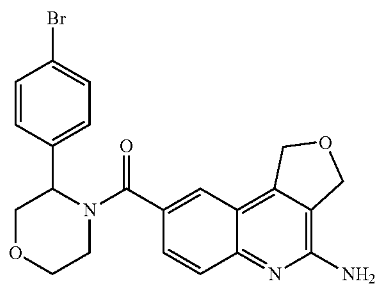 | (4-amino-1,3-dihydrofuro[3,4-c]quinolin-8-yl)-[rac-(3S)-3-(4-bromophenyl)morpholin-4-yl]methanone | PyBroP | 454.1 and 456.0 |
| 368 | 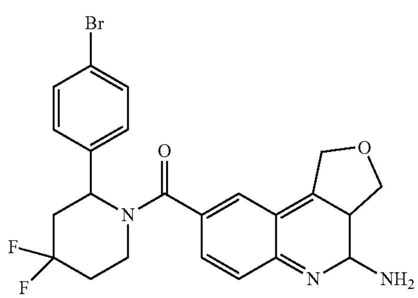 [SMILES: NC1N=c2ccc(C(=O)N3CCC(F)(F)CC3c3ccc(Br)cc3)cc2=C2COCC21] | (4-amino-1,3-dihydrofuro[3,4-c]quinolin-8-yl)-[rac-(2R)-2-(4-bromophenyl)-4,4-difluoro-1-piperidyl]methanone | PyBroP | 488.0 and 490.0 |
| 369 | 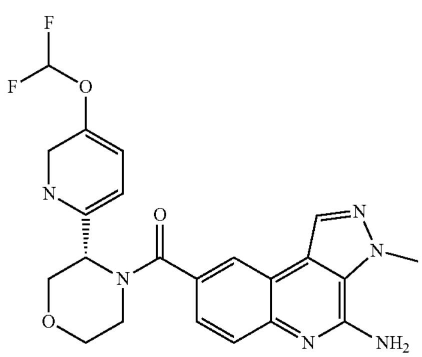 [SMILES: Cn1ncc2c3cc(C(=O)N4CCOC[C@@H]4C4=CC=C(OC(F)F)CN4)ccc3nc(N)c21] | (4-amino-3-methyl-3H-pyrazolo[3,4-c]quinolin-8-yl)((3S)-3-(5-(difluoromethoxy)-2-pyridinyl)-4-morpholinyl)methanone | PyBroP | 455.2 |

TABLE 7-continued

| Ex. | Structure | Name | Coupling Reagent | m/z (ESI): [M + H]+ |
|---|---|---|---|---|
| 370 | 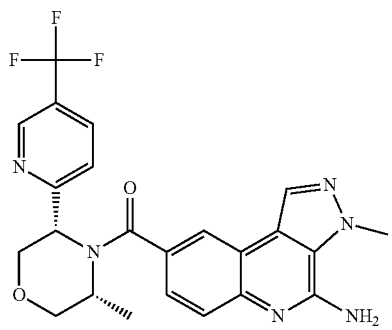 [SMILES: C[C@@H]1COC[C@H](c2ccc(C(F)(F)F)cn2)N1C(=O)c1ccc2nc(N)c3c(cnn3C)c2c1] | (4-amino-3-methyl-3H-pyrazolo[3,4-c]quinolin-8-yl)((3R,5S)-3-methyl-5-(5-(trifluoromethyl)-2-pyridinyl)-4-morpholinyl)methanone | PyBroP | 471.2 |
| 371 | 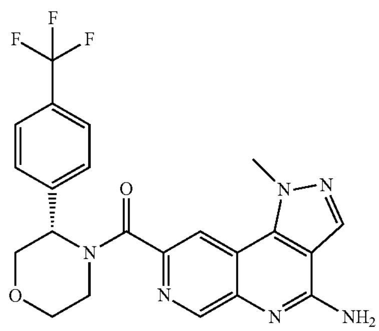 [SMILES: Cn1ncc2c(N)nc3cnc(C(=O)N4CCOC[C@@H]4c4ccc(C(F)(F)F)cc4)cc3c21] | (4-amino-1-methyl-1H-pyrazolo[4,3-c][1,7]naphthyridin-8-yl)((3S)-3-(4-(trifluoromethyl)phenyl)-4-morpholinyl)methanone | PyBroP | 457.2 |
| 372 | | ((3R)-4-amino-3-methyl-1,3-dihydrofuro[3,4-c]quinolin-8-yl)((3R,5S)-3-methyl-5-(5-(trifluoromethyl)-2-pyridinyl)-4-morpholinyl)methanone and ((3R)-4-amino-3-methyl-1,3-dihydrofuro[3,4-c]quinolin-8-yl)((3S,5R)-3-methyl-5-(5-(trifluoromethyl)-2-pyridinyl)-4-morpholinyl)methanone | PyBroP | 473.1 |

TABLE 7-continued

| Ex. | Structure | Name | Coupling Reagent | m/z (ESI): [M + H]+ |
|---|---|---|---|---|
| 373 | | ((3R)-4-amino-3-methyl-1,3-dihydrofuro[3,4-c]quinolin-8-yl)((3R)-3-(4-fluoro-3-(trifluoromethoxy)phenyl)-4-morpholinyl)methanone and ((3R)-4-amino-3-methyl-1,3-dihydrofuro[3,4-c]quinolin-8-yl)((3S)-3-(4-fluoro-3-(trifluoromethoxy)phenyl)-4-morpholinyl)methanone | PyBroP | 492.0 |
| 374 | | ((3R)-4-amino-3-methyl-1,3-dihydrofuro [3,4-c]quinolin-8-yl)((3R)-3-(4-fluoro-3-(trifluoromethyl)phenyl)-4-morpholinyl)methanone and ((3R)-4-amino-3-methyl-1,3-dihydrofuro[3,4-c]quinolin-8-yl)((3S)-3-(4-fluoro-3-(trifluoromethyl)phenyl)-4-morpholinyl)methanone | PyBroP | 476.1 |
| 375 | 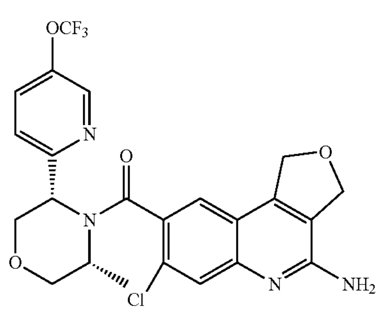 [SMILES: C[C@@H]1COC[C@H](c2ccc(OC(F)(F)F)cn2)N1C(=O)c1cc2c3c(c(N)nc2cc1Cl)COC3] | (4-amino-7-chloro-1,3-dihydrofuro[3,4-c]quinolin-8-yl)((3R,5S)-3-methyl-5-(5-(trifluoromethoxy)-2-pyridinyl)-4-morpholinyl)methanone and (4-amino-7-chloro-1,3-dihydrofuro[3,4-c]quinolin-8-yl)((3S,5R)-3-methyl-5-(5-(trifluoromethoxy)-2-pyridinyl)-4-morpholinyl)methanone | PyBroP | 509.0 |

| Ex. | Structure | Name | Coupling Reagent | m/z (ESI): [M + H]+ |
|---|---|---|---|---|
| | (structure with OCF3 pyridine, methyl morpholine, chloro dihydrofuroquinolin-amine) | | | |
| 376 | (structure) | (4-amino-1,3-dihydrofuro[3,4-c]quinolin-8-yl)((3R,5S)-3-methyl-5-(5-(trifluoromethoxy)-2-pyridinyl)-4-morpholinyl)methanone and (4-amino-1,3-dihydrofuro[3,4-c]quinolin-8-yl)((3S,5R)-3-methyl-5-(5-(trifluoromethoxy)-2-pyridinyl)-4-morpholinyl)methanone | PyBroP | 475.1 |
| 377 | (structure) | ((3R)-4-amino-3-methyl-1,3-dihydrofuro[3,4-c]quinolin-8-yl)((3R,5S)-3-methyl-5-(5-(trifluoromethoxy)-2-pyridinyl)-4-morpholinyl)methanone and ((3R)-4-amino-3-methyl-1,3-dihydrofuro[3,4-c]quinolin-8-yl)((3S,5R)-3-methyl-5-(5-(trifluoromethoxy)-2-pyridinyl)-4-morpholinyl)methanone | PyBroP | 489.2 |

TABLE 7-continued

| Ex. | Structure | Name | Coupling Reagent | m/z (ESI): [M + H]⁺ |
|---|---|---|---|---|
| 378 | | (4-amino-7-fluoro-1,3-dihydrofuro[3,4-c]quinolin-8-yl)((3R,5S)-3-methyl-5-(5-(trifluoromethoxy)-2-pyridinyl)-4-morpholinyl)methanone and (4-amino-7-fluoro-1,3-dihydrofuro[3,4-c]quinolin-8-yl)((3S,5R)-3-methyl-5-(5-(trifluoromethoxy)-2-pyridinyl)-4-morpholinyl)methanone | PyBroP | 493.0 |
| 379 | | ((3S)-4-amino-3-methyl-1,3-dihydrofuro[3,4-c][1,7]naphthyridin-8-yl)((3R,5S)-3-methyl-5-(5-(trifluoromethoxy)-2-pyridinyl)-4-morpholinyl)methanone and ((3S)-4-amino-3-methyl-1,3-dihydrofuro[3,4-c][1,7]naphthyridin-8-yl)((3S,5R)-3-methyl-5-(5-(trifluoromethoxy)-2-pyridinyl)-4-morpholinyl)methanone | PyBroP | 490.0 |

| Ex. | Structure | Name | Coupling Reagent | m/z (ESI): [M + H]+ |
|---|---|---|---|---|
| 380 | | ((3R)-4-amino-3-methyl-1,3-dihydrofuro[3,4-c][1,7]naphthyridin-8-yl)((3R,5S)-3-methyl-5-(5-(trifluoromethoxy)-2-pyridinyl)-4-morpholinyl)methanone and ((3R)-4-amino-3-methyl-1,3-dihydrofuro[3,4-c][1,7]naphthyridin-8-yl)((3S,5R)-3-methyl-5-(5-(trifluoromethoxy)-2-pyridinyl)-4-morpholinyl)methanone | PyBroP | 490.0 |
| 381 | | (4-amino-1,3-dihydrofuro[3,4-c][1,7]naphthyridin-8-yl)((3R,5S)-3-(6-(difluoromethoxy)-3-pyridazinyl)-5-methyl-4-morpholinyl)methanone and (4-amino-1,3-dihydrofuro[3,4-c][1,7]naphthyridin-8-yl)((3S,5R)-3-(6-(difluoromethoxy)-3-pyridazinyl)-5-methyl-4-morpholinyl)methanone | PyBroP | 459.0 |
| 382 | 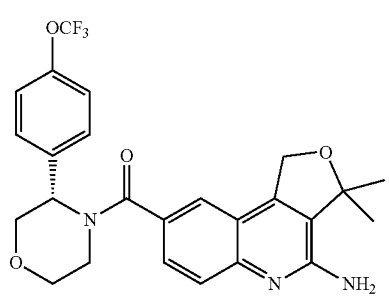 [SMILES: CC1(C)OCc2c1c(N)nc1ccc(C(=O)N3CCOC[C@@H]3c3ccc(OC(F)(F)F)cc3)cc21] | (4-amino-3,3-dimethyl-1H-furo[3,4-c]quinolin-8-yl)-[(3S)-3-[4-(trifluoromethoxy)phenyl]morpholin-4-yl]methanone | PyBroP | 488.2 |

TABLE 7-continued

| Ex. | Structure | Name | Coupling Reagent | m/z (ESI): [M + H]+ |
|---|---|---|---|---|
| 383 | 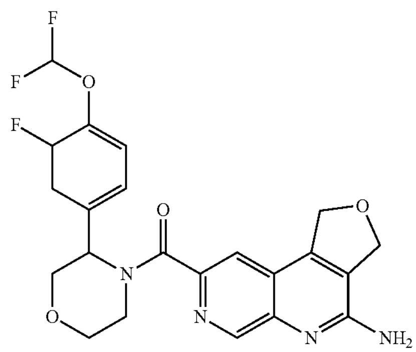 [SMILES: Nc1nc2cnc(C(=O)N3CCOCC3C3=CC=C(OC(F)F)C(F)C3)cc2c2c1COC2] | (4-amino-1,3-dihydrofuro[3,4-c][1,7]naphthyridin-8-yl)((3R)-3-(4-(difluoromethoxy)-3-fluorophenyl)-4-morpholinyl)methanone and (4-amino-1,3-dihydrofuro[3,4-c][1,7]naphthyridin-8-yl)((3S)-3-(4-(difluoromethoxy)-3-fluorophenyl)-4-morpholinyl)methanone | PyBroP | 461.0 |
| 384 | 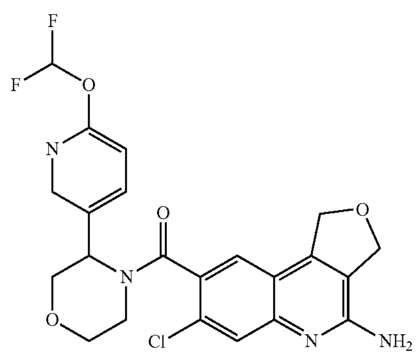 [SMILES: Nc1nc2cc(F)c(C(=O)N3CCOCC3C3=CC=C(OC(F)F)NC3)cc2c2c1COC2] | (4-amino-7-chloro-1,3-dihydrofuro[3,4-c]quinolin-8-yl)((3R)-3-(6-(difluoromethoxy)-3-pyridinyl)-4-morpholinyl)methanone and (4-amino-7-chloro-1,3-dihydrofuro[3,4-c]quinolin-8-yl)((3S)-3-(6-(difluoromethoxy)-3-pyridinyl)-4-morpholinyl)methanone | PyBroP | 477.1 |
| 385 | 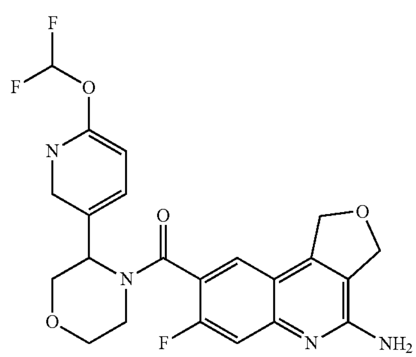 | (4-amino-7-fluoro-1,3-dihydrofuro[3,4-c]quinolin-8-yl)((3R)-3-(6-(difluoromethoxy)-3-pyridinyl)-4-morpholinyl)methanone and (4-amino-7-fluoro-1,3-dihydrofuro[3,4-c]quinolin-8-yl)((3S)-3-(6-(difluoromethoxy)-3-pyridinyl)-4-morpholinyl)methanone | PyBroP | 461.1 |
| 386 | 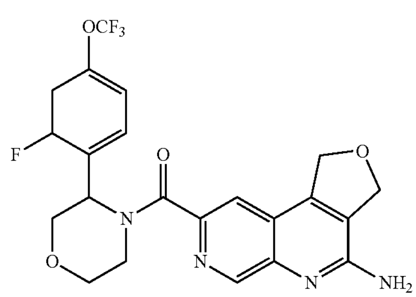 [SMILES: Nc1nc2cnc(C(=O)N3CCOCC3C3=CC=C(OC(F)(F)F)CC3F)cc2c2c1COC2] | (4-amino-1,3-dihydrofuro[3,4-c][1,7]naphthyridin-8-yl)((3R)-3-(2-fluoro-4-(trifluoromethoxy)phenyl)-4-morpholinyl)methanone and (4-amino-1,3-dihydrofuro[3,4-c][1,7]naphthyridin-8-yl)((3S)-3-(2-fluoro-4-(trifluoromethoxy)phenyl)-4-morpholinyl)methanone | PyBroP | 479.0 |

TABLE 7-continued

| Ex. | Structure | Name | Coupling Reagent | m/z (ESI): [M + H]+ |
|---|---|---|---|---|
| 387 | 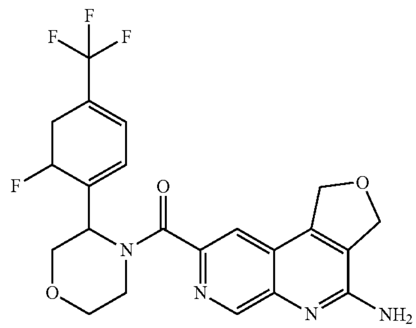 [SMILES: Nc1nc2cnc(C(=O)N3CCOCC3C3=CC=C(C(F)(F)F)CC3F)cc2c2c1COC2] | (4-amino-1,3-dihydrofuro[3,4-c][1,7]naphthyridin-8-yl)((3R)-3-(2-fluoro-4-(trifluoromethyl)phenyl)-4-morpholinyl)methanone and (4-amino-1,3-dihydrofuro[3,4-c][1,7]naphthyridin-8-yl)((3S)-3-(2-fluoro-4-(trifluoromethyl)phenyl)-4-morpholinyl)methanone | PyBroP | 463.2 |
| 388 | 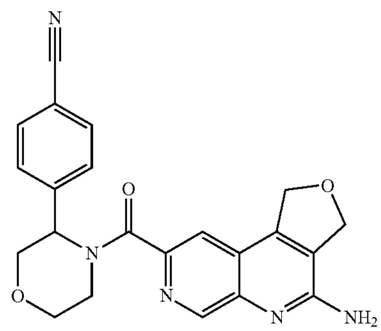 [SMILES: N#Cc1ccc(C2COCCN2C(=O)c2cc3c4c(c(N)nc3cn2)COC4)cc1] | 4-((3R)-4-((4-amino-1,3-dihydrofuro[3,4-c][1,7]naphthyridin-8-yl)carbonyl)-3-morpholinyl)benzonitrile and 4-((3S)-4-((4-amino-1,3-dihydrofuro[3,4-c][1,7]naphthyridin-8-yl)carbonyl)-3-morpholinyl)benzonitrile | PyBroP | 402.2 |
| 389 | 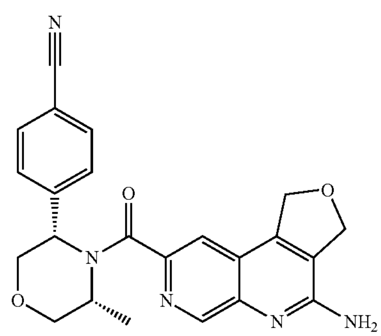 [SMILES: C[C@@H]1COC[C@H](c2ccc(C#N)cc2)N1C(=O)c1cc2c3c(c(N)nc2cn1)COC3] | 4-((3R,5S)-4-((4-amino-1,3-dihydrofuro[3,4-c][1,7]naphthyridin-8-yl)carbonyl)-5-methyl-3-morpholinyl)benzonitrile and 4-((3S,5R)-4-((4-amino-1,3-dihydrofuro[3,4-c][1,7]naphthyridin-8-yl)carbonyl)-5-methyl-3-morpholinyl)benzonitrile | PyBroP | 416.2 |

TABLE 7-continued

| Ex. | Structure | Name | Coupling Reagent | m/z (ESI): [M + H]+ |
|---|---|---|---|---|
| 390 | 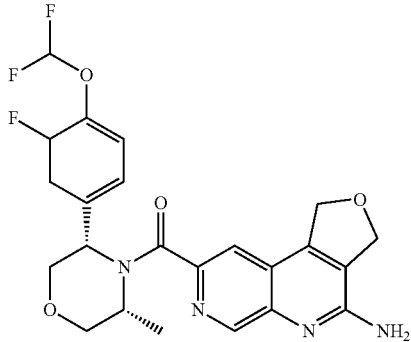 [SMILES: C[C@@H]1COC[C@H](C2=CC=C(OC(F)F)C(F)C2)N1C(=O)c1cc2c3c(c(N)nc2cn1)COC3] | (4-amino-1,3-dihydrofuro[3,4-c][1,7]naphthyridin-8-yl)((3R,5S)-3-(4-(difluoromethoxy)-3-fluorophenyl)-5-methyl-4-morpholinyl)methanone and (4-amino-1,3-dihydrofuro[3,4-c][1,7]naphthyridin-8-yl)((3S,5R)-3-(4-(difluoromethoxy)-3-fluorophenyl)-5-methyl-4-morpholinyl)methanone | PyBroP | 475.2 |
| 391 | 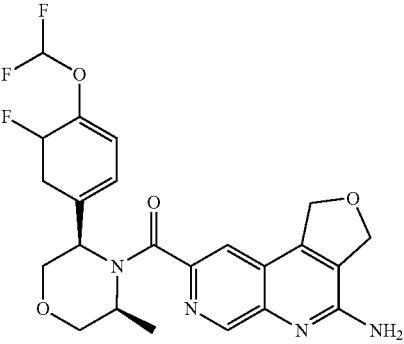 [SMILES: C[C@H]1COC[C@@H](C2=CC=C(OC(F)F)C(F)C2)N1C(=O)c1cc2c3c(c(N)nc2cn1)COC3] | (4-amino-7-chloro-1,3-dihydrofuro[3,4-c]quinolin-8-yl)((3R)-3-(6-ethoxy-3-pyridazinyl)-4-morpholinyl)methanone and (4-amino-7-chloro-1,3-dihydrofuro[3,4-c]quinolin-8-yl)((3S)-3-(6-ethoxy-3-pyridazinyl)-4-morpholinyl)methanone | PyBroP | 456.1 |
| 392 | 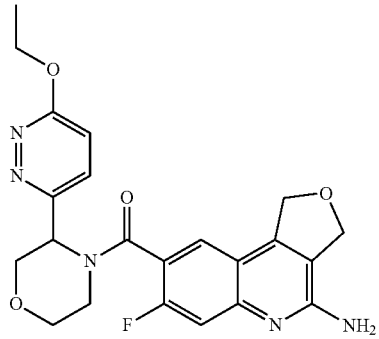 [SMILES: CCOc1ccc(C2COCCN2C(=O)c2cc3c4c(c(N)nc3cc2F)COC4)nn1] | (4-amino-7-fluoro-1,3-dihydrofuro[3,4-c]quinolin-8-yl)((3R)-3-(6-ethoxy-3-pyridazinyl)-4-morpholinyl)methanone and (4-amino-7-fluoro-1,3-dihydrofuro[3,4-c]quinolin-8-yl)((3S)-3-(6-ethoxy-3-pyridazinyl)-4-morpholinyl)methanone | PyBroP | 440.2 |

TABLE 7-continued

| Ex. | Structure | Name | Coupling Reagent | m/z (ESI): [M + H]+ |
|---|---|---|---|---|
| 393 | 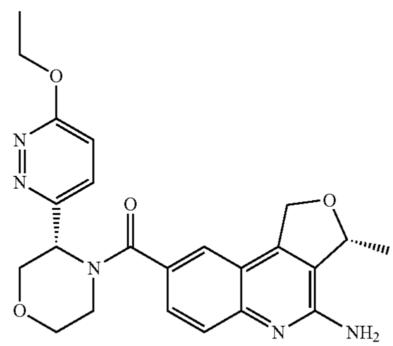 [SMILES: CCOc1ccc([C@H]2COCCN2C(=O)c2ccc3nc(N)c4c(c3c2)CO[C@@H]4C)nn1] | ((3R)-4-amino-3-methyl-1,3-dihydrofuro[3,4-c]quinolin-8-yl)((3R)-3-(6-ethoxy-3-pyridazinyl)-4-morpholinyl)methanone and ((3R)-4-amino-3-methyl-1,3-dihydrofuro[3,4-c]quinolin-8-yl)((3S)-3-(6-ethoxy-3-pyridazinyl)-4-morpholinyl)methanone | PyBroP | 436.2 |
| 394 | 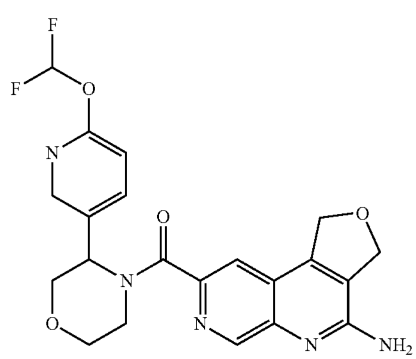 [SMILES: Nc1nc2cnc(C(=O)N3CCOCC3C3=CC=C(OC(F)F)NC3)cc2c2c1COC2] | (4-amino-1,3-dihydrofuro[3,4-c][1,7]naphthyridin-8-yl)((3R)-3-(6-(difluoromethoxy)-3-pyridinyl)-4-morpholinyl)methanone (4-amino-1,3-dihydrofuro[3,4-c][1,7]naphthyridin-8-yl)((3S)-3-(6-(difluoromethoxy)-3-pyridinyl)-4-morpholinyl)methanone | PyBroP | 444.1 |
| 395 | 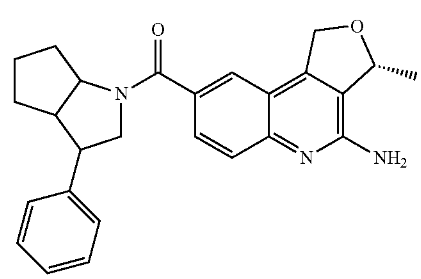 [SMILES: C[C@H]1OCc2c1c(N)nc1ccc(C(=O)N3CC(c4ccccc4)C4CCCC43)cc21] | ((3R)-4-amino-3-methyl-1,3-dihydrofuro[3,4-c]quinolin-8-yl)(3-phenylhexahydrocyclopenta[b]pyrrol-1(2H)-yl)methanone | TBTU | 414.2 |

TABLE 7-continued

| Ex. | Structure | Name | Coupling Reagent | m/z (ESI): [M + H]+ |
|---|---|---|---|---|
| 396 | 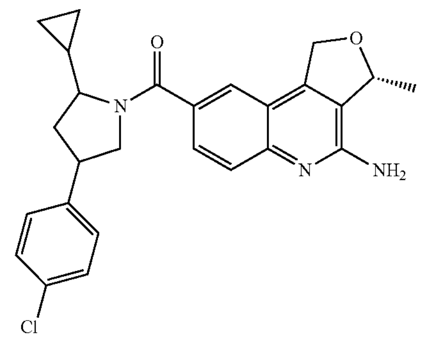 [SMILES: C[C@H]1OCc2c1c(N)nc1ccc(C(=O)N3CC(c4ccc(Cl)cc4)CC3C3CC3)cc21] | ((3R)-4-amino-3-methyl-1,3-dihydrofuro[3,4-c]quinolin-8-yl)(4-(4-chlorophenyl)-2-cyclopropylpyrrolidin-1-yl)methanone | TBTU | 448.2 |
| 397 | 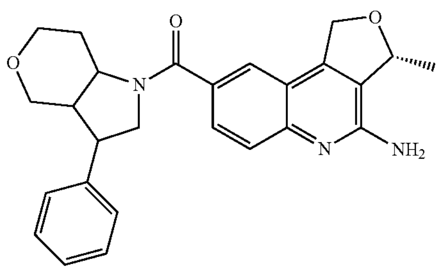 [SMILES: C[C@H]1OCc2c1c(N)nc1ccc(C(=O)N3CC(c4ccccc4)C4COCCC43)cc21] | ((3R)-4-amino-3-methyl-1,3-dihydrofuro[3,4-c]quinolin-8-yl)(3-phenylhexahydropyrano[4,3-b]pyrrol-1(4H)-yl)methanone | TBTU | 430.2 |
| 398 | 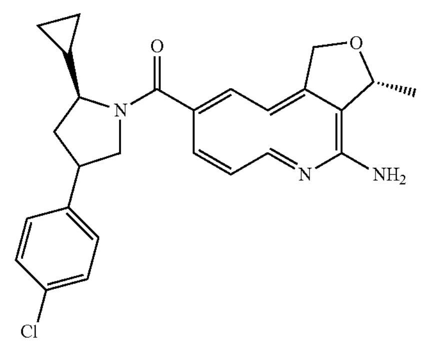 [SMILES: C[C@H]1OCc2ccc(C(=O)N3CC(c4ccc(Cl)cc4)C[C@H]3C3CC3)cccnc(N)c21] | ((3R)-4-amino-3-methyl-1,3-dihydrofuro[3,4-c]quinolin-8-yl)((2S,4S)-4-(4-chlorophenyl)-2-cyclopropyl-1-pyrrolidinyl)methanone | TBTU | 448.2 |
| 399 | 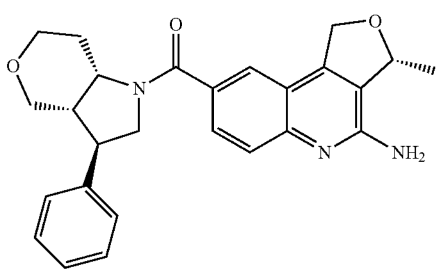 [SMILES: C[C@H]1OCc2c1c(N)nc1ccc(C(=O)N3C[C@@H](c4ccccc4)[C@@H]4COCC[C@@H]43)cc21] | ((3R)-4-amino-3-methyl-1,3-dihydrofuro[3,4-c]quinolin-8-yl)((3R,3aS,7aS)-3-phenylhexahydropyrano[4,3-b]pyrrol-1(4H)-yl)methanone | TBTU | 430.2 |
| 400 | 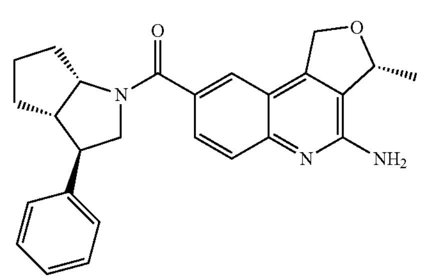 [SMILES: C[C@H]1OCc2c1c(N)nc1ccc(C(=O)N3C[C@@H](c4ccccc4)[C@@H]4CCC[C@@H]43)cc21] | ((3R)-4-amino-3-methyl-1,3-dihydrofuro[3,4-c]quinolin-8-yl)((3R,3aS,6aS)-3-phenylhexahydrocyclopenta[b]pyrrol-1(2H)-yl)methanone | TBTU | 414.2 |

TABLE 7-continued

| Ex. | Structure | Name | Coupling Reagent | m/z (ESI): [M + H]+ |
|---|---|---|---|---|
| 401 | 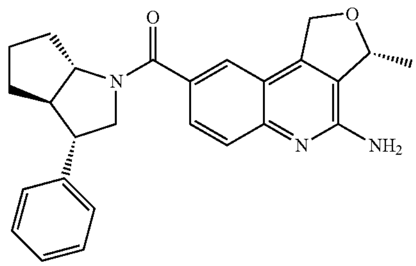 [SMILES: C[C@H]1OCc2c1c(N)nc1ccc(C(=O)N3C[C@H](c4ccccc4)[C@H]4CCC[C@@H]43)cc21] | ((3R)-4-amino-3-methyl-1,3-dihydrofuro[3,4-c]quinolin-8-yl)((3S,3aR,6aS)-3-phenylhexahydrocyclopenta[b]pyrrol-1(2H)-yl)methanone | TBTU | 414.2 |
| 402 | 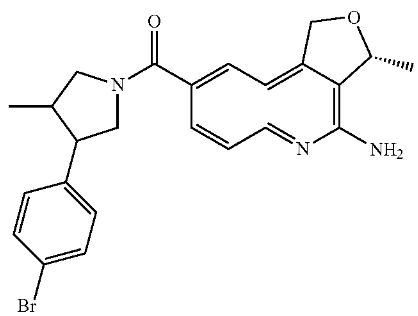 | ((3R)-4-amino-3-methyl-1,3-dihydrofuro[3,4-c]quinolin-8-yl)(3-(4-bromophenyl)-4-methylpyrrolidin-1-yl)methanone | TBTU | 465.8 and 467.8 |
| 403 | 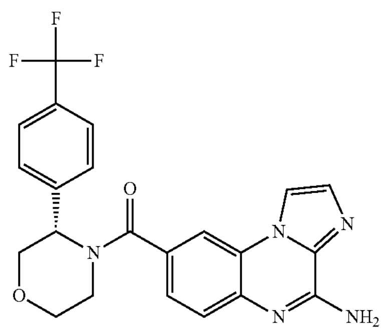 [SMILES: Nc1nc2ccc(C(=O)N3CCOC[C@@H]3c3ccc(C(F)(F)F)cc3)cc2n2ccnc12] | (4-aminoimidazo[1,2-a]quinoxalin-8-yl)((3S)-3-(4-(trifluoromethyl)phenyl)-4-morpholinyl)methanone | HATU | 442.1 |
| 404 | 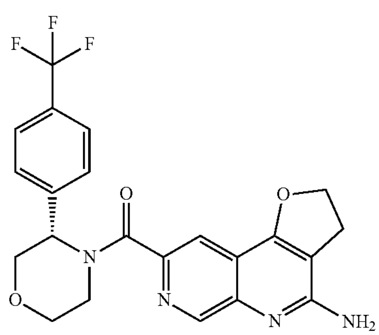 [SMILES: Nc1nc2cnc(C(=O)N3CCOC[C@@H]3c3ccc(C(F)(F)F)cc3)cc2c2c1CCO2] | (4-amino-2,3-dihydrofuro[3,2-c][1,7]naphthyridin-8-yl)((3S)-3-(4-(trifluoromethyl)phenyl)-4-morpholinyl)methanone | HATU | 445.2 |
| 405 | 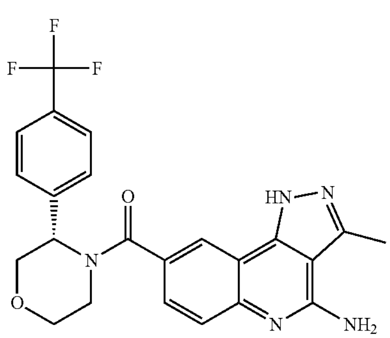 [SMILES: Cc1n[nH]c2c1c(N)nc1ccc(C(=O)N3CCOC[C@@H]3c3ccc(C(F)(F)F)cc3)cc12] | (4-amino-3-methyl-1H-pyrazolo[4,3-d]quinolin-8-yl)((3S)-3-(4-(trifluoromethyl)phenyl)-4-morpholinyl)methanone | HATU | 455.9 |

TABLE 7-continued

| Ex. | Structure | Name | Coupling Reagent | m/z (ESI): [M + H]+ |
|---|---|---|---|---|
| 406 | 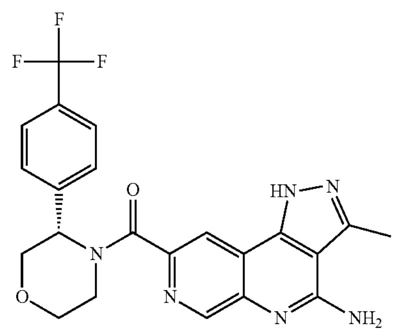 [SMILES: Cc1n[nH]c2c1c(N)nc1cnc(C(=O)N3CCOC[C@@H]3c3ccc(C(F)(F)F)cc3)cc12] | (4-amino-3-methyl-1H-pyrazolo[4,3-c][1,7]naphthyridin-8-yl)((3S)-3-(4-(trifluoromethyl)phenyl)-4-morpholinyl)methanone | HATU | 456.9 |
| 407 | 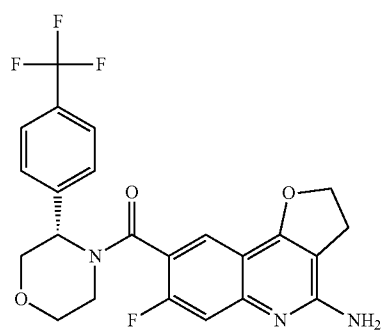 | (4-amino-7-fluoro-2,3-dihydrofuro[3,2-c]quinolin-8-yl)((3S)-3-(4-(trifluoromethyl)phenyl)-4-morpholinyl)methanone | HATU | 462.1 |
| 408 | 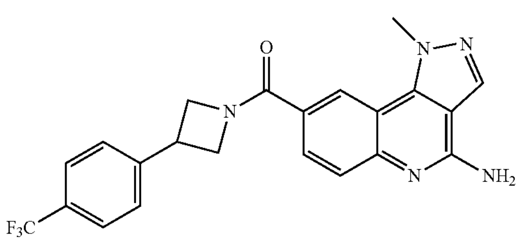 [SMILES: Cn1ncc2c(N)nc3ccc(C(=O)N4CC(c5ccc(C(F)(F)F)cc5)C4)cc3c21] | (4-amino-1-methyl-1H-pyrazolo[4,3-c]quinolin-8-yl)(3-(4-(trifluoromethyl)phenyl)-1-azetidinyl)methanone | HATU | 426.0 |
| 409 | 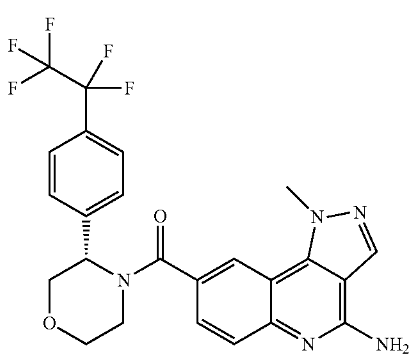 [SMILES: Cn1ncc2c(N)nc3ccc(C(=O)N4CCOC[C@@H]4c4ccc(C(F)(F)C(F)(F)F)cc4)cc3c21] | (4-amino-1-methyl-1H-pyrazolo[4,3-c]quinolin-8-yl)((3S)-3-(4-(pentafluoroethyl)phenyl)-4-morpholinyl)methanone | HATU | 506.0 |

TABLE 7-continued

| Ex. | Structure | Name | Coupling Reagent | m/z (ESI): [M + H]+ |
|---|---|---|---|---|
| 410 | 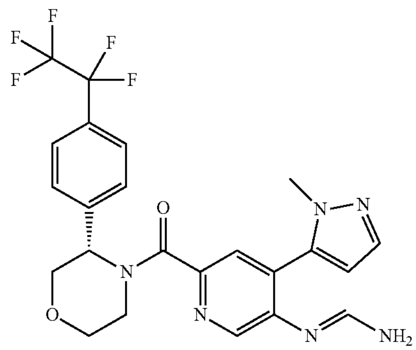 [SMILES: Cn1nccc1-c1cc(C(=O)N2CCOC[C@@H]2c2ccc(C(F)(F)C(F)(F)F)cc2)ncc1/N=C/N] | (4-amino-1-methyl-1H-pyrazolo[4,3-c][1,7]naphthyridin-8-yl)((3S)-3-(4-(pentafluoroethyl)phenyl)-4-morpholinyl)methanone | HATU | 507.0 |
| 411 | 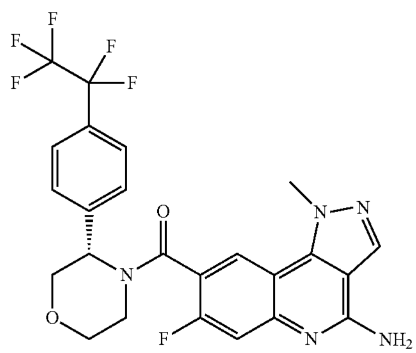 [SMILES: Cn1ncc2c(N)nc3cc(F)c(C(=O)N4CCOC[C@@H]4c4ccc(C(F)(F)C(F)(F)F)cc4)cc3c21] | (4-amino-7-fluoro-1-methyl-1H-pyrazolo[4,3-c]quinolin-8-yl)((3S)-3-(4-(pentafluoroethyl)phenyl)-4-morpholinyl)methanone | HATU | 524.0 |
| 412 | 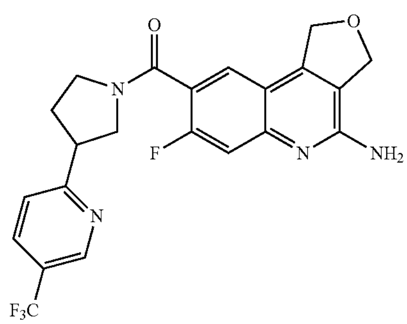 [SMILES: Nc1nc2cc(F)c(C(=O)N3CCC(c4ccc(C(F)(F)F)cn4)C3)cc2c2c1COC2] | (4-amino-7-fluoro-1,3-dihydrofuro[3,4-c]quinolin-8-yl)((3R)-3-(5-(trifluoromethyl)-2-pyridinyl)-1-pyrrolidinyl)methanone and (4-amino-7-fluoro-1,3-dihydrofuro [3,4-c]quinolin-8-yl)((3S)-3-(5-(trifluoromethyl)-2-pyridinyl)-1-pyrrolidinyl)methanone | TBTU | 447.1 |
| 413 | 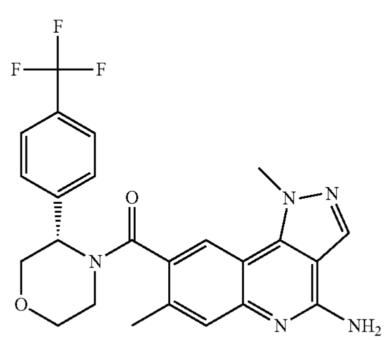 | (4-amino-1,7-dimethyl-1H-pyrazolo[4,3-c]quinolin-8-yl)((3S)-3-(4-(trifluoromethyl)phenyl)-4-morpholinyl)methanone | TBTU | 470.2 |

TABLE 7-continued

| Ex. | Structure | Name | Coupling Reagent | m/z (ESI): [M + H]+ |
|---|---|---|---|---|
| 414 | 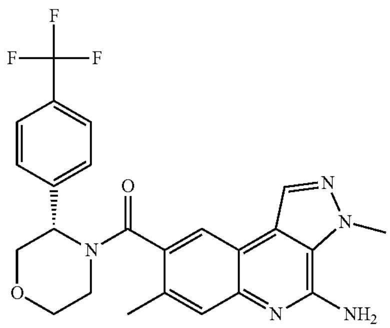 [SMILES: Cc1cc2nc(N)c3c(cnn3C)c2cc1C(=O)N1CCOC[C@@H]1c1ccc(C(F)(F)F)cc1] | (4-amino-3,7-dimethyl-3H-pyrazolo[3,4-c]quinolin-8-yl)((3S)-3-(4-(trifluoromethyl)phenyl)-4-morpholinyl)methanone | TBTU | 470.2 |
| 415 | 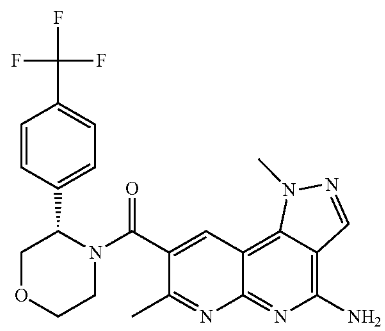 [SMILES: Cc1nc2nc(N)c3cnn(C)c3c2cc1C(=O)N1CCOC[C@@H]1c1ccc(C(F)(F)F)cc1] | (4-amino-1,7-dimethyl-1H-pyrazolo[4,3-c][1,8]naphthyridin-8-yl)((3S)-3-(4-(trifluoromethyl)phenyl)-4-morpholinyl)methanone | TBTU | 471.2 |
| 416 | 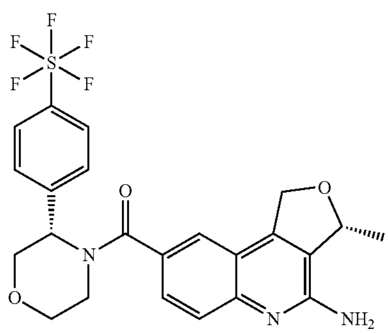 [SMILES: C[C@H]1OCc2c1c(N)nc1ccc(C(=O)N3CCOC[C@@H]3c3ccc(S(F)(F)(F)(F)F)cc3)cc21] | ((3R)-4-amino-3-methyl-1,3-dihydrofuro[3,4-c]quinolin-8-yl)((3S)-3-(4-(pentafluoro-lambda~6~-sulfanyl)phenyl)-4-morpholinyl)methanone | TBTU | 515.0 |
| 417 | 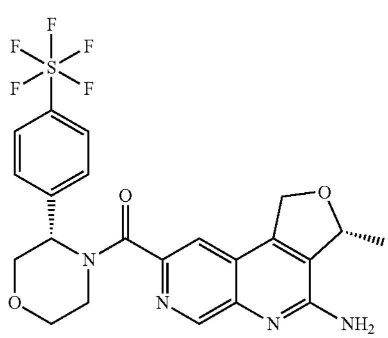 [SMILES: C[C@H]1OCc2c1c(N)nc1cnc(C(=O)N3CCOC[C@@H]3c3ccc(S(F)(F)(F)(F)F)cc3)cc21] | ((3R)-4-amino-3-methyl-1,3-dihydrofuro[3,4-c][1,7]naphthyridin-8-yl)((3S)-3-(4-(pentafluoro-lambda~6~-sulfanyl)phenyl)-4-morpholinyl)methanone | TBTU | 517.2 |

TABLE 7-continued

| Ex. | Structure | Name | Coupling Reagent | m/z (ESI): [M + H]+ |
|---|---|---|---|---|
| 418 | 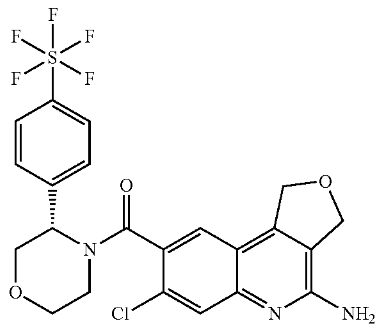 [SMILES: Nc1nc2cc(Cl)c(C(=O)N3CCOC[C@@H]3c3ccc(S(F)(F)(F)(F)F)cc3)cc2c2c1COC2] | (4-amino-7-chloro-1,3-dihydrofuro[3,4-c]quinolin-8-yl)((3S)-3-(4-(pentafluoro-lambda~6~-sulfanyl)phenyl)-4-morpholinyl)methanone | TBTU | 535.8 |
| 419 | 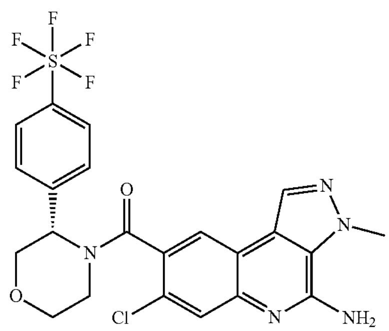 [SMILES: Cn1ncc2c3cc(C(=O)N4CCOC[C@@H]4c4ccc(S(F)(F)(F)(F)F)cc4)c(Cl)cc3nc(N)c21] | (4-amino-7-chloro-3-methyl-3H-pyrazolo[3,4-c]quinolin-8-yl)((3S)-3-(4-(pentafluoro-lambda~6~-sulfanyl)phenyl)-4-morpholinyl)methanone | TBTU | 548.2 |
| 420 | 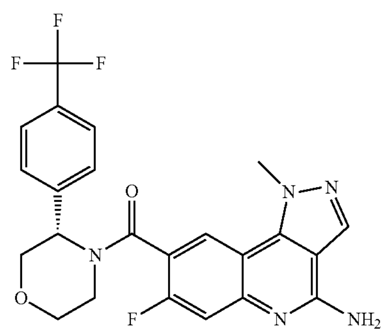 [SMILES: Cn1ncc2c(N)nc3cc(F)c(C(=O)N4CCOC[C@@H]4c4ccc(C(F)(F)F)cc4)cc3c21] | (4-amino-7-fluoro-1-methyl-1H-pyrazolo[4,3-c]quinolin-8-yl)((3S)-3-(4-(trifluoromethyl)phenyl)-4-morpholinyl)methanone | TBTU | 473.8 |
| 421 | 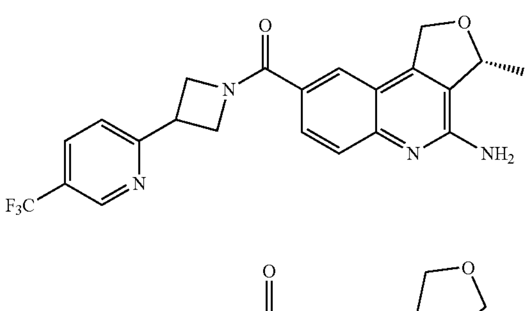 | ((3R)-4-amino-3-methyl-1,3-dihydrofuro[3,4-c]quinolin-8-yl)(3-(5-(trifluoromethyl)-2-pyridinyl)-1-azetidinyl)methanone | TBTU | 429.2 |
| 422 | 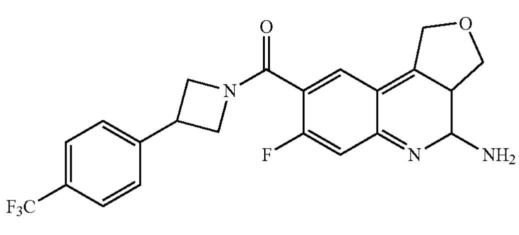 | (4-amino-7-fluoro-1,3-dihydrofuro[3,4-c]quinolin-8-yl)(3-(4-(trifluoromethyl)phenyl)-1-azetidinyl)methanone | TBTU | 432.2 |

TABLE 7-continued

| Ex. | Structure | Name | Coupling Reagent | m/z (ESI): [M + H]+ |
|---|---|---|---|---|
| 423 | 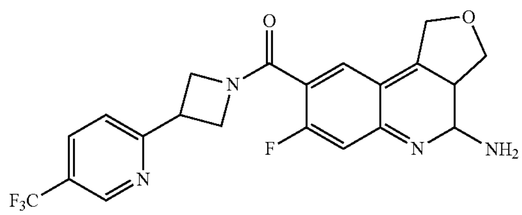 [SMILES: NC1N=c2cc(F)c(C(=O)N3CC(c4ccc(C(F)(F)F)cn4)C3)cc2=C2COCC21] | (4-amino-7-fluoro-1,3-dihydrofuro[3,4-c]quinolin-8-yl)(3-(5-(trifluoromethyl)-2-pyridinyl)-1-azetidinyl)methanone | TBTU | 433.2 |
| 424 | | (4-amino-7-chloro-1,3-dihydrofuro[3,4-c]quinolin-8-yl)((3R,4S)-3-ethyl-4-(4-methylphenyl)-1-pyrrolidinyl)methanone and (4-amino-7-chloro-1,3-dihydrofuro[3,4-c]quinolin-8-yl)((3S,4R)-3-ethyl-4-(4-methylphenyl)-1-pyrrolidinyl)methanone | TBTU | 436.9 |
| 425 | 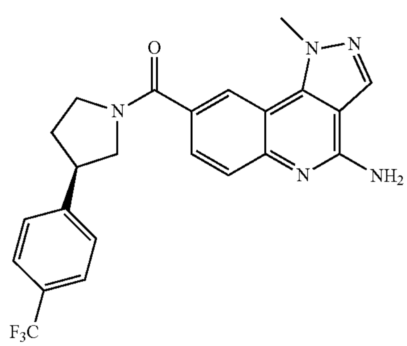 [SMILES: Cn1ncc2c(N)nc3ccc(C(=O)N4CC[C@H](c5ccc(C(F)(F)F)cc5)C4)cc3c21] | (4-amino-1-methyl-1H-pyrazolo[4,3-c]quinolin-8-yl)((3R)-3-(4-(trifluoromethyl)phenyl)-1-pyrrolidinyl)methanone | TBTU | 440.9 |
| 426 | 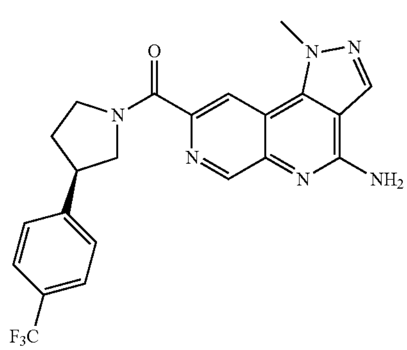 | (4-amino-1-methyl-1H-pyrazolo[4,3-c][1,7]naphthyridin-8-yl)((3R)-3-(4-(trifluoromethyl)phenyl)-1-pyrrolidinyl)methanone | TBTU | 441.9 |

TABLE 7-continued

| Ex. | Structure | Name | Coupling Reagent | m/z (ESI): [M + H]+ |
|---|---|---|---|---|
| 427 | 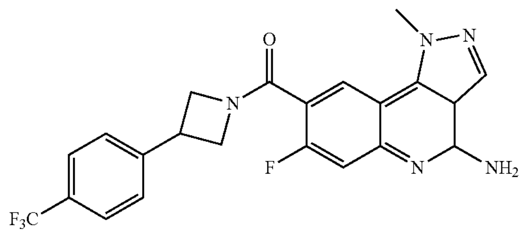 [SMILES: CN1N=CC2C1=c1cc(C(=O)N3CC(c4ccc(C(F)(F)F)cc4)C3)c(F)cc1=NC2N] | (4-amino-7-fluoro-1-methyl-1H-pyrazolo[4,3-c]quinolin-8-yl)(3-(4-(trifluoromethyl)phenyl)-1-azetidinyl)methanone | TBTU | 444.9 |
| 428 | 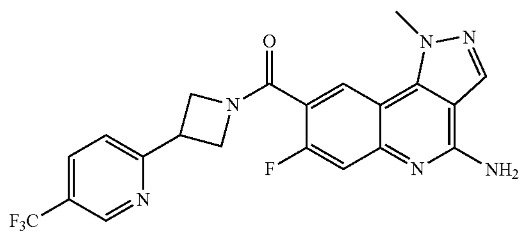 [SMILES: Cn1ncc2c(N)nc3cc(F)c(C(=O)N4CC(c5ccc(C(F)(F)F)cn5)C4)cc3c21] | (4-amino-7-fluoro-1-methyl-1H-pyrazolo[4,3-c]quinolin-8-yl)(3-(5-(trifluoromethyl)-2-pyridinyl)-1-azetidinyl)methanone | TBTU | 445.9 |
| 429 | 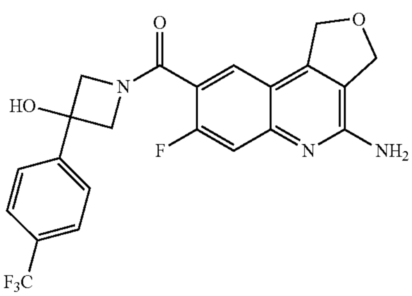 [SMILES: Nc1nc2cc(F)c(C(=O)N3CC(O)(c4ccc(C(F)(F)F)cc4)C3)cc2c2c1COC2] | (4-amino-7-fluoro-1,3-dihydrofuro[3,4-c]quinolin-8-yl)(3-hydroxy-3-(4-(trifluoromethyl)phenyl)-1-azetidinyl)methanone | TBTU | 447.9 |
| 430 | 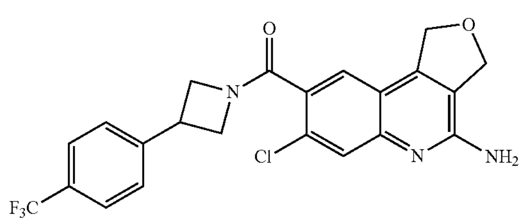 [SMILES: Nc1nc2cc(Cl)c(C(=O)N3CC(c4ccc(C(F)(F)F)cc4)C3)cc2c2c1COC2] | (4-amino-7-chloro-1,3-dihydrofuro[3,4-c]quinolin-8-yl)(3-(4-(trifluoromethyl)phenyl)-1-azetidinyl)methanone | TBTU | 448.2 |
| 431 | | ((3R)-4-amino-3-methyl-1,3-dihydrofuro[3,4-c]quinolin-8-yl)((3R,4R)-3,4-diphenyl-1-pyrrolidinyl)methanone and ((3R)-4-amino-3-methyl-1,3-dihydrofuro[3,4-c]quinolin-8-yl)((3S,4S)-3,4-diphenyl-1-pyrrolidinyl)methanone | TBTU | 450.8 |

TABLE 7-continued

| Ex. | Structure | Name | Coupling Reagent | m/z (ESI): [M + H]+ |
|---|---|---|---|---|
| 432 | 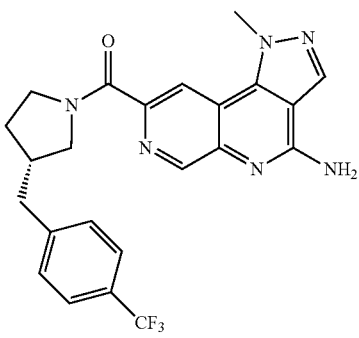 [SMILES: Cn1ncc2c(N)nc3cnc(C(=O)N4CC[C@@H](Oc5ccc(C(F)(F)F)cc5)C4)cc3c21] | (4-amino-1-methyl-1H-pyrazolo[4,3-c][1,7]naphthyridin-8-yl)((3R)-3-(4-(trifluoromethyl)benzyl)-1-pyrrolidinyl)methanone and (4-amino-1-methyl-1H-pyrazolo[4,3-c][1,7]naphthyridin-8-yl)((3S)-3-(4-(trifluoromethyl)benzyl)-1-pyrrolidinyl)methanone | TBTU | 455.9 |
| 433 | 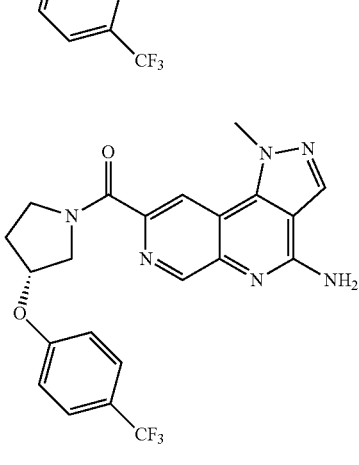 | (4-amino-1-methyl-1H-pyrazolo[4,3-c][1,7]naphthyridin-8-yl)((3R)-3-(4-(trifluoromethyl)phenoxy)-1-pyrrolidinyl)methanone and (4-amino-1-methyl-1H-pyrazolo[4,3-c][1,7]naphthyridin-8-yl)((3S)-3-(4-(trifluoromethyl)phenoxy)-1-pyrrolidinyl)methanone | TBTU | 457.9 |

TABLE 7-continued

| Ex. | Structure | Name | Coupling Reagent | m/z (ESI): [M + H]⁺ |
|---|---|---|---|---|
| 434 | 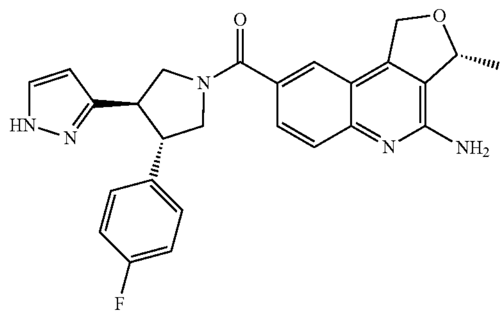 [SMILES: C[C@H]1OCc2c1c(N)nc1ccc(C(=O)N3C[C@H](c4ccc(F)cc4)[C@@H](c4cc[nH]n4)C3)cc21] | ((3R)-4-amino-3-methyl-1,3-dihydrofuro[3,4-c]quinolin-8-yl)((3R,4S)-3-(4-fluorophenyl)-4-(1H-pyrazol-3-yl)-1-pyrrolidinyl)methanone and ((3R)-4-amino-3-methyl-1,3-dihydrofuro[3,4-c]quinolin-8-yl)((3S,4R)-3-(4-fluorophenyl)-4-(1H-pyrazol-3-yl)-1-pyrrolidinyl)methanone | TBTU | 458.2 |
| 435 | 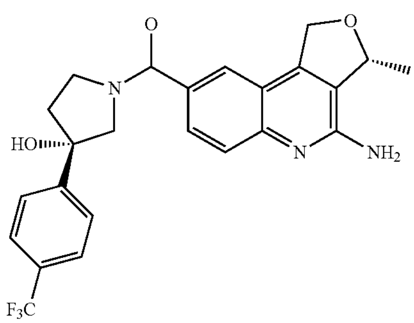 [SMILES: C[C@H]1OCc2c1c(N)nc1ccc(C(O)N3CC[C@](O)(c4ccc(C(F)(F)F)cc4)C3)cc21] | ((3R)-4-amino-3-methyl-1,3-dihydrofuro[3,4-c]quinolin-8-yl)((3S)-3-hydroxy-3-(4-(trifluoromethyl)phenyl)-1-pyrrolidinyl)methanone | TBTU | 458.9 |
| 436 | 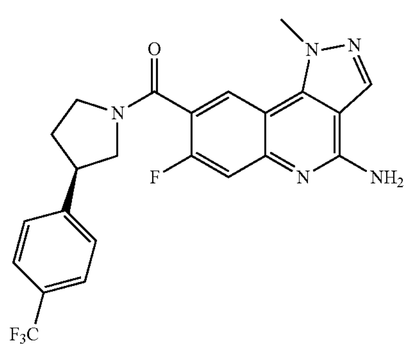 [SMILES: Cn1ncc2c(N)nc3cc(F)c(C(=O)N4CC[C@H](c5ccc(C(F)(F)F)cc5)C4)cc3c21] | (4-amino-7-fluoro-1-methyl-1H-pyrazolo[4,3-c]quinolin-8-yl)((3R)-3-(4-(trifluoromethyl)phenyl)-1-pyrrolidinyl)methanone | TBTU | 458.2 |

TABLE 7-continued

| Ex. | Structure | Name | Coupling Reagent | m/z (ESI): [M + H]+ |
|---|---|---|---|---|
| 437 | 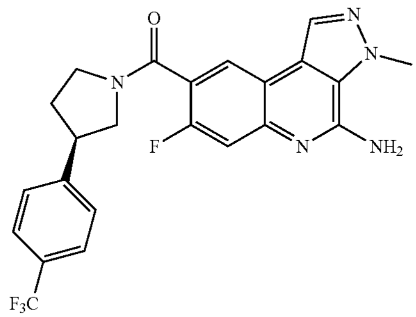 [SMILES: Cn1ncc2c3cc(C(=O)N4CC[C@H](c5ccc(C(F)(F)F)cc5)C4)c(F)cc3nc(N)c21] | (4-amino-7-fluoro-3-methyl-3H-pyrazolo[3,4-c]quinolin-8-yl)((3R)-3-(4-(trifluoromethyl)phenyl)-1-pyrrolidinyl)methanone | TBTU | 458.9 |
| 438 | 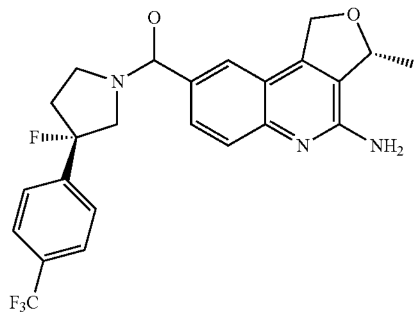 [SMILES: C[C@H]1OCc2c1c(N)nc1ccc(C(O)N3CC[C@](F)(c4ccc(C(F)(F)F)cc4)C3)cc21] | ((3R)-4-amino-3-methyl-1,3-dihydrofuro[3,4-c]quinolin-8-yl)((3S)-3-fluoro-3-(4-(trifluoromethyl)phenyl)-1-pyrrolidinyl)methanone | TBTU | 460.9 |
| 439 | 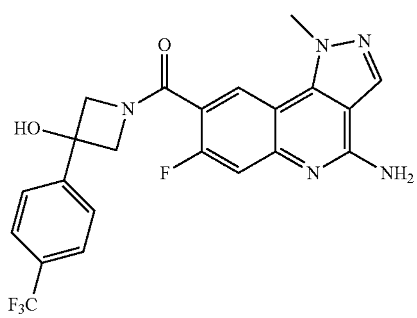 [SMILES: Cn1ncc2c(N)nc3cc(F)c(C(=O)N4CC(O)(c5ccc(C(F)(F)F)cc5)C4)cc3c21] | (4-amino-7-fluoro-1-methyl-1H-pyrazolo[4,3-c]quinolin-8-yl)(3-hydroxy-3-(4-(trifluoromethyl)phenyl)-1-azetidinyl)methanone | TBTU | 460.9 |
| 440 | 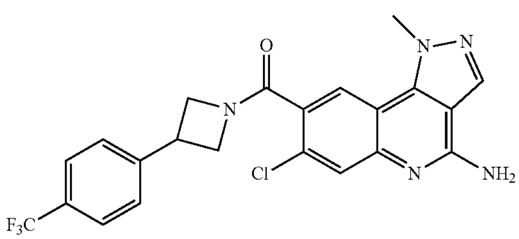 | (4-amino-7-chloro-1-methyl-1H-pyrazolo[4,3-c]quinolin-8-yl)(3-(4-(trifluoromethyl)phenyl)-1-azetidinyl)methanone | TBTU | 460.9 |
| 441 | 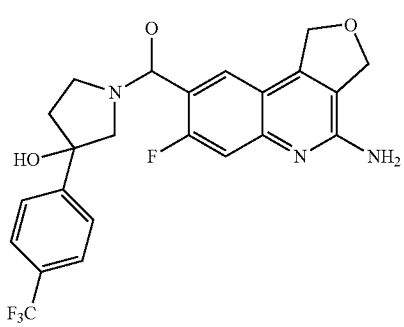 [SMILES: Nc1nc2cc(F)c(C(O)N3CCC(O)(c4ccc(C(F)(F)F)cc4)C3)cc2c2c1COC2] | (4-amino-7-fluoro-1,3-dihydrofuro[3,4-c]quinolin-8-yl)((3R)-3-hydroxy-3-(4-(trifluoromethyl)phenyl)-1-pyrrolidinyl)methanone and (4-amino-7-fluoro-1,3-dihydrofuro[3,4-c]quinolin-8-yl)((3S)-3-hydroxy-3-(4-(trifluoromethyl)phenyl)-1-pyrrolidinyl)methanone | TBTU | 462.8 |

TABLE 7-continued

| Ex. | Structure | Name | Coupling Reagent | m/z (ESI): [M + H]+ |
|---|---|---|---|---|
| 442 | 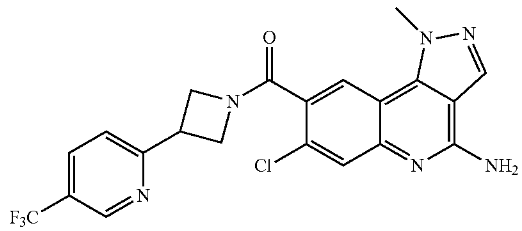 | (4-amino-7-chloro-1-methyl-1H-pyrazolo[4,3-c]quinolin-8-yl)(3-(5-(trifluoromethyl)-2-pyridinyl)-1-azetidinyl)methanone | TBTU | 461.8 |
| 443 | 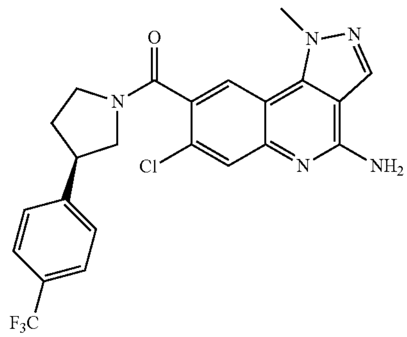 | (4-amino-7-chloro-1-methyl-1H-pyrazolo[4,3-c]quinolin-8-yl)((3R)-3-(4-(trifluoromethyl)phenyl)-1-pyrrolidinyl)methanone | TBTU | 474.9 |
| 444 | 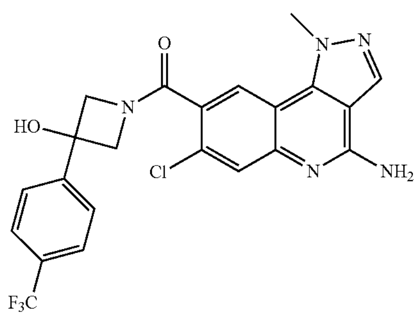 [SMILES: Cn1ncc2c(N)nc3cc(Cl)c(C(=O)N4CC(O)(c5ccc(C(F)(F)F)cc5)C4)cc3c21] | (4-amino-7-chloro-1-methyl-1H-pyrazolo[4,3-c]quinolin-8-yl)(3-hydroxy-3-(4-(trifluoromethyl)phenyl)-1-azetidinyl)methanone | TBTU | 476.9 |
| 445 | 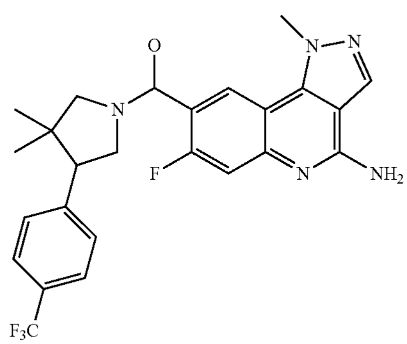 [SMILES: Cn1ncc2c(N)nc3cc(F)c(C(O)N4CC(c5ccc(C(F)(F)F)cc5)C(C)(C)C4)cc3c21] | (4-amino-7-fluoro-1-methyl-1H-pyrazolo[4,3-c]quinolin-8-yl)((4R)-3,3-dimethyl-4-(4-(trifluoromethyl)phenyl)-1-pyrrolidinyl)methanone and (4-amino-7-fluoro-1-methyl-1H-pyrazolo[4,3-c]quinolin-8-yl)((4S)-3,3-dimethyl-4-(4-(trifluoromethyl)phenyl)-1-pyrrolidinyl)methanone | TBTU | 486.9 |
| 446 | 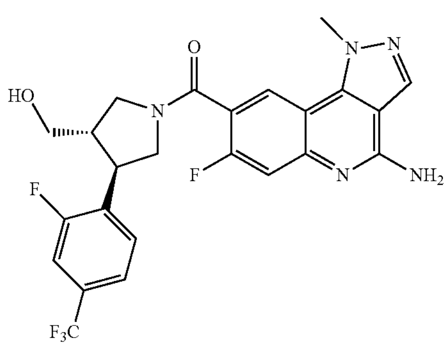 [SMILES: Cn1ncc2c(N)nc3cc(F)c(C(=O)N4C[C@@H](CO)[C@H](c5ccc(C(F)(F)F)cc5F)C4)cc3c21] | (4-amino-7-fluoro-1-methyl-1H-pyrazolo[4,3-c]quinolin-8-yl)((3R,4S)-3-(2-fluoro-4-(trifluoromethyl)phenyl)-4-(hydroxymethyl)-1-pyrrolidinyl)methanone | TBTU | 506.9 |

TABLE 7-continued

| Ex. | Structure | Name | Coupling Reagent | m/z (ESI): [M + H]+ |
|---|---|---|---|---|
| 447 | 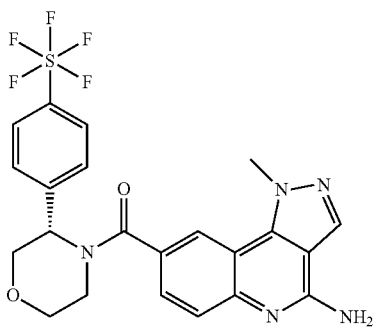 [SMILES: Cn1ncc2c(N)nc3ccc(C(=O)N4CCOC[C@@H]4c4ccc(S(F)(F)(F)(F)F)cc4)cc3c21] | (4-amino-1-methyl-1H-pyrazolo [4,3-c]quinolin-8-yl)((3S)-3-(4-(pentafluoro-lambda~6~-sulfanyl)phenyl)-4-morpholinyl)methanone | TBTU | 514.2 |
| 448 | 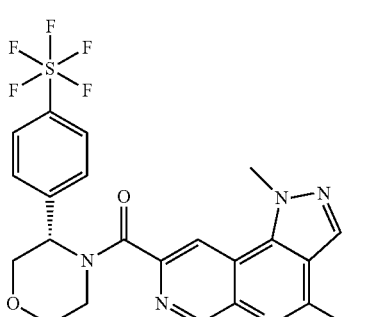 | (4-amino-1-methyl-1H-pyrazolo [4,3-c][1,7]naphthyridin-8-yl)((3S)-3-(4-(pentafluoro-lambda~6~-sulfanyl)phenyl)-4-morpholinyl)methanone | TBTU | 515.2 |
| 449 | 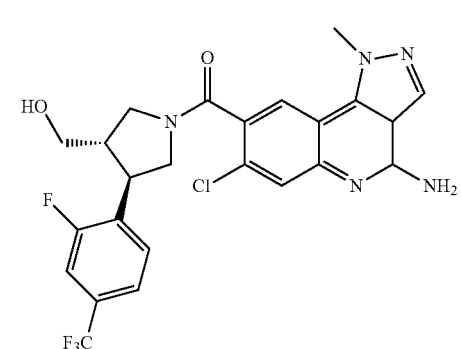 | (4-amino-7-chloro-1-methyl-1H-pyrazolo[4,3-c]quinolin-8-yl)((3R,4S)-3-(2-fluoro-4-(trifluoromethyl)phenyl)-4-(hydroxymethyl)-1-pyrrolidinyl)methanone | TBTU | 522.9 |
| 450 | 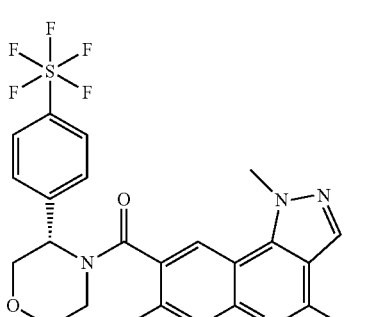 | (4-amino-7-fluoro-1-methyl-1H-pyrazolo [4,3-c]quinolin-8-yl)((3S)-3-(4-(pentafluoro-lambda~6~-sulfanyl)phenyl)-4-morpholinyl)methanone | TBTU | 532.2 |

TABLE 7-continued

| Ex. | Structure | Name | Coupling Reagent | m/z (ESI): [M + H]+ |
|---|---|---|---|---|
| 451 | 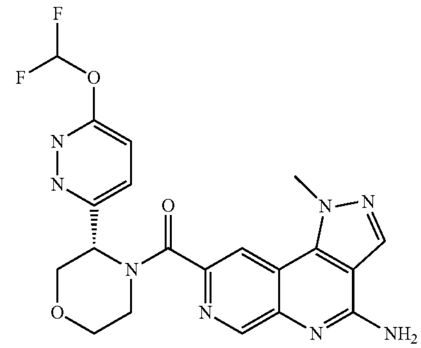 [SMILES: Cn1ncc2c(N)nc3cnc(C(=O)N4CCOC[C@@H]4C4=CC=C(OC(F)F)NN4)cc3c21] | (4-amino-1-methyl-1H-pyrazolo[4,3-c][1,7]naphthyridin-8-yl)((3S)-3-(6-(difluoromethoxy)-3-pyridazinyl)-4-morpholinyl)methanone | TBTU | 457.1 |

Examples 452 and 453: ((R)-4-amino-3-methyl-1,3-dihydrofuro[3,4-c][1,7]naphthyridin-8-yl)((S)-3-(4-(trifluoromethyl)phenyl)morpholino)methanone and ((S)-4-amino-3-methyl-1,3-dihydrofuro[3,4-c][1,7]naphthyridin-8-yl)((S)-3-(4-(trifluoromethyl)phenyl)morpholino)methanone

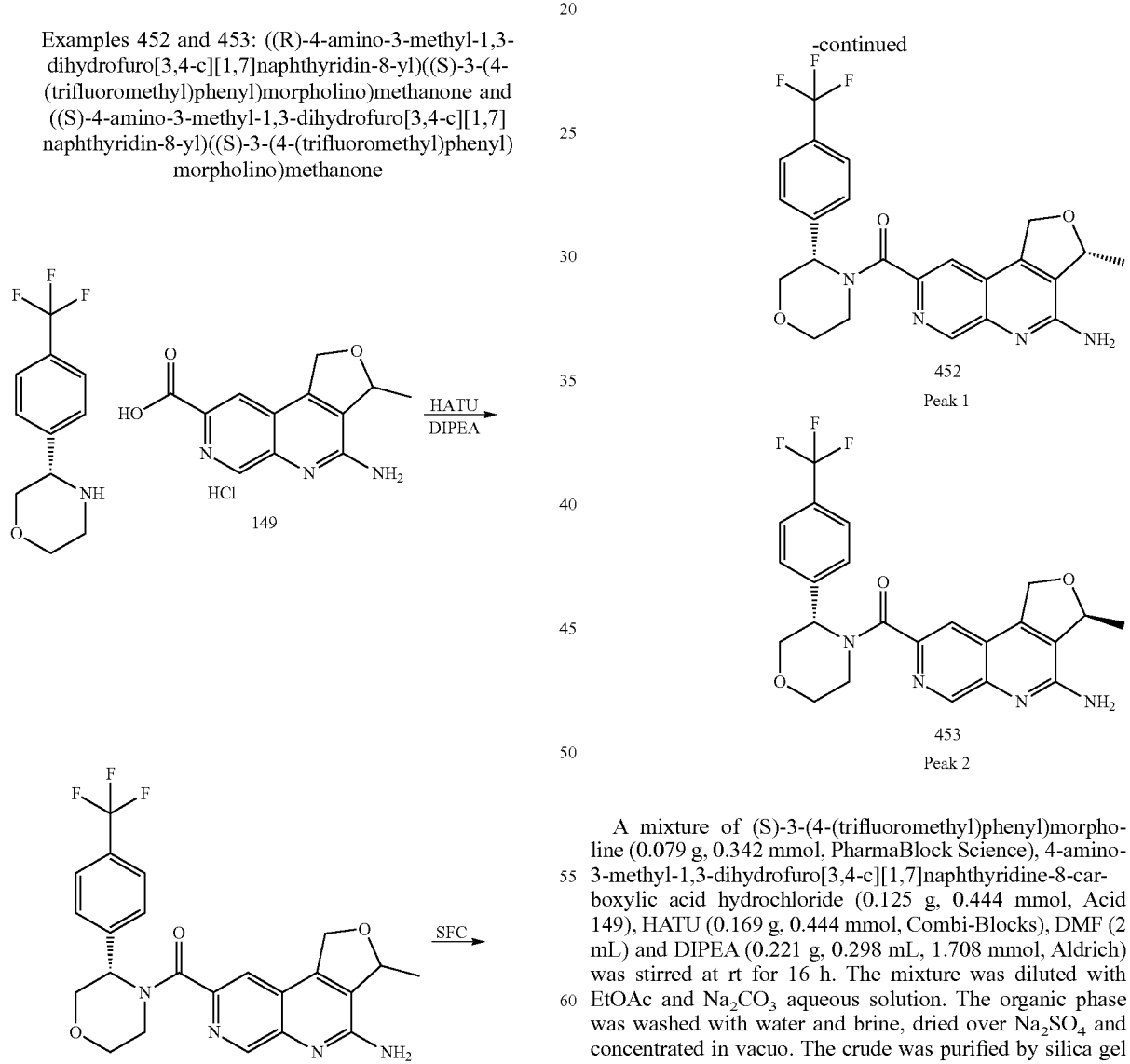

452
Peak 1

453
Peak 2

A mixture of (S)-3-(4-(trifluoromethyl)phenyl)morpholine (0.079 g, 0.342 mmol, PharmaBlock Science), 4-amino-3-methyl-1,3-dihydrofuro[3,4-c][1,7]naphthyridine-8-carboxylic acid hydrochloride (0.125 g, 0.444 mmol, Acid 149), HATU (0.169 g, 0.444 mmol, Combi-Blocks), DMF (2 mL) and DIPEA (0.221 g, 0.298 mL, 1.708 mmol, Aldrich) was stirred at rt for 16 h. The mixture was diluted with EtOAc and Na$_2$CO$_3$ aqueous solution. The organic phase was washed with water and brine, dried over Na$_2$SO$_4$ and concentrated in vacuo. The crude was purified by silica gel chromatography: 0-100% EtOAc/EtOH (3/1) in heptane. The racemate product was obtained as off-white solid (0.108 g, 69%). m/z (ESI): 459 [M+H]+.

100 mg of the racemate product was purified via preparative SFC using a Chiral Technologies OJ column (250×21 mm, 5 mm) with a mobile phase of 75% liquid $CO_2$ and 25% MeOH with 0.2% TEA using a flowrate of 80 mL/min. to generate 39.7 mg of peak 1 with an ee of >99% and 40.5 mg of peak 2 with an ee of 99.8%. Peak assignment determined by SFC with OJ column with 25% MeOH with 0.2% TEA. Stereochemistry is assigned arbitrarily.

Peak 1: $^1$H NMR (500 MHz, DMSO-$d_6$) δ ppm 8.73-8.92 (m, 1H), 7.84 (s, 1H), 7.59-7.81 (m, 4H), 6.98 (br s, 2H), 5.57-5.79 (m, 1H), 5.42-5.50 (m, 1H), 5.35-5.40 (m, 1H), 5.22-5.34 (m, 1H), 4.38-4.58 (m, 1H), 3.69-3.94 (m, 3H), 3.57 (br s, 1H), 3.17 (d, J=5.0 Hz, 1H), 1.33-1.48 (m, 3H).

Peak 2: $^1$H NMR (500 MHz, DMSO-$d_6$) δ ppm 8.71-8.97 (m, 1H), 7.82-7.86 (m, 1H), 7.59-7.82 (m, 4H), 6.98 (br s, 2H), 5.63-5.80 (m, 1H), 5.46 (br s, 1H), 5.25-5.41 (m, 2H), 4.23-4.59 (m, 1H), 3.71-3.99 (m, 3H), 3.56 (br s, 1H), 3.17 (d, J=5.0 Hz, 1H), 1.41 (br d, J=6.2 Hz, 3H).

Examples in Table 8 were prepared in a manner similar to that described above for example 452 and 453 using the indicated amide coupling reagent in the table and purification conditions.

TABLE 8

| Ex. | Structure | Name | Coupling Reagent | m/z (ESI): [M + H]$^+$ | SFC Conditions |
|---|---|---|---|---|---|
| 454 | 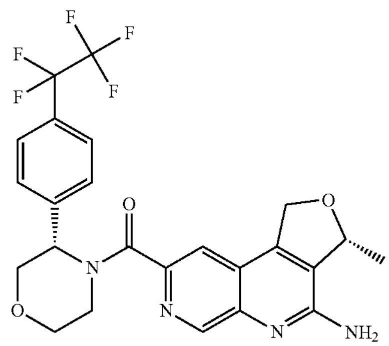 [SMILES: C[C@H]1OCc2c1c(N)nc1cnc(C(=O)N3CCOC[C@@H]3c3ccc(C(F)(F)C(F)(F)F)cc3)cc21] | ((3R)-4-amino-3-methyl-1,3-dihydrofuro[3,4-c][1,7]naphthyridin-8-yl)((3S)-3-(4-(pentafluoroethyl)phenyl)-4-morpholinyl)methanone | HATU | 509.0 | 1$^{st}$ peak, Chiral Technologies OJ column (250 X 21 mm, 5 μm) with a mobile phase of 75% Liquid CO$_2$ and 25% MeOH with 0.2% TEA using a flowrate of 80 mL/min. |
| 455 | 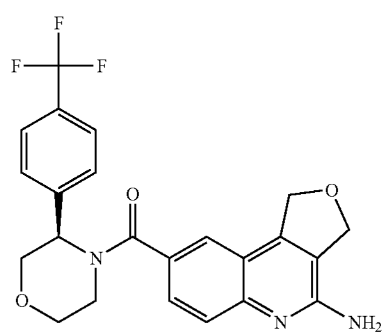 [SMILES: Nc1nc2ccc(C(=O)N3CCOC[C@H]3c3ccc(C(F)(F)F)cc3)cc2c2c1COC2] | (4-amino-1,3-dihydrofuro[3,4-c]quinolin-8-yl)-[(3R)-3-[4-(trifluoromethyl)phenyl]morpholin-4-yl]methanone | PyBroP | 444.4 | 1$^{st}$ peak, Chiral Technologies AZ column (250 X 21 mm, 5 μm) with a mobile phase of 50% Liquid CO$_2$ and 50% MeOH with 0.2% TEA using a flowrate of 50 mL/min. |
| 456 | 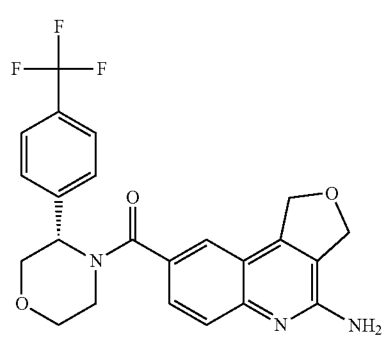 | (4-amino-1,3-dihydrofuro[3,4-c]quinolin-8-yl)-[(3S)-3-[4-(trifluoromethyl)phenyl]morpholin-4-yl]methanone | PyBroP | 444.4 | 2$^{nd}$ peak, Chiral Technologies AZ column (250 X 21 mm, 5 μm) with a mobile phase of 50% Liquid CO$_2$ and 50% MeOH with 0.2% TEA using a flowrate of 50 mL/min. |

TABLE 8-continued

| Ex. | Structure | Name | Coupling Reagent | m/z (ESI): [M + H]+ | SFC Conditions |
|---|---|---|---|---|---|
| 457 | 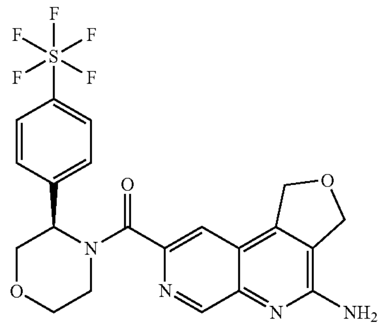 [SMILES: Nc1nc2cnc(C(=O)N3CCOC[C@H]3c3ccc(S(F)(F)(F)(F)F)cc3)cc2c2c1COC2] | (R)-(4-amino-1,3-dihydrofuro[3,4-c][1,7]naphthyridin-8-yl)(3-(4-(pentafluoro-16-sulfaneyl)phenyl)morpholino)methanone | TBTU | 503.8 | 1st peak, Chiral Technologies IC column (250 X 21 nun, 5 mm) with a mobile phase of 65% Liquid CO$_2$ and 35% MeOH with 0.2% TEA using a flowrate of 80 mL/min |
| 458 | 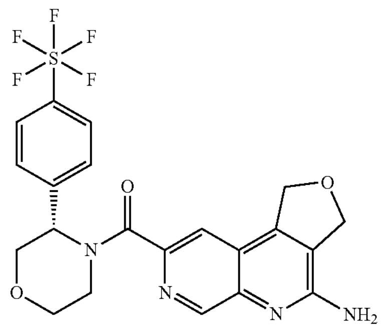 [SMILES: Nc1nc2cnc(C(=O)N3CCOC[C@@H]3c3ccc(S(F)(F)(F)(F)F)cc3)cc2c2c1COC2] | (S)-(4-amino-1,3-dihydrofuro[3,4-c][1,7]naphthyridin-8-yl)(3-(4-(pentafluoro-16-sulfaneyl)phenyl)morpholino)methanone | TBTU | 503.8 | 2nd peak, Chiral Technologies IC column (250 X 21 nun, 5 mm) with a mobile phase of 65% Liquid CO$_2$ and 35% MeOH with 0.2% TEA using a flowrate of 80 mL/min |
| 459 | 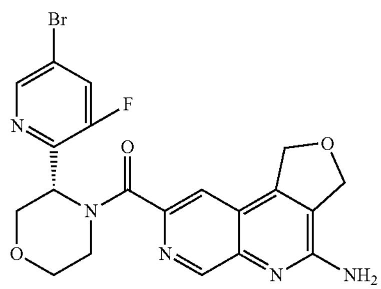 [SMILES: Nc1nc2cnc(C(=O)N3CCOC[C@@H]3c3ncc(Br)cc3F)cc2c2c1COC2] | (4-amino-1,3-dihydrofuro[3,4-c][1,7]naphthyridin-8-yl)((3S)-3-(5-bromo-3-fluoro-2-pyridinyl)-4-morpholinyl)methanone | PyBroP | 474.00 and 476.00 | 1st peak, Chiralpak AD column (21 x 150 mm, 5 micron) with a mobile phase of 55% Liquid CO$_2$ and 45% methanol with 0.2% diethylamine using a flowrate of 80 ml/min |
| 460 | 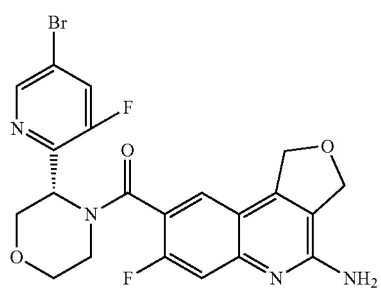 [SMILES: Nc1nc2cc(F)c(C(=O)N3CCOC[C@@H]3c3ncc(Br)cc3F)cc2c2c1COC2] | (4-amino-7-fluoro-1,3-dihydrofuro[3,4-c]quinolin-8-yl)((3S)-3-(5-bromo-3-fluoro-2-pyridinyl)-4-morpholinyl)methanone | PyBroP | 491.00 and 493.00 | 1st peak, (S,S) Whelk-O 1 column, (21 x 250 mm) with a mobile phase of 60% Liquid CO$_2$ and 40% MeOH with 0.2% diethylamine using a flowrate of 80 ml/min |
| 461 | 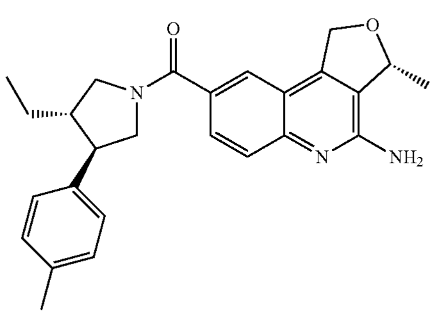 [SMILES: CC[C@@H]1CN(C(=O)c2ccc3nc(N)c4c(c3c2)CO[C@@H]4C)C[C@H]1c1ccc(C)cc1] | ((3R)-4-amino-3-methyl-1,3-dihydrofuro[3,4-c]quinolin-8-yl)((3S,4R)-3-ethyl-4-(4-methylphenyl)-1-pyrrolidinyl)methanone | TBTU | 416.2 | 1st peak, Chiralpak AD column (21 x 150 mm, 5 micron) with a mobile phase of 65% Liquid CO$_2$ and 35% methanol with 0.2% diethylamine using a flowrate of 80 ml/min) |

TABLE 8-continued

| Ex. | Structure | Name | Coupling Reagent | m/z (ESI): [M + H]+ | SFC Conditions |
|---|---|---|---|---|---|
| 462 | 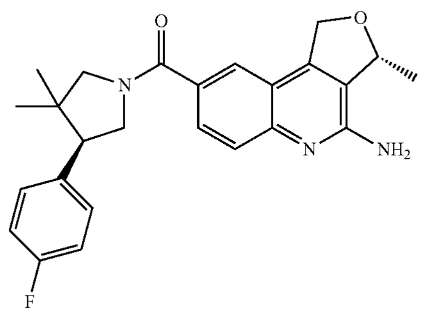 [SMILES: C[C@H]1OCc2c1c(N)nc1ccc(C(=O)N3C[C@@H](c4ccc(F)cc4)C(C)(C)C3)cc21] | ((3R)-4-amino-3-methyl-1,3-dihydrofuro[3,4-c]quinolin-8-yl)((4S)-4-(4-fluorophenyl)-3,3-dimethyl-1-pyrrolidinyl)methanone | TBTU | 420.1 | 1st peak, Chiralcel OJ column (30 x 250 mm, 5 micron) with a mobile phase of 75% Liquid CO2 and 25% MeOH w/ 0.2% diethylamine using a flowrate of 80 ml/min |
| 463 | 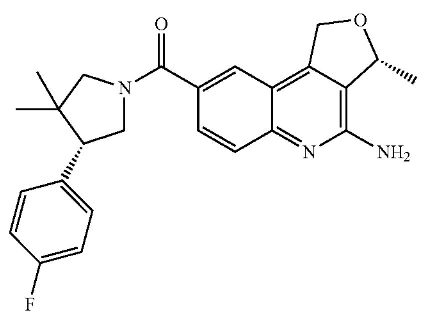 [SMILES: C[C@H]1OCc2c1c(N)nc1ccc(C(=O)N3C[C@H](c4ccc(F)cc4)C(C)(C)C3)cc21] | ((3R)-4-amino-3-methyl-1,3-dihydrofuro[3,4-c]quinolin-8-yl)((4R)-4-(4-fluorophenyl)-3,3-dimethyl-1-pyrrolidinyl)methanone | TBTU | 420.1 | 2nd peak, Chiralcel OJ column (30 x 250 mm, 5 micron) with a mobile phase of 75% Liquid CO2 and 25% MeOH w/ 0.2% diethylamine using a flowrate of 80 ml/min |
| 464 | 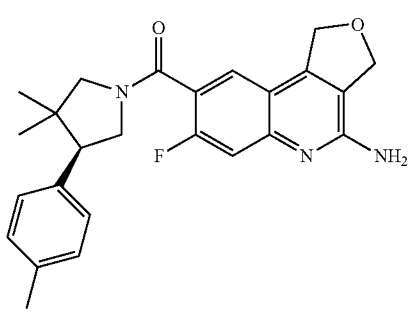 [SMILES: Cc1ccc([C@@H]2CN(C(=O)c3cc4c5c(c(N)nc4cc3F)COC5)CC2(C)C)cc1] | (4-amino-7-fluoro-1,3-dihydrofuro[3,4-c]quinolin-8-yl)((4S)-3,3-dimethyl-4-(4-methylphenyl)-1-pyrrolidinyl)methanone | TBTU | 420.2 | 2nd peak, Chiralcel OJ column (2 x 25 cm, 5 micron) with a mobile phase of 80% Liquid CO2 and 20% methanol with 0.1% triethylamine using a flowrate of 70 ml/min |
| 465 | 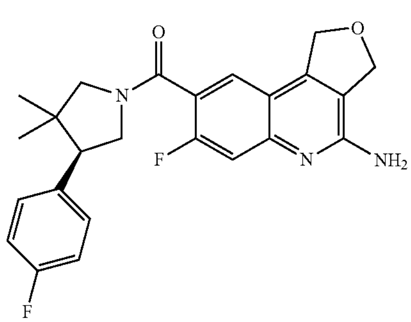 [SMILES: CC1(C)CN(C(=O)c2cc3c4c(c(N)nc3cc2F)COC4)C[C@H]1c1ccc(F)cc1] | (4-amino-7-fluoro-1,3-dihydrofuro[3,4-c]quinolin-8-yl)((4S)-4-(4-fluorophenyl)-3,3-dimethyl-1-pyrrolidinyl)methanone | TBTU | 424.1 | 2nd peak, Chiralcel OJ column (2 x 25 cm, 5 micron) with a mobile phase of 80% Liquid CO2 and 20% methanol with 0.1% triethylamine using a flowrate of 70 ml/min |
| 466 | 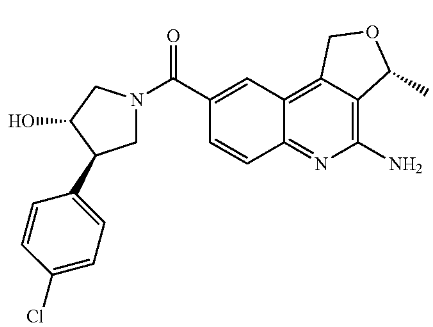 [SMILES: C[C@H]1OCc2c1c(N)nc1ccc(C(=O)N3C[C@@H](O)[C@H](c4ccc(Cl)cc4)C3)cc21] | ((3R)-4-amino-3-methyl-1,3-dihydrofuro[3,4-c]quinolin-8-yl)((3R,4S)-3-(4-chlorophenyl)-4-hydroxy-1-pyrrolidinyl)methanone | TBTU | 424.9 | 1st peak, Chiralcel OD column (21 x 250 mm, 5 micron) with a mobile phase of 75% Liquid CO2 and 25% MeOH with 0.2% DEA using a flowrate of 80 ml/min |

TABLE 8-continued

| Ex. | Structure | Name | Coupling Reagent | m/z (ESI): [M + H]+ | SFC Conditions |
|---|---|---|---|---|---|
| 467 | 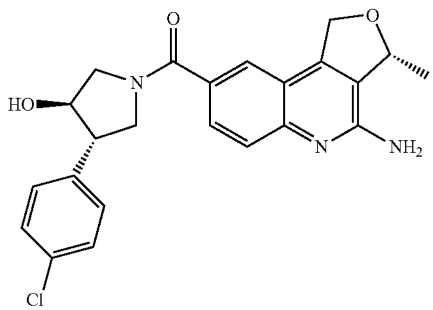 [SMILES: C[C@H]1OCc2c1c(N)nc1ccc(C(=O)N3C[C@H](c4ccc(Cl)cc4)[C@@H](O)C3)cc21] | ((3R)-4-amino-3-methyl-1,3-dihydrofuro[3,4-c]quinolin-8-yl)((3S,4R)-3-(4-chlorophenyl)-4-hydroxy-1-pyrrolidinyl)methanone | TBTU | 424.9 | 2nd peak, Chiralcel OD column (21 x 250 mm, 5 micron) with a mobile phase of 75% Liquid $CO_2$ and 25% MeOH with 0.2% DEA using a flowrate of 80 mL/min |
| 468 | 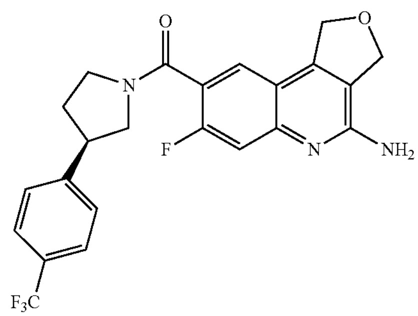 [SMILES: Nc1nc2cc(F)c(C(=O)N3CC[C@H](c4ccc(C(F)(F)F)cc4)C3)cc2c2c1COC2] | (4-amino-7-fluoro-1,3-dihydrofuro[3,4-c]quinolin-8-yl)((3R)-3-(4-(trifluoromethyl)phenyl)-1-pyrrolidinyl)methanone | TBTU | 446.8 | 2nd peak, Chiralcel OJ column (21 x 250 mm, 5 micron) with a mobile phase of 75% Liquid $CO_2$ and 25% MeOH with 0.2% diethylamine using a flowrate of 80 mL/min |
| 469 | 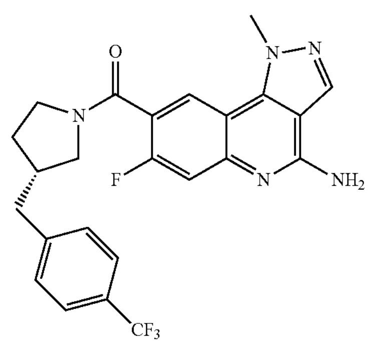 [SMILES: Cn1ncc2c(N)nc3cc(F)c(C(=O)N4CC[C@@H](Cc5ccc(C(F)(F)F)cc5)C4)cc3c21] | (4-amino-7-fluoro-1-methyl-1H-pyrazolo[4,3-c]quinolin-8-yl)((3R)-3-(4-(trifluoromethyl)benzyl)-1-pyrrolidinyl)methanone | TBTU | 472.9 | 1st peak, Chiralcel OD column, (2 x 25 cm, 5 micron) with a mobile phase of 70% Liquid $CO_2$ and 30% methanol w/ 0.1% diethylamine using a flowrate of 60 mL/min |
| 470 | 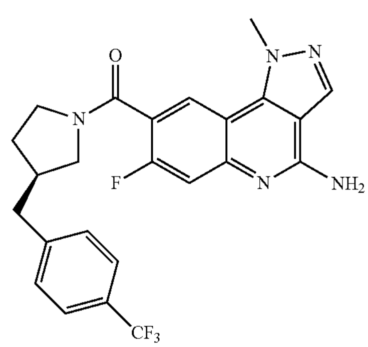 [SMILES: Cn1ncc2c(N)nc3cc(F)c(C(=O)N4CC[C@H](Cc5ccc(C(F)(F)F)cc5)C4)cc3c21] | (4-amino-7-fluoro-1-methyl-1H-pyrazolo[4,3-c]quinolin-8-yl)((3S)-3-(4-(trifluoromethyl)benzyl)-1-pyrrolidinyl)methanone | TBTU | 472.9 | 2nd peak, Chiralcel OD column, (2 x 25 cm, 5 micron) with a mobile phase of 70% Liquid $CO_2$ and 30% methanol w/ 0.1% diethylamine using a flowrate of 60 mL/min |

TABLE 8-continued

| Ex. | Structure | Name | Coupling Reagent | m/z (ESI): [M + H]+ | SFC Conditions |
|---|---|---|---|---|---|
| 471 | 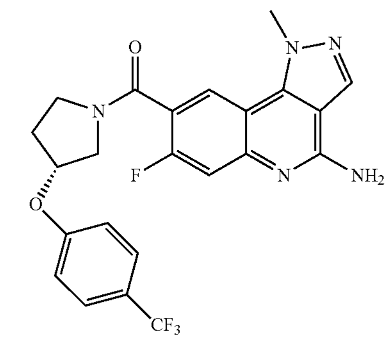 | (4-amino-7-fluoro-1-methyl-1H-pyrazolo[4,3-c]quinolin-8-yl)((3R)-3-(4-(trifluoromethyl)phenoxy)-1-pyrrolidinyl)methanone | TBTU | 474.9 | 1st peak, Chiralpak IC column, (2 x 15 cm, 5 micron) with a mobile phase of 60% Liquid CO2 and 40% methanol w/ 0.1% diethylamine using a flowrate of 55 mL/min |
| 472 | 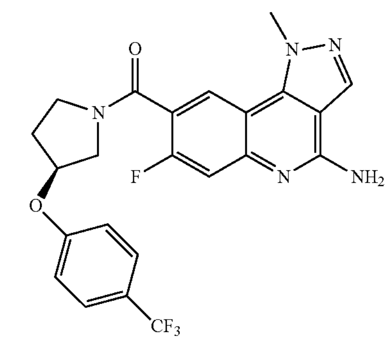 [SMILES: Cn1ncc2c(N)nc3cc(F)c(C(=O)N4CC[C@H](Oc5ccc(C(F)(F)F)cc5)C4)cc3c21] | (4-amino-7-fluoro-1-methyl-1H-pyrazolo[4,3-c]quinolin-8-yl)((3S)-3-(4-(trifluoromethyl)phenoxy)-1-pyrrolidinyl)methanone | TBTU | 474.9 | 2nd peak, Chiralpak IC column, (2 x 15 cm, 5 micron) with a mobile phase of 60% Liquid CO2 and 40% methanol w/ 0.1% diethylamine using a flowrate of 55 mL/min |
| 473 | 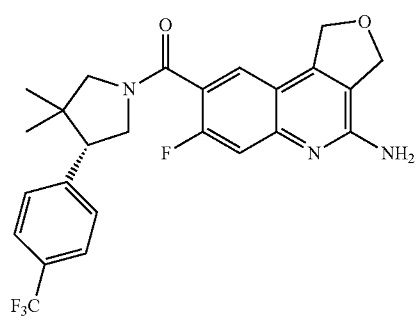 [SMILES: CC1(C)CN(C(=O)c2cc3c4c(c(N)nc3cc2F)COC4)C[C@@H]1c1ccc(C(F)(F)F)cc1] | (4-amino-7-fluoro-1,3-dihydrofuro[3,4-c]quinolin-8-yl)((4R)-3,3-dimethyl-4-(4-(trifluoromethyl)phenyl)-1-pyrrolidinyl)methanone | TBTU | 474.8 | 2nd peak, Chiralcel OJ column (21 x 250 mm, 5 micron) with a mobile phase of 75% Liquid CO2 and 25% methanol with 0.2% diethylamine using a flowrate of 80 ml/min |
| 474 | 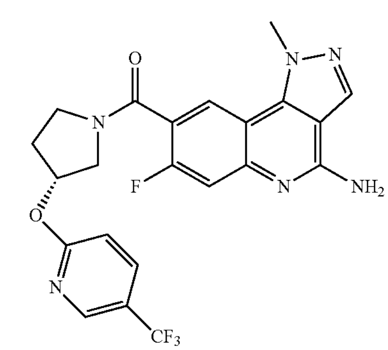 [SMILES: Cn1ncc2c(N)nc3cc(F)c(C(=O)N4CC[C@@H](Oc5ccc(C(F)(F)F)cn5)C4)cc3c21] | (4-amino-7-fluoro-1-methyl-1H-pyrazolo[4,3-c]quinolin-8-yl)((3R)-3-((5-(trifluoromethyl)-2-pyridinyl)oxy)-1-pyrrolidinyl)methanone | TBTU | 475.0 | 1st peak, Chiralpak IC column, (2 x 15 cm, 5 micron) with a mobile phase of 60% Liquid CO2 and 40% methanol w/ 0.1% diethylamine using a flowrate of 55 mL/min |

TABLE 8-continued

| Ex. | Structure | Name | Coupling Reagent | m/z (ESI): [M + H]+ | SFC Conditions |
|---|---|---|---|---|---|
| 475 | 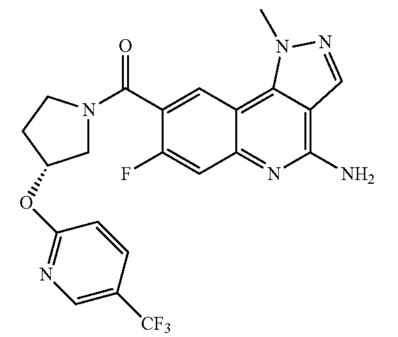 [SMILES: Cn1ncc2c(N)nc3cc(F)c(C(=O)N4CC[C@@H](Oc5ccc(C(F)(F)F)cn5)C4)cc3c21] | (4-amino-7-fluoro-1-methyl-1H-pyrazolo[4,3-c]quinolin-8-yl)((3S)-3-((5-(trifluoromethyl)-2-pyridinyl)oxy)-1-pyrrolidinyl)methanone | TBTU | 475.0 | 2nd peak, Chiralpak IC column, (2 x 15 cm, 5 micron) with a mobile phase of 60% Liquid $CO_2$ and 40% methanol w/ 0.1% diethylamine using a flowrate of 55 mL/min |
| 476 | 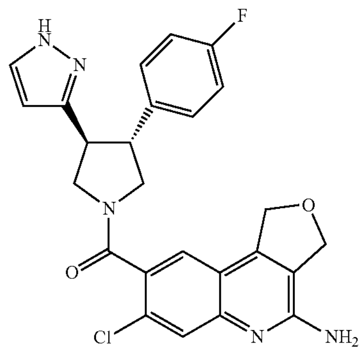 [SMILES: Nc1nc2cc(Cl)c(C(=O)N3C[C@@H](c4ccc(F)cc4)[C@H](c4cc[nH]n4)C3)cc2c2c1COC2] | (4-amino-7-chloro-1,3-dihydrofuro[3,4-c]quinolin-8-yl)((3R,4S)-3-(4-fluorophenyl)-4-(1H-pyrazol-3-yl)-1-pyrrolidinyl)methanone | TBTU | 476.0 | 1st peak, Whelk-O-S,S column (250 X 21 mm, 5 um), with a mobile phase of 60% Liquid $CO_2$ and 40% methanol with 0.2% TEA using a flowrate 80 mL/min |
| 477 | 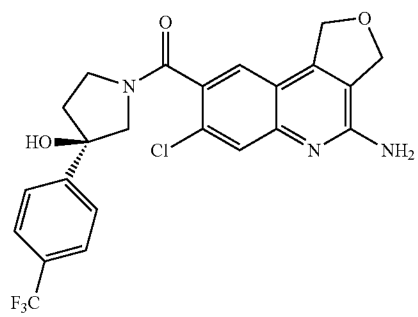 [SMILES: Nc1nc2cc(Cl)c(C(=O)N3CC[C@@](O)(c4ccc(C(F)(F)F)cc4)C3)cc2c2c1COC2] | (4-amino-7-chloro-1,3-dihydrofuro[3,4-c]quinolin-8-yl)((3R)-3-hydroxy-3-(4-(trifluoromethyl)phenyl)-1-pyrrolidinyl)methanone | TBTU | 478.8 | 2nd peak, Chiral Technologies OJ column (250 X 21 mm, 5 mm) with a mobile phase of 80% Liquid $CO_2$ and 20% MeOH with 0.2% TEA using a flowrate of 80 mL/min |
| 478 | 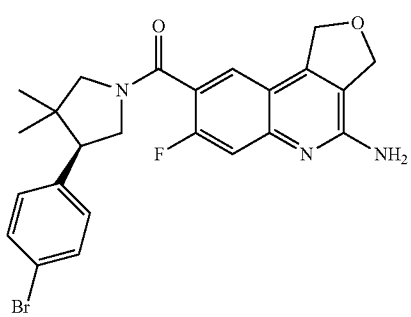 [SMILES: CC1(C)CN(C(=O)c2cc3c4c(c(N)nc3cc2F)COC4)C[C@H]1c1ccc(Br)cc1] | (4-amino-7-fluoro-1,3-dihydrofuro[3,4-c]quinolin-8-yl)((4S)-4-(4-bromophenyl)-3,3-dimethyl-1-pyrrolidinyl)methanone | TBTU | 483.9/ 485.8 (1:1) | 2nd peak, Chiralcel OJ column, (2 x 25 cm, 5 micron) with a mobile phase of 80% Liquid $CO_2$ and 20% methanol with 0.1% triethylamine using a flowrate of 70 mL/min |

TABLE 8-continued

| Ex. | Structure | Name | Coupling Reagent | m/z (ESI): [M + H]+ | SFC Conditions |
|---|---|---|---|---|---|
| 479 | 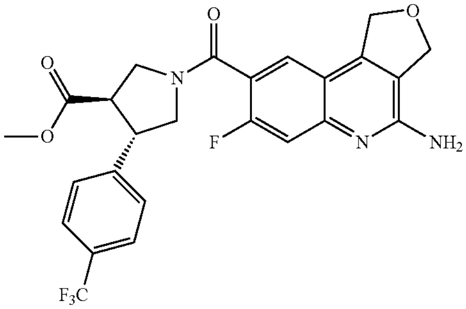 [SMILES: COC(=O)[C@H]1CN(C(=O)c2cc3c4c(c(N)nc3cc2F)COC4)C[C@@H]1c1ccc(C(F)(F)F)cc1] | methyl (3R,4S)-1-((4-amino-7-fluoro-1,3-dihydrofuro[3,4-c]quinolin-8-yl)carbonyl)-4-(4-(trifluoromethyl)phenyl)-3-pyrrolidine-carboxylate | TBTU | 504.2 | 1st peak, Chiralcel OJ column, (21 x 400 mm) with a mobile phase of 80% Liquid CO2 and 20% methanol w/ 0.2% diethylamine using a flow rate of 60 ml/min |
| 480 | 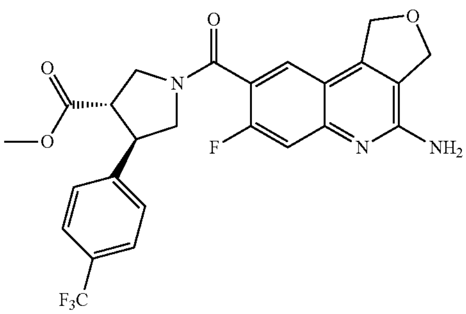 [SMILES: COC(=O)[C@@H]1CN(C(=O)c2cc3c4c(c(N)nc3cc2F)COC4)C[C@H]1c1ccc(C(F)(F)F)cc1] | methyl (3S,4R)-1-((4-amino-7-fluoro-1,3-dihydrofuro[3,4-c]quinolin-8-yl)carbonyl)-4-(4-(trifluoromethyl)phenyl)-3-pyrrolidine-carboxylate | TBTU | 504.2 | 2nd peak, Chiralcel OJ column, (21 x 400 mm) with a mobile phase of 80% Liquid CO2 and 20% methanol w/ 0.2% diethylamine using a flow rate of 60 ml/min |

Examples 481 and 482: (4-amino-1,3-dihydrofuro[3,4-c][1,7]naphthyridin-8-yl)(3-(4-(trifluoromethyl)phenyl)morpholino)methanone

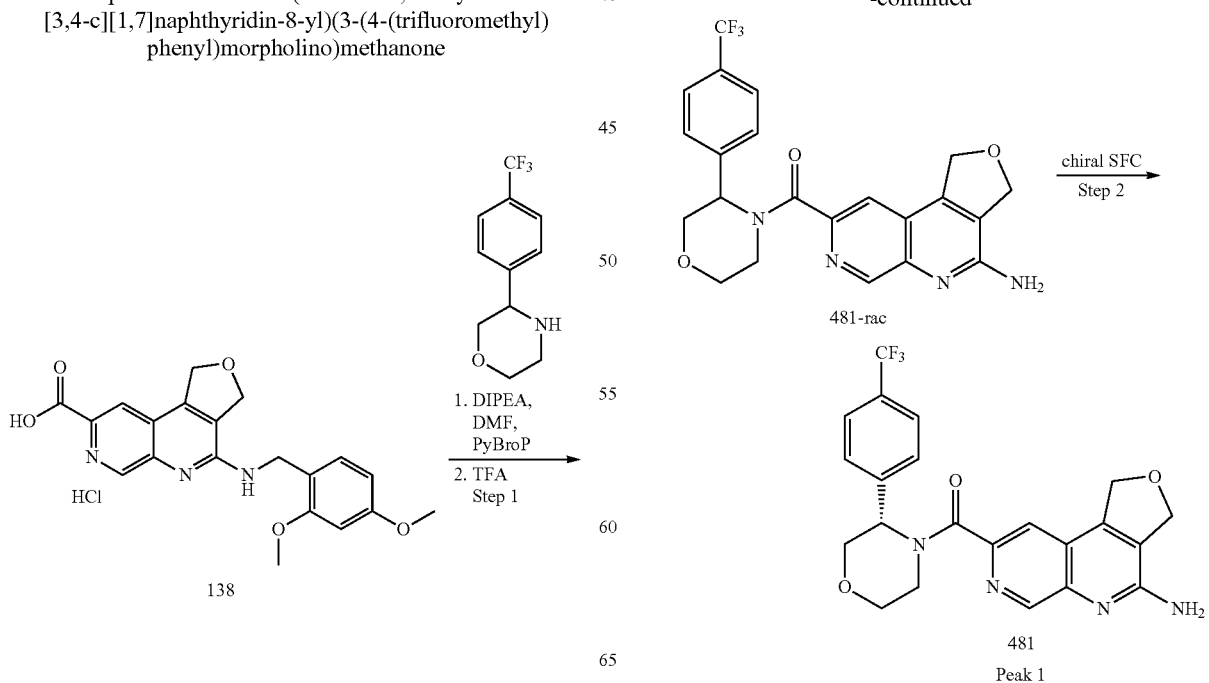

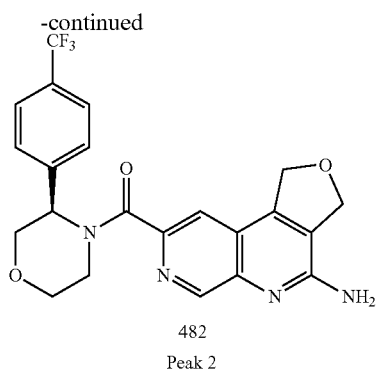

482
Peak 2

Step 1: To a solution of 3-(4-(trifluoromethyl)phenyl) morpholine (0.100 g, 0.432 mmol, Enamine), 4-((2,4-dimethoxybenzyl)amino)-1,3-dihydrofuro[3,4-c][1,7]naphthyridine-8-carboxylic acid hydrochloride (138) (0.271 g, 0.649 mmol) and 1,1'-dimethyltriethylamine (0.559 g, 0.755 mL, 4.32 mmol, Sigma-Aldrich Corporation) in DMF (4 mL) was added bromotripyrrolidinophosphonium hexafluorophosphate (0.202 g, 0.432 mmol, Sigma-Aldrich Corporation) and the resulting mixture was heated at 50° C. for 30 min. The reaction was brought to rt, diluted with water, sat·NaHCO$_3$ and extracted with EtOAc (3×). The combined organics were dried over Na$_2$SO$_4$, filtered and concentrated. The residue was then chromatographed on silica gel using 0-50% 3:1 EtOAc/EtOH in heptane to afford (4-((2,4-dimethoxybenzyl)amino)-1,3-dihydrofuro[3,4-c][1,7]naphthyridin-8-yl)(3-(4-(trifluoromethyl)phenyl)morpholino)methanone (0.160 g, 0.269 mmol, 62.2% yield) as a light yellow solid. m/z (ESI): 595 (M+H)$^+$.

To a solution of (4-((2,4-dimethoxybenzyl)amino)-1,3-dihydrofuro[3,4-c][1,7]naphthyridin-8-yl)(3-(4-(trifluoromethyl)phenyl)morpholino)methanone (0.160 g, 0.269 mmol, 62.2% yield) in DCM (2 mL) was added TFA (14.80 g, 10 mL, 130 mmol, Aldrich) and the resulting mixture was heated at 50° C. for 1 h. The reaction was concentrated, washed with 10% Na$_2$CO$_3$ and extracted with DCM. The combined organics were concentrated and chromatographed on silica gel using 0-50% 3:1 EtOAc/EtOH in heptane to afford (4-amino-1,3-dihydrofuro[3,4-c][1,7]naphthyridin-8-yl)(3-(4-(trifluoromethyl)phenyl)morpholino)methanone as the TFA salt (0.078 g, 0.140 mmol, 32.3% yield) as an off-white solid. m/z (ESI): 445 (M+H)$^+$.

Step 2: (S)-(4-amino-1,3-dihydrofuro[3,4-c][1,7]naphthyridin-8-yl)(3-(4-(trifluoromethyl)phenyl)morpholino)methanone and (R)-(4-amino-1,3-dihydrofuro[3,4-c][1,7]naphthyridin-8-yl)(3-(4-(trifluoromethyl)phenyl)morpholino)methanone (4-amino-1,3-dihydrofuro[3,4-c][1,7]naphthyridin-8-yl)(3-(4-(trifluoromethyl)phenyl)morpholino)methanone 2,2,2-trifluoroacetate were separated via preparative SFC using a Chiral Technologies AD column (150×21 mm, 5 mm) with a mobile phase of 60% Liquid CO$_2$ and 40% MeOH with 0.2% TEA using a flowrate of 80 mL/min to generate peak 1, (S)-(4-amino-1,3-dihydrofuro[3,4-c][1,7]naphthyridin-8-yl)(3-(4-(trifluoromethyl)phenyl)morpholino)methanone with an ee of >99%, and peak 2, (R)-(4-amino-1,3-dihydrofuro[3,4-c][1,7]naphthyridin-8-yl)(3-(4-(trifluoromethyl)phenyl)morpholino)methanone with an ee of 99.28%. Peak assignment determined by SFC with AD column with 60% Liquid CO$_2$ and 40% MeOH with 0.2% TEA and absolute stereochemistry was arbitrarily assigned.

Peak 1: (S)-(4-amino-1,3-dihydrofuro[3,4-c][1,7]naphthyridin-8-yl)(3-(4-(trifluoromethyl)phenyl)morpholino)methanone (481) as a white solid. m/z (ESI): 445 (M+H)$^+$. $^1$H NMR (400 MHz, DMSO-d$_6$) δ ppm 8.67-9.03 (m, 1H), 7.85 (s, 1H), 7.77 (br s, 4H), 7.07 (br s, 2H), 5.75 (s, 1H), 5.37 (br s, 2H), 5.04 (br s, 2H), 4.46-4.61 (m, 1H), 3.89 (br dd, J=12.2, 3.3 Hz, 4H), 3.58 (br d, J=5.8 Hz, 1H). $^{19}$F NMR (377 MHz, DMSO-d6) δ ppm −60.90 (br s, 3 F).

Peak 2: (R)-(4-amino-1,3-dihydrofuro[3,4-c][1,7]naphthyridin-8-yl)(3-(4-(trifluoromethyl)phenyl)morpholino)methanone (482) as a white solid. m/z (ESI): 445 (M+H)$^+$. $^1$H NMR (400 MHz, DMSO-d$_6$) δ ppm 8.88 (br s, 1H), 7.85 (s, 1H), 7.77 (br d, J=1.7 Hz, 4H), 7.07 (br s, 2H), 5.69-5.78 (m, 1H), 5.37 (br s, 2H), 5.04 (br s, 2H), 4.45-4.61 (m, 1H), 3.89 (br dd, J=12.4, 3.3 Hz, 4H), 3.51-3.64 (m, 1H). $^{19}$F NMR (DMSO-d6, 377 MHz) δ−60.90 (s, 3 F).

Example 483: rac-(4-amino-1,3-dihydrofuro[3,4-c][1,8]naphthyridin-8-yl)(3-(4-(trifluoromethyl)phenyl)morpholino)methanone

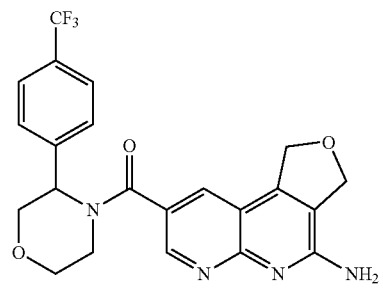

Example 483 was prepared in a manner similar to compound 481-rac above. m/z (ESI): 445.1 [M+H]$^+$ Example 484: (5-amino-2,4-dihydro-1H-pyrano[3,4-c]quinolin-9-yl)-[(3S)-3-[4-(trifluoromethoxy)phenyl]morpholin-4-yl]methanone

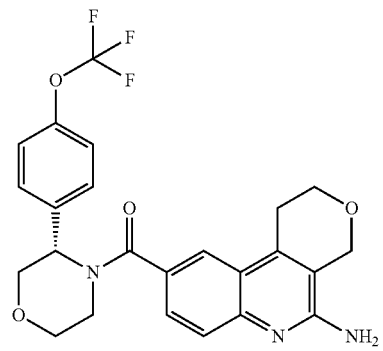 [SMILES: Nc1nc2ccc(C(=O)N3CCOC[C@@H]3c3ccc(OC(F)(F)F)cc3)cc2c2c1COCC2]

Example 484 was prepared in a manner similar to compound 481-rac above using commercial enantiopure (3)-3-[4-(Trifluoromethoxy)phenyl]morpholine hydrochloride (NetChem, CAS #1391448-60-4). m/z (ESI): 474.0 [M+H]$^+$ Examples below were prepared in a manner similar to that described for Example 481 and 482.

TABLE 9

| Ex. | Structure | Name | m/z (ESI): [M + H]+ | SFC Conditions |
|---|---|---|---|---|
| 485 | 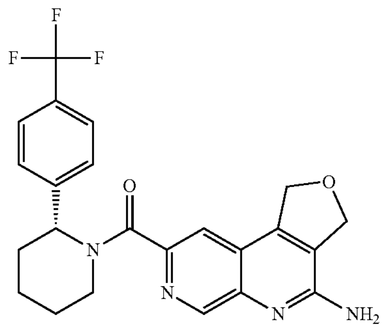 [SMILES: Nc1nc2cnc(C(=O)N3CCCC[C@@H]3c3ccc(C(F)(F)F)cc3)cc2c2c1COC2] | (4-amino-1,3-dihydrofuro[3,4-c][1,7]naphthyridin-8-yl)-[(2R)-2-[4-(trifluoromethyl)phenyl]-1-piperidyl]methanone | 443.0 | 1st peak, Chiral Technologies AS column (250 x 21 mm, 5 mm) with a mobile phase of 75% Liquid $CO_2$ and 25% MeOH with 0.2% TEA using a flowrate of 80 mL/min. |
| 486 | 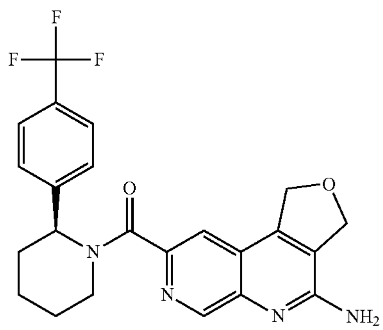 [SMILES: Nc1nc2cnc(C(=O)N3CCCC[C@H]3c3ccc(C(F)(F)F)cc3)cc2c2c1COC2] | (4-amino-1,3-dihydrofuro[3,4-c][1,7]naphthyridin-8-yl)-[(2S)-2-[4-(trifluoromethyl)phenyl]-1-piperidyl]methanone | 443.0 | 2nd peak, Chiral Technologies AS column (250 x 21 mm, 5 mm) with a mobile phase of 75% Liquid $CO_2$ and 25% MeOH with 0.2% TEA using a flowrate of 80 mL/min. |
| 487 | 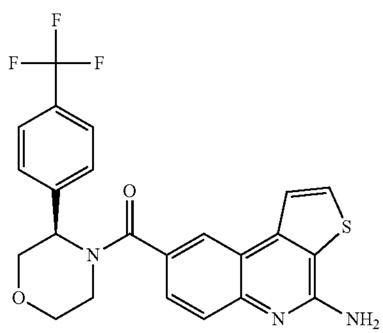 [SMILES: Nc1nc2ccc(C(=O)N3CCOC[C@H]3c3ccc(C(F)(F)F)cc3)cc2c2ccsc12] | (4-aminothieno[2,3-c]quinolin-8-yl)-[(3R)-3-[4-(trifluoromethyl)phenyl]morpholin-4-yl]methanone | 458.0 | $1^{st}$ peak, Chiral Technologies OJ column (250 X 21 mm, 5 mm) with a mobile phase of 70% Liquid $CO_2$ and 30% MeOH with 0.2% TEA using a flowrate of 80 mL/min. |
| 488 | 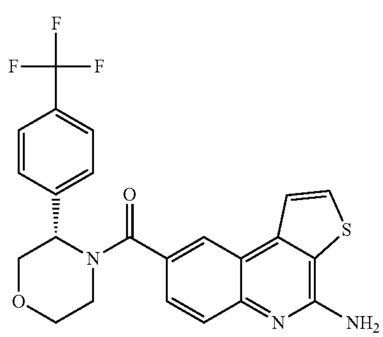 [SMILES: Nc1nc2ccc(C(=O)N3CCOC[C@@H]3c3ccc(C(F)(F)F)cc3)cc2c2ccsc12] | (4-aminothieno[2,3-c]quinolin-8-yl)-[(3S)-3-[4-(trifluoromethyl)phenyl]morpholin-4-yl]methanone | 458.0 | $2^{nd}$ peak, Chiral Technologies OJ column (250 X 21 mm, 5 mm) with a mobile phase of 70% Liquid $CO_2$ and 30% MeOH with 0.2% TEA using a flowrate of 80 mL/min. |

TABLE 9-continued

| Ex. | Structure | Name | m/z (ESI): [M + H]+ | SFC Conditions |
|---|---|---|---|---|
| 489 | 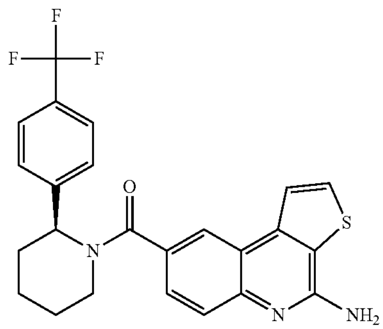 [SMILES: Nc1nc2ccc(C(=O)N3CCCC[C@H]3c3ccc(C(F)(F)F)cc3)cc2c2ccsc12] | (4-aminothieno[2,3-c]quinolin-8-yl)-[(2S)-2-[4-(trifluoromethyl)phenyl]-1-piperidyl]methanone | 456.0 | 1st peak, Chiral Technologies AS column (250 X 21 mm, 5 mm) with a mobile phase of 65% Liquid CO₂ and 35% MeOH with 0.2% TEA using a flowrate of 80 mL/min. |
| 490 | 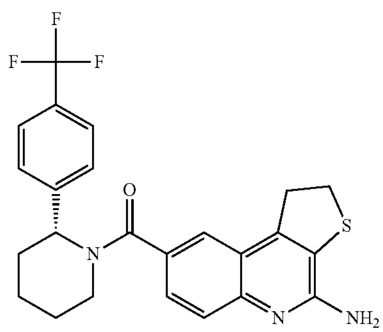 [SMILES: Nc1nc2ccc(C(=O)N3CCCC[C@@H]3c3ccc(C(F)(F)F)cc3)cc2c2c1SCC2] | (4-aminothieno[2,3-c]quinolin-8-yl)-[(2R)-2-[4-(trifluoromethyl)phenyl]-1-piperidyl]methanone | 456.0 | 2nd peak, Chiral Technologies AS column (250 X 21 mm, 5 mm) with a mobile phase of 65% Liquid CO₂ and 35% MeOH with 0.2% TEA using a flowrate of 80 mL/min. |

Example 491: (4-amino-1,3-dihydrofuro[3,4-c][1,7]naphthyridin-8-yl)((3S,5R)-3-(6-methoxypyridazin-3-yl)-5-methylmorpholino)methanone

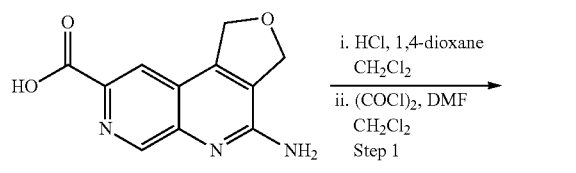

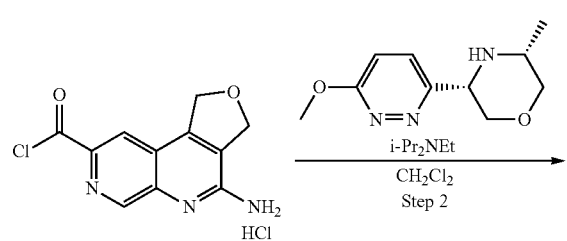

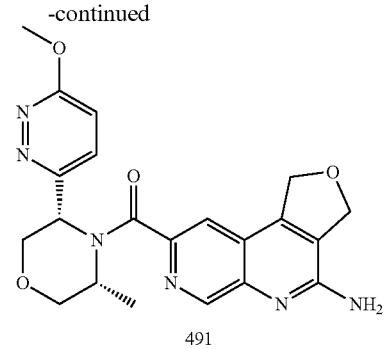

Step 1. To a stirred suspension of 4-amino-1,3-dihydrofuro[3,4-c][1,7]naphthyridine-8-carboxylic acid (500 mg, 2.163 mmol) in CH₂Cl₂ (10.0 mL) was added 4 M HCl in 1,4-dioxane (1.62 mL, 6.49 mmol) and the resulting suspension was allowed to stir at room temperature for 30 min. The mixture was concentrated under reduced pressure, then co-evaporated with toluene (2×5 mL). The obtained crude material was re-suspended in dichloromethane (20.0 mL), cooled to 0° C., and treated with oxalyl chloride (2.0 M in CH₂Cl₂, 4.33 mL, 8.65 mmol) followed by DMF (5 drops). The reaction vessel was flushed with nitrogen and the reaction mixture was allowed to stir at room temperature under nitrogen overnight. After 16 h, the reaction mixture was concentrated under reduced pressure, and the obtained crude residue was rinsed with heptane (30 mL) and dried in vacuo to give 4-amino-1,3-dihydrofuro[3,4-c][1,7]naphthyridine-8-carbonyl chloride hydrochloride (463 mg, 1.62 mmol, 75% yield) as a tan solid; m/z (ESI): 246.1 [M+H]+ was observed for the corresponding methyl ester after quenching of an aliquot with MeOH.

Step 2. A vial was charged with (3S,5R)-3-(6-methoxypyridazin-3-yl)-5-methylmorpholine (35.9 mg, 0.172 mmol), 4-amino-1,3-dihydrofuro[3,4-c][1,7]naphthyridine-8-carbonyl chloride hydrochloride (63.8 mg, 0.223 mmol) and dichloromethane (3.43 mL). To the resulting suspension was added N,N-diisopropylethylamine (111 mg, 150 µL, 0.858 mmol), and the resulting mixture was stirred at rt for 16 h. The reaction was quenched by addition of sat. aq. NaHCO$_3$ (10 mL), transferred to a separatory funnel with brine (10 mL) and CH$_2$Cl$_2$ (20 mL), and extracted with CH$_2$Cl$_2$ (2×20 mL). The combined organic layers were dried over anhydrous Na$_2$SO$_4$, filtered, and concentrated to dryness. The resulting crude residue was purified by flash chromatography (0 to 100% 3:1 EtOAc:EtOH in heptane) to afford (4-amino-1,3-dihydrofuro[3,4-c][1,7]naphthyridin-8-yl)((3S,5R)-3-(6-methoxypyridazin-3-yl)-5-methylmorpholino)methanone (59.8 mg, 0.142 mmol, 83% yield) as an off-white solid. $^1$H NMR (400 MHz, CHLOROFORM-d) δ ppm 9.03 (br s, 1H), 7.94 (br s, 1H), 7.72 (br d, J=7.1 Hz, 1H), 6.99 (d, J=9.2 Hz, 1H), 5.97 (d, J=3.8 Hz, 1H), 5.50 (t, J=3.7 Hz, 2H), 5.29-5.44 (m, 1H), 5.15-5.23 (m, 2H), 4.97 (s, 2H), 4.37-4.65 (m, 1H), 4.17 (s, 3H), 3.68-3.99 (m, 3H), 1.05 (d, J=7.1 Hz, 3H); m/z (ESI): 423.25 [M+H]+.

Examples below were prepared in a manner similar to that described for Example 491.

TABLE 10

| Ex. | Structure | Name | m/z (ESI): [M + H]+ |
| --- | --- | --- | --- |
| 492 | 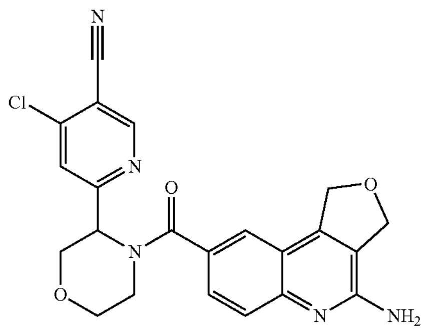 [SMILES: N#Cc1cnc(C2COCCN2C(=O)c2ccc3nc(N)c4c(c3c2)COC4)cc1Cl] | 4-chloro-6-[rac-(3S)-4-(4-amino-1,3-dihydrofuro[3,4-c]quinoline-8-carbonyl)morpholin-3-yl]pyridine-3-carbonitrile | 436.0 |
| 493 | 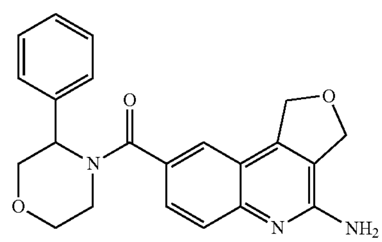 [SMILES: Nc1nc2ccc(C(=O)N3CCOCC3c3ccccc3)cc2c2c1COC2] | (4-amino-1,3-dihydrofuro[3,4-c]quinolin-8-yl)-[rac-(3S)-3-phenylmorpholin-4-yl]methanone | 376.1 |
| 494 | 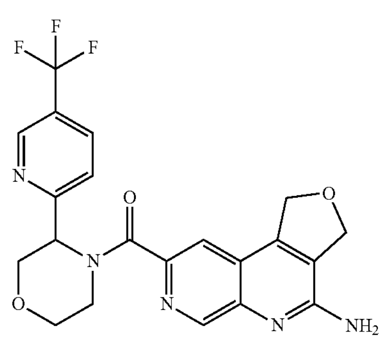 [SMILES: Nc1nc2cnc(C(=O)N3CCOCC3c3ccc(C(F)(F)F)cn3)cc2c2c1COC2] | (4-amino-1,3-dihydrofuro[3,4-c][1,7]naphthyridin-8-yl)-[rac-(3S)-3-[5-(trifluoromethyl)-2-pyridyl]morpholin-4-yl]methanone | 446.0 |

TABLE 10-continued

| Ex. | Structure | Name | m/z (ESI): [M + H]+ |
|---|---|---|---|
| 495 | 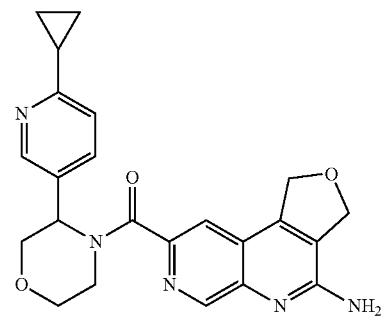 [SMILES: Nc1nc2cnc(C(=O)N3CCOCC3c3ccc(C4CC4)nc3)cc2c2c1COC2] | (4-amino-1,3-dihydrofuro[3,4-c][1,7]naphthyridin-8-yl)-[rac-(3S)-3-(6-cyclopropyl-3-pyridyl)morpholin-4-yl]methanone | 418.2 |
| 496 | 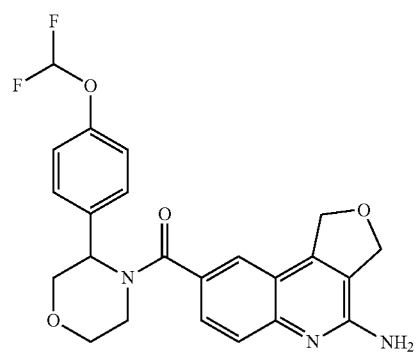 [SMILES: Nc1nc2ccc(C(=O)N3CCOCC3c3ccc(OC(F)F)cc3)cc2c2c1COC2] | (4-amino-1,3-dihydrofuro[3,4-c]quinolin-8-yl)((3R)-3-(4-(difluoromethoxy)phenyl)-4-morpholinyl)methanone and (4-amino-1,3-dihydrofuro[3,4-c]quinolin-8-yl)((3S)-3-(4-(difluoromethoxy)phenyl)-4-morpholinyl)methanone | 442.2 |
| 497 | 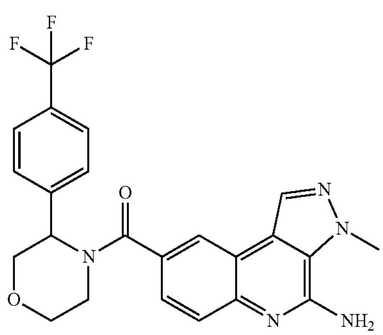 [SMILES: Cn1ncc2c3cc(C(=O)N4CCOCC4c4ccc(C(F)(F)F)cc4)ccc3nc(N)c21] | (4-amino-3-methyl-3H-pyrazolo[3,4-c]quinolin-8-yl)((3R)-3-(4-(trifluoromethyl)phenyl)-4-morpholinyl)methanone and (4-amino-3-methyl-3H-pyrazolo[3,4-c]quinolin-8-yl)((3S)-3-(4-(trifluoromethyl)phenyl)-4-morpholinyl)methanone | 456.1 |
| 498 | 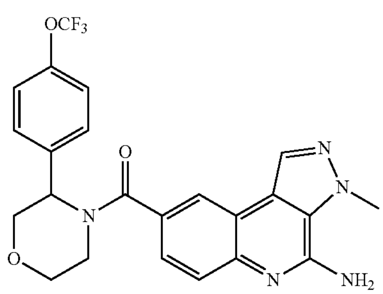 [SMILES: Cn1ncc2c3cc(C(=O)N4CCOCC4c4ccc(OC(F)(F)F)cc4)ccc3nc(N)c21] | (4-amino-3-methyl-3H-pyrazolo[3,4-c]quinolin-8-yl)((3R)-3-(4-(trifluoromethoxy)phenyl)-4-morpholinyl)methanone and (4-amino-3-methyl-3H-pyrazolo[3,4-c]quinolin-8-yl)((3S)-3-(4-(trifluoromethoxy)phenyl)-4-morpholinyl)methanone | 472.1 |

TABLE 10-continued

| Ex. | Structure | Name | m/z (ESI): [M + H]+ |
|---|---|---|---|
| 499 | 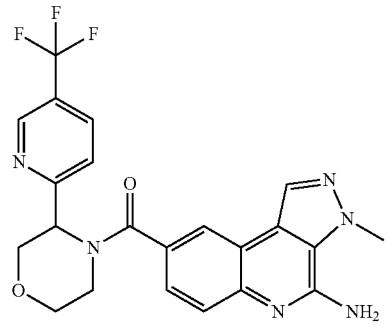 | (4-amino-3-methyl-3H-pyrazolo[3,4-c]quinolin-8-yl)((3R)-3-(5-(trifluoromethyl)-2-pyridinyl)-4-morpholinyl)methanone and (4-amino-3-methyl-3H-pyrazolo[3,4-c]quinolin-8-yl)((3S)-3-(5-(trifluoromethyl)-2-pyridinyl)-4-morpholinyl)methanone | 457.1 |
| 500 | 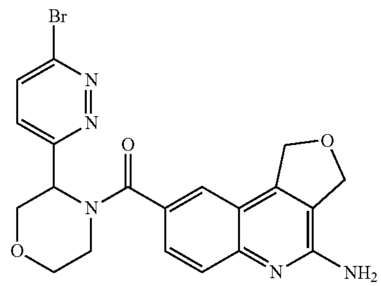 [SMILES: Nc1nc2ccc(C(=O)N3CCOCC3c3ccc(Br)nn3)cc2c2c1COC2] | (4-amino-1,3-dihydrofuro[3,4-c]quinolim-8-yl)-[rac-(3S)-3-(6-bromopyridazin-3-yl)morpholin-4-yl]methanone | 454.0, 456.0 |
| 501 | 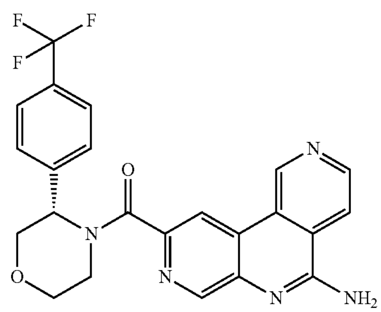 [SMILES: Nc1nc2cnc(C(=O)N3CCOC[C@@H]3c3ccc(C(F)(F)F)cc3)cc2c2cnccc12] | (5-aminopyrido[4,3-c][1,7]naphthyridin-9-yl)((3S)-3-(4-(trifluoromethyl)phenyl)-4-morpholinyl)methanone | 454.1 |
| 502 | 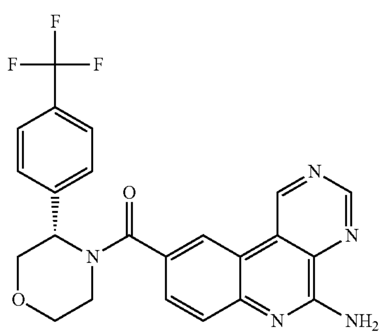 [SMILES: Nc1nc2ccc(C(=O)N3CCOC[C@@H]3c3ccc(C(F)(F)F)cc3)cc2c2cncnc12] | (5-aminopyrimido[4,5-c]quinolin-9-yl)((3S)-3-(4-(trifluoromethyl)phenyl)-4-morpholinyl)methanone | 454.0 |
| 503 | 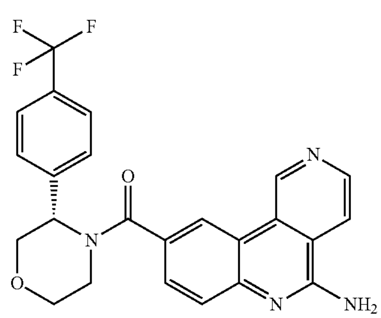 [SMILES: Nc1nc2ccc(C(=O)N3CCOC[C@@H]3c3ccc(C(F)(F)F)cc3)cc2c2cnccc12] | (5-aminobenzo[c][2,6]naphthyridin-9-yl)((3S)-3-(4-(trifluoromethyl)phenyl)-4-morpholinyl)methanone | 453.1 |

TABLE 10-continued

| Ex. | Structure | Name | m/z (ESI): [M + H]+ |
|---|---|---|---|
| 504 | 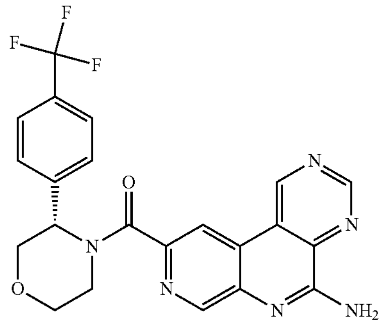 [SMILES: Nc1nc2cnc(C(=O)N3CCOC[C@@H]3c3ccc(C(F)(F)F)cc3)cc2c2cncnc12] | (5-aminopyrimido[4,5-c][1,7]naphthyridin-9-yl)((3S)-3-(4-(trifluoromethyl)phenyl)-4-morpholinyl)methanone | 455.1 |
| 505 | 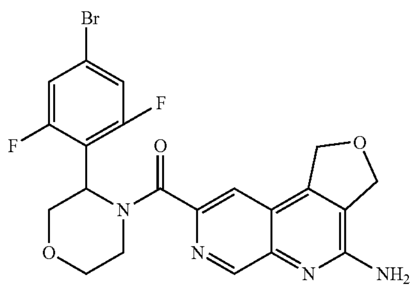 | (4-amino-1,3-dihydrofuro[3,4-c][1,7]naphthyridin-8-yl)((3R)-3-(4-bromo-2,6-difluorophenyl)-4-morpholinyl)methanone and (4-amino-1,3-dihydrofuro[3,4-c][1,7]naphthyridin-8-yl)((3S)-3-(4-bromo-2,6-difluorophenyl)-4-morpholinyl)methanone | 491.00 and 493.00 |
| 506 | 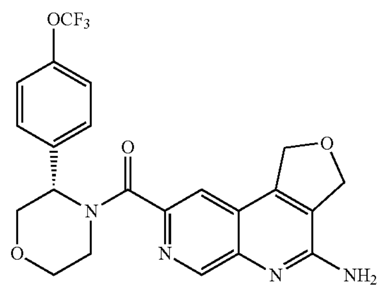 [SMILES: Nc1nc2cnc(C(=O)N3CCOC[C@@H]3c3ccc(OC(F)(F)F)cc3)cc2c2c1COC2] | (4-amino-1,3-dihydrofuro[3,4-c][1,7]naphthyridin-8-yl)-[(3S)-3-[4-(trifluoromethoxy)phenyl]morpholin-4-yl]methanone | 461.0 |
| 507 | 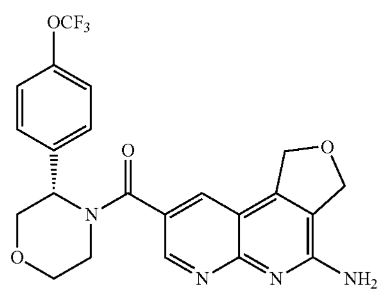 | (4-amino-1,3-dihydrofuro[3,4-c][1,8]naphthyridin-8-yl)-[(3S)-3-[4-(trifluoromethoxy)phenyl]morpholin-4-yl]methanone | 461.0 |
| 508 | 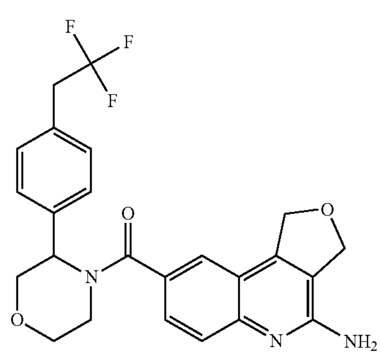 [SMILES: Nc1nc2ccc(C(=O)N3CCOCC3c3ccc(CC(F)(F)F)cc3)cc2c2c1COC2] | (4-amino-1,3-dihydrofuro[3,4-c]quinolin-8-yl)((3R)-3-(4-(2,2,2-trifluoroethyl)phenyl)-4-morpholinyl)methanone and (4-amino-1,3-dihydrofuro[3,4-c]quinolin-8-yl)((3S)-3-(4-(2,2,2-trifluoroethyl)phenyl)-4-morpholinyl)methanone | 458.0 |

TABLE 10-continued

| Ex. | Structure | Name | m/z (ESI): [M + H]+ |
|---|---|---|---|
| 509 | 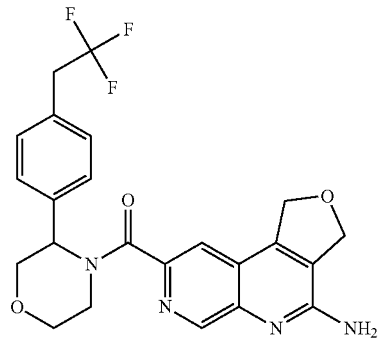 [SMILES: Nc1nc2cnc(C(=O)N3CCOCC3c3ccc(CC(F)(F)F)cc3)cc2c2c1COC2] | (4-amino-1,3-dihydrofuro[3,4-c][1,7]naphthyridin-8-yl)((3R)-3-(4-(2,2,2-trifluoroethyl)phenyl)-4-morpholinyl)methanone and (4-amino-1,3-dihydrofuro[3,4-c][1,7]naphthyridin-8-yl)((3S)-3-(4-(2,2,2-trifluoroethyl)phenyl)-4-morpholinyl)methanone | 459.0 |
| 510 | 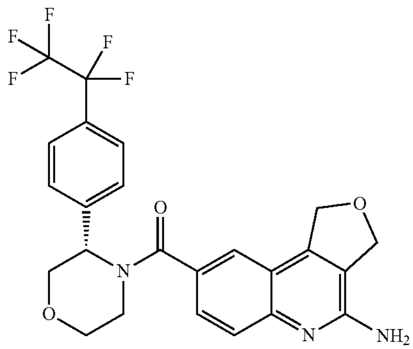 [SMILES: Nc1nc2ccc(C(=O)N3CCOC[C@@H]3c3ccc(C(F)(F)C(F)(F)F)cc3)cc2c2c1COC2] | (4-amino-1,3-dihydrofuro[3,4-c]quinolin-8-yl)((3S)-3-(4-(pentafluoroethyl)phenyl)-4-morpholinyl)methanone | 494.0 |
| 511 | 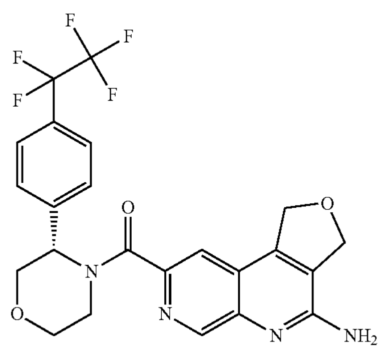 [SMILES: Nc1nc2cnc(C(=O)N3CCOC[C@@H]3c3ccc(C(F)(F)C(F)(F)F)cc3)cc2c2c1COC2] | (4-amino-1,3-dihydrofuro[3,4-c][1,7]naphthyridin-8-yl)(3S)-3-(4-(pentafluoroethyl)phenyl)-4-morpholinyl)methanone | 495.0 |
| 512 | 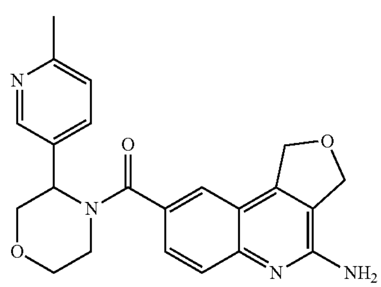 [SMILES: Cc1ccc(C2COCCN2C(=O)c2ccc3nc(N)c4c(c3c2)COC4)cn1] | (4-amino-1,3-dihydrofuro[3,4-c]quinolin-8-yl)-[rac-(3R)-3-(6-methyl-3-pyridyl)morpholin-4-yl]methanone | 391.2 |

TABLE 10-continued

| Ex. | Structure | Name | m/z (ESI): [M + H]+ |
|---|---|---|---|
| 513 | 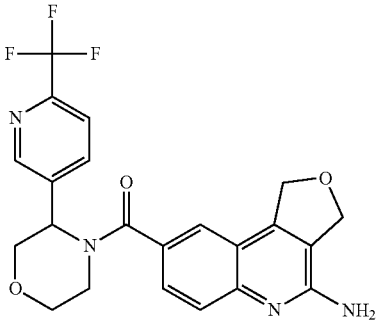 [SMILES: Nc1nc2ccc(C(=O)N3CCOCC3c3ccc(C(F)(F)F)nc3)cc2c2c1COC2] | (4-amino-1,3-dihydrofuro[3,4-c]quinolin-8-yl)-[rac-(3S)-3-[6-(trifluoromethyl)-3-pyridyl]morpholin-4-yl]methanone | 445.0 |
| 514 | 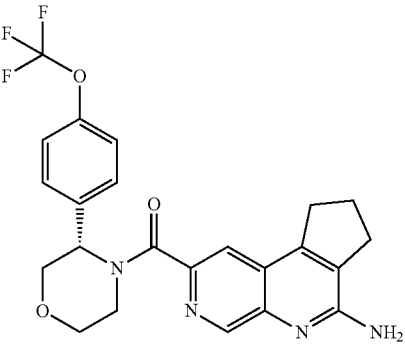 [SMILES: Nc1nc2cnc(C(=O)N3CCOC[C@@H]3c3ccc(OC(F)(F)F)cc3)cc2c2c1CCC2] | (6-amino-8,9-dihydro-7H-cyclopenta[c][1,7]naphthyridin-2-yl)((3S)-3-(4-(trifluoromethoxy)phenyl)-4-morpholinyl)methanone | 459.0 |
| 515 | 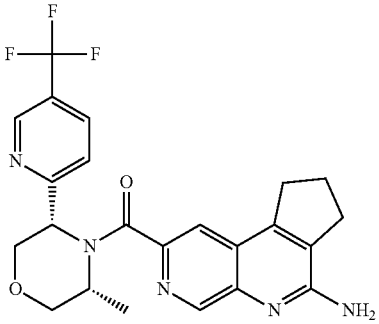 [SMILES: C[C@@H]1COC[C@H](c2ccc(C(F)(F)F)cn2)N1C(=O)c1cc2c3c(c(N)nc2cn1)CCC3] | (6-amino-8,9-dihydro-7H-cyclopenta[c][1,7]naphthyridin-2-yl)((3R,5S)-3-methyl-5-(5-(trifluoromethyl)-2-pyridinyl)-4-morpholinyl)methanone | 458.2 |
| 516 | 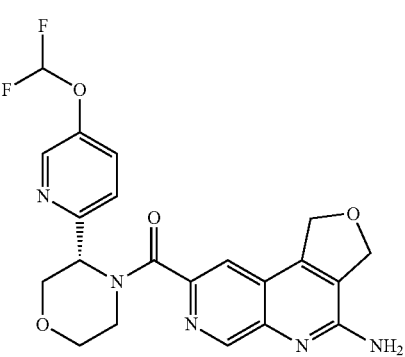 | (4-amino-1,3-dihydrofuro[3,4-c][1,7]naphthyridin-8-yl)((3S)-3-(5-(difluoromethoxy)-2-pyridinyl)-4-morpholinyl)methanone | 444.2 |

TABLE 10-continued

| Ex. | Structure | Name | m/z (ESI): [M + H]+ |
|---|---|---|---|
| 517 | 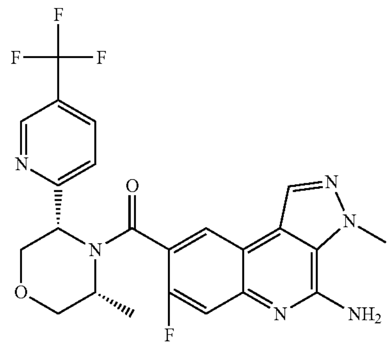 [SMILES: C[C@@H]1COC[C@H](c2ccc(C(F)(F)F)cn2)N1C(=O)c1cc2c(cc1F)nc(N)c1c2cnn1C] | (4-amino-7-fluoro-3-methyl-3H-pyrazolo[3,4-c]quinolin-8-yl)((3R,5S)-3-methyl-5-(5-(trifluoromethyl)-2-pyridinyl)-4-morpholinyl)methanone | 489.2 |
| 518 | 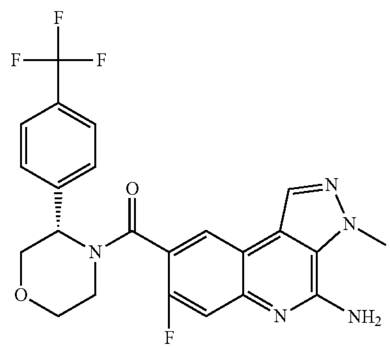 [SMILES: Cn1ncc2c3cc(C(=O)N4CCOC[C@@H]4c4ccc(C(F)(F)F)cc4)c(F)cc3nc(N)c21] | (4-amino-7-fluoro-3-methyl-3H-pyrazolo[3,4-c]quinolin-8-yl)((3S)-3-(4-(trifluoromethyl)phenyl)-4-morpholinyl)methanone | 474.2 |
| 519 | 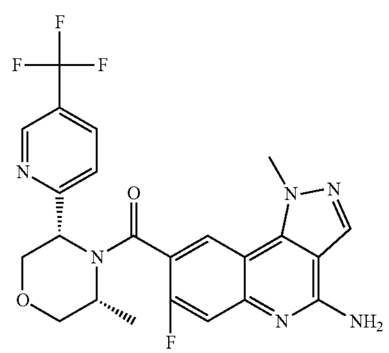 [SMILES: C[C@@H]1COC[C@H](c2ccc(C(F)(F)F)cn2)N1C(=O)c1cc2c(cc1F)nc(N)c1cnn(C)c12] | (4-amino-7-fluoro-1-methyl-1H-pyrazolo[4,3-c]quinolin-8-yl)((3R,5S)-3-methyl-5-(5-(trifluoromethyl)-2-pyridinyl)-4-morpholinyl)methanone | 489.2 |
| 520 | 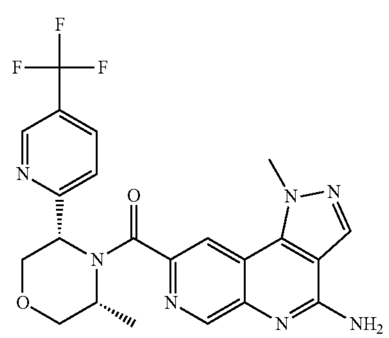 [SMILES: C[C@@H]1COC[C@H](c2ccc(C(F)(F)F)cn2)N1C(=O)c1cc2c(cn1)nc(N)c1cnn(C)c12] | (4-amino-1-methyl-1H-pyrazolo[4,3-c][1,7]naphthyridin-8-yl)((3R,5S)-3-methyl-5-(5-(trifluoromethyl)-2-pyridinyl)-4-morpholinyl)methanone | 472.2 |

TABLE 10-continued

| Ex. | Structure | Name | m/z (ESI): [M + H]+ |
|---|---|---|---|
| 521 | 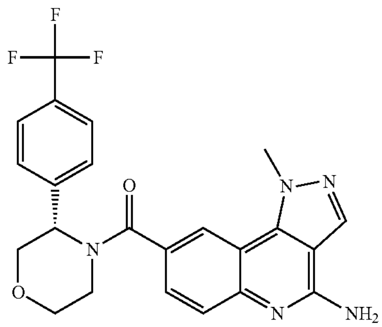 [SMILES: Cn1ncc2c(N)nc3ccc(C(=O)N4CCOC[C@@H]4c4ccc(C(F)(F)F)cc4)cc3c21] | (4-amino-1-methyl-1H-pyrazolo[4,3-c]quinolin-8-yl)((3S)-3-(4-(trifluoromethyl)phenyl)-4-morpholinyl)methanone | 456.2 |
| 522 | 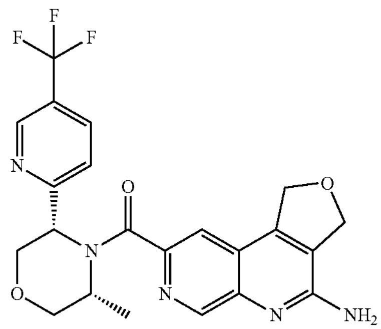 [SMILES: C[C@@H]1COC[C@H](c2ccc(C(F)(F)F)cn2)N1C(=O)c1cc2c3c(c(N)nc2cn1)COC3] | (4-amino-1,3-dihydrofuro[3,4-c][1,7]naphthyridin-8-yl)((3R,5S)-3-methyl-5-(5-(trifluoromethyl)-2-pyridinyl)-4-morpholinyl)methanone | 460.2 |
| 523 | 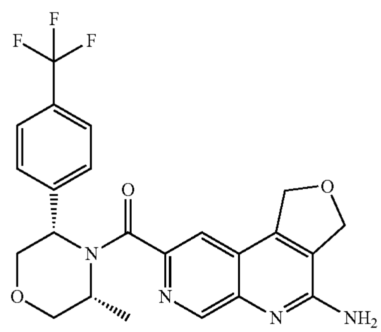 | (4-amino-1,3-dihydrofuro[3,4-c][1,7]naphthyridin-8-yl)((3R,5S)-3-methyl-5-(4-(trifluoromethyl)phenyl)-4-morpholinyl)methanone | 458.8 |
| 524 | 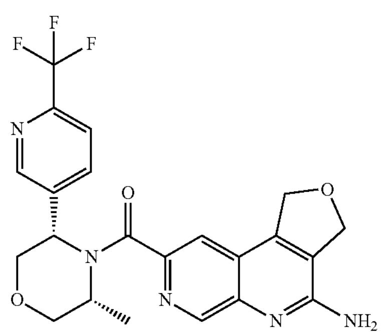 | (4-amino-1,3-dihydrofuro[3,4-c][1,7]naphthyridin-8-yl)((3R,5S)-3-methyl-5-(6-(trifluoromethyl)-3-pyridinyl)-4-morpholinyl)methanone | 459.8 |

TABLE 10-continued

| Ex. | Structure | Name | m/z (ESI): [M + H]+ |
|---|---|---|---|
| 525 | 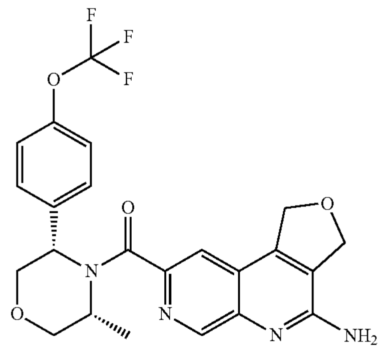 [SMILES: C[C@@H]1COC[C@H](c2ccc(OC(F)(F)F)cc2)N1C(=O)c1cc2c3c(c(N)nc2cn1)COC3] | (4-amino-1,3-dihydrofuro[3,4-c][1,7]naphthyridin-8-yl)((3R,5S)-3-methyl-5-(4-(trifluoromethoxy)phenyl)-4-morpholinyl)methanone | 475.2 |
| 526 | 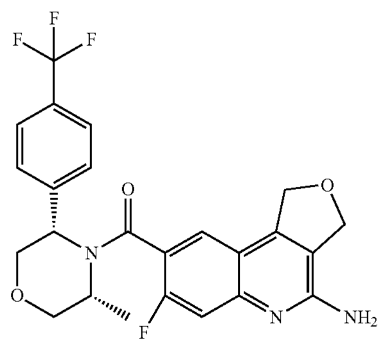 [SMILES: C[C@@H]1COC[C@H](c2ccc(C(F)(F)F)cc2)N1C(=O)c1cc2c3c(c(N)nc2cc1F)COC3] | (4-amino-7-fluoro-1,3-dihydrofuro[3,4-c]quinolin-8-yl)((3R,5S)-3-methyl-5-(4-(trifluoromethyl)phenyl)-4-morpholinyl)methanone | 476.1 |
| 527 | 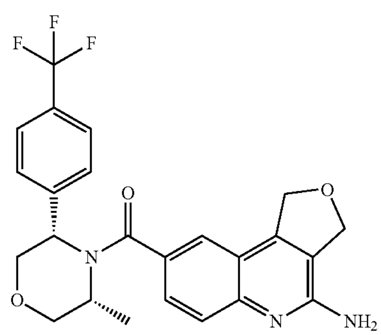 | (4-amino-1,3-dihydrofuro[3,4-c]quinolin-8-yl)((3R,5S)-3-methyl-5-(4-(trifluoromethyl)phenyl)-4-morpholinyl)methanone | 458.1 |
| 528 | 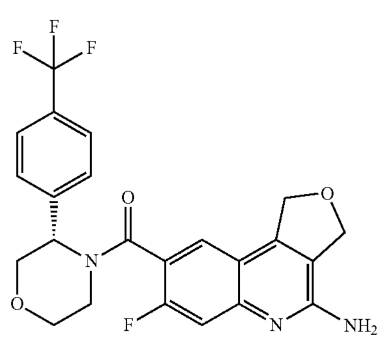 | (4-amino-7-fluoro-1,3-dihydrofuro[3,4-c]quinolin-8-yl)((3S)-3-(4-(trifluoromethyl)phenyl)-4-morpholinyl)methanone | 462.1 |

TABLE 10-continued

| Ex. | Structure | Name | m/z (ESI): [M + H]+ |
|---|---|---|---|
| 529 | 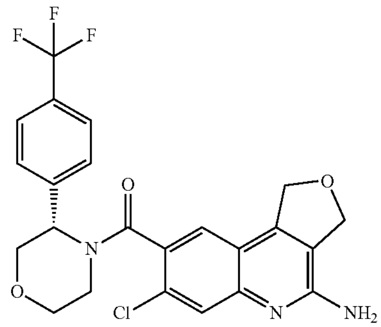 [SMILES: Nc1nc2cc(Cl)c(C(=O)N3CCOC[C@@H]3c3ccc(C(F)(F)F)cc3)cc2c2c1COC2] | (4-amino-7-chloro-1,3-dihydrofuro[3,4-c]quinolin-8-yl)((3S)-3-(4-(trifluoromethyl)phenyl)-4-morpholinyl)methanone | 478.0 |
| 530 | 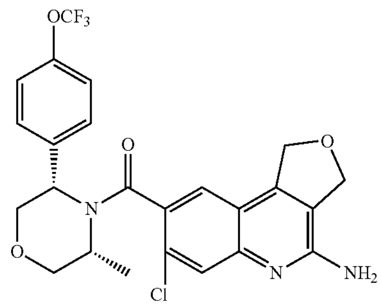 [SMILES: C[C@@H]1COC[C@H](c2ccc(OC(F)(F)F)cc2)N1C(=O)c1cc2c3c(c(N)nc2cc1Cl)COC3] | (4-amino-7-chloro-1,3-dihydrofuro[3,4-c]quinolin-8-yl)((3R,5S)-3-methyl-5-(4-(trifluoromethoxy)phenyl)-4-morpholinyl)methanone | 508.0 |
| 531 | 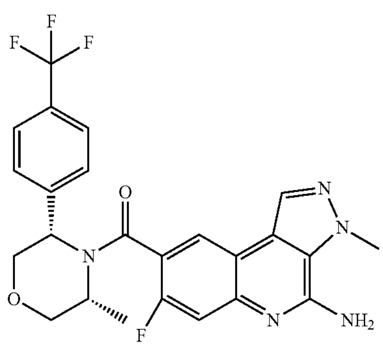 [SMILES: C[C@@H]1COC[C@H](c2ccc(C(F)(F)F)cc2)N1C(=O)c1cc2c(cc1F)nc(N)c1c2cnn1C] | (4-amino-7-fluoro-3-methyl-3H-pyrazolo[3,4-c]quinolin-8-yl)((3R,5S)-3-methyl-5-(4-(trifluoromethyl)phenyl)-4-morpholinyl)methanone | 488.1 |
| 532 | 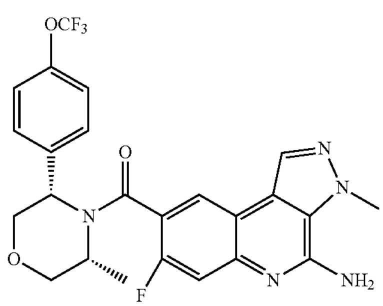 [SMILES: C[C@@H]1COC[C@H](c2ccc(OC(F)(F)F)cc2)N1C(=O)c1cc2c(cc1F)nc(N)c1c2cnn1C] | (4-amino-7-fluoro-3-methyl-3H-pyrazolo[3,4-c]quinolin-8-yl)((3R,5S)-3-methyl-5-(4-(trifluoromethoxy)phenyl)-4-morpholinyl)methanone | 504.1 |

TABLE 10-continued

| Ex. | Structure | Name | m/z (ESI): [M + H]+ |
|---|---|---|---|
| 533 | 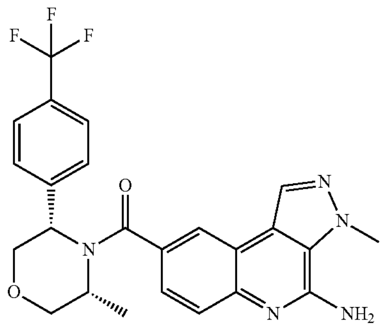 [SMILES: C[C@@H]1COC[C@H](c2ccc(C(F)(F)F)cc2)N1C(=O)c1ccc2nc(N)c3c(cnn3C)c2c1] | (4-amino-3-methyl-3H-pyrazolo[3,4-c]quinolin-8-yl)((3R,5S)-3-methyl-5-(4-(trifluoromethyl)phenyl)-4-morpholinyl)methanone | 469.9 |
| 534 | 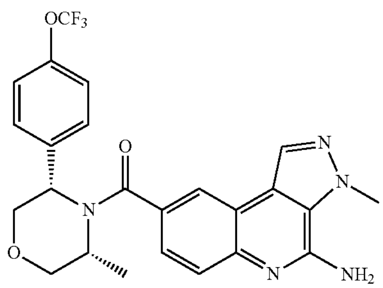 [SMILES: C[C@@H]1COC[C@H](c2ccc(OC(F)(F)F)cc2)N1C(=O)c1ccc2nc(N)c3c(cnn3C)c2c1] | (4-amino-3-methyl-3H-pyrazolo[3,4-c]quinolin-8-yl)((3R,5S)-3-methyl-5-(4-(trifluoromethoxy)phenyl)-4-morpholinyl)methanone | 486.0 |
| 535 | 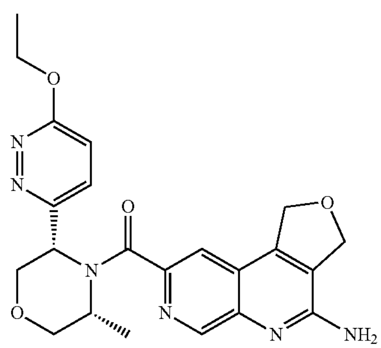 [SMILES: CCOc1ccc([C@H]2COC[C@@H](C)N2C(=O)c2cc3c4c(c(N)nc3cn2)COC4)nn1] | (4-amino-1,3-dihydrofuro[3,4-c][1,7]naphthyridin-8-yl)((3S,5R)-3-(6-ethoxy-3-pyridazinyl)-5-methyl-4-morpholinyl)methanone | 437.2 |
| 536 | 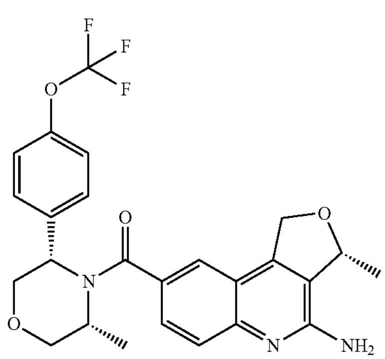 [SMILES: C[C@@H]1COC[C@H](c2ccc(OC(F)(F)F)cc2)N1C(=O)c1ccc2nc(N)c3c(c2c1)CO[C@@H]3C] | ((3R)-4-amino-3-methyl-1,3-dihydrofuro[3,4-c]quinolin-8-yl)((3R,5S)-3-methyl-5-(4-(trifluoromethoxy)phenyl)-4-morpholinyl)methanone | 488.2 |

TABLE 10-continued

| Ex. | Structure | Name | m/z (ESI): [M + H]+ |
|---|---|---|---|
| 537 | 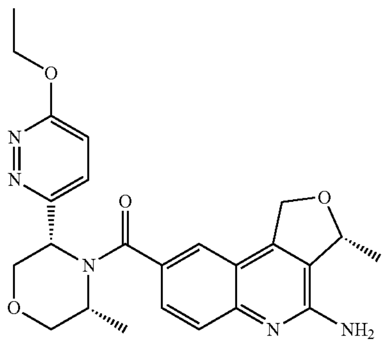 [SMILES: CCOc1ccc([C@H]2COC[C@@H](C)N2C(=O)c2ccc3nc(N)c4c(c3c2)CO[C@@H]4C)nn1] | ((3R)-4-amino-3-methyl-1,3-dihydrofuro[3,4-c]quinolin-8-yl)((3S,5R)-3-(6-ethoxy-3-pyridazinyl)-5-methyl-4-morpholinyl)methanone | 450.1 |
| 538 | 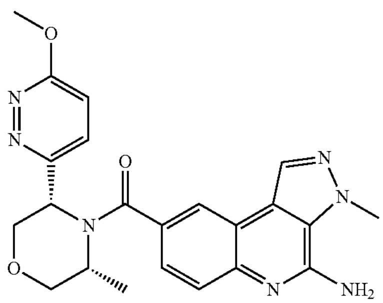 [SMILES: COc1ccc([C@H]2COC[C@@H](C)N2C(=O)c2ccc3nc(N)c4c(cnn4C)c3c2)nn1] | (4-amino-3-methyl-3H-pyrazolo[3,4-c]quinolin-8-yl)((3S,5R)-3-(6-methoxy-3-pyridazinyl)-5-methyl-4-morpholinyl)methanone | 434.2 |
| 539 | 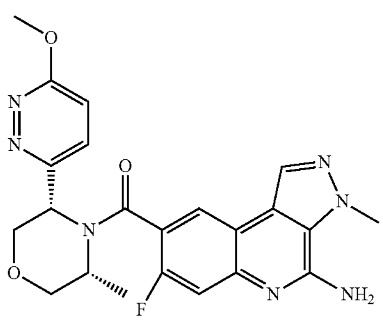 [SMILES: COc1ccc([C@H]2COC[C@@H](C)N2C(=O)c2cc3c(cc2F)nc(N)c2c3cnn2C)nn1] | (4-amino-7-fluoro-3-methyl-3H-pyrazolo[3,4-c]quinolin-8-yl)((3S,5R)-3-(6-methoxy-3-pyridazinyl)-5-methyl-4-morpholinyl)methanone | 452.2 |
| 540 | 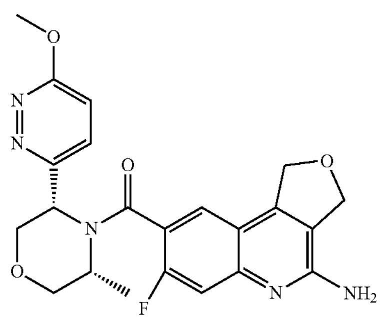 [SMILES: COc1ccc([C@H]2COC[C@@H](C)N2C(=O)c2cc3c4c(c(N)nc3cc2F)COC4)nn1] | (4-amino-7-fluoro-1,3-dihydrofuro[3,4-c]quinolin-8-yl)((3S,5R)-3-(6-methoxy-3-pyridazinyl)-5-methyl-4-morpholinyl)methanone | 440.2 |

TABLE 10-continued

| Ex. | Structure | Name | m/z (ESI): [M + H]+ |
|---|---|---|---|
| 541 | 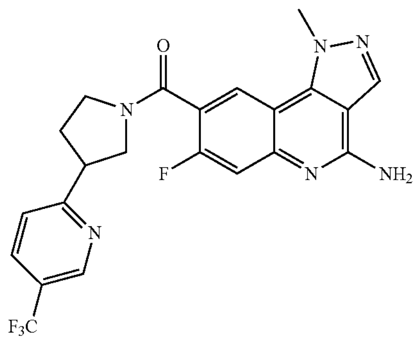 [SMILES: Cn1ncc2c(N)nc3cc(F)c(C(=O)N4CCC(c5ccc(C(F)(F)F)cn5)C4)cc3c21] | (4-amino-7-fluoro-1-methyl-1H-pyrazolo[4,3-c]quinolin-8-yl)((3R)-3-(5-(trifluoromethyl)-2-pyridinyl)-1-pyrrolidinyl)methanone and (4-amino-7-fluoro-1-methyl-1H-pyrazolo[4,3-c]quinolin-8-yl)((3S)-3-(5-(trifluoromethyl)-2-pyridinyl)-1-pyrrolidinyl)methanone | 459.1 |
| 542 | 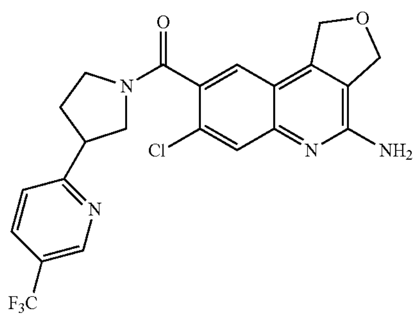 [SMILES: Nc1nc2cc(Cl)c(C(=O)N3CCC(c4ccc(C(F)(F)F)cn4)C3)cc2c2c1COC2] | (4-amino-7-chloro-1,3-dihydrofuro[3,4-c]quinolin-8-yl)((3R)-3-(5-(trifluoromethyl)-2-pyridinyl)-1-pyrrolidinyl)methanone and (4-amino-7-chloro-1,3-dihydrofuro[3,4-c]quinolin-8-yl)((3S)-3-(5-(trifluoromethyl)-2-pyridinyl)-1-pyrrolidinyl)methanone | 463.2 |
| 543 | 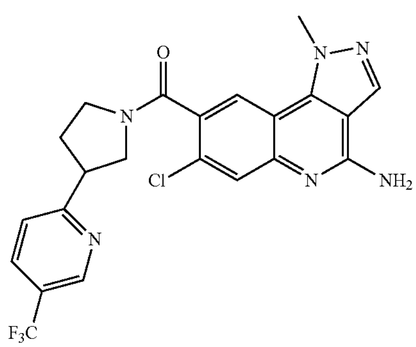 [SMILES: Cn1ncc2c(N)nc3cc(Cl)c(C(=O)N4CCC(c5ccc(C(F)(F)F)cn5)C4)cc3c21] | (4-amino-7-chloro-1-methyl-1H-pyrazolo[4,3-c]quinolin-8-yl)((3R)-3-(5-(trifluoromethyl)-2-pyridinyl)-1-pyrrolidinyl)methanone and (4-amino-7-chloro-1-methyl-1H-pyrazolo[4,3-c]quinolin-8-yl)((3S)-3-(5-(trifluoromethyl)-2-pyridinyl)-1-pyrrolidinyl)methanone | 475.2 |
| 544 | 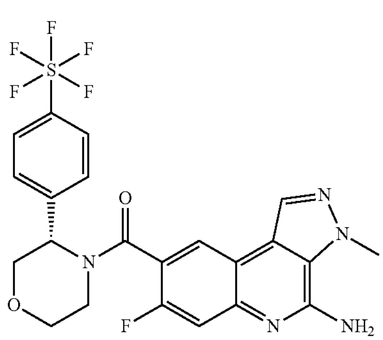 [SMILES: Cn1ncc2c3cc(C(=O)N4CCOC[C@@H]4c4ccc(S(F)(F)(F)(F)F)cc4)c(F)cc3nc(N)c21] | (4-amino-7-fluoro-3-methyl-3H-pyrazolo[3,4-c]quinolin-8-yl)((3S)-3-(4-(pentafluoro-lambda~6~-sulfanyl)phenyl)-4-morpholinyl)methanone | 532.0 |

TABLE 10-continued

| Ex. | Structure | Name | m/z (ESI): [M + H]⁺ |
|---|---|---|---|
| 545 | 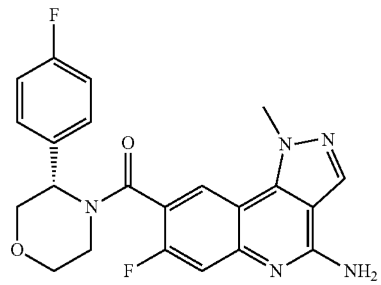 [SMILES: Cn1ncc2c(N)nc3cc(F)c(C(=O)N4CCOC[C@@H]4c4ccc(F)cc4)cc3c21] | (4-amino-7-fluoro-1-methyl-1H-pyrazolo[4,3-c]quinolin-8-yl)((3S)-3-(4-fluorophenyl)-4-morpholinyl)methanone | 424.1 |
| 546 | 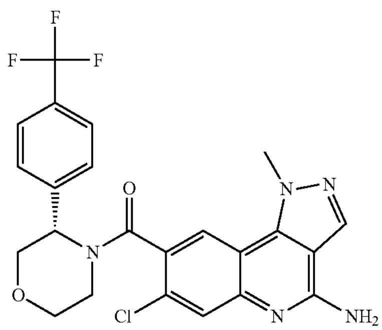 [SMILES: Cn1ncc2c(N)nc3cc(Cl)c(C(=O)N4CCOC[C@@H]4c4ccc(C(F)(F)F)cc4)cc3c21] | (4-amino-7-chloro-1-methyl-1H-pyrazolo[4,3-c]quinolin-8-yl)((3S)-3-(4-(trifluorometliyl)phenyl)-4-morpholinyl)methanone | 489.9 |
| 547 | 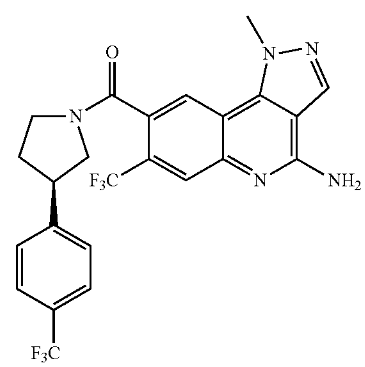 [SMILES: Cn1ncc2c(N)nc3cc(C(F)(F)F)c(C(=O)N4CC[C@H](c5ccc(C(F)(F)F)cc5)C4)cc3c21] | (4-amino-1-methyl-7-(trifluoromethyl)-1H-pyrazolo[4,3-c]quinolin-8-yl)((3R)-3-(4-(trifluoromethyl)phenyl)-1-pyrrolidinyl)methanone | 507.9 |
| 548 | 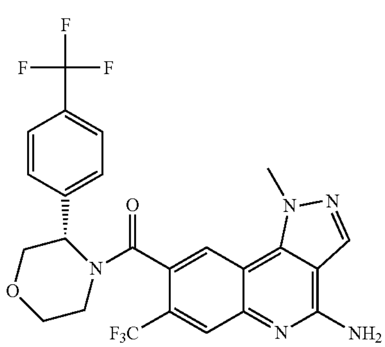 [SMILES: Cn1ncc2c(N)nc3cc(C(F)(F)F)c(C(=O)N4CCOC[C@@H]4c4ccc(C(F)(F)F)cc4)cc3c21] | (4-amino-1-methyl-7-(trifluoromethyl)-1H-pyrazolo[4,3-c]quinolin-8-yl)((3S)-3-(4-(trifluoromethyl)phenyl)-4-morpholinyl)methanone | 523.8 |

TABLE 10-continued

| Ex. | Structure | Name | m/z (ESI): [M + H]+ |
|---|---|---|---|
| 549 | 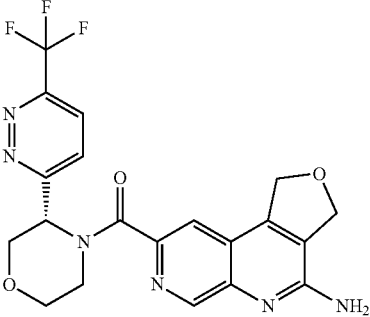 | (4-amino-1,3-dihydrofuro[3,4-c][1,7]naphthyridin-8-yl)((3S)-3-(6-(trifluoromethyl)-3-pyridazinyl)-4-morpholinyl)methanone | 446.8 |
| 550 | 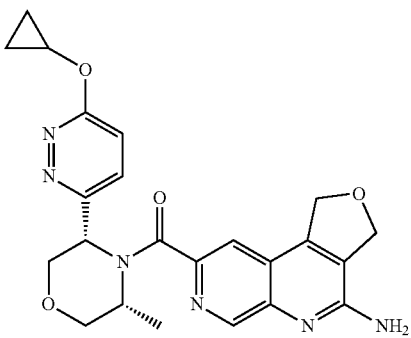 [SMILES: C[C@@H]1COC[C@H](c2ccc(OC3CC3)nn2)N1C(=O)c1cc2c3c(c(N)nc2cn1)COC3] | (4-amino-1,3-dihydrofuro[3,4-c][1,7]naphthyridin-8-yl)((3S,5R)-3-(6-(cyclopropyloxy)-3-pyridazinyl)-5-methyl-4-morpholinyl)methanone | 449.2 |
| 551 | 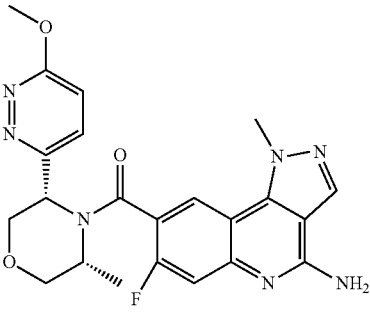 [SMILES: COc1ccc([C@H]2COC[C@@H](C)N2C(=O)c2cc3c(cc2F)nc(N)c2cnn(C)c23)nn1] | (4-amino-7-fluoro-1-methyl-1H-pyrazolo[4,3-c]quinolin-8-yl)((3S,5R)-3-(6-methoxy-3-pyridazinyl)-5-methyl-4-morpholinyl)methanone | 452.2 |
| 552 | 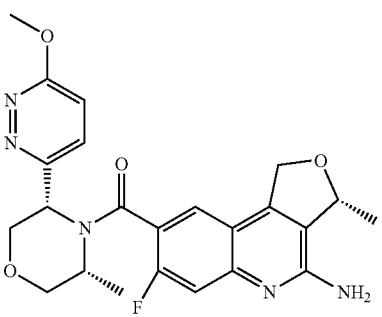 [SMILES: COc1ccc([C@H]2COC[C@@H](C)N2C(=O)c2cc3c4c(c(N)nc3cc2F)[C@@H](C)OC4)nn1] | ((3R)-4-amino-7-fluoro-3-methyl-1,3-dihydrofuro[3,4-c]quinolin-8-yl)((3S,5R)-3-(6-methoxy-3-pyridazinyl)-5-methyl-4-morpholinyl)methanone | 454.2 |

TABLE 10-continued

| Ex. | Structure | Name | m/z (ESI): [M + H]⁺ |
|---|---|---|---|
| 553 | 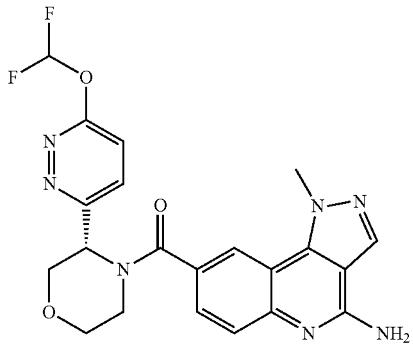 [SMILES: Cn1ncc2c(N)nc3ccc(C(=O)N4CCOC[C@@H]4c4ccc(OC(F)F)nn4)cc3c21] | (4-amino-1-methyl-1H-pyrazolo[4,3-c]quinolin-8-yl)((3S)-3-(6-(difluoromethoxy)-3-pyridazinyl)-4-morpholinyl)methanone | 456.0 |
| 554 | 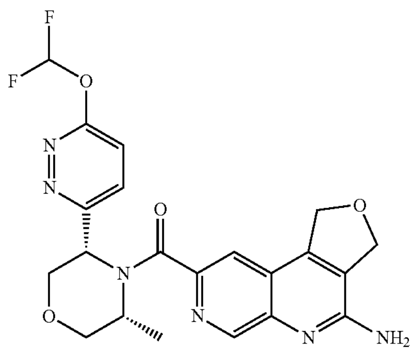 | (4-amino-1,3-dihydrofuro[3,4-c][1,7]naphthyridin-8-yl)((3S,5R)-3-(6-(difluoromethoxy)-3-pyridazinyl)-5-methyl-4-morpholinyl)methanone | 459.1 |
| 555 | 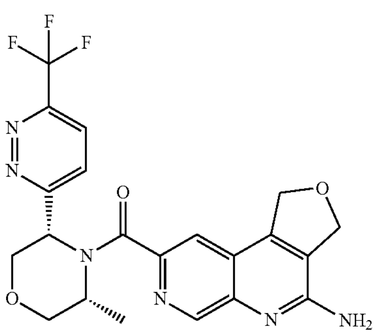 | (4-amino-1,3-dihydrofuro[3,4-c][1,7]naphthyridin-8-yl)((3R,5S)-3-methyl-5-(6-(trifluoromethyl)-3-pyridazinyl)-4-morpholinyl)methanone | 461.1 |
| 556 | 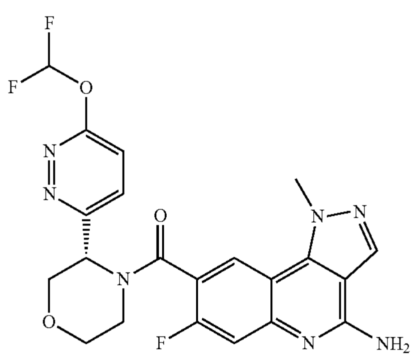 | (4-amino-7-fluoro-1-methyl-1H-pyrazolo[4,3-c]quinolin-8-yl)((3S)-3-(6-(difluoromethoxy)-3-pyridazinyl)-4-morpholinyl)methanone | 474.1 |

TABLE 10-continued

| Ex. | Structure | Name | m/z (ESI): [M + H]+ |
|---|---|---|---|
| 557 | 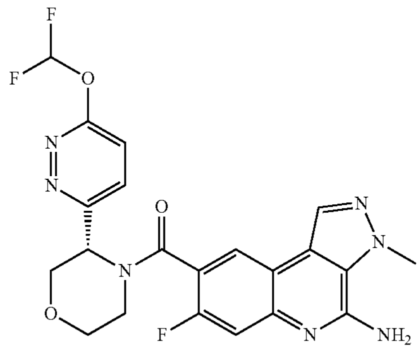 [SMILES: Cn1ncc2c3cc(C(=O)N4CCOC[C@@H]4c4ccc(OC(F)F)nn4)c(F)cc3nc(N)c21] | (4-amino-7-fluoro-3-methyl-3H-pyrazolo[3,4-c]quinolin-8-yl)((3S)-3-(6-(difluoromethoxy)-3-pyridazinyl)-4-morpholinyl)methanone | 474.1 |
| 558 | 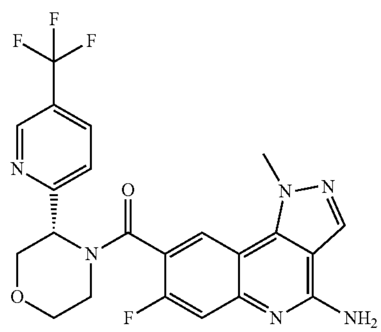 [SMILES: Cn1ncc2c(N)nc3cc(F)c(C(=O)N4CCOC[C@@H]4c4ccc(C(F)(F)F)cn4)cc3c21] | (4-amino-7-fluoro-1-methyl-1H-pyrazolo[4,3-c]quinolin-8-yl)((3S)-3-(5-(trifluoromethyl)-2-pyridinyl)-4-morpholinyl)methanone | 475.1 |
| 559 | 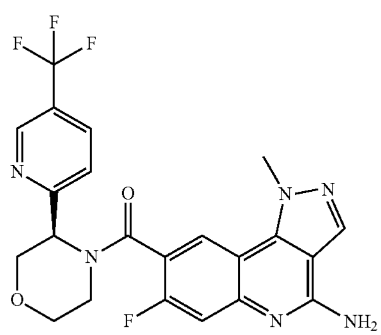 [SMILES: Cn1ncc2c(N)nc3cc(F)c(C(=O)N4CCOC[C@H]4c4ccc(C(F)(F)F)cn4)cc3c21] | (4-amino-7-fluoro-1-methyl-1H-pyrazolo[4,3-c]quinolin-8-yl)((3R)-3-(5-(trifluoromethyl)-2-pyridinyl)-4-morpholinyl)methanone | 475.2 |
| 560 | 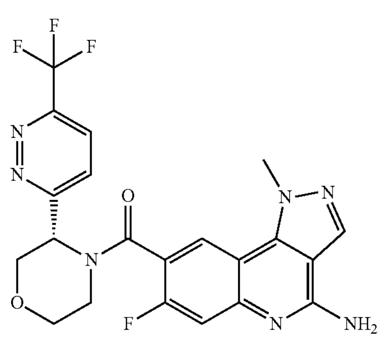 [SMILES: Cn1ncc2c(N)nc3cc(F)c(C(=O)N4CCOC[C@@H]4c4ccc(C(F)(F)F)nn4)cc3c21] | (4-amino-7-fluoro-1-methyl-1H-pyrazolo[4,3-c]quinolin-8-yl)((3S)-3-(6-(trifluoromethyl)-3-pyridazinyl)-4-morpholinyl)methanone | 476.1 |

TABLE 10-continued

| Ex. | Structure | Name | m/z (ESI): [M + H]+ |
|---|---|---|---|
| 561 | 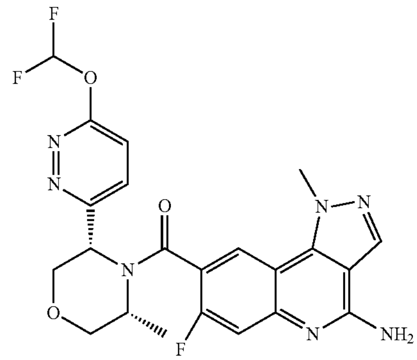 [SMILES: C[C@@H]1COC[C@H](c2ccc(OC(F)F)nn2)N1C(=O)c1cc2c(cc1F)nc(N)c1cnn(C)c12] | (4-amino-7-fluoro-1-methyl-1H-pyrazolo[4,3-c]quinolin-8-yl)((3S,5R)-3-(6-(difluoromethoxy)-3-pyridazinyl)-5-methyl-4-morpholinyl)methanone | 488.2 |
| 562 | 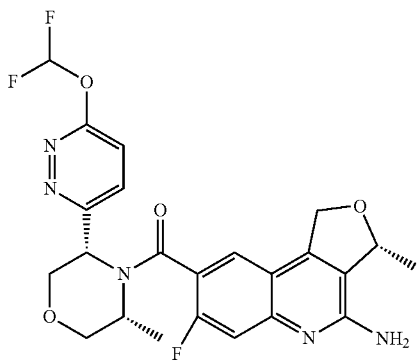 [SMILES: C[C@@H]1COC[C@H](c2ccc(OC(F)F)nn2)N1C(=O)c1cc2c3c(c(N)nc2cc1F)[C@@H](C)OC3] | ((3R)-4-amino-7-fluoro-3-methyl-1,3-dihydrofuro[3,4-c]quinolin-8-yl)((3S,5R)-3-(6-(difluoromethoxy)-3-pyridazinyl)-5-methyl-4-morpholinyl)methanone | 490.2 |
| 563 | 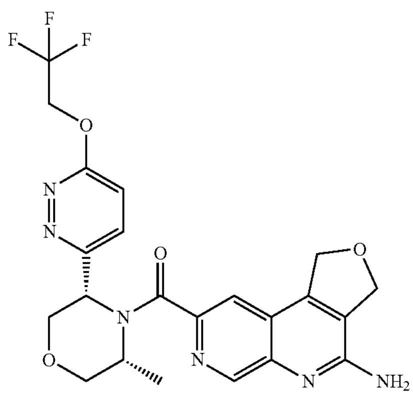 [SMILES: C[C@@H]1COC[C@H](c2ccc(OCC(F)(F)F)nn2)N1C(=O)c1cc2c3c(c(N)nc2cn1)COC3] | (4-amino-1,3-dihydrofuro[3,4-c][1,7]naphthyridin-8-yl)((3R,5S)-3-methyl-5-(6-(2,2,2-trifluoroethoxy)-3-pyridazinyl)-4-morpholinyl)methanone | 491.1 |
| 564 | 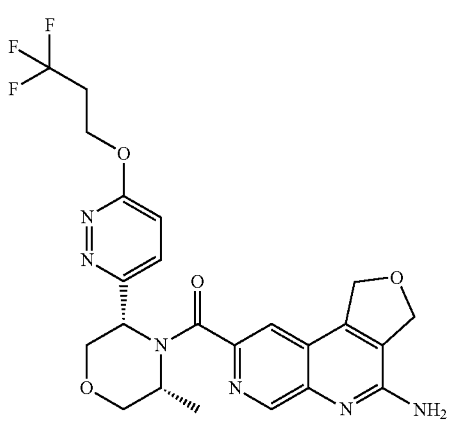 [SMILES: C[C@@H]1COC[C@H](c2ccc(OCCC(F)(F)F)nn2)N1C(=O)c1cc2c3c(c(N)nc2cn1)COC3] | (4-amino-1,3-dihydrofuro[3,4-c][1,7]naphthyridin-8-yl)((3R,5S)-3-methyl-5-(6-(3,3,3-trifluoropropoxy)-3-pyridazinyl)-4-morpholinyl)methanone | 505.2 |

TABLE 10-continued

| Ex. | Structure | Name | m/z (ESI): [M + H]+ |
|---|---|---|---|
| 565 | 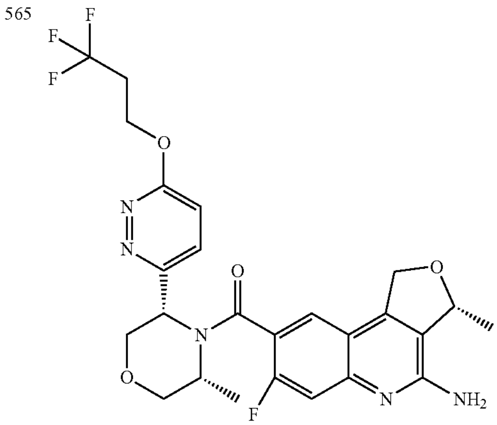 | ((3R)-4-amino-7-fluoro-3-methyl-1,3-dihydrofuro[3,4-c]quinolin-8-yl)((3R,5S)-3-methyl-5-(6-(3,3,3-trifluoropropoxy)-3-pyridazinyl)-4-morpholinyl)methanone | 536.2 |

Examples 566 and 567: (4-amino-1,3-dihydrofuro[3,4-c][1,7]naphthyridin-8-yl)((3R,5S)-3-isobutyl-5-(4-(trifluoromethyl)phenyl)morpholino)methanone and (4-amino-1,3-dihydrofuro[3,4-c][1,7]naphthyridin-8-yl)((3S,5R)-3-isobutyl-5-(4-(trifluoromethyl)phenyl)morpholino) methanone

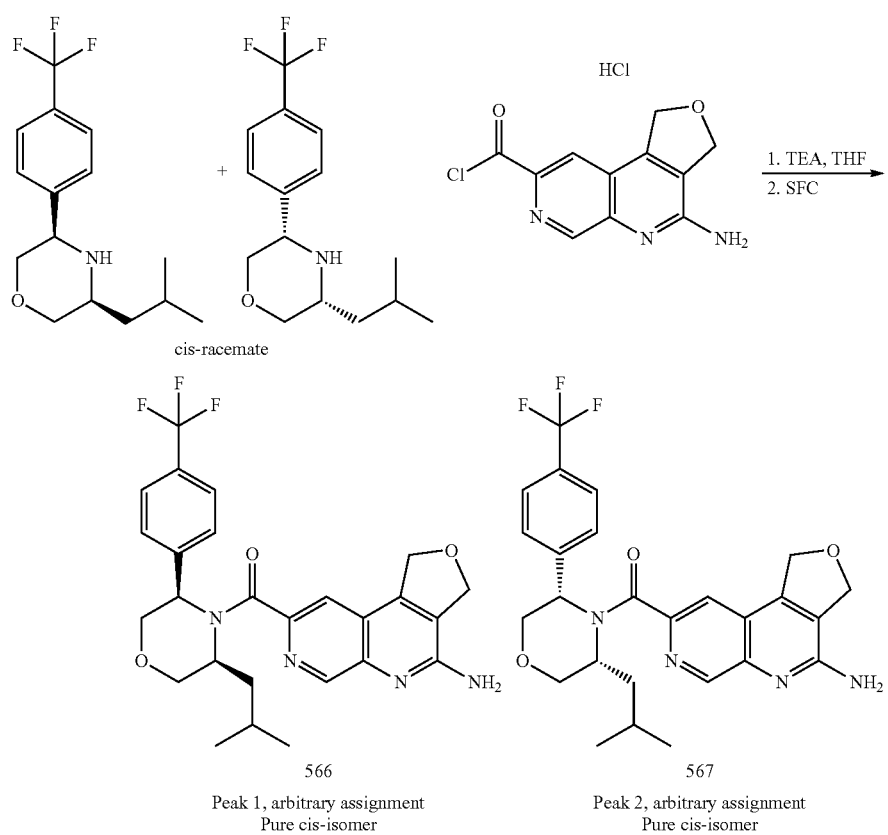

A mixture of 4-amino-1,3-dihydrofuro[3,4-c][1,7]naphthyridine-8-carbonyl chloride hydrochloride (71 mg, 0.25 mmol, From Ex. 491, Step 1), triethylamine (97 mg, 130 µL, 0.96 mmol, Aldrich) and racemic cis-3-isobutyl-5-(4-(trifluoromethyl)phenyl)morpholine (55 mg, 0.19 mmol, prepared by following the procedure described in Bode, J. W.; et. al.; Org. Lett.; 2014, pp. 1236-1239.) was stirred in THF (1.9 mL) for 4.5 h. The reaction was then concentrated and the residue was dissolved in DMSO and purified by reverse phase preparatory HPLC (C18, 10 to 100% MeCN:Water (+0.1% TFA) to give racemic (4-amino-1,3-dihydrofuro[3,4-c][1,7]naphthyridin-8-yl)((3R,5S)-3-isobutyl-5-(4-(trifluoromethyl)phenyl)morpholino)methanone (2,2,2-trifluoroacetate (80 mg, 0.055 mmol, 49% yield). This racemic mixture was then submitted for chiral separation. The sample was purified by SFC using column Chiralpak IC (250×21 mm, 5 µm), with a modifier of 25% MeOH+ TEA using a flowrate of 100 mL/min. Submitted sample was 70 mg dissolved in 10 mL MeOH:DCM 1:1 (7 mg/mL). From the dissolved sample, 16.7 mg of peak 1 with an ee of >99% (chemical purity >99%) and 20.6 mg of peak 2 with an ee of >99% (chemical purity>99%) were isolated and then arbitrarily assigned as the cis-enantiomers (4-amino-1,3-dihydrofuro[3,4-c][1,7]naphthyridin-8-yl)((3S,5R)-3-isobutyl-5-(4-(trifluoromethyl)phenyl)morpholino)methanone 2 (Peak 1, chiral column) (17 mg, 0.033 mmol, 17% yield) and (4-amino-1,3-dihydrofuro[3,4-c][1,7]naphthyridin-8-yl)((3R,5S)-3-isobutyl-5-(4-(trifluoromethyl)phenyl)morpholino)methanone 3 (Peak 2, chiral column) (21 mg, 0.041 mmol, 22% yield) $^1$H NMR (400 MHz, METHANOL-$d_4$) δ ppm 9.14 (s, 1H), 8.10 (br s, 1H), 7.88-8.00 (m, 2H), 7.62-7.76 (m, 2H), 5.76-5.99 (m, 1H), 5.47-5.63 (m, 2H), 5.24 (t, J=3.9 Hz, 2H), 4.62-4.88 (m, 1H), 3.82-4.08 (m, 4H), 1.13-1.35 (m, 2H), 1.00-1.08 (m, 1H), 0.25 (br d, J=1.5 Hz, 6H). m/z (ESI): 501.0 [M+H]$^+$.

Examples in Table 11 were prepared in a manner similar to that described for Example 566 and 567.

TABLE 11

| Ex. | Structure | Name | m/z (ESI): [M + H]$^+$ | SFC Conditions |
|-----|-----------|------|------------------------|----------------|
| 568 | 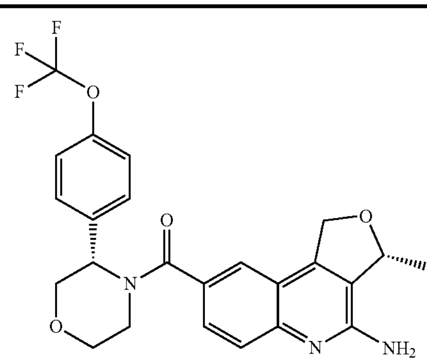 | [(3R-4-amino-3-methyl-1,3-dihydrofuro[3,4-c]quinolin-8-yl]-[(3S)-3-[4-(trifluoromethoxy)phenyl]morpholin-4-yl]methanone | 474 | 1$^{st}$ peak, Chiral Tech OJ Column (250 × 21 mm, 5 um) with a mobile phase of 65% liquid CO$_2$ and 35% MeOH with 0.2% TEA using a flowrate of 80 mL/min |
| 569 | 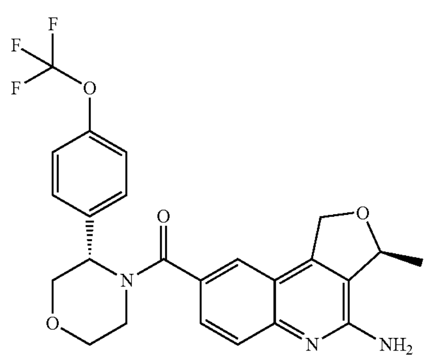 [SMILES: C[C@@H]1OCc2c1c(N)nc1ccc(C(=O)N3CCOC[C@@H]3c3ccc(OC(F)(F)F)cc3)cc21] | [(3S)-4-amino-3-methyl-1,3-dihydrofuro[3,4-c]quinolin-8-yl]-[(3S)-3-[4-(trifluoromethoxy)phenyl]morpholin-4-yl]methanone | 474 | 2$^{nd}$ peak, Chiral Tech OJ Column (250 × 21 mm, 5 um) with a mobile phase of 65% liquid CO$_2$ and 35% MeOH with 0.2% TEA using a flowrate of 80 mL/min |
| 570 | 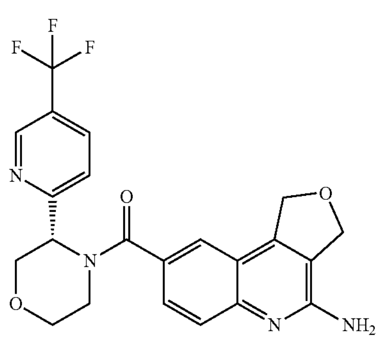 [SMILES: Nc1nc2ccc(C(=O)N3CCOC[C@@H]3c3ccc(C(F)(F)F)cn3)cc2c2c1COC2] | (4-amino-1,3-dihydrofuro[3,4-c]quinolin-8-yl)-[(3S)-3-[5-(trifluoromethyl)-2-pyridyl]morpholin-4-yl]methanone | 445.2 | 1$^{st}$ peak: Chiral Tech AD Column (250 × 21 mm, 5 um) with a mobile phase of 60% liquid CO$_2$ and 40% MeOH with 0.2% TEA using a flowrate of 80 mL/min |

TABLE 11-continued

| Ex. | Structure | Name | m/z (ESI): [M + H]+ | SFC Conditions |
|---|---|---|---|---|
| 571 | 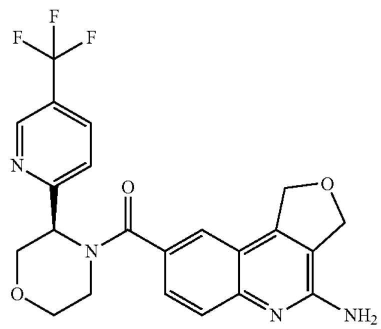 [SMILES: Nc1nc2ccc(C(=O)N3CCOC[C@H]3c3ccc(C(F)(F)F)cn3)cc2c2c1COC2] | (4-amino-1,3-dihydrofuro[3,4-c]quinolin-8-yl)-[(3R)-3-[5-(trifluoromethyl)-2-pyridyl]morpholin-4-yl]methanone | 445.2 | 2nd peak, Chiral Tech AD Column (250 × 21 mm, 5 um) with a mobile phase of 60% liquid CO$_2$ and 40% MeOH with 0.2% TEA using a flowrate of 80 mL/min |
| 572 | 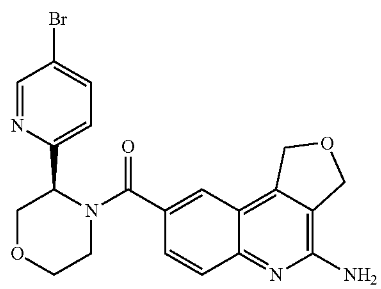 [SMILES: Nc1nc2ccc(C(=O)N3CCOC[C@H]3c3ccc(Br)cn3)cc2c2c1COC2] | (4-amino-1,3-dihydrofuro[3,4-c]quinolin-8-yl)-[(3R)-3-(5-bromo-2-pyridyl)morpholin-4-yl]methanone | 455 | 1st peak, Chiral Tech OJ Column (250 × 21 mm, 5 um) with a mobile phase of 50% liquid CO$_2$ and 50% MeOH with 0.2% TEA using a flowrate of 60 mL/min |
| 573 | 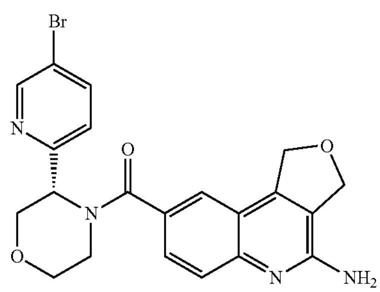 | (4-amino-1,3-dihydrofuro[3,4-c]quinolin-8-yl)-[(3S)-3-(5-bromo-2-pyridyl)morpholin-4-yl]methanone | 455 | 2nd peak, Chiral Tech OJ Column (250 × 21 mm, 5 um) with a mobile phase of 50% liquid CO$_2$ and 50% MeOH with 0.2% TEA using a flowrate of 60 mL/min |
| 574 | 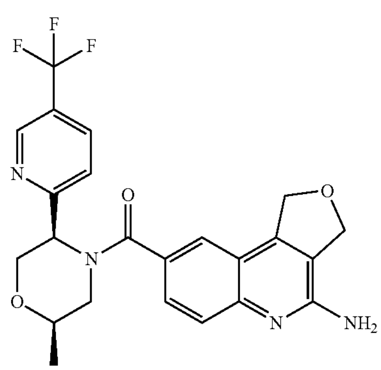 [SMILES: C[C@@H]1CN(C(=O)c2ccc3nc(N)c4c(c3c2)COC4)[C@H](c2ccc(C(F)(F)F)cn2)CO1] | (4-amino-1,3-dihydrofuro[3,4-c]quinolin-8-yl)-[(2R,SR)-2-methyl-5-[5-(trifluoromethyl)-2-pyridyl]morpholin-4-yl]methanone | 459.2 | 1st peak, Chiral Tech OD Column (250 × 21 mm, 5 mm) with a mobile phase of 85% liquid CO$_2$ and 15% MeOH with 0.2% TEA using a flowrate of 80 mL/min |

TABLE 11-continued

| Ex. | Structure | Name | m/z (ESI): [M + H]+ | SFC Conditions |
|---|---|---|---|---|
| 575 | 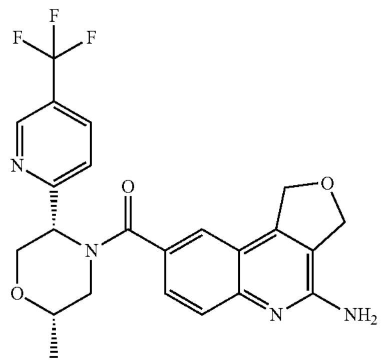 [SMILES: C[C@H]1CN(C(=O)c2ccc3nc(N)c4c(c3c2)COC4)[C@@H](c2ccc(C(F)(F)F)cn2)CO1] | (4-amino-1,3-dihydrofuro[3,4-c]quinolin-8-yl)-[(2S,5S)-2-methyl-5-[5-(trifluoromethyl)-2-pyridyl]morpholin-4-yl]methanone | 459.2 | 2$^{nd}$ peak, Chiral Tech OD Column (250 × 21 mm, 5 mm) with a mobile phase of 85% liquid CO$_2$ and 15% MeOH with 0.2% TEA using a flowrate of 80 mL/min |
| 576 | 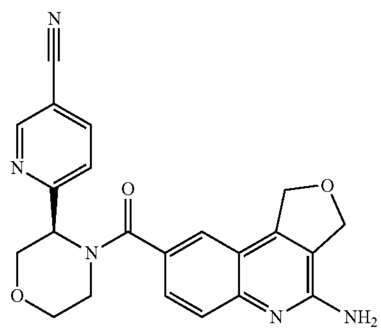 [SMILES: N#Cc1ccc([C@@H]2COCCN2C(=O)c2ccc3nc(N)c4c(c3c2)COC4)nc1] | 6-[(3R)-4-(4-amino-1,3-dihydrofuro[3,4-c]quinoline-8-carbonyl)morpholin-3-yl]pyridine-3-carbonitrile | 402.2 | 1$^{st}$ peak, Chiral Tech OJ Column (250 × 21 mm, 5 mm) with a mobile phase of 50% liquid CO$_2$ and 50% MeOH with 0.2% TEA using a flowrate of 50 mL/min |
| 577 | 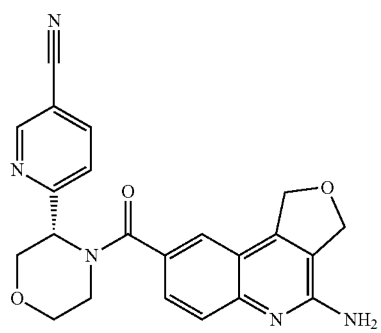 [SMILES: N#Cc1ccc([C@H]2COCCN2C(=O)c2ccc3nc(N)c4c(c3c2)COC4)nc1] | 6-[(3S)-4-(4-amino-1,3-dihydrofuro[3,4-c]quinoline-8-carbonyl)morpholin-3-yl]pyridine-3-carbonitrile | 402.2 | 2$^{nd}$ peak, Chiral Tech OJ Column (250 × 21 mm, 5 mm) with a mobile phase of 50% liquid CO$_2$ and 50% MeOH with 0.2% TEA using a flowrate of 50 mL/min |
| 578 | 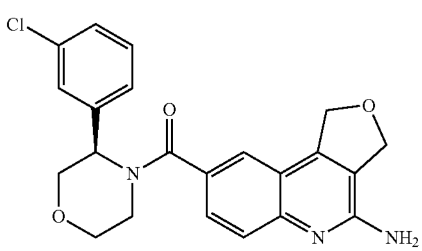 [SMILES: Nc1nc2ccc(C(=O)N3CCOC[C@H]3c3cccc(Cl)c3)cc2c2c1COC2] | (4-amino-1,3-dihydrofuro[3,4-c]quinolin-8-yl)-[(3R)-3-(3-chlorophenyl)morpholin-4-yl]methanone | 410 | 1$^{st}$ peak, Chiral Tech AD Column (250 × 21 mm, 5 um) with a mobile phase of 73% liquid CO$_2$ and 27% MeOH with 0.2% TEA using a flowrate of 80 mL/min |
| 579 | 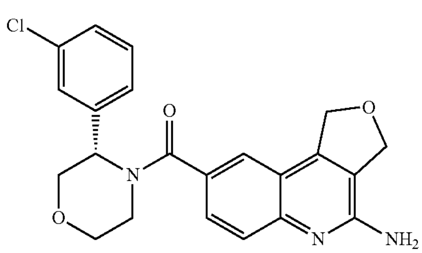 [SMILES: Nc1nc2ccc(C(=O)N3CCOC[C@@H]3c3cccc(Cl)c3)cc2c2c1COC2] | (4-amino-1,3-dihydrofuro[3,4-c]quinolin-8-yl)-[(3S)-3-(3-chlorophenyl)morpholin-4-yl]methanone | 410.1 | 2$^{nd}$ peak, Chiral Tech AD Column (250 × 21 mm, 5 um) with a mobile phase of 73% liquid CO$_2$ and 27% MeOH with 0.2% TEA using a flowrate of 80 mL/min |

TABLE 11-continued

| Ex. | Structure | Name | m/z (ESI): [M + H]+ | SFC Conditions |
|---|---|---|---|---|
| 580 | 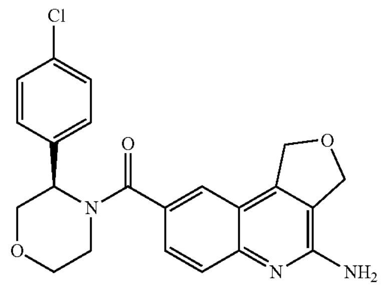 [SMILES: Nc1nc2ccc(C(=O)N3CCOC[C@H]3c3ccc(Cl)cc3)cc2c2c1COC2] | (4-amino-1,3-dihydrofuro[3,4-c]quinolin-8-yl)-[(3R)-3-(4-chlorophenyl)morpholin-4-yl]methanone | 410.2 | 1st peak, Chiral Tech AD Column (250 × 21 mm, 5 um) with a mobile phase of 65% liquid CO$_2$ and 35% MeOH with 0.2% TEA using a flowrate of 80 mL/min |
| 581 | 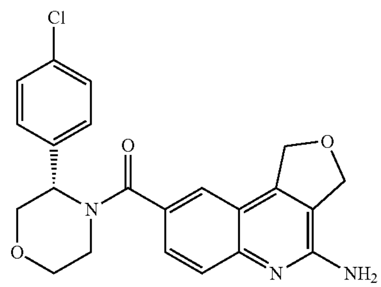 [SMILES: Nc1nc2ccc(C(=O)N3CCOC[C@@H]3c3ccc(Cl)cc3)cc2c2c1COC2] | (4-amino-1,3-dihydrofuro[3,4-c]quinolin-8-yl)-[(3S)-3-(4-chlorophenyl)morpholin-4-yl]methanone | 410.2 | 2nd peak, Chiral Tech AD Column (250 × 21 mm, 5 um) with a mobile phase of 65% liquid CO$_2$ and 35% MeOH with 0.2% TEA using a flowrate of 80 mL/min |
| 582 | 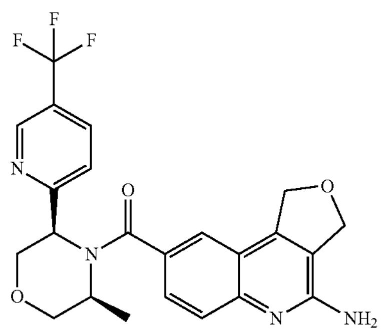 [SMILES: C[C@H]1COC[C@@H](c2ccc(C(F)(F)F)cn2)N1C(=O)c1ccc2nc(N)c3c(c2c1)COC3] | (4-amino-1,3-dihydrofuro[3,4-c]quinolin-8-yl)-[(3S,5R)-3-methyl-5-[5-(trifluoromethyl)-2-pyridyl]morpholin-4-yl]methanone | 459.2 | 1st peak, Chiral Tech OJ Column (250 × 21 mm, 5 um) with a mobile phase of 70% liquid CO$_2$ and 30% MeOH with 0.2% TEA using a flowrate of 80 mL/min |
| 583 | 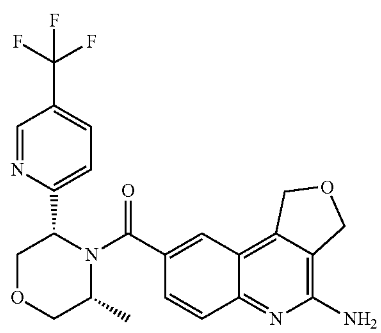 [SMILES: C[C@@H]1COC[C@H](c2ccc(C(F)(F)F)cn2)N1C(=O)c1ccc2nc(N)c3c(c2c1)COC3] | (4-amino-1,3-dihydrofuro[3,4-c]quinolin-8-yl)-[(3S,5S)-3-methyl-5-[5-(trifluoromethyl)-2-pyridyl]morpholin-4-yl]methanone | 459.2 | 2nd peak, Chiral Tech OJ Column (250 × 21 mm, 5 um) with a mobile phase of 70% liquid CO$_2$ and 30% MeOH with 0.2% TEA using a flowrate of 80 mL/min |
| 584 | 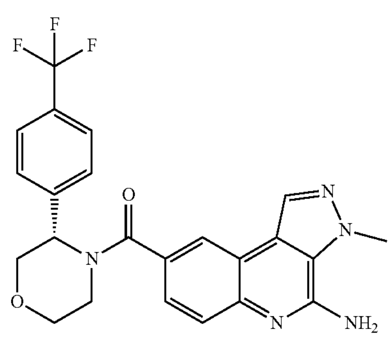 [SMILES: Cn1ncc2c3cc(C(=O)N4CCOC[C@@H]4c4ccc(C(F)(F)F)cc4)ccc3nc(N)c21] | (4-amino-3-methyl-3H-pyrazolo[3,4-c]quinolin-8-yl)((3S)-3-(4-(trifluoromethyl)phenyl)-4-morpholinyl)methanone | 456.2 | 2nd peak, Chiral Technologies IC column (250 × 21 mm, 5 mm) with a mobile phase of 65% Liquid CO$_2$ and 35% MeOH with 0.2% TEA using a flowrate of 80 mL/min. Peak assignment determined by SFC with IC column with 35% MeOH |

TABLE 11-continued

| Ex. | Structure | Name | m/z (ESI): [M + H]+ | SFC Conditions |
|---|---|---|---|---|
| 585 | 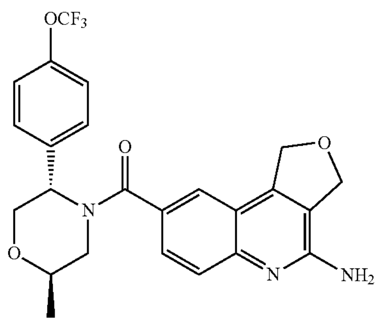 [SMILES: C[C@@H]1CN(C(=O)c2ccc3nc(N)c4c(c3c2)COC4)[C@@H](c2ccc(OC(F)(F)F)cc2)CO1] | (4-amino-1,3-dihydrofuro[3,4-c]quinolin-8-yl)-[(2R,5S)-2-methyl-5-[4-(trifluoromethoxy)phenyl]morpholin-4-yl]methanone | 473.9 | 1st peak, Chiral Technologies AD column (250 × 21 mm, 5 mm) with a mobile phase of 82% Liquid $CO_2$ and 18% MeOH with 0.2% TEA using a flowrate of 80 mL/min |
| 586 | 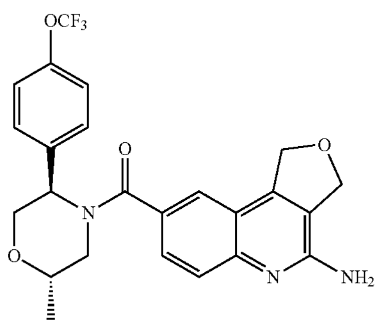 [SMILES: C[C@H]1CN(C(=O)c2ccc3nc(N)c4c(c3c2)COC4)[C@H](c2ccc(OC(F)(F)F)cc2)CO1] | (4-amino-1,3-dihydrofuro[3,4-c]quinolin-8-yl)-[(2S,5R)-2-methyl-5-[4-(trifluoromethoxy)phenyl]morpholin-4-yl]methanone | 473.9 | 2nd peak, Chiral Technologies AD column (250 × 21 mm, 5 mm) with a mobile phase of 82% Liquid $CO_2$ and 18% MeOH with 0.2% TEA using a flowrate of 80 mL/min |
| 587 | 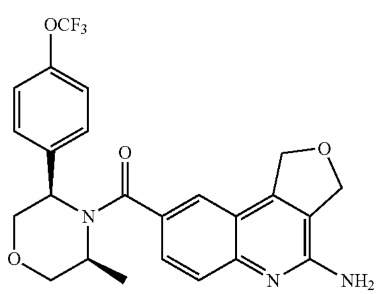 [SMILES: C[C@H]1COC[C@@H](c2ccc(OC(F)(F)F)cc2)N1C(=O)c1ccc2nc(N)c3c(c2c1)COC3] | (4-amino-1,3-dihydrofuro[3,4-c]quinolin-8-yl)-[(3S,5R)-3-methyl-5-[4-(trifluoromethoxy)phenyl]morpholin-4-yl]methanone | 473.9 | 1st peak, Chiralpak AS-H column (250 × 21 mm, 5 um), with a mobile phase of 85% Liquid $CO_2$ and 15% MeOH + TEA using a flowrate of 80 mL/min |
| 588 | 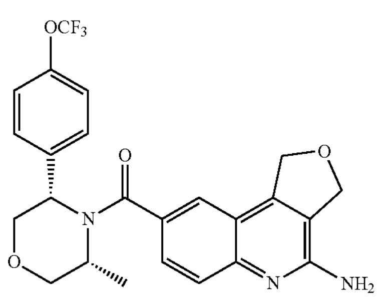 | (4-amino-1,3-dihydrofuro[3,4-c]quinolin-8-yl)-[(3R,5S)-3-methyl-5-[4-(trifluoromethoxy)phenyl]morpholin-4-yl]methanone | 473.9 | 2nd peak, Chiralpak AS-H column (250 × 21 mm, 5 um), with a mobile phase of 85% Liquid $CO_2$ and 15% MeOH + TEA using a flowrate of 80 mL/min |

TABLE 11-continued

| Ex. | Structure | Name | m/z (ESI): [M + H]+ | SFC Conditions |
|---|---|---|---|---|
| 589 | 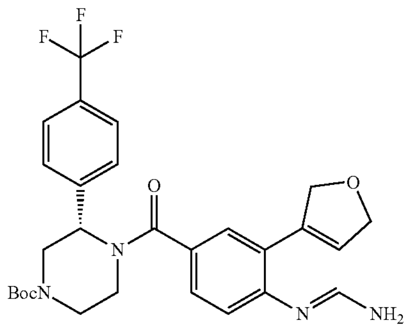 [SMILES: CC(C)(C)OC(=O)N1CCN(C(=O)c2ccc(/N=C/N)c(C3=CCOC3)c2)[C@@H](c2ccc(C(F)(F)F)cc2)C1] | tert-butyl (3S)-4-(4-amino-1,3-dihydrofuro[3,4-c][1,7]naphthyridine-8-carbonyl)-3-[4-(trifluoromethyl)phenyl]piperazine-1-carboxylate | 544.2 | 1st peak, Chiralcel OJ-H column, with a mobile phase of 70% Liquid $CO_2$ and 30% MeOH |
| 590 | 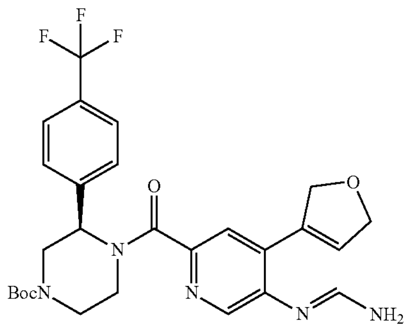 [SMILES: CC(C)(C)OC(=O)N1CCN(C(=O)c2cc(C3=CCOC3)c(/N=C/N)cn2)[C@H](c2ccc(C(F)(F)F)cc2)C1] | tert-butyl (3R)-4-(4-amino-1,3-dihydrofuro[3,4-c][1,7]naphthyridine-8-carbonyl)-3-[4-(trifluoromethyl)phenyl]piperazine-1-carboxylate | 544.2 | 2nd peak, Chiralcel OJ-H column, with a mobile phase of 70% Liquid $CO_2$ and 30% MeOH |
| 591 | 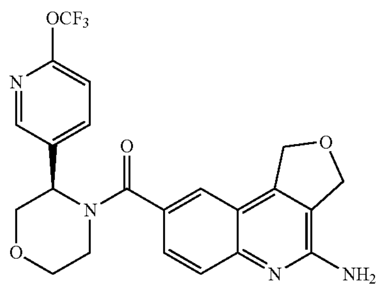 [SMILES: Nc1nc2ccc(C(=O)N3CCOC[C@H]3c3ccc(OC(F)(F)F)nc3)cc2c2c1COC2] | (4-amino-1,3-dihydrofuro[3,4-c]quinolin-8-yl)-[(3R)-3-[6-(trifluoromethoxy)-3-pyridyl]morpholin-4-yl]methanone | 461.1 | 1st peak, Chiralcel OJ-H column, with a mobile phase of 60% Liquid $CO_2$ and 40% MeOH |
| 592 | 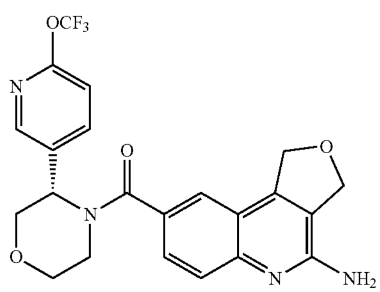 [SMILES: Nc1nc2ccc(C(=O)N3CCOC[C@@H]3c3ccc(OC(F)(F)F)nc3)cc2c2c1COC2] | (4-amino-1,3-dihydrofuro[3,4-c]quinolin-8-yl)-[(3S)-3-[6-(trifluoromethoxy)-3-pyridyl]morpholin-4-yl]methanone | 461.1 | 2nd peak, Chiralcel OJ-H column, with a mobile phase of 60% Liquid $CO_2$ and 40% MeOH |
| 593 | 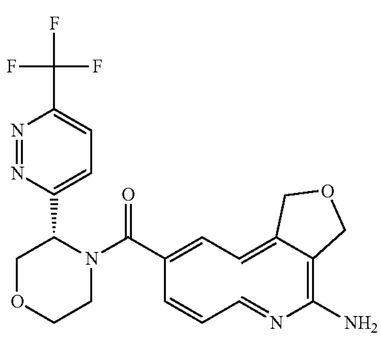 [SMILES: Nc1ncccc(C(=O)N2CCOC[C@@H]2c2ccc(C(F)(F)F)nn2)ccc2c1COC2] | (4-amino-1,3-dihydrofuro[3,4-c]quinolin-8-yl)((3S)-3-(6-(trifluoromethyl)-3-pyridazinyl)-4-morpholinyl)methanone | 446.1 | 2nd peak, ChiralPak OD-H column with a mobile phase of 60% Liquid $CO_2$ and 40% iPrOH with 0.5% DEA |

TABLE 11-continued

| Ex. | Structure | Name | m/z (ESI): [M + H]+ | SFC Conditions |
|---|---|---|---|---|
| 594 | 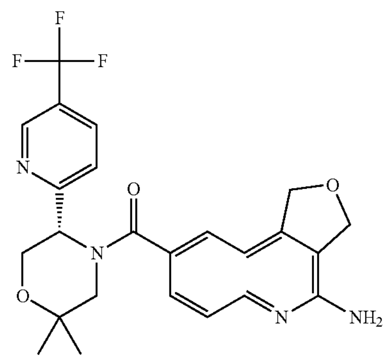 [SMILES: CC1(C)CN(C(=O)c2cccnc(N)c3c(cc2)COC3)[C@@H](c2ccc(C(F)(F)F)cn2)CO1] | (4-amino-1,3-dihydrofuro[3,4-c]quinolin-8-yl)((5S)-2,2-dimethyl-5-(5-(trifluoromethyl)-2-pyridinyl)-4-morpholinyl)methanone | 473.3 | 2nd peak, ChiralPak OD-H column with a mobile phase of 70% Liquid CO2 and 30% MeOH |
| 595 | 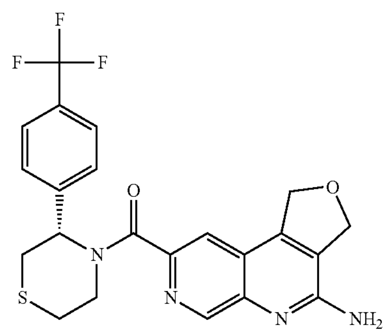 | (4-amino-1,3-dihydrofuro[3,4-c][1,7]naphthyridin-8-yl)((3S)-3-(4-(trifluoromethyl)phenyl)-4-thiomorpholinyl)methanone or (4-amino-1,3-dihydrofuro[3,4-c][1,7]naphthyridin-8-yl)((3R)-3-(4-(trifluoromethyl)phenyl)-4-thiomorpholinyl)methanone | 461.1 | 2nd peak, ChiralPak IC column with a mobile phase of 60% Liquid CO2 and 40% MeOH |
| 596 | 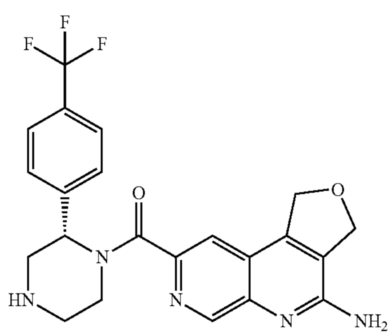 [SMILES: Nc1nc2cnc(C(=O)N3CCNC[C@@H]3c3ccc(C(F)(F)F)cc3)cc2c2c1COC2] | (4-amino-1,3-dihydrofuro[3,4-c][1,7]naphthyridin-8-yl)((2S)-2-(4-(trifluoromethyl)phenyl)-1-piperazinyl)methanone or (4-amino-1,3-dihydrofuro[3,4-c][1,7]naphthyridin-8-yl)((2R)-2-(4-(trifluoromethyl)phenyl)-1-piperazinyl)methanone | 444.1 | 2nd peak, Lux C3 column with a mobile phase of 60% Liquid CO2 and 40% MeOH w/ 0.5% DEA |
| 597 | 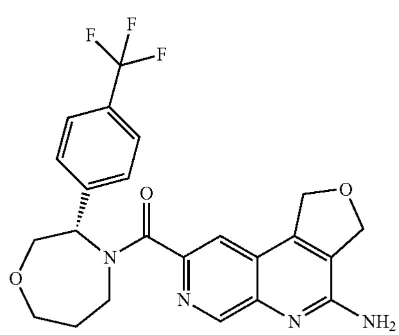 [SMILES: Nc1nc2cnc(C(=O)N3CCCOC[C@@H]3c3ccc(C(F)(F)F)cc3)cc2c2c1COC2] | (4-amino-1,3-dihydrofuro[3,4-c][1,7]naphthyridin-8-yl)((3S)-3-(4-(trifluoromethyl)phenyl)-1,4-oxazepan-4-yl)methanone or (4-amino-1,3-dihydrofuro[3,4-c][1,7]naphthyridin-8-yl)((3R)-3-(4-(trifluoromethyl)phenyl)-1,4-oxazepan-4-yl)methanone | 459.1 | 2nd peak, Chiralpak IC column with a mobile phase of 60% Liquid CO2 and 40% MeOH |

TABLE 11-continued

| Ex. | Structure | Name | m/z (ESI): [M + H]+ | SFC Conditions |
|---|---|---|---|---|
| 598 | 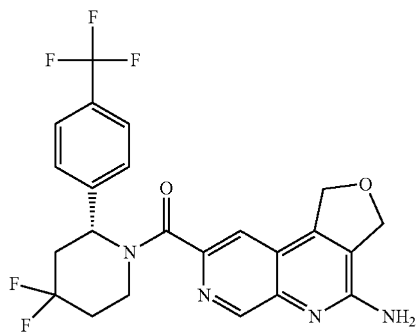 [SMILES: Nc1nc2cnc(C(=O)N3CCC(F)(F)C[C@@H]3c3ccc(C(F)(F)F)cc3)cc2c2c1COC2] | (4-amino-1,3-dihydrofuro[3,4-c][1,7]naphthyridin-8-yl)-[(2R)-4,4-difluoro-2-[4-(trifluoromethyl)phenyl]-1-piperidyl]methanone | 479 | 1$^{st}$ peak, Chiral Technologies AS column (250 × 21 mm, 5 mm) with a mobile phase of 75% Liquid CO$_2$ and 25% MeOH with 0.2% TEA using a flowrate of 80 mL/min |
| 599 | 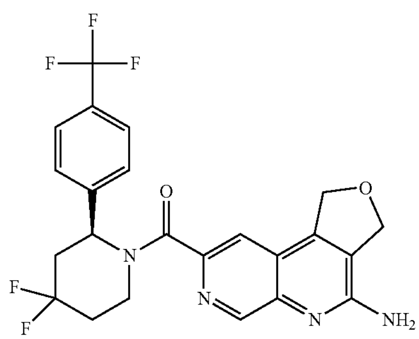 [SMILES: Nc1nc2cnc(C(=O)N3CCC(F)(F)C[C@H]3c3ccc(C(F)(F)F)cc3)cc2c2c1COC2] | (4-amino-1,3-dihydrofuro[3,4-c][1,7]naphthyridin-8-yl)-[(2S)-4,4-difluoro-2-[4-(trifluoromethyl)phenyl]-1-piperidyl]methanone | 479 | 2$^{nd}$ peak, Chiral Technologies AS column (250 × 21 mm, 5 mm) with a mobile phase of 75% Liquid CO$_2$ and 25% MeOH with 0.2% TEA using a flowrate of 80 mL/min |
| 600 | 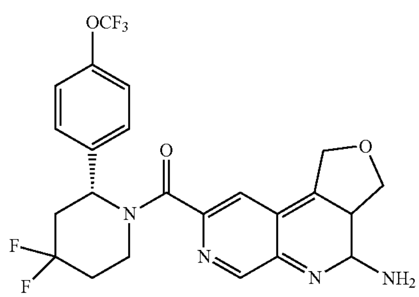 [SMILES: NC1N=c2cnc(C(=O)N3CCC(F)(F)C[C@@H]3c3ccc(OC(F)(F)F)cc3)cc2=C2COCC21] | (4-amino-1,3-dihydrofuro[3,4-c][1,7]naphthyridin-8-yl)-[(2R)-4,4-difluoro-2-[4-(trifluoromethoxy)phenyl]-1-piperidyl]methanone | 495 | 1$^{st}$ peak, Chiral Technologies AS column (250 × 21 mm, 5 mm) with a mobile phase of 80% Liquid CO$_2$ and 20% MeOH with 0.2% TEA using a flowrate of 80 mL/min |
| 601 | 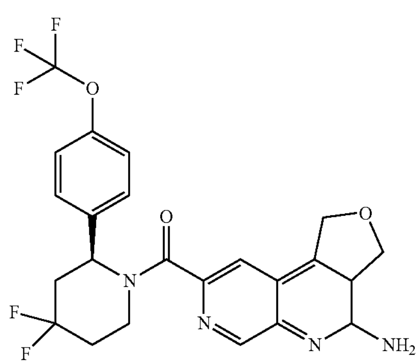 [SMILES: NC1N=c2cnc(C(=O)N3CCC(F)(F)C[C@H]3c3ccc(OC(F)(F)F)cc3)cc2=C2COCC21] | (4-amino-1,3-dihydrofuro[3,4-c][1,7]naphthyridin-8-yl)-[(2S)-4,4-difluoro-2-[4-(trifluoromethoxy)phenyl]-1-piperidyl]methanone | 495 | 2$^{nd}$ peak, Chiral Technologies AS column (250 × 21 mm, 5 mm) with a mobile phase of 80% Liquid CO$_2$ and 20% MeOH with 0.2% TEA using a flowrate of 80 mL/min |

TABLE 11-continued

| Ex. | Structure | Name | m/z (ESI): [M + H]+ | SFC Conditions |
|---|---|---|---|---|
| 602 | 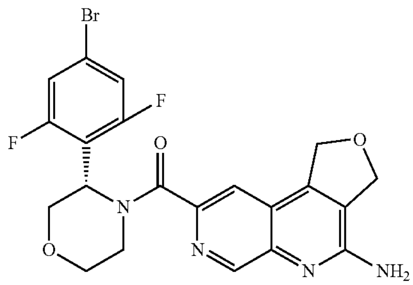 [SMILES: Nc1nc2cnc(C(=O)N3CCOC[C@@H]3c3c(F)cc(Br)cc3F)cc2c2c1COC2] | (4-amino-1,3-dihydrofuro[3,4-c][1,7]naphthyridin-8-yl)((3S)-3-(4-bromo-2,6-difluorophenyl)-4-morpholinyl)methanone | 491.00 and 493.00 | 1st peak, Chiral Technologies OJ column (250 × 21 mm, 5 mm) with a mobile phase of 85% Liquid $CO_2$ and 15% MeOH with 0.2% TEA using a flowrate of 80 mL/min. |
| 603 | 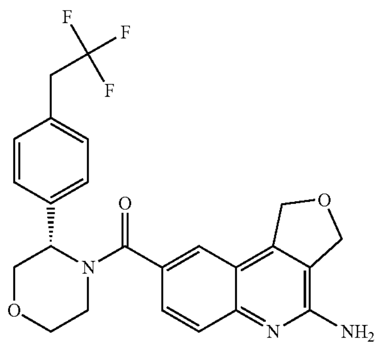 [SMILES: Nc1nc2ccc(C(=O)N3CCOC[C@@H]3c3ccc(CC(F)(F)F)cc3)cc2c2c1COC2] | (4-amino-1,3-dihydrofuro[3,4-c]quinolin-8-yl)((3S)-3-(4-(2,2,2-trifluoroethyl)phenyl)-4-morpholinyl)methanone | 458 | 1st peak, Chiralcel AS-H column (250 × 21 mm, 5 um) with a mobile phase of 80% Liquid $CO_2$ and 20% MeOH + TEA using a flowrate of 80 mL/min |
| 604 | 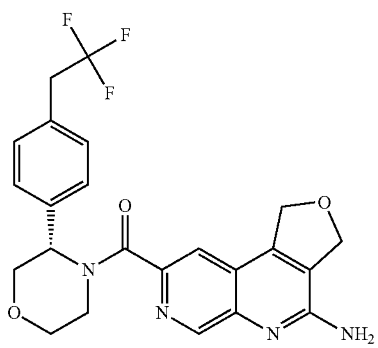 | (4-amino-1,3-dihydrofuro[3,4-c][1,7]naphthyridin-8-yl)((3S)-3-(4-(2,2,2-trifluoroethyl)phenyl)-4-morpholinyl)methanone | 459 | 1st peak, Chiral Technologies AS column (250 × 21 mm, 5 mm) with a mobile phase of 80% Liquid $CO_2$ and 20% MeOH with 0.2% TEA using a flowrate of 80 mL/min. |
| 605 | 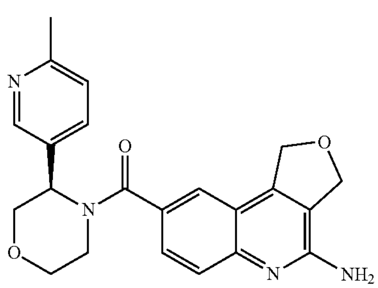 | (4-amino-1,3-dihydrofuro[3,4-c]quinolin-8-yl)-[(3R)-3-(6-methyl-3-pyridyl)morpholin-4-yl]methanone | 391.2 | 2nd peak, Chiral Technologies OJ column (250 × 21 mm, 5 mm) with a mobile phase of 70% Liquid $CO_2$ and 30% MeOH with 0.2% TEA using a flowrate of 80 mL/min. |
| 606 | 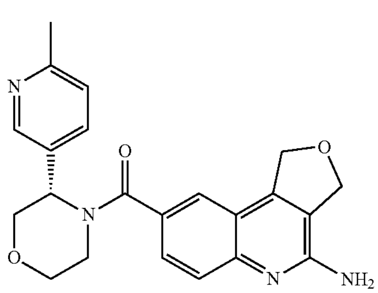 | (4-amino-1,3-dihydrofuro[3,4-c]quinolin-8-yl)-[(3S)-3-(6-methyl-3-pyridyl)morpholin-4-yl]methanone | 391.2 | 1st peak, Chiral Technologies OJ column (250 × 21 mm, 5 mm) with a mobile phase of 70% Liquid $CO_2$ and 30% MeOH with 0.2% TEA using a flowrate of 80 mL/min. |

TABLE 11-continued

| Ex. | Structure | Name | m/z (ESI): [M + H]⁺ | SFC Conditions |
|---|---|---|---|---|
| 607 | 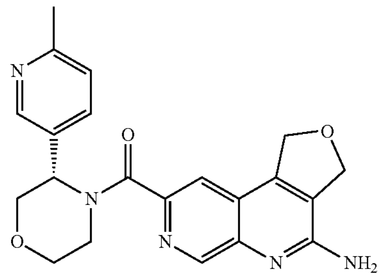 [SMILES: Cc1ccc([C@H]2COCCN2C(=O)c2cc3c4c(c(N)nc3cn2)COC4)cn1] | (4-amino-1,3-dihydrofuro[3,4-c][1,7]naphthyridin-8-yl)-[(3S)-3-(6-methyl-3-pyridyl)morpholin-4-yl]methanone | 392.2 | 1st peak, Regis (S,S) Whelk-01 column (250 × 21 mm, 5 mm) with a mobile phase of 70% Liquid CO$_2$ and 30% MeOH with 0.2% TEA using a flowrate of 80 mL/min. |
| 608 | 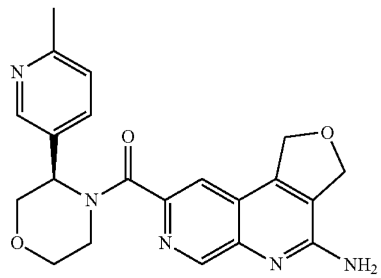 [SMILES: Cc1ccc([C@@H]2COCCN2C(=O)c2cc3c4c(c(N)nc3cn2)COC4)cn1] | (4-amino-1,3-dihydrofuro[3,4-c][1,7]naphthyridin-8-yl)-[(3R)-3-(6-methyl-3-pyridyl)morpholin-4-yl]methanone | 392.2 | 2nd peak, Regis (S,S) Whelk-01 column (250 × 21 mm, 5 mm) with a mobile phase of 70% Liquid CO$_2$ and 30% MeOH with 0.2% TEA using a flowrate of 80 mL/min. |
| 609 | 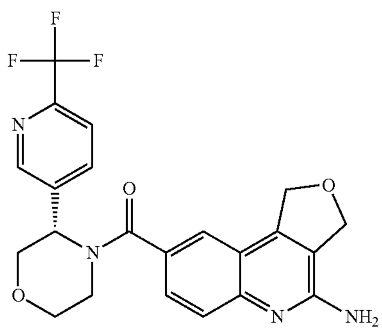 | (4-amino-1,3-dihydrofuro[3,4-c]quinolin-8-yl)-[(3S)-3-[6-(trifluoromethyl)-3-pyridyl]morpholin-4-yl]methanone | 445 | 1st peak, Chiral Technologies ID column (250 × 21 mm, 5 mm) with a mobile phase of 60% Liquid CO$_2$ and 40% MeOH with 0.2% TEA using a flowrate of 70 mL/min. |
| 610 | 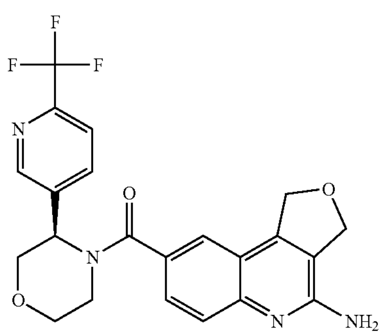 | (R)-(4-amino-1,3-dihydrofuro[3,4-c]quinolin-8-yl)(3-(6-(trifluoromethyl)pyridin-3-yl)morpholino)methanone | 445 | 2nd peak, Chiral Technologies ID column (250 × 21 mm, 5 mm) with a mobile phase of 60% Liquid CO$_2$ and 40% MeOH with 0.2% TEA using a flowrate of 70 mL/min. |
| 611 | 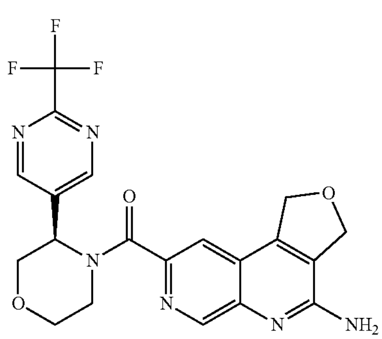 | (4-amino-1,3-dihydrofuro[3,4-c][1,7]naphthyridin-8-yl)-[(3R)-3-[2-(trifluoromethyl)pyrimidin-5-yl]morpholin-4-yl]methanone | 447 | 2nd peak, ChromegaChiral CC4 column (250 × 21 mm, 5 um) and Chiralcel OJ-H column (250 × 21 mm, 5 um), with a mobile phase of 65% Liquid CO$_2$ and 35% MeOH + TEA using a flowrate of 80 mL/min. |

TABLE 11-continued

| Ex. | Structure | Name | m/z (ESI): [M + H]+ | SFC Conditions |
|---|---|---|---|---|
| 612 | 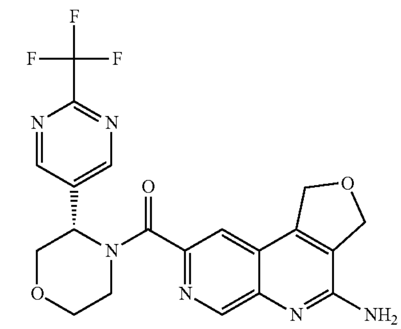 | (4-amino-1,3-dihydrofuro[3,4-c][1,7]naphthyridin-8-yl)-[(3S)-3-[2-(trifluoromethyl)pyrimidin-5-yl]morpholin-4-yl]methanone | 447 | 1st peak, ChromegaChiral CC4 column (250 × 21 mm, 5 um) and Chiralcel OJ-H column (250 × 21 mm, 5 um), with a mobile phase of 65% Liquid $CO_2$ and 35% MeOH + TEA using a lowrate of 80 mL/min. |
| 613 | 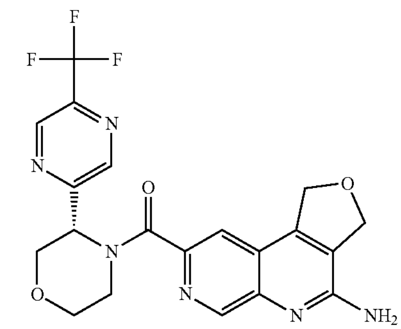 | (4-amino-1,3-dihydrofuro[3,4-c][1,7]naphthyridin-8-yl)-[(3S)-3-[5-(trifluoromethyl)pyrazin-2-yl]morpholin-4-yl]methanone | 447 | 1st peak, Chiral Technologies OJ column (250 × 21 mm, 5 mm) with a mobile phase of 75% Liquid $CO_2$ and 25% MeOH with 0.2% TEA using a of 80 mL/min. |
| 614 | 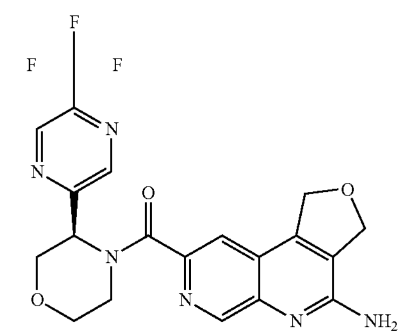 | (4-amino-1,3-dihydrofuro[3,4-c][1,7]naphthyridin-8-yl)-[(3R)-3-[5-(trifluoromethy)pyrazin-2-yl]morpholin-4-yl]methanone | 447 | 2nd peak, Chiral Technologies OJ column (250 × 21 mm, 5 mm) with a mobile phase of 75% Liquid $CO_2$ and 25% MeOH with 0.2% TEA using a flowrate of 80 mL/min. |
| 615 | 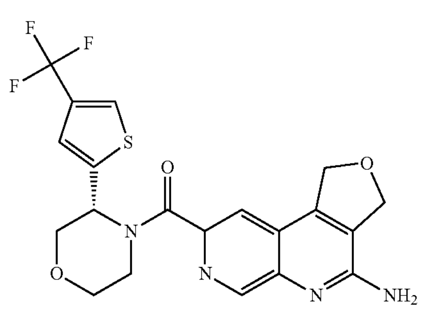 [SMILES: Nc1nc2c(c3c1COC3)=CC(C(=O)N1CCOC[C@@H]1c1cc(C(F)(F)F)cs1)NC=2] | (4-amino-1,3-dihydrofuro[3,4-c][1,7]naphthyridin-8-yl)((3R)-3-(4-(trifluoromethyl)-2-thiophenyl)-4-morpholinyl)methanone | 451.2 | 1st peak, Chiral Technologies OX column (250 × 21 mm, 5 mm) with a mobile phase of 65% Liquid $CO_2$ and 35% MeOH with 0.2% TEA using a flowrate of 80 mL/min. |

TABLE 11-continued

| Ex. | Structure | Name | m/z (ESI): [M + H]+ | SFC Conditions |
|---|---|---|---|---|
| 616 | 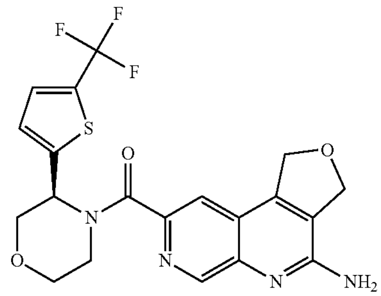 [SMILES: Nc1nc2cnc(C(=O)N3CCOC[C@H]3c3ccc(C(F)(F)F)s3)cc2c2c1COC2] | (4-amino-1,3-dihydrofuro[3,4-c][1,7]naphthyridin-8-yl)((3S)-3-(5-(trifluoromethyl)-2-thiophenyl)-4-morpholinyl)methanone | 451.2 | 1st peak, Chiral Technologies IC column (250 × 21 mm, 5 mm) with a mobile phase of 70% Liquid $CO_2$ and 30% MeOH with 0.2% TEA using a flowrate of 80 mL/min |
| 617 | 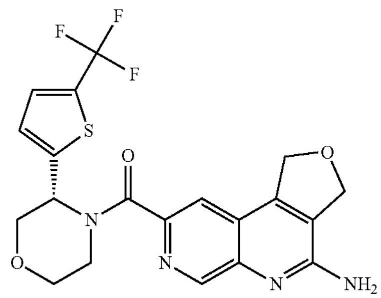 [SMILES: Nc1nc2cnc(C(=O)N3CCOC[C@@H]3c3ccc(C(F)(F)F)s3)cc2c2c1COC2] | (4-amino-1,3-dihydrofuro[3,4-c][1,7]naphthyridin-8-yl)((3R)-3-(5-(trifluoromethyl)-2-thiophenyl)-4-morpholinyl)methanone | 451.2 | 2nd peak, Chiral Technologies IC column (250 × 21 mm, 5 mm) with a mobile phase of 70% Liquid $CO_2$ and 30% MeOH with 0.2% TEA using a flowrate of 80 mL/min |
| 618 | 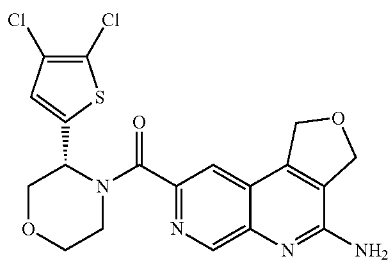 [SMILES: Nc1nc2cnc(C(=O)N3CCOC[C@@H]3c3cc(Cl)c(Cl)s3)cc2c2c1COC2] | (4-amino-1,3-dihydrofuro[3,4-c][1,7]naphthyridin-8-yl)((3R)-3-(4,5-dichloro-2-thiophenyl)-4-morpholinyl)methanone | 451.4 | 1st peak, Chiral Technologies OJ column (250 × 21 mm, 5 mm) with a mobile phase of 60% Liquid $CO_2$ and 40% MeOH with 0.2% TEA using a flowrate of 60 mL/min |
| 619 | 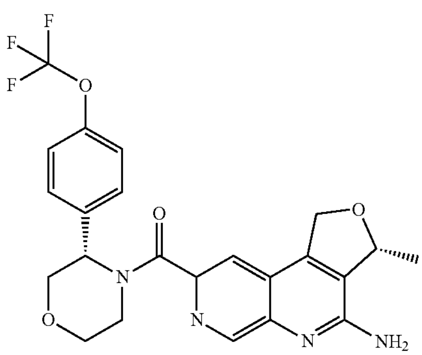 [SMILES: C[C@H]1OCc2c1c(N)nc1c2=CC(C(=O)N2CCOC[C@@H]2c2ccc(OC(F)(F)F)cc2)NC=1] | ((3R)-4-amino-3-methyl-1,3-dihydrofuro[3,4-c][1,7]naphthyridin-8-yl)((3S)-3-(4-(trifluoromethoxy)phenyl)-4-morpholinyl)methanone | 474.8 | 2nd Peak, Chiralcel OJ-H column with a mobile phase of 80% Liquid $CO_2$ and 20% MeOH + TEA using flowrate of 80 mL/min |
| 620 | 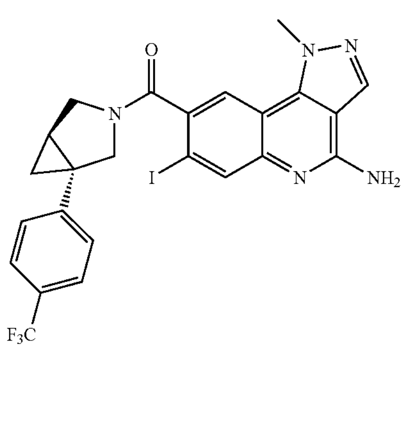 [SMILES: Cn1ncc2c(N)nc3cc(I)c(C(=O)N4C[C@@H]5C[C@]5(c5ccc(C(F)(F)F)cc5)C4)cc3c21] | (4-amino-7-fluoro-1-methyl-1H-pyrazolo[4,3-c]quinolin-8-yl)((1S,5R)-1-(4-(trifluoromethyl)phenyl)-3-azabicyclo[3.1.0]hexan-3-yl)methanone | 470.2 | 1st Peak, SFC using a Chiralcel OJ, 2 × 25 cm, 5 micron column, with a mobile phase of 75% Liquid $CO_2$ and 25% methanol w/ 0.1% diethylamine using a flowrate of 60 mL/min |

TABLE 11-continued

| Ex. | Structure | Name | m/z (ESI): [M + H]+ | SFC Conditions |
|---|---|---|---|---|
| 621 | 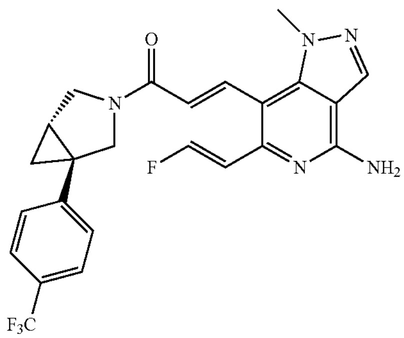 [SMILES: Cn1ncc2c(N)nc(/C=C/F)c(/C=C/C(=O)N3C[C@H]4C[C@@]4(c4ccc(C(F)(F)F)cc4)C3)c21] | (4-amino-7-fluoro-1-methyl-1H-pyrazolo[4,3-c]quinolin-8-yl)((1R,5S)-1-(4-(trifluoromethyl)phenyl)-3-azabicyclo[3.1.0]hexan-3-yl)methanone | 470.2 | $2^{nd}$ Peak, SFC using a Chiralcel OJ, 2 × 25 cm, 5 micron column, with a mobile phase of 75% Liquid $CO_2$ and 25% methanol w/ 0.1% diethylamine using a flowrate of 60 mL/min |
| 622 | 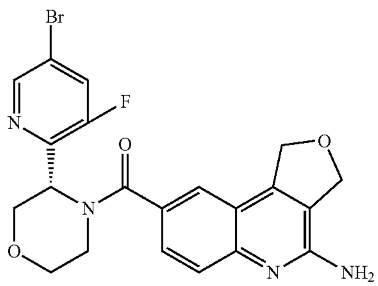 [SMILES: Nc1nc2ccc(C(=O)N3CCOC[C@@H]3c3ncc(Br)cc3F)cc2c2c1COC2] | (4-amino-1,3-dihydrofuro[3,4-c]quinolin-8-yl)((3S)-3-(5-bromo-3-fluoro-2-pyridinyl)-4-morpholinyl)methanone | 473.00 and 475.00 | $2^{nd}$ peak, Chiral Technologies OJ column (250 × 21 mm, 5 mm) with a mobile phase of 75% Liquid $CO_2$ and 25% MeOH with 0.2% TEA using a flowrate of 80 mL/min |

Example 623: (4-Amino-1,3-dihydrofuro[3,4-c][1,7]naphthyridin-8-yl)((3S)-1-oxido-3-(4-(trifluoromethyl)phenyl)thiomorpholino)methanone

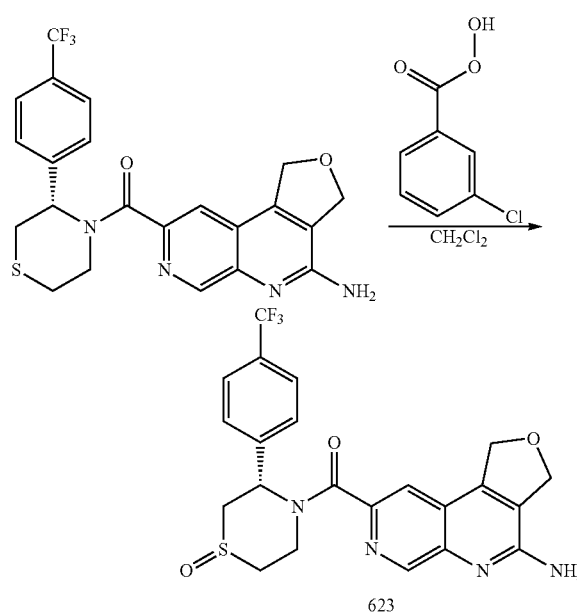

To a solution of (S)-(4-amino-1,3-dihydrofuro[3,4-c][1,7]naphthyridin-8-yl)(3-(4-(trifluoromethyl)phenyl)thiomorpholino)methanone (30 mg, 0.065 mmol) in 1.5 mL of DCM at RT was added 3-chloroperoxybenzoic acid (36.5 mg, 0.163 mmol, Sigma-Aldrich Corporation). The mixture was stirred at RT for 2 h (LCMS showed a mixture of sulfone and sulfoxide was formed) then partitioned between 2.5 mL of 0.5 N NaOH and 25 mL of DCM. The organic phase was separated and concentrated. The residue was purified via RP-HPLC (10-90% 0.1% TFA mediated $CH_3CN$ in water) to give (4-amino-1,3-dihydrofuro[3,4-c][1,7]naphthyridin-8-yl)((3S)-1-oxido-3-(4-(trifluoromethyl)phenyl)thiomorpholino)methanone 2,2,2-trifluoroacetate (2 mg, 3.39 µmol, 5.2% yield) as an off-white solid. m/z (ESI): 476.9 [M+H]+. $^{19}F$ NMR (METHANOL-$d_4$, 376 MHz) δ –64.16 (s, 3F), –77.26 (s, 3F). $^1H$ NMR (METHANOL-$d_4$, 400 MHz) δ 9.04 (s, 1H), 8.11 (s, 1H), 7.78 (m, 4H), 6.34 (m, 1H), 5.56 (m, 2H), 5.23 (t, J=3.9 Hz, 2H), 4.05 (dd, J=5.4, 13.2 Hz, 1H), 3.45 (m, 3H), 3.13 (m, 2H).

Example 624: (S)-1-(4-(4-Amino-1,3-dihydrofuro[3,4-c][1,7]naphthyridine-8-carbonyl)-3-(4-(trifluoromethyl)phenyl)piperazin-1-yl)ethan-1-one

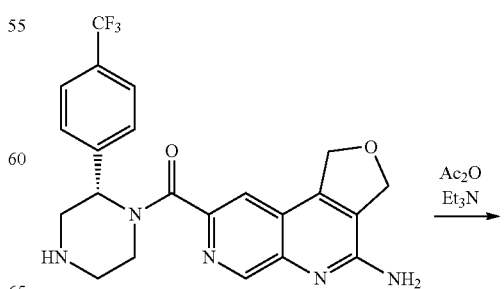

-continued

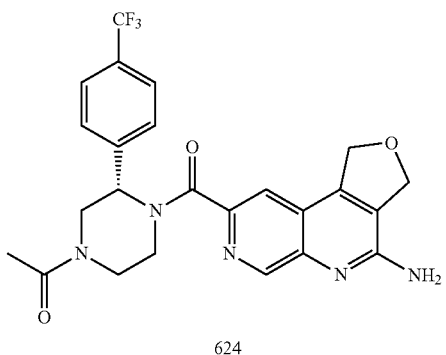

624

To a solution of (S)-(4-amino-1,3-dihydrofuro[3,4-c][1,7]naphthyridin-8-yl)(2-(4-(trifluoromethyl)phenyl)piperazin-1-yl)methanone (50 mg, 0.113 mmol) in 1.5 mL of DCM at 0° C. was added acetic acid anhydride (13.81 mg, 0.135 mmol, Sigma-Aldrich Corporation) followed by triethylamine (31.7 μL, 0.226 mmol, Sigma-Aldrich Corporation). The mixture was stirred at 0° C. for 20 min followed by RT for 10 min then partitioned between 1 mL of 0.5 N NaOH and 10 mL of DCM. The organic phase was washed with 1 mL of brine, concentrated, and the residue was purified on a RP-HPLC (10-90% 0.1% TFA mediated $CH_3CN$ in water) to give (S)-1-(4-(4-amino-1,3-dihydrofuro[3,4-c][1,7]naphthyridine-8-carbonyl)-3-(4-(trifluoromethyl)phenyl)piperazin-1-yl)ethan-1-one bis(2,2,2-trifluoroacetate) (55 mg, 0.077 mmol, 68.4% yield) as a brown solid. m/z (ESI): 486.1 [M+H]$^+$. $^{19}$F NMR (DMSO-d$_6$, 376 MHz) δ −60.88 (s, 3F), −74.63 (s, 6F). $^1$H-NMR was a mixture of rotamers (1/3 ratio). $^1$H NMR (DMSO-d$_6$, 400 MHz) δ 9.00 (br s, 0.75H), 8.86 (br s, 0.25H), 7.97 (m, 2H), 7.78 (m, 3H), 7.63 (m, 2H), 5.86 (br s, 0.75H), 5.64 (br s, 0.25H), 5.42 (br s, 1.5H), 5.37 (br s, 0.5H), 5.09 (br s, 2H), 3.8-4.0 (m, 6H), 2.8-3.0 (m, 2H), 1.96 (br s, 3H).

Example 625: (S)-(4-amino-1,3-dihydrofuro[3,4-c]quinolin-8-yl)(3-(4-(trifluoromethyl)phenyl)morpholino)methanethione

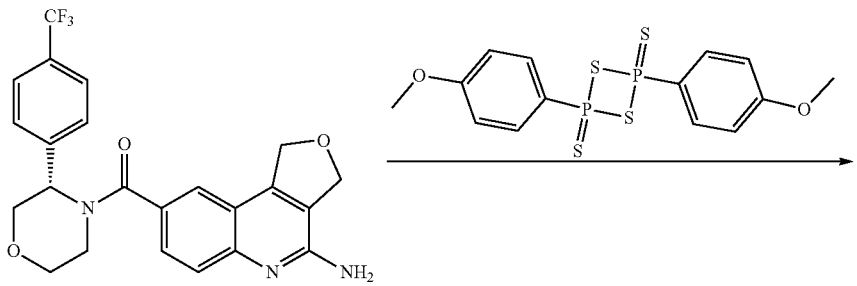

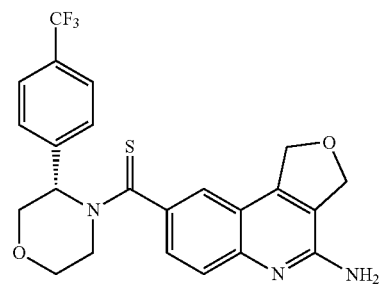

625

A mixture of Lawesson's reagent (63.8 mg, 0.158 mmol, Aldrich) and (S)-(4-amino-1,3-dihydrofuro[3,4-c]quinolin-8-yl)(3-(4-(trifluoromethyl)phenyl)morpholino)methanone (70 mg, 0.158 mmol) in 1 mL of THF in a sealed glass tube was heated in a microwave at 95° C. for 6 h. RP-HPLC purification of the crude mixture (10-90% 0.1% TFA mediated $CH_3CN$ in water) afforded (S)-(4-amino-1,3-dihydrofuro[3,4-c]quinolin-8-yl)(3-(4-(trifluoromethyl)phenyl)morpholino)methanethione 2,2,2-trifluoroacetate (69.7 mg, 0.122 mmol, 77% yield) as a yellow solid. m/z (ESI): 460.3 $[M+H]^+$. $^{19}F$ NMR (METHANOL-$d_4$, 376 MHz) δ −64.14 (s, 3F), −77.05 (s, 3F). $^1H$ NMR (400 MHz, METHANOL-$d_4$) δ ppm 7.91 (m, 1H), 7.69-7.83 (m, 3H), 7.64 (m, 1H), 7.51 (br s, 1H), 7.05 (br s, 1H), 5.52 (br s, 2H), 5.20 (br s, 2H), 4.90-5.06 (m, 2H), 4.73 (m, 1H), 4.11 (m, 1H), 3.89 (m, 1H), 3.81 (m, 1H), 3.71 (m, 1H).

Example 626: (4-amino-1,3-dihydrofuro[3,4-c][1,7]naphthyridin-8-yl)((3S)-3-(4-(trifluoromethyl)phenyl)-4-morpholinyl)methanethione

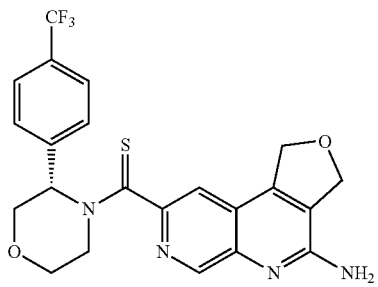

Example 626 was prepared in an identical manner to example 625. m/z (ESI): 461.10 $[M+H]^+$ HCT116 Proliferation Activity To assess selective anti-proliferative activity of compounds of the invention in cells that have loss expression of MTAP, an HCT-116 isogenic cell line pair was utilized where one cell line was engineered to genetically knockout both MTAP alleles. Cell viability was then assessed in both the parent HCT-116 cell line and the MTAP null cell line after 6 days of treatment with compounds of the present invention. Selective anti-proliferative activity in the MTAP null cell line indicates MTA-cooperative inhibition of PRMT5 and ability to inhibit growth of cancer cells that have loss of MTAP.

HCT116 MTAP null and WT cells were seeded in 96-well tissue culture plates in RPMI 1640 media+10% fetal bovine serum. Plates were incubated overnight at 37° C. and 5% $CO_2$. Cells were then treated with an 8- or 9-point serial dilution of compound, using a top concentration of 1, or 10 μM, 1:3 serial dilution steps and, a DMSO-only control. Cells were incubated in the presence of drug for 6 days. Effects on cell viability were measured with the CellTiter-Glo® Luminescent Cell Viability Assay (Promega) per manufacturer's recommendation. Assay plates were read on an EnVision™ Multilabel Reader using the Ultra-Sensitive luminescence module. $IC_{50}$ values were calculated with GraphPad Prism v 5.01 using symmetrical sigmoidal dose-response least squares fit with Hill slope fixed to −1 and top constrain to 100% or GeneData Screener using a 4-parameter logistic model to fit dose response curves.

Alternatively, compounds could be assayed with a 384 well plate format:

Compounds were pre-spotted into 384 well plates with a 22-point serial dilution of compound, using a top concentration of 10 or 50 μM, 1:2 serial dilution steps and, a DMSO-only control. HCT116 MTAP null and WT cells were then seeded as above and after 6 days effects on cell viability were measured with the CellTiter-Glo® Luminescent Cell Viability Assay (Promega). Assay plates were read as above and $IC_{50}$ values were calculated with GeneData Screener using a 4-parameter logistic model to fit dose response curves. The reported $IC_{50}$ represents the value where the curve transits 50% of control.

TABLE 12

| HCT116-MTAP null and WT cell line proliferation | | |
| --- | --- | --- |
| Ex. | HCT-116 MTAP null $IC_{50}$ (μM) | HCT-116 WT $IC_{50}$ (μM) |
| 300 | >1 | >10 |
| 301 | 0.006 | 0.060 |
| 302 | 0.011 | 0.167 |
| 303 | 0.134 | 2.860 |
| 304 | 0.710 | 0.572 |
| 305 | 0.049 | 0.611 |
| 306 | 0.096 | 2.130 |
| 307 | 0.022 | 0.492 |
| 308 | 0.046 | 1.720 |
| 309 | 0.040 | 0.688 |
| 310 | 0.066 | 3.230 |
| 311 | 0.148 | 6.740 |
| 312 | 0.071 | 3.000 |
| 313 | 0.033 | 0.850 |
| 314 | 0.015 | 0.606 |
| 315 | 0.106 | 4.747 |
| 316 | 0.035 | 1.130 |
| 317 | 0.053 | 2.370 |
| 318 | 0.082 | 2.780 |
| 319 | 0.145 | 5.575 |
| 320 | 0.101 | 3.675 |
| 321 | 0.093 | 4.955 |
| 322 | 0.006 | 0.279 |
| 323 | 0.397 | |
| 324 | 0.186 | |
| 325 | 0.771 | >10 |
| 326 | 0.072 | 2.580 |
| 327 | 0.043 | 2.400 |
| 328 | 0.049 | 1.000 |
| 329 | 0.050 | 1.520 |
| 330 | 0.403 | 20.900 |
| 331 | 0.035 | 0.897 |
| 332 | 0.536 | 23.300 |
| 333 | 0.058 | 1.445 |
| 334 | 0.027 | 0.706 |
| 335 | 0.091 | 2.690 |
| 336 | 0.039 | 1.625 |
| 337 | 0.030 | 1.465 |
| 338 | 0.100 | 5.020 |
| 339 | 0.020 | 0.497 |
| 340 | 0.071 | 6.445 |
| 341 | 0.871 | 13.200 |
| 342 | 0.117 | 6.170 |
| 343 | 0.308 | 16.250 |
| 344 | 0.058 | 1.410 |
| 345 | 0.346 | 19.100 |
| 346 | 0.062 | 1.950 |
| 347 | 0.325 | 4.700 |
| 348 | 0.784 | 13.000 |
| 349 | 0.505 | 20.800 |
| 350 | 0.107 | 2.890 |
| 351 | 0.129 | 6.005 |
| 352 | 0.717 | 20.700 |
| 353 | 0.234 | 6.890 |
| 354 | 0.487 | >10 |
| 355 | 4.060 | >10 |

TABLE 12-continued

HCT116-MTAP null and WT cell line proliferation

| Ex. | HCT-116 MTAP null IC$_{50}$ (μM) | HCT-116 WT IC$_{50}$ (μM) |
|---|---|---|
| 356 | 0.257 | >10 |
| 357 | 0.175 | 9.390 |
| 358 | 0.313 | 14.000 |
| 359 | 0.022 | 0.765 |
| 360 | 1.050 | |
| 361 | 0.839 | |
| 362 | 3.410 | >10 |
| 363 | 1.910 | >10 |
| 364 | 3.480 | >10 |
| 365 | 1.560 | >10 |
| 366 | 0.363 | |
| 367 | 0.368 | |
| 368 | 0.457 | 2.030 |
| 369 | 0.340 | 15.400 |
| 370 | 0.030 | 2.020 |
| 371 | 0.022 | 0.707 |
| 372 | 0.023 | 0.613 |
| 373 | 0.442 | 7.820 |
| 374 | 0.161 | 9.890 |
| 375 | 0.003 | 0.058 |
| 376 | 0.029 | 1.220 |
| 377 | 0.037 | 1.106 |
| 378 | 0.015 | 0.190 |
| 379 | 0.927 | >10 |
| 380 | 0.048 | 0.906 |
| 381 | 0.084 | 2.570 |
| 382 | 0.786 | >10 |
| 383 | 0.437 | 13.900 |
| 384 | 0.023 | 1.680 |
| 385 | 0.151 | 5.830 |
| 386 | 0.344 | 5.020 |
| 387 | 0.193 | 7.250 |
| 388 | 0.838 | 32.750 |
| 389 | 0.052 | 1.610 |
| 390 | 0.165 | 6.360 |
| 391 | 0.073 | 3.390 |
| 392 | 0.216 | >10 |
| 393 | 0.971 | >50 |
| 394 | 0.624 | 36.400 |
| 395 | 0.303 | 8.240 |
| 396 | 0.866 | 13.300 |
| 397 | 0.380 | 32.000 |
| 398 | 0.609 | 13.150 |
| 399 | 0.197 | 13.050 |
| 400 | 0.159 | 6.995 |
| 401 | 0.677 | 17.550 |
| 402 | 0.833 | 13.300 |
| 403 | 0.765 | 0.673 |
| 404 | 0.872 | 9.760 |
| 405 | 0.181 | 2.700 |
| 406 | 0.155 | 5.640 |
| 407 | 0.416 | 4.210 |
| 408 | 0.118 | 6.360 |
| 409 | 0.029 | 1.670 |
| 410 | 0.015 | 0.444 |
| 411 | 0.008 | 0.352 |
| 412 | 0.725 | 20.800 |
| 413 | 0.022 | 0.413 |
| 414 | 0.056 | 2.800 |
| 415 | 0.073 | 3.340 |
| 416 | 0.033 | 0.867 |
| 417 | 0.017 | 0.523 |
| 418 | 0.010 | 0.243 |
| 419 | 0.023 | 0.548 |
| 420 | 0.012 | 0.338 |
| 421 | 0.914 | >50 |
| 422 | 0.633 | 12.500 |
| 423 | 0.653 | 33.300 |
| 424 | 0.345 | 5.690 |
| 425 | 0.147 | 4.400 |
| 426 | 0.097 | 4.760 |
| 427 | 0.040 | 2.540 |
| 428 | 0.074 | 8.403 |
| 429 | 0.382 | 20.600 |
| 430 | 0.445 | 12.600 |
| 431 | 0.337 | 11.400 |
| 432 | 0.616 | 22.700 |
| 433 | 0.421 | 14.600 |
| 434 | 0.468 | 8.220 |
| 435 | 0.251 | 3.760 |
| 436 | 0.029 | 1.720 |
| 437 | 0.924 | 16.000 |
| 438 | 0.878 | 15.200 |
| 439 | 0.021 | 0.887 |
| 440 | 0.014 | 0.602 |
| 441 | 0.683 | 15.600 |
| 442 | 0.040 | 3.610 |
| 443 | 0.013 | 0.793 |
| 444 | 0.018 | 0.499 |
| 445 | 0.011 | 0.240 |
| 446 | 0.014 | 0.240 |
| 447 | 0.013 | 0.602 |
| 448 | 0.006 | 0.130 |
| 449 | 0.007 | 0.145 |
| 450 | 0.005 | 0.040 |
| 451 | 0.162 | 15.350 |
| 452 | 0.049 | 3.458 |
| 453 | 2.175 | 40.300 |
| 454 | 0.024 | 0.778 |
| 455 | >1 | >10 |
| 456 | 0.102 | 4.355 |
| 457 | 8.710 | 18.600 |
| 458 | 0.018 | 0.454 |
| 459 | 0.072 | 6.140 |
| 460 | 0.030 | 1.813 |
| 461 | 0.864 | 14.600 |
| 462 | 0.595 | 14.100 |
| 463 | 0.122 | 6.550 |
| 464 | 0.195 | 5.470 |
| 465 | 0.071 | 3.510 |
| 466 | 0.189 | 16.600 |
| 467 | 0.982 | 31.200 |
| 468 | 0.417 | 37.400 |
| 469 | 0.243 | 4.950 |
| 470 | 0.340 | 5.300 |
| 471 | 0.283 | 6.010 |
| 472 | 0.190 | 4.470 |
| 473 | 0.017 | 0.556 |
| 474 | 0.842 | 6.420 |
| 475 | 0.175 | 9.490 |
| 476 | 0.068 | 1.560 |
| 477 | 0.547 | >50 |
| 478 | 0.031 | 1.950 |
| 479 | 0.577 | 18.900 |
| 480 | 0.092 | 1.750 |
| 481 | 0.107 | 4.330 |
| 482 | >1 | >10 |
| 483 | >1 | >10 |
| 484 | 0.656 | >10 |
| 485 | 0.040 | 1.740 |
| 486 | >1 | >10 |
| 487 | >1 | >10 |
| 488 | >1 | 7.490 |
| 489 | >1 | 5.320 |
| 490 | >1 | 4.800 |
| 491 | 0.108 | 4.385 |
| 492 | 0.764 | 0.318 |
| 493 | >1 | >10 |
| 494 | 0.352 | 13.985 |
| 495 | 0.502 | |
| 496 | 0.486 | 19.800 |
| 497 | 0.477 | 26.000 |
| 498 | 0.711 | 21.500 |
| 499 | 1.097 | 36.600 |
| 500 | >1 | >10 |
| 501 | 0.037 | 0.689 |
| 502 | 0.819 | 11.600 |
| 503 | 0.039 | 0.867 |

TABLE 12-continued

HCT116-MTAP null and WT cell line proliferation

| Ex. | HCT-116 MTAP null IC$_{50}$ (μM) | HCT-116 WT IC$_{50}$ (μM) |
|---|---|---|
| 504 | 0.810 | 6.380 |
| 505 | 0.330 | 21.500 |
| 506 | 0.061 | 2.530 |
| 507 | 0.843 | >10 |
| 508 | 0.603 | 6.610 |
| 509 | 0.325 | 10.600 |
| 510 | 0.043 | 1.580 |
| 511 | 0.043 | 1.130 |
| 512 | >1 | >10 |
| 513 | 0.380 | >10 |
| 514 | 0.210 | 2.590 |
| 515 | 0.047 | 0.541 |
| 516 | 0.211 | 9.120 |
| 517 | 0.008 | 0.151 |
| 518 | 0.086 | 4.690 |
| 519 | 0.004 | 0.026 |
| 520 | 0.018 | 0.120 |
| 521 | 0.030 | 2.083 |
| 522 | 0.030 | 0.509 |
| 523 | 0.009 | 0.213 |
| 524 | 0.031 | 1.240 |
| 525 | 0.019 | 0.372 |
| 526 | 0.006 | 0.120 |
| 527 | 0.027 | 0.503 |
| 528 | 0.029 | 1.210 |
| 529 | 0.018 | 0.502 |
| 530 | 0.004 | 0.060 |
| 531 | 0.013 | 0.215 |
| 532 | 0.019 | 0.400 |
| 533 | 0.045 | 2.480 |
| 534 | 0.044 | 2.610 |
| 535 | 0.064 | 3.163 |
| 536 | 0.019 | 0.646 |
| 537 | 0.055 | 2.503 |
| 538 | 0.282 | 13.300 |
| 539 | 0.027 | 1.270 |
| 540 | 0.019 | 0.579 |
| 541 | 0.056 | 5.330 |
| 542 | 0.235 | 12.500 |
| 543 | 0.018 | 1.860 |
| 544 | 0.024 | 1.010 |
| 545 | 0.031 | 1.430 |
| 546 | 0.013 | 0.198 |
| 547 | 0.396 | 3.850 |
| 548 | 0.269 | 8.110 |
| 549 | 0.558 | 21.500 |
| 550 | 0.073 | 3.147 |
| 551 | 0.006 | 0.150 |
| 552 | 0.013 | 0.369 |
| 553 | 0.513 | 32.450 |
| 554 | 0.028 | 1.100 |
| 555 | 0.041 | 1.230 |
| 556 | 0.039 | 3.580 |
| 557 | 0.697 | 37.100 |
| 558 | 0.017 | 0.630 |
| 559 | 0.575 | 12.000 |
| 560 | 0.042 | 2.877 |
| 561 | 0.006 | 0.120 |
| 562 | 0.006 | 0.084 |
| 563 | 0.032 | 1.057 |
| 564 | 0.028 | 0.708 |
| 565 | 0.006 | 0.072 |
| 566 | >10 | >10 |
| 567 | 2.140 | >10 |
| 568 | 0.036 | 1.790 |
| 569 | >1 | >10 |
| 570 | 0.221 | 8.765 |
| 571 | >1 | >10 |
| 572 | >1 | >10 |
| 573 | 0.241 | >10 |
| 574 | >1 | >10 |
| 575 | 0.357 | 8.480 |
| 576 | >1 | >10 |
| 577 | 0.873 | >10 |
| 578 | >1 | >10 |
| 579 | 0.182 | 7.570 |
| 580 | >1 | >10 |
| 581 | 0.183 | 6.570 |
| 582 | >1 | >10 |
| 583 | 0.017 | 0.616 |
| 584 | 0.236 | 11.700 |
| 585 | >1 | >10 |
| 586 | 0.082 | 2.915 |
| 587 | >1 | >10 |
| 588 | 0.014 | 0.466 |
| 589 | 5.100 | >10 |
| 590 | 0.056 | 1.800 |
| 591 | 6.160 | >10 |
| 592 | 0.145 | 8.900 |
| 593 | 0.936 | >10 |
| 594 | 0.099 | |
| 595 | 0.138 | 8.01 |
| 596 | 0.580 | >10 |
| 597 | 0.866 | >10 |
| 598 | 0.807 | >10 |
| 599 | >10 | >10 |
| 600 | 0.921 | >10 |
| 601 | >10 | >10 |
| 602 | 0.149 | 10 |
| 603 | 0.420 | 10.2 |
| 604 | 0.087 | 7.27 |
| 605 | >1 | >10 |
| 606 | 1.030 | >10 |
| 607 | >1 | >10 |
| 608 | >1 | >10 |
| 609 | 0.207 | 9.11 |
| 610 | >1 | >10 |
| 611 | >1 | >10 |
| 612 | >1 | >10 |
| 613 | 1.830 | >10 |
| 614 | >10 | >10 |
| 615 | 0.241 | 3.46 |
| 616 | 3.240 | >10 |
| 617 | 0.228 | 5.73 |
| 618 | 0.300 | >10 |
| 619 | 0.049 | 1.98 |
| 620 | 0.634 | 4.23 |
| 621 | 0.175 | 4.41 |
| 622 | 0.239 | 7.945001 |
| 623 | 0.843 | 25.7 |
| 624 | 0.343 | 8.573333 |
| 625 | 0.882 | 7.26 |
| 626 | 0.394 | 12.9 |

All publications and patent applications cited in this specification are hereby incorporated by reference herein in their entireties and for all purposes as if each individual publication or patent application were specifically and individually indicated as being incorporated by reference and as if each reference was fully set forth in its entirety. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

The invention claimed is:
1. A compound of Formula I

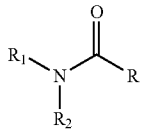

a tautomer thereof, a stereoisomer thereof, or a pharmaceutically acceptable salt of any of the foregoing:
wherein $R_1$, $R_2$ and the nitrogen atom to which they are attached form a five, six or seven membered ring that may be saturated or partially saturated, and comprises 0, 1 or 2 additional heteroatoms, independently selected from O, N and S, wherein the S atom is optionally substituted with one or two oxo groups;
wherein the ring formed by $R_1$, $R_2$ and the nitrogen atom to which they are attached can be substituted with 0, 1, 2 or 3 $R^3$;
wherein $R^3$ is in each instance selected independently from $C_{1-6}$ alkyl, halo, $C_{1-6}$ haloalkyl, —$OC_{1-6}$ alkyl, —$OC_{1-6}$ haloalkyl, —$C(O)C_{1-6}$ alkyl, —$C(O)C_{1-6}$ haloalkyl, —$C(O)OC_{1-6}$ alkyl, —$C(O)OC_{1-6}$ haloalkyl, and five or six membered cycle that may be saturated, partially saturated, or aromatic, and comprises 0, 1 or 2 heteroatoms, independently selected from O, N and S, wherein the cycle may be optionally substituted with one or more $R^a$,
wherein $R^a$ is in each instance independently selected from halo, CN, $C_{1-6}$ alkyl, $C_{1-6}$ haloalkyl, pentafluorosulfanyl, —$OC_{1-3}$ alkyl, and —$OC_{1-3}$ haloalkyl;
wherein R is a tricycle selected from the formulae IA and IB:

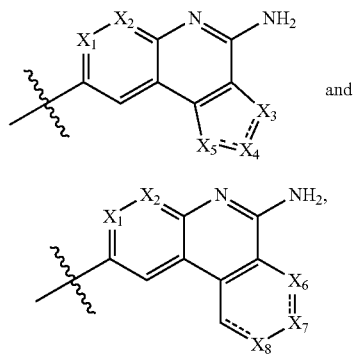

wherein ⚏ is a single or double bond,
$X_1$ and $X_2$ are each selected from N and C, wherein both $X_1$ and $X_2$ cannot be N at the same time; and if $X_1$ is C, it can be optionally substituted with $C_{1-3}$ alkyl or halo;
$X_6$, $X_7$ and $X_8$ are in each instance independently selected from optionally substituted N and C, wherein substituents on N or C are independently selected from $C_{1-3}$ alkyl;
both $X_6$ and $X_7$, and $X_7$ and $X_8$ cannot be N at the same time;
$X_3$, $X_4$ and $X_5$ are at each instance independently selected from O, S, optionally substituted C, and optionally substituted N, wherein the substituents on C or N are independently selected from $C_{1-3}$ alkyl, and $C_{1-3}$ alkyl(OH), wherein alkyl can be optionally substituted with halo.

2. The compound of claim 1, the tautomer thereof, the stereoisomer thereof, or the pharmaceutically acceptable salt of any of the foregoing, wherein R is a tricycle of Formula IA

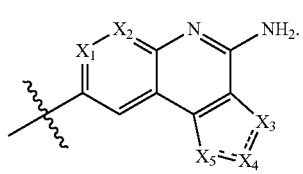

3. The compound of claim 2, the tautomer thereof, the stereoisomer thereof, or the pharmaceutically acceptable salt of any of the foregoing, wherein R is

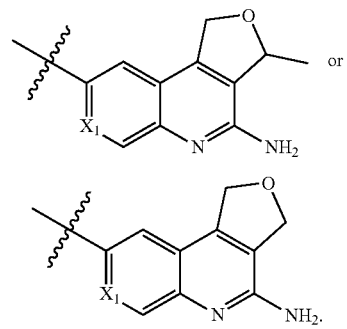

4. The compound of claim 3, the tautomer thereof, the stereoisomer thereof, or the pharmaceutically acceptable salt of any of the foregoing, wherein R is

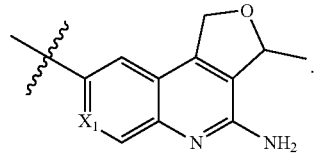

5. The compound of claim 3, the tautomer thereof, the stereoisomer thereof, or the pharmaceutically acceptable salt of any of the foregoing, wherein R is

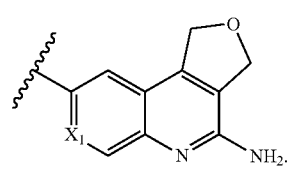

6. The compound of claim 2, the tautomer thereof, the stereoisomer thereof, or the pharmaceutically acceptable salt of any of the foregoing, wherein R is

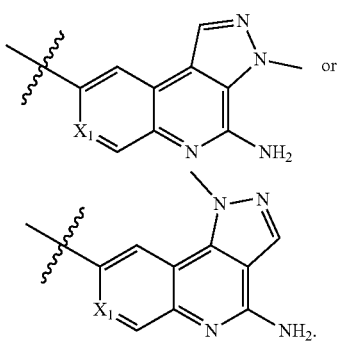

or

7. The compound of claim 6, the tautomer thereof, the stereoisomer thereof, or the pharmaceutically acceptable salt of any of the foregoing, wherein R is

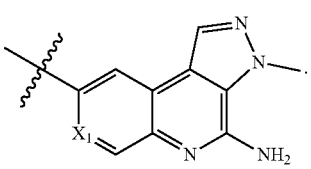

8. The compound of claim 6, the tautomer thereof, the stereoisomer thereof, or the pharmaceutically acceptable salt of any of the foregoing, wherein R is

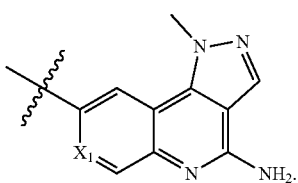

9. The compound as in any of claims 4, 5, 7 and 8, the tautomer thereof, the stereoisomer thereof, or the pharmaceutically acceptable salt of any of the foregoing, wherein $X_1$ is C.

10. The compound of claim 9, the tautomer thereof, the stereoisomer thereof, or the pharmaceutically acceptable salt of any of the foregoing, wherein $X_1$ is substituted with halo.

11. The compound as in any of claims 4, 5, 7 and 8, the tautomer thereof, the stereoisomer thereof, or the pharmaceutically acceptable salt of any of the foregoing, wherein $X_1$ is N.

12. The compound of claim 1, the tautomer thereof, the stereoisomer thereof, or the pharmaceutically acceptable salt of any of the foregoing, wherein R is a tricycle of Formula IB

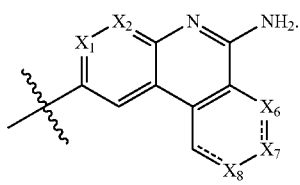

13. The compound of claim 12, the tautomer thereof, the stereoisomer thereof, or the pharmaceutically acceptable salt of any of the foregoing, wherein $X_1$ is N.

14. The compound of claim 13, the tautomer thereof, the stereoisomer thereof, or the pharmaceutically acceptable salt of any of the foregoing, wherein $X_7$ is N.

15. The compound of claim 1, the tautomer thereof, the stereoisomer thereof, or the pharmaceutically acceptable salt of any of the foregoing, wherein R is

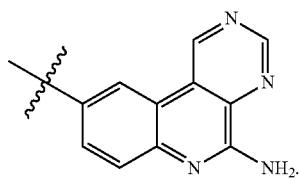 [SMILES: *c1ccc2nc(N)c3ncncc3c2c1]

16. The compound of claim 1, the tautomer thereof, the stereoisomer thereof, or the pharmaceutically acceptable salt of any of the foregoing, wherein R is

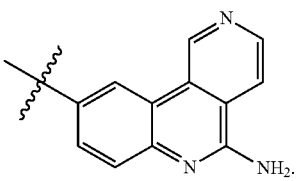

17. The compound of claim 12, the tautomer thereof, the stereoisomer thereof, or the pharmaceutically acceptable salt of any of the foregoing, wherein $R_1$, $R_2$ and the nitrogen atom to which they are attached form a six membered ring that may be saturated or partially saturated, and comprises 0, 1 or 2 additional heteroatoms independently selected from O, N or S, wherein the six membered ring is

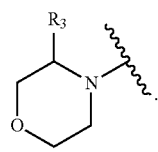

18. The compound of claim 17, the tautomer thereof, the stereoisomer thereof, or the pharmaceutically acceptable salt of any of the foregoing, wherein $R^3$ is selected from phenyl, pyridinyl, pyrazidinyl, or pyrimidinyl, optionally independently substituted with one or more $R^a$.

19. The compound of claim 18, the tautomer thereof, the stereoisomer thereof, or the pharmaceutically acceptable salt of any of the foregoing, wherein $R^3$ is phenyl, optionally independently substituted with one or more $R^a$.

20. The compound of claim 19, the tautomer thereof, the stereoisomer thereof, or the pharmaceutically acceptable salt of any of the foregoing, wherein $R^a$ is C1.6 haloalkyl or —$OC_{1-3}$ haloalkyl.

21. The compound of claim 5, the tautomer thereof, the stereoisomer thereof, or the pharmaceutically acceptable salt of any of the foregoing, wherein $X_1$ is C, optionally substituted with halo.

22. The compound of claim 21, the tautomer thereof, the stereoisomer thereof, or the pharmaceutically acceptable salt of any of the foregoing, wherein halo is Cl or F.

23. The compound of claim 21, the tautomer thereof, the stereoisomer thereof, or the pharmaceutically acceptable salt of any of the foregoing, wherein $R_1$, $R_2$ and the nitrogen atom to which they are attached form a six membered ring that may be saturated or partially saturated, and comprises 0, 1 or 2 additional heteroatoms selected from O, N or S, wherein the six membered ring is

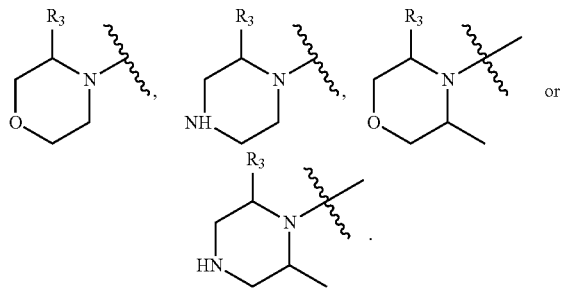

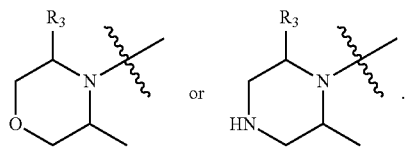

24. The compound of claim 21, the tautomer thereof, the stereoisomer thereof, or the pharmaceutically acceptable salt of any of the foregoing, wherein the six membered ring is 25. The compound of claim 23, the tautomer thereof, the stereoisomer thereof, or the pharmaceutically acceptable salt of any of the foregoing, wherein $R^3$ is independently selected from phenyl, pyridinyl, pyrazidinyl or pyrimidinyl, optionally independently substituted with one or more $R^a$.

26. The compound of claim 21, the tautomer thereof, the stereoisomer thereof, or the pharmaceutically acceptable salt of any of the foregoing, wherein $R_1$, $R_2$ and the nitrogen atom to which they are attached form pyrrolidinyl.

27. The compound of claim 25, the tautomer thereof, the stereoisomer thereof, or the pharmaceutically acceptable salt of any of the foregoing, wherein $R^3$ is phenyl, optionally independently substituted with one or more $R^a$.

28. The compound of claim 27, the tautomer thereof, the stereoisomer thereof, or the pharmaceutically acceptable salt of any of the foregoing, wherein $R^a$ is $C_{1-6}$ haloalkyl or —$OC_{1-3}$ haloalkyl.

29. The compound of claim 6, the tautomer thereof, the stereoisomer thereof, or the pharmaceutically acceptable salt of any of the foregoing, wherein $X_1$ is C, optionally substituted with $C_{1-3}$ alkyl or halo.

30. The compound of claim 29, the tautomer thereof, the stereoisomer thereof, or the pharmaceutically acceptable salt of any of the foregoing, wherein $C_{1-3}$ alkyl is methyl.

31. The compound of claim 29, the tautomer thereof, the stereoisomer thereof, or the pharmaceutically acceptable salt of any of the foregoing, wherein halo is Cl or Br.

32. The compound of claim 6, the tautomer thereof, the stereoisomer thereof, or the pharmaceutically acceptable salt of any of the foregoing, wherein $X_1$ is N.

33. The compound of claim 29, wherein $R_1$, $R_2$ and the nitrogen atom to which they are attached form a six membered ring that may be saturated or partially saturated, and comprises 0, 1 or 2 additional heteroatoms selected from O, N or S, wherein the six membered ring is

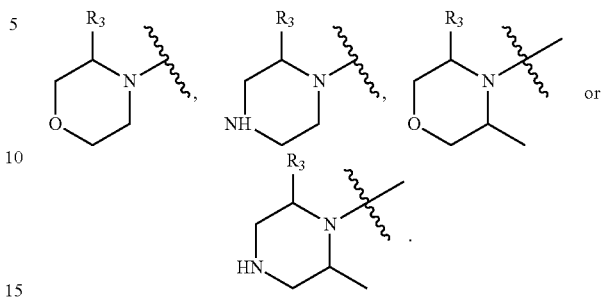

34. The compound of claim 33, the tautomer thereof, the stereoisomer thereof, or the pharmaceutically acceptable salt of any of the foregoing, wherein $R^3$ is independently selected from phenyl, pyridinyl, pyrazidinyl and pyrimidinyl, optionally substituted with one or more $R^a$.

35. The compound of claim 34, the tautomer thereof, the stereoisomer thereof, or the pharmaceutically acceptable salt of any of the foregoing, wherein $R^a$ is in each instance selected from halo, CN, $C_{1-6}$ alkyl, $C_{1-6}$ haloalkyl, —$OC_{1-3}$ alkyl, and —$OC_{1-3}$ haloalkyl.

36. The compound of claim 32, wherein $R_1$, $R_2$ and the nitrogen atom to which they are attached form a six membered ring that may be saturated or partially saturated, and comprises 0, 1 or 2 additional heteroatoms selected from O, N or S, wherein the six membered ring is

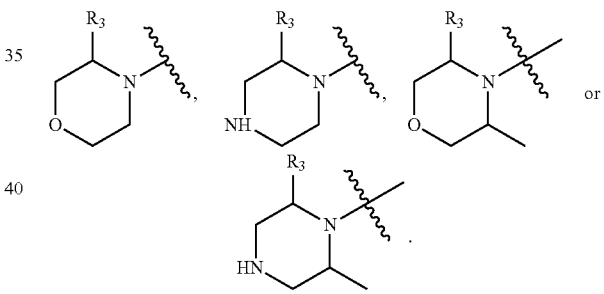

37. The compound of claim 36, the tautomer thereof, the stereoisomer thereof, or the pharmaceutically acceptable salt of any of the foregoing, wherein $R^3$ is independently selected from phenyl, pyridinyl, pyrazidinyl and pyrimidinyl, optionally substituted with one or more $R^a$.

38. The compound of claim 37, the tautomer thereof, the stereoisomer thereof, or the pharmaceutically acceptable salt of any of the foregoing, wherein $R^a$ is in each instance independently selected from halo, CN, $C_{1-6}$ alkyl, $C_{1-6}$ haloalkyl, —$OC_{1-3}$ alkyl, and —$OC_{1-3}$ haloalkyl.

39. A compound, the tautomer thereof, the stereoisomer thereof, or the pharmaceutically acceptable salt of any of the foregoing, wherein the compound is selected from:
(4-amino-1-methyl-1H-pyrazolo[4,3-c][1,7]naphthyridin-8-yl)((3S)-3-(4-(trifluoromethyl)phenyl)-4-morpholinyl)methanone;
(4-amino-1,3-dihydrofuro[3,4-c][1,7]naphthyridin-8-yl)((3S,5R)-3-(6-(cyclopropyloxy)-3-pyridazinyl)-5-methyl-4-morpholinyl)methanone;
(4-amino-1,3-dihydrofuro[3,4-c][1,7]naphthyridin-8-yl)((3R,5S)-3-methyl-5-(6-(2,2,2-trifluoroethoxy)-3-pyridazinyl)-4-morpholinyl)methanone;

((3R)-4-amino-3-methyl-1,3-dihydrofuro[3,4-c]quinolin-8-yl)((3S,5R)-3-(6-ethoxy-3-pyridazinyl)-5-methyl-4-morpholinyl)methanone;

(4-amino-1,3-dihydrofuro[3,4-c][1,7]naphthyridin-8-yl)((3S,5R)-3-(6-(difluoromethoxy)-3-pyridazinyl)-5-methyl-4-morpholinyl)methanone;

(4-amino-1-methyl-1H-pyrazolo[4,3-c]quinolin-8-yl)((3S)-3-(4-(pentafluoro-lambda~6~-sulfanyl)phenyl)-4-morpholinyl)methanone;

(4-amino-1,3-dihydrofuro[3,4-c]quinolin-8-yl)-[(3S)-3-[4-(trifluoromethyl)phenyl]morpholin-4-yl]methanone;

(4-amino-1,3-dihydrofuro[3,4-c]quinolin-8-yl)-[(3S,5S)-3-methyl-5-[5-(trifluoromethyl)-2-pyridyl]morpholin-4-yl]methanone;

(4-amino-1,3-dihydrofuro[3,4-c]quinolin-8-yl)-[(3S)-3-[6-(trifluoromethyl)-3-pyridyl]morpholin-4-yl]methanone;

(4-amino-1,3-dihydrofuro[3,4-c]quinolin-8-yl)-[(3S)-3-[5-(trifluoromethyl)-2-pyridyl]morpholin-4-yl]methanone;

((3R)-4-amino-3-methyl-1,3-dihydrofuro[3,4-c][1,7]naphthyridin-8-yl)((3S)-3-(4-(trifluoromethyl)phenyl)-4-morpholinyl)methanone;

[(3R)-4-amino-3-methyl-1,3-dihydrofuro[3,4-c]quinolin-8-yl]-[(3S)-3-[4-(trifluoromethoxy)phenyl]morpholin-4-yl]methanone;

(4-amino-1,3-dihydrofuro[3,4-c]quinolin-8-yl)-[(3S)-3-[4-(trifluoromethoxy)phenyl]morpholin-4-yl]methanone;

(4-amino-3-methyl-3H-pyrazolo[3,4-c]quinolin-8-yl)((3R,5S)-3-methyl-5-(5-(trifluoromethyl)-2-pyridinyl)-4-morpholinyl)methanone;

(4-amino-1-methyl-1H-pyrazolo[4,3-c]quinolin-8-yl)((3S)-3-(4-(trifluoromethyl)phenyl)-4-morpholinyl)methanone;

(4-amino-7-fluoro-1-methyl-1H-pyrazolo[4,3-c]quinolin-8-yl)((3S)-3-(6-(difluoromethoxy)-3-pyridazinyl)-4-morpholinyl)methanone;

(4-amino-7-fluoro-1-methyl-1H-pyrazolo[4,3-c]quinolin-8-yl)((3S)-3-(6-(trifluoromethyl)-3-pyridazinyl)-4-morpholinyl)methanone;

(4-amino-7-fluoro-1-methyl-1H-pyrazolo[4,3-c]quinolin-8-yl)((3R)-3-(4-(trifluoromethyl)phenyl)-1-pyrrolidinyl)methanone; and (4-amino-1,3-dihydrofuro[3,4-c][1,7]naphthyridin-8-yl)-[(3S)-3-[4-(trifluoromethyl)phenyl]morpholin-4-yl]methanone.

40. A compound, or the pharmaceutically acceptable salt of any of the foregoing, wherein the compound is selected from:

(4-amino-1-methyl-1H-pyrazolo[4,3-c][1,7]naphthyridin-8-yl)((3S)-3-(4-(trifluoromethyl)phenyl)-4-morpholinyl)methanone;

(4-amino-1,3-dihydrofuro[3,4-c][1,7]naphthyridin-8-yl)((3S,5R)-3-(6-(cyclopropyloxy)-3-pyridazinyl)-5-methyl-4-morpholinyl)methanone;

(4-amino-1,3-dihydrofuro[3,4-c][1,7]naphthyridin-8-yl)((3R,5S)-3-methyl-5-(6-(2,2,2-trifluoroethoxy)-3-pyridazinyl)-4-morpholinyl)methanone;

((3R)-4-amino-3-methyl-1,3-dihydrofuro[3,4-c]quinolin-8-yl)((3S,5R)-3-(6-ethoxy-3-pyridazinyl)-5-methyl-4-morpholinyl)methanone;

(4-amino-1,3-dihydrofuro[3,4-c][1,7]naphthyridin-8-yl)((3S,5R)-3-(6-(difluoromethoxy)-3-pyridazinyl)-5-methyl-4-morpholinyl)methanone;

(4-amino-1-methyl-1H-pyrazolo[4,3-c]quinolin-8-yl)((3S)-3-(4-(pentafluoro-lambda~6~-sulfanyl)phenyl)-4-morpholinyl)methanone;

(4-amino-1,3-dihydrofuro[3,4-c]quinolin-8-yl)-[(3S)-3-[4-(trifluoromethyl)phenyl]morpholin-4-yl]methanone;

(4-amino-1,3-dihydrofuro[3,4-c]quinolin-8-yl)-[(3S,5S)-3-methyl-5-[5-(trifluoromethyl)-2-pyridyl]morpholin-4-yl]methanone;

(4-amino-1,3-dihydrofuro[3,4-c]quinolin-8-yl)-[(3S)-3-[6-(trifluoromethyl)-3-pyridyl]morpholin-4-yl]methanone;

(4-amino-1,3-dihydrofuro[3,4-c]quinolin-8-yl)-[(3S)-3-[5-(trifluoromethyl)-2-pyridyl]morpholin-4-yl]methanone;

((3R)-4-amino-3-methyl-1,3-dihydrofuro[3,4-c][1,7]naphthyridin-8-yl)((3S)-3-(4-(trifluoromethyl)phenyl)-4-morpholinyl)methanone;

[(3R)-4-amino-3-methyl-1,3-dihydrofuro[3,4-c]quinolin-8-yl]-[(3S)-3-[4-(trifluoromethoxy)phenyl]morpholin-4-yl]methanone;

(4-amino-1,3-dihydrofuro[3,4-c]quinolin-8-yl)-[(3S)-3-[4-(trifluoromethoxy)phenyl]morpholin-4-yl]methanone;

(4-amino-3-methyl-3H-pyrazolo[3,4-c]quinolin-8-yl)((3R,5S)-3-methyl-5-(5-(trifluoromethyl)-2-pyridinyl)-4-morpholinyl)methanone;

(4-amino-1-methyl-1H-pyrazolo[4,3-c]quinolin-8-yl)((3S)-3-(4-(trifluoromethyl)phenyl)-4-morpholinyl)methanone;

(4-amino-7-fluoro-1-methyl-1H-pyrazolo[4,3-c]quinolin-8-yl)((3S)-3-(6-(difluoromethoxy)-3-pyridazinyl)-4-morpholinyl)methanone;

(4-amino-7-fluoro-1-methyl-1H-pyrazolo[4,3-c]quinolin-8-yl)((3S)-3-(6-(trifluoromethyl)-3-pyridazinyl)-4-morpholinyl)methanone;

(4-amino-7-fluoro-1-methyl-1H-pyrazolo[4,3-c]quinolin-8-yl)((3R)-3-(4-(trifluoromethyl)phenyl)-1-pyrrolidinyl)methanone; and (4-amino-1,3-dihydrofuro[3,4-c][1,7]naphthyridin-8-yl)-[(3S)-3-[4-(trifluoromethyl)phenyl]morpholin-4-yl]methanone.

41. A pharmaceutical composition comprising a compound of any of claims 1, 39 or 40, the tautomer thereof, the stereoisomer thereof, or the pharmaceutically acceptable salt of any of the foregoing and a pharmaceutically acceptable carrier.

42. A compound or the pharmaceutically acceptable salt thereof, wherein the compound is (5-aminopyrimido[4,5-c][1,7]naphthyridin-9-yl)((3S)-3-(4-(trifluoromethyl)phenyl)-4-morpholinyl)methanone.

43. A compound or the pharmaceutically acceptable salt thereof, wherein the compound is (4-amino-1,3-dihydrofuro[3,4-c]quinolin-8-yl)((3S)-3-(4-(pentafluoroethyl)phenyl)-4-morpholinyl)methanone.

44. A compound, or the pharmaceutically acceptable salt thereof, wherein the compound is (4-amino-1,3-dihydrofuro[3,4-c][1,7]naphthyridin-8-yl)(3-(4-(trifluoromethyl)phenyl)morpholino)methanone.

45. A compound, or the pharmaceutically acceptable salt thereof, wherein the compound is (S)-(4-amino-1,3-dihydrofuro[3,4-c][1,7]naphthyridin-8-yl)(3-(4-(trifluoromethyl)phenyl)morpholino)methanone.

46. A compound, or the pharmaceutically acceptable salt thereof, wherein the compound is (R)-(4-amino-1,3-dihydrofuro[3,4-c][1,7]naphthyridin-8-yl)(3-(4-(trifluoromethyl)phenyl)morpholino)methanone.

* * * * *